US012618091B2

(12) United States Patent
Jennewein et al.

(10) Patent No.: US 12,618,091 B2
(45) Date of Patent: *May 5, 2026

(54) PRODUCTION OF HUMAN MILK OLIGOSACCHARIDES IN MICROBIAL HOSTS WITH ENGINEERED IMPORT/EXPORT

(71) Applicant: Chr. Hansen A/S, Hoersholm (DK)

(72) Inventors: Stefan Jennewein, Bad Honnef (DE); Dirk Wartenberg, Bonn (DE)

(73) Assignee: Chr. Hansen A/S, Hoersholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/733,787

(22) Filed: Jun. 4, 2024

(65) Prior Publication Data

US 2024/0318216 A1 Sep. 26, 2024

Related U.S. Application Data

(62) Division of application No. 17/323,737, filed on May 18, 2021, now Pat. No. 12,037,622, which is a division of application No. 15/758,653, filed as application No. PCT/EP2016/071420 on Sep. 12, 2016, now Pat. No. 11,046,985.

(30) Foreign Application Priority Data

Sep. 12, 2015 (EP) ..................................... 15184968

(51) Int. Cl.
| | |
|---|---|
| *C07H 3/06* | (2006.01) |
| *A23L 2/84* | (2006.01) |
| *C12N 9/10* | (2006.01) |
| *C12N 15/70* | (2006.01) |
| *C12P 19/00* | (2006.01) |
| *C12P 19/04* | (2006.01) |
| *C12P 19/18* | (2006.01) |

(52) U.S. Cl.
CPC ............ *C12P 19/18* (2013.01); *C12N 9/1051* (2013.01); *C12N 15/70* (2013.01); *C12Y 204/01146* (2013.01)

(58) Field of Classification Search
CPC .. C12P 19/18; C07H 3/06; C12N 9/10; C12N 15/70; A23L 2/84
See application file for complete search history.

(56) References Cited

U.S. PATENT DOCUMENTS

| | | | |
|---|---|---|---|
| 8,652,808 B2 | 2/2014 | Jennewein et al. | |
| 9,512,433 B2 | 12/2016 | Jennewein et al. | |
| 11,046,985 B2 | 6/2021 | Jennewein et al. | |
| 2011/0236934 A1 | 9/2011 | Samain et al. | |
| 2012/0135467 A1 | 5/2012 | Jennewein et al. | |
| 2014/0120611 A1 | 5/2014 | Jennewein et al. | |

FOREIGN PATENT DOCUMENTS

| | | |
|---|---|---|
| CN | 103060252 B | 4/2015 |
| EP | 2722394 A1 | 4/2014 |
| JP | 2003504072 A | 2/2003 |
| JP | 2007525186 A | 9/2007 |
| JP | 2012529274 A | 11/2012 |
| RU | 2473695 C2 | 1/2013 |
| WO | 2007101862 A1 | 9/2007 |
| WO | 2010142305 A1 | 6/2010 |
| WO | 2014122328 A1 | 8/2014 |
| WO | 2015032413 A1 | 3/2015 |
| WO | 2015106943 A1 | 7/2015 |
| WO | 2015117812 A1 | 8/2015 |
| WO | 2015150328 A1 | 10/2015 |
| WO | 2017042382 A1 | 3/2017 |

OTHER PUBLICATIONS

PCT International Search Report for PCT/EP2016/071420, mailed Oct. 28, 2016.
Weichert, et al., "Bioengineered 2'-fucosyllactose and 3-fucosyl-lactose inhibit the adhesion of Pseudomonas aeruginosa and enteric pathogens to human intestinal and respiratory cell lines," Nutrition Research, (2013), vol. 33: 831-838.
Jennewein: "Abschlussbericht zum Forderprojekl Entwicklung eines innovativen Produklionsverfahrens fur Fucosyllctosen Mit dem," Jennewein Biotechnologie GmbH, Project Report, 2012, pp. 1-31.
Khushnuma Koita, "Optimizing Pentose Sugar Utilization in *Escherichia coli* for the Production of Biofuels," University of Illinois at Urbana-Champaign Dissertation, 2012.
Koita, et al., "Identification and Analysis of the Putative Pentose Sugar Efflux Transporters in *Escherichia coli*," PLOS One, (2012), vol. 7, No. 8: pp. 1-10.
Baumgartner, et al., "Construction of *Escherichia coli* strains with chromosomally integrated expression cassettes for the synthesis of 2'-fucosyllactose," Microbial Cell Factories, (2013), vol. 12: 1-13.
Petschacher, et al., "Biotechnological production of fucosylated human milk oligosaccharides: Prokaryotic fucosyltransferases and their use in biocatalytic cascades or whole cell conversion systems," Journal of Biotechnology, (2016), vol. 235: 61-83.
Baumgartner, et al., "Synthesis of fucosylated lacto-N-tetraose using whole-cell biotransformation," Bioorganic & Medicinal Chemistry, (2015), vol. 23: 6799-6806.
Saumonneau et al., "Design of an alpha-L-transfucosidase for the synthesis of fucosylated HMOs," Glycobiology, (2016), vol. 26, No. 3: 261-269.

(Continued)

*Primary Examiner* — Maryam Monshipouri
(74) *Attorney, Agent, or Firm* — Kelly K. Reynolds

(57) ABSTRACT

The present invention relates to methods for the production of oligosaccharides in genetically modified bacterial host cells, as well as to the genetically modified host cells used in the methods. The genetically modified host cell comprises at least one recombinant glycosyltransferase, and at least one nucleic acid sequence coding for a protein enabling the export of the oligosaccharide.

7 Claims, 6 Drawing Sheets

Specification includes a Sequence Listing.

(56)         References Cited

OTHER PUBLICATIONS

Bernard Priem, et al., "A new fermentation process allows large-scale production of human milk oligosaccharides by metabolically engineered bacteria," Glycobiology, (2002), vol. 12, No. 4: 235-240.

Florian Baumgartner, "Synthesis of the Human Milk Oligosaccaride Lacto-N-Tetraose in Metabolically Engineered, Plasmid-Free *E. coli*," ChemBioChem Communications, (2015), vol. 15(13), 1896-1900.

Baumgartner, et al., "Galactose-limited fed-batch cultivation of *Escherichia coli* for the production of lacto-N-tetraose," Enzyme and Microbial Technology (2015), 75-76: 37-43.

Han, et al., "Biotechnological production of human milk oligosaccharides," Biotechnology Advances (2012), 30(6): 1268-1278.

Koita, Dissertation, University of Illinois at Urbana Champaign (2012), pp. 1-121.

Pao, et al. , "Major Facilitator Superfamily," Microbiology and Molecular Biology Reviews (1998), 62(1): 1-34.

Mncent, et al., "Structure and Kinetics of a Monomeric Glucosamine 6-Phosphate Deaminase," JBC (2005), 280 (20): 19649-19655.

Smilovitz et al.; Breast milk oligosaccharides: structure-function relationships in the neonate; Annu. Rev. Nutr. 2014) 34: 143-169.

Neichert, et al., "Bioengineered 2'—fucosyllactose and 3-fucosyl-lactose inhibit the adhesion of Pseudomonas aeruginosa and enteric pathogens to human intestinal and respiratory cell lines," Nutrition Research, (2013), vol. 33: 831-838.

Witkowski et al., 1999, Biochemistry, 38, 11643-11650.

PRODUCTION OF HUMAN MILK OLIGOSACCHARIDES IN MICROBIAL HOSTS WITH ENGINEERED IMPORT/EXPORT

CROSS-REFERENCE TO RELATED APPLICATIONS

This application is a divisional application of U.S. application Ser. No. 17/323,737, published as U.S. patent application publication 2021/0277435 on Sep. 9, 2021, which is a divisional of U.S. application Ser. No. 15/758,653, now U.S. Pat. No. 11,046,985 issued on Jun. 29, 2021, which is a 35 U.S.C. 371 national application of international application no. PCT/EP2016/071420 filed Sep. 12, 2016 and published as International patent application publication WO2017/042385 on Mar. 16, 2017, which claims priority or the benefit under 35 U.S.C. 119 of European application no. 15184968.4 filed Sep. 15, 2015, the contents of which are fully incorporated herein by reference.

REFERENCE TO A SEQUENCE LISTING

This application contains a Sequence Listing in computer readable form. The contents of the electronic sequence listing created on Jun. 4, 2022, named SQ_ST26.xml and 333 KB in size, is hereby incorporated by reference in its entirety.

BACKGROUND

Human milk is regarded as the best diet for the development of infants. It is composed of fats, proteins, vitamins, minerals, trace elements and a complex carbohydrate mixture which comprises lactose and approximately 150 structurally diverse oligosaccharides (Human milk oligosaccharides, HMO).

Efforts to produce HMO chemically or by biotechnological approaches mainly attracted common attention due to their beneficial impact on the development of the gastrointestinal flora of infants, thus, advocating their use as nutritional additives. Besides these prebiotic properties, many other positive effects of HMO could be observed so far, expanding their field of application.

However, extensive scientific studies demand pure single compounds which are hardly achievable. This is especially true for complex free neutral and acidic oligosaccharides for which competitive large-scale production processes are still lacking. (e.g. lacto-N-tetraose (Gal($\beta$1-3)GlcNAc($\beta$1-3)Gal ($\beta$1-4)Gluc), lacto-N-neotetraose (Gal($\beta$1-4)GlcNAc($\beta$1-3) Gal($\beta$1-4)Gluc), lacto-N-fucopentaose I (Fuc($\alpha$1-2)Gal($\beta$1-3)GlcNAc($\beta$1-3)Gal($\beta$1-4)Gluc) lacto-N-neofucopenaose I (Fuc($\alpha$1-2)Gal($\beta$1-4)GlcNAc($\beta$1-3)Gal($\beta$1-4)Gluc) (Lacto-N-sialylpentaose a (LST-a; Neu5Ac($\alpha$2-3)Gal($\beta$1-3) GlcNAc($\beta$1-3)Gal($\beta$1-4)Gluc)) The metabolic engineering of a microorganism to produce these compounds represents the most promising approach since chemical methods are rather inefficient to produce these molecules at multi-ton scale.

Several fermentative approaches were already developed for the structural simpler HMOs such as 2'-fucosyllactose, 3-fucosyllactose or 3'-sialyllactose, using mainly metabolically engineered *Escherichia coli* strains.

However, large-scale quantities are only achievable through boosting the oligosaccharide export out of the bacterial cell, thus, (i) enhancing the productivity and (ii) allowing the recovering of the desired oligosaccharide from the culture broth. The need for solving the export problem seems to enlarge with the size of the produced sugar. Also, with the currently available fermentation processes, upon production of more complex oligosaccharides, the problem of an unwanted export of oligosaccharide precursors from the producing cell occurs, leading to an undesirable mix of product and precursor oligosaccharides in the fermentation medium. Whereas multiple transporter proteins are known to transfer mono- or disaccharides across the membrane, hardly any knowledge exists on the transport of larger oligosaccharides (e.g., trisaccharides and larger oligosaccharides).

For example, the genome of the often used fermentation model organism *E. coli* encodes more than 500 distinct transporter proteins (Busch and Saier, Crit Rev Biochem Mol Biol. 2002; 37(5):287-337). The classification of those membrane transport proteins is quite diverse and subgroups may vary in translocation mechanisms, protein structures or evolutionary origins.

Classically energy-driven active transporters perform substrate movement against its concentration or electrochemical gradient, while kinetics and direction of the substrate flow through channels primarily follows such gradients. Depending on the source of energy used for the translocation, pumps can be principally divided into primary active and secondary active transporters, exploiting metabolic energy like ATP or the electrochemical potential, respectively (Davidson and Maloney, Trends Microbiol. 2007 October; 15(10):448-55; Forrest et al, Biochim Biophys Acta. 2011 February; 1807(2):167-88). Although in-depth knowledge was achieved for several membrane proteins permitting energy generation, the import of carbohydrates and the efflux of proteins and antibacterial substances, however, keen insights into mechanistic processes or information on natural or probable substrates were gained only for a minor portion of annotated bacterial transporters so far.

The *E. coli* lactose permease LacY probably represents the most intensively characterized solute transporter (Guan and Kaback, Annu Rev Biophys Biomol Struct. 2006; 35:67-91) and is a member of the large and exceptionally diverse major facilitator superfamily (MFS)—that belongs to the secondary active transporter class—transporting sugars, drugs, hydrophobic molecules, peptides, organic ions, etc. by uniport, symport or antiport (Saier et al., J Mol Microbiol Biotechnol. 1999 November; 1(2):257-79). Apart from a few exceptions a common structural feature of MFS transporters are two six-helical subdomains that transverse the cytoplasmic membrane. The existence of functionally homologous amino acid positions between related H$^+$-coupled MFS symporters further suggests a similar kinetic mechanism as determined for the lactose permease (Madej and Kaback, Proc Natl Acad Sci USA. 2013 Dec. 10; 110(50):E4831-8).

Since decades, enormous knowledge about the import of carbohydrates into bacteria could be acquired. But regarding the export of carbohydrates, especially about molecules that are non-surface-associated, only little information is available. This is not unexpected since sugars actually depict a favourable carbon- and energy source, thus, once in the cell they shouldn't be released to a competitive environment.

However, the natural function of sugar exporters probably involve the reduction of osmotic or sugar-phosphate stress which might point to a flexible substrate spectrum. Interestingly, the export of a variety of galactosides like IPTG, TMG and lactose was shown for members of the so called sugar efflux transporter family (SET), which belong to the group of MFS transporters (Liu et al., J Biol Chem. 1999 Aug. 13; 274(33):22977-84; Liu et al., Mol Microbiol. 1999 March; 31(6):1845-51).

The *E. coli* transport protein SetA was even described to transfer the human milk oligosaccharide 3-fucosyllactose resulting in an improved production of said compound during fermentation of a recombinant *E. coli* strain overexpressing setA (see applicant's international patent application WO 2010/142305). Similarly, the expression of a sugar efflux transporter from Yersinia was shown to enable the export of the human milk oligosaccharide 2'-fucosyllactose out of an engineered *E. coli* production strain.

Apart from this, from a mechanistic and energetic point of view, only the ion-gradient-driven transport systems have the potential to translocate solutes in both directions across the membrane. This is exemplarily true for the above mentioned LacY, a galactoside/H⁺ symporter, which is part of the bacterial lac operon that allows the metabolism of lactose in *E. coli*. This permease primarily imports lactose into the cell but it is also capable to transfer its substrate in the opposite direction.

Besides the major facilitator superfamily, which represents the largest group of transporters, bacteria possess further mechanisms to excrete solutes-often summarized in the classes of multidrug efflux pumps. Alike for the MFS, the activities of the small multidrug resistance superfamily (SMR), the multidrug and toxic compound extrusion superfamily (MATE) and the resistance-nodulation-cell division superfamily (RND) rely on the electrochemical gradient. The fifth class is the adenosine triphosphate (ATP)-binding cassette superfamily (ABC) which uses ATP as energy source to drive molecules from the cell. As for the MFS, members of SMR, MATE, RND and ABC transport structurally diverse molecules. Further, most of their so far identified substrates are not naturally occurring, and, thus, their preferences are hardly predictable.

Although chemical synthesizing processes are known for human milk oligosaccharides, these processes are very cost-intensive and do not lead to satisfying amounts. On the other hand, fermentation processes using genetically modified microorganisms still have the drawback that the export of larger oligosaccharides (tetra-, penta-, hexasaccharides) represents a major limitation for the establishment of cost effective production processes. As a consequence, there still is the need for improved processes for the production of large-scale human oligosaccharides.

SUMMARY OF THE INVENTION

According to the invention, this and other objects are solved by the methods and microbial host cell(s) as claimed in the attached claims.

With the methods and host cells according to the invention it is possible to produce a desired oligosaccharide, preferably an oligosaccharide that is not produced in an unmodified host cell, and also preferably an oligosaccharide belonging to the human milk oligosaccharides, in large amounts obtainable from the medium. As such, the oligosaccharide is, so to say, obtainable in free from in the medium; it is not bound to a surface protein or membrane protein or other protein of the surface of the host cell.

According to the invention, a method for the production of a desired oligosaccharide by a genetically modified microbial host cell, comprising the steps of a) providing a genetically modified microbial host cell that comprises at least one recombinant glycosyltransferase, and that has the expression or activity of at least one endogenous sugar export protein modified such, that the expression or activity of the sugar export protein is either (i) increased or (ii) decreased or inactivated as compared to an genetically unmodified host cell, so that (i) the export of a oligosaccharide into the medium is either decreased or abolished, or (ii) the transport of a desired oligosaccharide is increased, respectively, as compared to an genetically unmodified host cell, b) cultivating the host cell in a medium under conditions permissive for the production of the desired oligosaccharide, whereby the desired oligosaccharide is transported into the medium. The method may further comprise the step of c) obtaining the desired oligosaccharide from the medium.

In the method according to the invention, it is preferred if the desired oligosaccharide is a human milk oligosaccharide comprising a lacto-N-triose II (LNT-II; GlcNAc(β1-3)Gal (β1-4)Gluc) as a core trisaccharide. In this connection, an oligosaccharide having a "core trisaccharide" is meant to comprise the specific trisaccharide representing the reducing end of a desired oligosaccharide, and comprising, as the case may be, additional saccharide moieties, with the specific trisaccharide representing the major moiety.

Accordingly, in an embodiment of the method and the host cell according to the invention, the desired oligosaccharide is selected from the group consisting of: lacto-N-triose II, lacto-N-tetraose, lacto-N-neotetraose, lacto-N-fucopentaose I, lacto-N-fucopentaose II, lacto-N-fucopentaose III, lacto-N-fucopentaose V, lacto-N-difucosylhexose I, lacto-N-difucosylhexaose II, lacto-N-sialylpentaose LSTa, LSTb, LSTc, disialyllacto-N-tetraose, disialyllacto-N-neotetraose.

In order to overcome the above mentioned drawbacks of limited oligosaccharide export the object is further solved by a method according to the invention, wherein the host cell comprises: at least one homologous or heterologous nucleic acid sequence coding for a protein enabling the export of a desired oligosaccharide into the culture medium, wherein said host cell has been modified such, that the expression of the homologous or heterologous nucleic acid sequence is overexpressed or under control of a promoter enabling the overexpression of the nucleic acid sequence; and/or the deletion, disruption, diminishment or inactivation of at least one endogenous nucleic acid sequence coding for an exporter protein that exports precursors of the desired oligosaccharide outside the host cell; and/or at least one homologous or heterologous nuclei acid sequence coding for a protein mediating the import of a precursor of a desired oligosaccharide into said host cell, wherein preferably the nucleic acid sequence is overexpressed, and wherein preferably the precursor is larger than a disaccharide.

The genetically modified microbial host cell comprising the characteristics as set forth herein are cultured in the presence of glucose, sucrose, glycerin or a combination thereof—using these substrates as carbon- and energy sources—as well as in the presence of lactose or oligosaccharides larger than disaccharides, e.g., LNT-II.

In a preferred embodiment of this method and host cell, said protein enabling the export of a desired oligosaccharide belongs to the class of secondary active transporters, and more preferably effects the export of an oligosaccharide comprising at least three moieties.

According to preferred embodiments, for the export of desired oligosaccharides a suitable exporter is expressed in addition to the genes that are responsible for intracellular oligosaccharide biosynthesis.

According to one aspect of the method and host cell of the invention, the at least one nucleic acid sequence coding for a protein enabling the export of a desired oligosaccharide is an endogenous or a recombinant nucleic acid.

In a preferred embodiment of the method and the host cell of the invention, the nucleic acid sequence coding for a protein enabling the export of a desired oligosaccharide is of bacterial, archeal, plant, yeast or animal origin; preferably, the at least one nucleic acid sequence coding for a protein enabling the export of a desired oligosaccharide is a gene selected from the group consisting of yebQ and yjhB from *Escherichia coli*, proP from *Mannheimia succiniciprod-ucens* and setA from *Cedecea neteri* or functional fragments thereof.

Preferably, the oligosaccharide exporter is a protein selected from at least one of the following: SetA, SetB, SetC, YdeA, Cmr, YnfM, MdtD, YfcJ, YhhS, EmrD, YdhC, YbdA, YdeE, MhpT, YebQ, YjhB, Bcr and YdeA of *E. coli*, or ProP from *Mannheimia succiniciproducens* and SetA from *Cedecea neteri* or variants or homologs thereof.

In yet another preferred embodiment, the recombinant glycosyltransferase is selected from at least one of the following: a galactosyltransferase, a sialyltransferase, an N-acetylglucosaminyltransferase and a fucosyltransferase, and is preferably selected from at least one of the following: β-1,3-N-acetylglucosaminyltransferase, β-1,3-galactosyl-transferase, β-1,4-galactosyltransferase, β-1,6-galactosyl-transferase, α-2,3-sialyltransferase, α-2,6-sialyltransferase, α-1,2-fucosyltransferase, or α-1,3-fucosyltransferase.

A preferred embodiment of the method and the host cell of the invention, concerns the a host cell or its provision, wherein the host cell comprises (i) a β-1,3-N-acetylglu-cosaminyltransferase, and (ii) a β-1,3-galactosyltransferase or a β-1,4-galactosyltransferase as glycosyltransferases. In this connection it is preferred, if said β-1,3-N-acetylglu-cosaminyltransferase has the activity of ligating N-acetyl-glucosamine to lactose generating lacto-N-triose II, and if said β-1,3-galactosyltransferase or said β-1,4-galactosyl-transferase, respectively, have the activity to galactosylate lacto-N-triose II thus generating lacto-N-tetraose or lacto-N-neotetraose, respectively. The here developed system is easily adaptable to even more complex oligosaccharides by the expression of further glycosyltransferases.

With the microbial cell and the method according to the invention, it is possible to ferment a desired oligosaccharide in large quantities, especially an oligosaccharide comprising LNT-II as core structure, and to recover it from the culture broth.

In a preferred embodiment, said β-1,3-N-acetylglu-cosaminyltransferase belongs to the class of lgtA of *Neis-seria meningitides* or PmnagT of *Pasteurella multocida*, or variants thereof.

Preferably, the glycosyltransferase is selected from a galactosyltransferase, a sialyltransferase, an N-acetylglu-cosaminyltransferase and a fucosyltransferase.

In yet another preferred embodiment, the lacto-N-tetraose generating β-1,3-galactosyltransferase is WbdO or a func-tional variant thereof. According to an aspect of the inven-tion, the β-1,3-galactosyltransferase is a β-1,3-galactosyl-transferase derived from *Salmonella enterica* (wbdO, acc. no. AY730594), and is preferably encoded by a gene selected from the group consisting of wbgO from *Escheri-chia coli* O55:H7 or furA from *Lutiella nitroferrum*, or a functional fragments thereof.

The invention also concerns a genetically modified micro-bial host cell, preferably a bacterial host cell, as described above in which the endogenous β-galactosidase gene is inactivated or deleted and in which a functional lactose permease gene is present.

Accordingly, in a preferred embodiment of the method and the host cell of the invention, a genetically modified host cell is provided, in which, where applicable, an endogenous β-galactosidase gene and a glucosamine-6-phosphate deaminase gene are inactivated or deleted, and wherein said genetically modified host cell comprises a nucleic acid sequence coding for a functional lactose permease protein, preferably LacY.

In a preferred embodiment, the genetically modified host cell comprises an increased UDP-N-acetylglucosamine and UDP-galactose, GDP-fucose or CMP-N-acetylneuraminic acid production capability as compared to a genetically unmodified host cell.

In a refinement of this embodiment of the method of and of the host cell of the invention, said increased UDP-N-acetylglucosamine and UDP-galactose production capabil-ity comprises the overexpression of one or more genes encoding for proteins comprising the following activities for a: L-glutamine:D-fructose-6-phosphate aminotransferase, N-acetyl glucosamine-1-phosphate uridyltransferase/glu-cosamine-1-phosphate acetyl transferase, phosphoglu-cosamine mutase, UDP-galactose-4-epimerase, phosphoglu-comutase, glucose-1-phosphate uridylyltransferase.

For the synthesis of, e.g. LNT, UDP-galactose and UDP-N-acetylglucosamine are required. UDP-galactose can be obtained by feeding galactose to the HMO producing bac-terial host cell via the fermentation medium. The galactose is then taken up by the cell, phosphorylated to galactose-1-phosphate and then converted to UDP-galactose. Genes encoding these enzymatic activities are well known in the literature (Grossiord et al., J. Bacteriol 2003 185(3) 870-878). The supply for UDP-galactose can be also obtained from the cells own metabolism, and the metabolism can be improved by further genetic modification, such as the over-expression of the UDP-galactose-4'-epimerase, or the UDP-galactose-4'-epimerase in combination with the glucose-1-phosphate-1-uridinyltransferase. UDP-N-acetylglucosamine can be also obtained from the bacterial host cell's own UDP-N-acetylglucosamine metabolism. The provision of UDP-N-acetylglucosamine for the synthesis of N-acetylglu-cosamine containing oligosaccharides can be improved by the inactivation of the N-acetylglucosamine catabolism within the producing cell.

According to one aspect of the invention, the genetically modified host cell is cultivated in the presence of glucose, sucrose, glycerol or a combination thereof, but neither by addition or in the presence of N-acetylglucosamine or galac-tose nor in a combination thereof.

In a preferred embodiment of the method and of the host cell of the invention, the desired oligosaccharide is lacto-N-triose II, which is produced by total fermentation from a simple carbon source in the host cell by the action of the heterologous expressed glycosyltransferases β-1,4-galacto-syltransferase and β-1,3-N-acetylglucosaminyltransferase.

The present invention, as already mentioned above, also concerns a genetically modified host cell for the production of a desired oligosaccharide, the oligosaccharide comprising a lacto-N-triose II (LNT-II; GlcNAc(β1-3)Gal(β1-4)Gluc) as a core trisaccharide, wherein the host cell comprises at least one recombinant glycosyltransferase, the glycosyl-transferase being preferably selected from a galactosyltrans-ferase, a sialyltransferase, and an N-acetylglucosaminyl-transferase, and has the expression or activity of at least endogenous sugar transport protein modified such, that the expression or activity of the endogenous sugar transport protein is functionally inactivated for the export of a pre-cursor of the desired oligosaccharide.

A preferred embodiment concerns a host cell as described above, comprising (i) a heterologous expressed β-1,3-N-acetylglucosaminyltransferase, and (ii) a heterologous expressed β-1,3-galactosyltransferase or a heterologous expressed β-1,4-galactosyltransferase as glycosyltransferases, wherein the host cell further preferably comprises at least one homologous or heterologous nucleic acid sequence coding for a protein enabling the export of the oligosaccharide into a culture medium the host cell is cultivated in, wherein said protein enabling the export of the desired oligosaccharide belongs to the class of secondary active transporters, wherein said host cell has been modified such, that the expression of the homologous or heterologous nucleic acid sequence is overexpressed or under control of a promoter enabling the overexpression of the nucleic acid sequence. In preferred embodiments of the host cell, said at least one nucleic acid sequence coding for a protein enabling the export of the desired oligosaccharide is an endogenous or a recombinant nucleic acid sequence.

As already outlined for the method according to the invention, it is also preferred in the host cell of the invention, if said nucleic acid sequence coding for a protein enabling the export of a desired oligosaccharide is of bacterial, archeal, plant, yeast or animal origin.

According to another aspect of the invention, the host cell as described above further comprises: the deletion, disruption, diminishment or inactivation of at least one endogenous nucleic acid sequence coding for an exporter protein that exports precursors of the desired oligosaccharide outside the host cell; and/or at least one homologous or heterologous nucleic acid sequence coding for a protein enabling the import of a precursor of a desired oligosaccharide into said host cell, wherein preferably the nucleic acid sequence is overexpressed, and wherein preferably the precursor is larger than a disaccharide.

With the overexpression of at least one homologous or heterologous nucleic acid sequence coding for a protein enabling the import of a precursor of a desired oligosaccharide into said host cell, it is possible to feed precursors of a desired oligosaccharide to the culture medium, which get imported into the host cell, such as, e.g., LNT-II.

According to one aspect of the invention, in the host cell said at least one nucleic acid sequence coding for a protein enabling the export of a desired oligosaccharide is a gene selected from the group consisting of yebQ and yjhB from *Escherichia coli*, proP from *Mannheimia succiniciproducens* and setA from *Cedecea neteri* or functional fragments thereof.

According to yet another preferred embodiment, the desired oligosaccharide is lacto-N-triose II, and the protein enabling the export of the oligosaccharide into a culture medium the host cell is cultivated in, is YjhB from *Escherichia coli*, ProP from *Mannheimia succiniciproducens* and SetA from *Cedecea neteri* or functional fragments thereof.

According to a preferred embodiment, the microbial host according to the invention is further modified not to express proteins exporting precursors of a desired oligosaccharide.

In a preferred embodiment of the host cell, the desired oligosaccharide is lacto-N-tetraose, the precursor is lacto-N-triose II, and the host cell has deleted, disrupted or inactivated at least one nucleic acid sequence coding for an exporter protein that is able to export lacto-N-triose II outside the host cell.

In this connection it is preferred, if the protein enabling the export of lacto-N-tetraose is selected from YebQ from *Escherichia coli* BL21 (DE3), SpoVB of *Bacillus amyloliquefaciens*, YabM of *Erwinia pyrilfolia*, Bcr of *E. coli*

MG1655, YdeA of *E. coli* MG1655, ProP2 of *Haemophilus parainfluenzae*, SetA of *Pectobacterium carotovorum*, FucP of *E. coli* MG1655, MdeA of *Staphylococcus aureus* Bmb9393, ImrA of *Lactococcus lactis*, SetA of *Pseudomonas* sp. MT-1 and SetA of *Beauveria bassiana* D1-5.

Preferably, the oligosaccharide exporter is a protein selected from at least one of the following: SetA, SetB, SetC, YdeA, Cmr, YnfM, MdtD, YfcJ, YhhS, EmrD, YdhC, YbdA, YdeE, MhpT, YebQ, YjhB, Bcr and YdeA of *E. coli*, or ProP from *Mannheimia succiniciproducens* and SetA from *Cedecea neteri* or variants or homologs thereof.

Presently, the term "nucleic acid" refers to a single- or double-stranded deoxyribonucleotide or ribonucleotide macromolecule and encompasses known analogues or natural or synthetically produced nucleotides that hybridize with the desired nucleic acid and that encode a certain polypeptide.

The term "recombinant" or "genetically modified", as used herein with reference to a microbial host cell indicates that the microbial host cell replicates a heterologous nucleic acid, or expresses a peptide or protein encoded by a heterologous nucleic acid (i.e., a sequence "foreign to said cell"). Recombinant cells can contain genes that are not found within the native (non-recombinant) form of the cell. Recombinant cells can also contain genes found in the native form of the cell wherein the genes are modified and reintroduced into the cell by artificial means. The term also encompasses cells that contain a nucleic acid endogenous to the cell that has been modified without removing the nucleic acid from the cell; such modifications include those obtained by gene replacement, site-specific mutation, and related techniques. Accordingly, a "recombinant polypeptide" is one which has been produced by a recombinant cell. A "heterologous sequence" or a "heterologous nucleic acid", as used herein, is one that originates from a source foreign to the particular host cell (e.g. from a different species), or, if from the same source, is modified from its original form. Thus, a heterologous nucleic acid operably linked to a promoter is from a source different from that from which the promoter was derived, or, if from the same source, is modified from its original form. The heterologous sequence may be stably introduced, e.g. by transfection, transformation, conjugation or transduction, into the genome of the host microbial host cell, thus representing a genetically modified host cell. Techniques may be applied which will depend on the host cell the sequence is to be introduced. Various techniques are known to a person skilled in the art and are, e.g., disclosed in Sambrook et al., Molecular Cloning: A Laboratory Manual, 2nd Ed., Cold Spring Harbor Laboratory Press, Cold Spring Harbor, N.Y. (1989).

Accordingly, a "microbial host cell" is presently understood as a microbial, preferably bacterial, cell which has been transformed or transfected, or is capable of transformation or transfection by an exogenous polynucleotide sequence.

Thus, the nucleic acid sequences as used in the present invention, may, e.g., be comprised in a vector which is to be stably transformed/transfected or otherwise introduced into host microorganism cells.

Presently, the term "operably linked" as used herein, shall mean a functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence. Accordingly, the term "Promoter" designates DNA sequences which usually "precede" a gene in a DNA polymer and provide a site for initiation of the transcription into mRNA. "Regulator" DNA sequences, also usually "upstream" of (i.e., preceding) a gene in a given DNA polymer, bind proteins that determine the frequency (or rate) of transcriptional initiation. Collectively referred to as "promoter/regulator" or "control" DNA sequence, these sequences which precede a selected gene (or series of genes) in a functional DNA polymer cooperate to determine whether the transcription (and eventual expression) of a gene will occur. DNA sequences which "follow" a gene in a DNA polymer and provide a signal for termination of the transcription into mRNA are referred to as transcription "terminator" sequences.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and to synthesize a polypeptide in a host may be used for expression in this regard. The appropriate DNA sequence may be inserted into the expression system by any of a variety of well-known and routine techniques, such as, for example, those set forth in Sambrook et al., supra.

The art is rich in patent and literature publications relating to "recombinant DNA" methodologies for the isolation, synthesis, purification and amplification of genetic materials for use in the transformation of selected host organisms. Thus, it is common knowledge to transform host organisms with "hybrid" viral or circular plasmid DNA which includes selected exogenous (i.e. foreign or "heterologous") DNA sequences. The procedures known in the art first involve generation of a transformation vector by enzymatically cleaving circular viral or plasmid DNA to form linear DNA strands. Selected foreign DNA strands usually including sequences coding for desired protein product are prepared in linear form through use of the same/similar enzymes. The linear viral or plasmid DNA is incubated with the foreign DNA in the presence of ligating enzymes capable of effecting a restoration process and "hybrid" vectors are formed which include the selected exogenous DNA segment "spliced" into the viral or circular DNA plasmid.

As used herein, the term "cultivating" means growing a bacterial cell in a medium and under conditions permissive and suitable for the production of the desired oligosaccharide(s). A couple of suitable bacterial host cells as well as mediums and conditions for their cultivation will be readily available for one skilled in the art upon reading the disclosure of this invention in connection with the skilled person's technical and expert background.

As used herein, the term "recovering" or "obtaining" means isolating, harvesting, purifying, collecting or otherwise separating from the host cell culture the oligosaccharide produced by the host cell according to the invention.

A "microbial" host cell according to the invention, and as generally understood, means any microorganism, including bacteria, fungi and archaea, which is generally suitable for cultivation in large amounts, and which can be genetically modified according to the invention in order to produce a desired oligosaccharide. Preferred microorganisms are bacteria, e.g. *Escherichia coli, Corynebacterium glutamicum* and the yeast *Saccharomyces* sp., which have the advantage that these microorganisms can be grown easily and inexpensively in laboratory settings, and the bacteria and yeast have been intensively investigated for over many years Generally, and throughout the present invention, the term "glycosyltransferase activity" or "glycosyltransferase" designates and encompasses enzymes that are responsible for the biosynthesis of disaccharides, oligosaccharides and polysaccharides, and they catalyze the transfer of monosaccharide moieties from an activated nucleotide monosaccharide/sugar (the "glycosyl donor") to a glycosyl acceptor molecule.

Generally, and throughout the present invention, the terms "exporter" or "exporter protein" or "protein enabling the export of a desired oligosaccharide", which terms are presently being used synonymously, designates one or more polypeptides that solely or as part of a multi-protein complex transfers an oligosaccharide from the intracellular milieu of a bacterial cell into the periplasm of said cell or the culture supernatant, thus, enabling the oligosaccharide to pass the cellular membrane and/or the cell wall of said cell.

Within the scope of the present invention, also nucleic acid/polynucleotide and polypeptide polymorphic variants, alleles, mutants, and interspecies homologs are comprised by those terms, that have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a wild type glycosyltransferase activity or oligosaccharide export displaying protein.

"Variant(s)" as the term is used herein, is a polynucleotide or polypeptide that differs from a reference polynucleotide or polypeptide, respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to the persons skilled in the art.

Accordingly, a "functional fragment" of any of the genes/proteins disclosed therein, is meant to designate sequence variants of the genes/proteins still retaining the same or somewhat lesser activity of the gene or protein the respective fragment is derived from.

In this connection, the term "nucleic acid sequence encoding . . . " generally refers to any polyribonucleotide or polydeoxyribonucleotide, which may be unmodified RNA or DNA or modified RNA or DNA, and generally represents a gene which encodes a certain polypeptide or protein.

In this context, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as "proteins". Polypeptides may contain amino acids other than the 20 gene encoded amino acids. "Polypeptide(s)" include those modified either by natural processes, such as processing and other post-translational modifications, but also by chemical modification techniques. It will be appreciated that the same type of modification may be present in the same or varying degree at several sites in a given polypeptide, without essentially altering the activity of the polypeptide. Also, a given polypeptide may contain many types of modifications. Modifications can occur anywhere in a polypeptide, including the peptide backbone, the amino acid side-chains, and the amino or carboxyl termini.

Further, with the expression "precursor" compounds are encompassed which are involved in the biosynthetic pathway of the oligosaccharide according to the invention or which are produced and naturally present in the host cell.

A "precursor that is larger than a disaccharide" is presently understood as a sugar moiety that comprises more than two monosaccharide residues.

The term "desired oligosaccharide" refers to a sugar polymer consisting of at least three moieties, thus, comprising trisaccharides, tetrasaccharides, pentasaccharides etc., preferably an oligosaccharide selected from at least one of the following: lacto-N-triose II, lacto-N-tetraose, lacto-N-neotetraose, lacto-N-fucopentaose I, lacto-N-fucopentaose II, lacto-N-fucopentaose III, lacto-N-fucopentaose V, lacto-N-difucosylhexose I, lacto-N-difucosylhexaose II, lacto-N-sialylpentaose LSTa, LSTb, LSTc, disialyllacto-N-tetraose, disialyllacto-N-neotetraose.

Presently, and as generally understood in the relevant field, the expression "homologous" refers to a nucleic acid sequence that encodes for a specific product or products and is derived from the same species, in which said nucleic acid sequence is inserted. Accordingly, the term "heterologous" refers to a nucleic acid sequence encoding for a specific product or products and being derived from a species other than those in which said nucleic acid sequence is inserted.

The term "endogenous" herein and generally within the field means that the nucleic acid encoding for an enzyme of interest is originating from the bacterial host cell and has not been introduced into said host cell, whereas a "recombinant" nucleic acid has been introduced into said host cell and does not originates from said host cell.

The expression "overexpressed", or "overexpressing" or "under control of a promoter sequence enabling the overexpression of said nucleic acid sequence" presently, and generally in the art, means the expression of a gene in greater-than-normal amounts, i.e. in increased quantity thus leading to an increased amount of the protein the nucleic acid sequence is coding for.

In some embodiments, the nucleic acid sequence is placed under the control of an inducible promoter, which is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the proteins used in the present invention. For *E. coli*, and other microbial host cells, inducible promoters are known to those of skill in the art.

Further advantages are evident from the description and the drawings.

It is understood that the features mentioned above and those yet to be explained below can be used not only in the respective combinations indicated, but also in other combinations or in isolation, without leaving the context of the present invention.

The invention will be described in more detail in the examples and the attached figures, in which FIG. 1 shows a schematic illustration for the production of either lacto-N-triose II or lacto-N-tetraose in a host cell cultivated in a medium;

Figure 8:
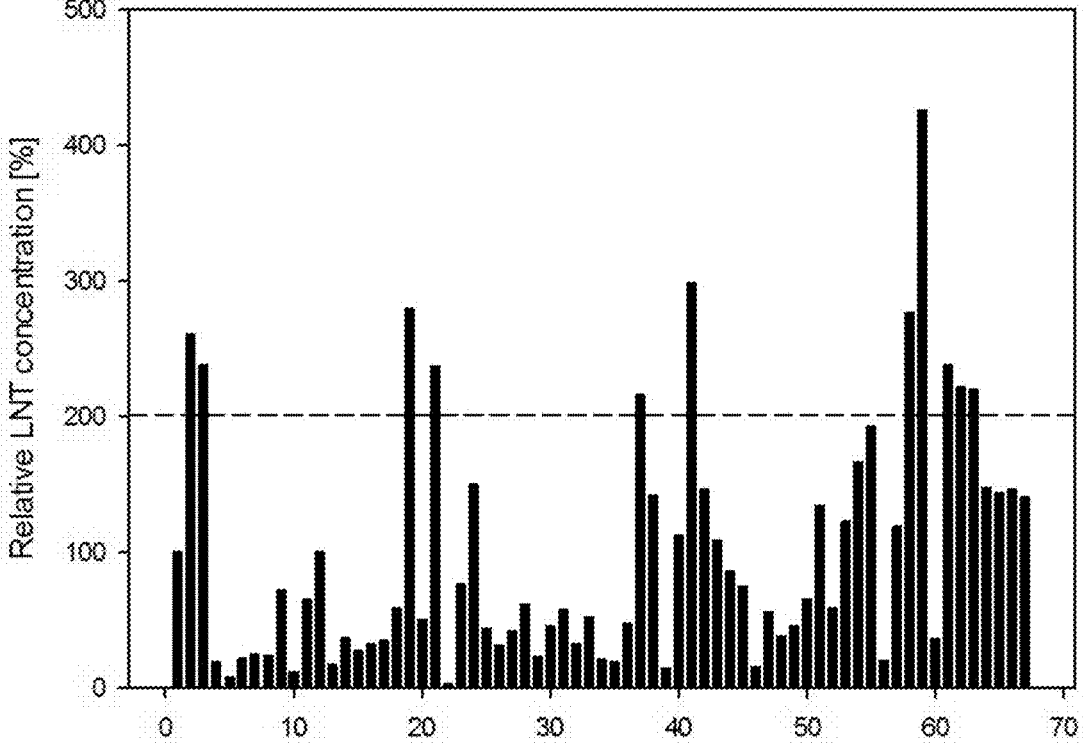
Figure 9:
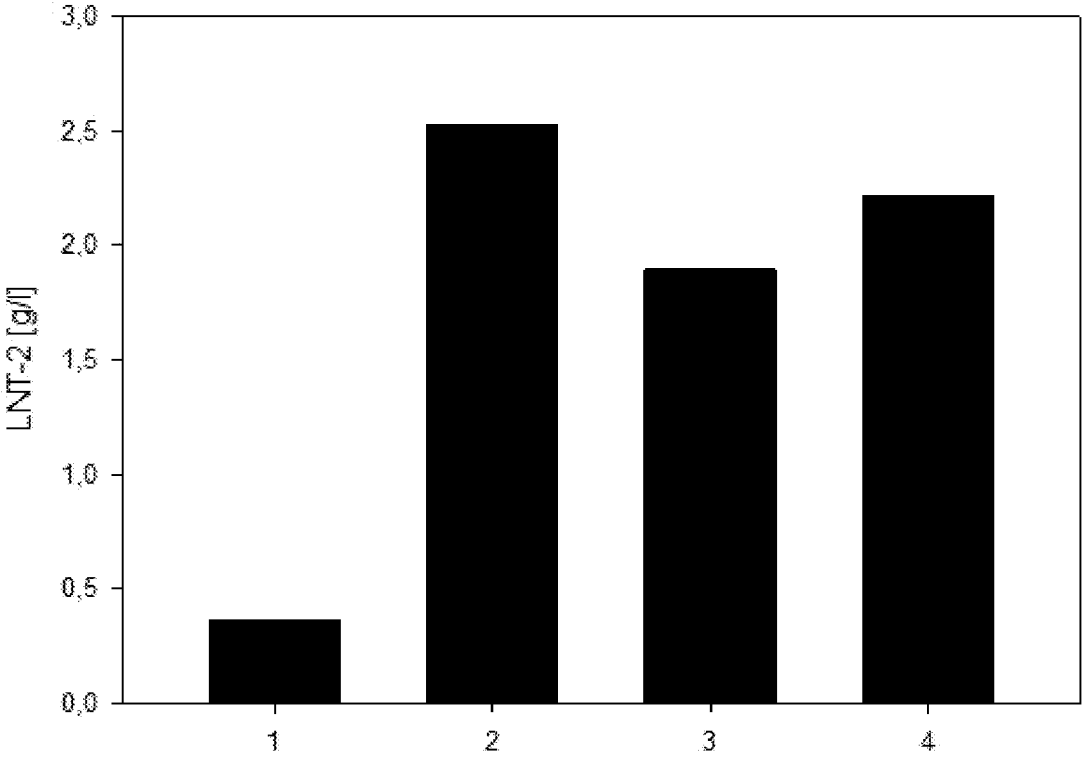

FIG. 8 shows a diagram depicting the relative concentration of lacto-N-tetraose in the supernatant of *E. coli* BL21 (DE3) strains overexpressing sugar efflux transporters compared to the control strain 1353; and FIG. 9 shows a diagram depicting concentrations of lacto-N-triose II in the supernatant of *E. coli* BL21 (DE3) strains overexpressing the sugar efflux transporters TP11 (2), YjhB (3) or TP70 (4).

EXAMPLES

Figure 1:
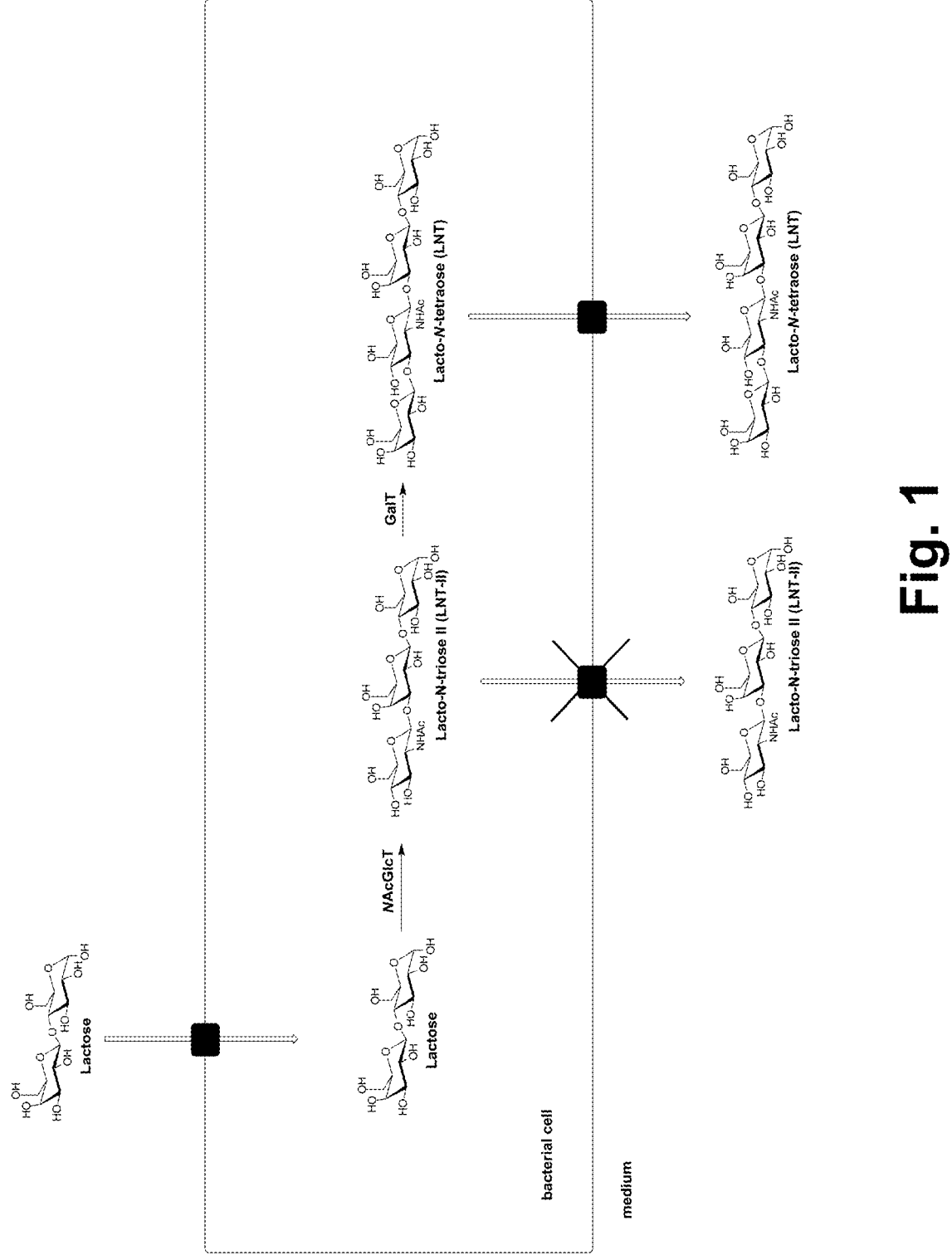

FIG. 1 shows a schematic drawing of an exemplary host cell 10 according to the invention, importing lactose and synthesizing lacto-N-triose II (LNT II) and lacto-N-tetraose (LNT). Lactose is imported from the medium the host cell is cultivated in into the cell via transporter 1. The enzyme N-acetylglucosaminyltransferase NacGlcT ligates N-acetyl-glucosamine to the acceptor substrate lactose, thus generating LNT-II. LNT-II is exported from the cell via exporter protein 20. Since LNT-II is a precursor of LNT or LNnT, the exporter exporting LNT-II represents an exporter protein exporting precursors of the latter oligosaccharides. As can further be seen from FIG. 1, the cell comprises a protein having β-1,3-galactosyltransferase activity enabling the galactosylation of LNT-II to intracellularly generate LNT; the cell may also and/or alternatively comprise or β-1,4-galactosyltransferase activity enabling the galactosylation of LNT-II to intracellularly generate lacto-N-neotetraose LNnt. LNT—or as the case may be LNnt—is then exported, via a oligosaccharide exporter from the cell into the culture medium the cell is cultivated in.

The exporters are membrane-bound, and their expression can be either overexpressed, which—in case of overexpression of the LNT-II exporter leads to an increased LNT-II export and to a decreased LNT export, whereas when the LNT-II exporting exporter protein is deleted or otherwise inactivated, this leads to an improved LNT-export. The LNT-II exporter preferably is an endogenous exporter protein, whereas the LNT-exporter protein preferably is a heterologous exporter protein.

Example 1

Development of an *E. coli* Lacto-N-Triose II Production Strain

*Escherichia coli* BL21(DE3) was used to construct a lacto-N-triose II (LNT-2) producing strain. Metabolic engineering included mutagenesis and deletions of specific genes, respectively, and genomic integrations of heterologous genes. The genes lacZ and araA were inactivated by mutagenesis using mismatch-oligonucleotides as described by Ellis et al., "High efficiency mutagenesis, repair, and engineering of chromosomal DNA using single-stranded oligonucleotides", Proc. Natl. Acad. Sci. USA 98:6742-6746 (2001).

Genomic deletions were performed according to the method of Datsenko and Warner (Proc. Natl. Acad. Sci. USA 97:6640-6645 (2000)). To prevent intracellular degradation of N-acetylglucosamine, genes encoding N-acetylglucosamine-6-phosphate deacetylase (nagA) and glucosamine-6-phosphate deaminase (nagB) were deleted from the genome of the *E. coli* strain BL21 (DE3) strain. Also genes wzxC-wcaJ were deleted. WcaJ encodes an UDP-glucose: undecaprenyl phosphate glucose-1-phosphate transferase catalysing the first step in colanic acid synthesis (Stevenson et al., J. Bacteriol. 1996, 178:4885-4893). In addition the genes fucI and fucK, coding for L-fucose isomerase and L-fuculose kinase, respectively, were removed.

Genomic integration of heterologous genes was performed by transposition. Either the EZ-Tn5™ transposase (Epicentre, USA) was used to integrate linear DNA-fragments or the hyperactive C9-mutant of the mariner transposase Himar1 (Lampe et al., Proc. Natl. Acad. Sci. 1999, USA 96:11428-11433) was employed for transposition. To produce EZ-Tn5 transposomes the gene of interest together with a FRT-site flanked antibiotic resistance marker was amplified with primer 1119 and 1120 (all primer used are listed in table 3 below); the resulting PCR-product carried on both sites the 19-bp Mosaic End recognition sites for the EZ-Tn5 transposase. For integration using Himar1 transposase expression constructs (operons) of interest were similarly cloned together with a FRT-site flanked antibiotic resistance marker into the pEcomar vector. The pEcomar vector encodes the hyperactive C9-mutant of the mariner transposase Himar1 under the control of the arabinose inducible promoter $P_{araB}$. The expression fragment $<P_{tet}$-lacY-FRT-aadA-FRT>$ (SeqID1) was integrated by using the EZ-Tn5 transposase. After successful integration of the gene for the lactose importer LacY from *E. coli* K12 TG1 acc. no.

ABN72583) the resistance gene was eliminated from streptomycin resistant clones by the FLP recombinase encoded on plasmid pCP20 (Datsenko and Warner, Proc. Natl. Acad. Sci. 2000, USA 97:6640-6645). The N-acetylglucosaminyltransferase gene lgtA from *Neisseria meningitidis* MC58 (acc. no. NP_274923) was codon-optimized for expression in *E. coli* and prepared synthetically by gene synthesis. Together with the gene galT, encoding a galactose-1-phosphate uridylyltransferase from *E. coli* K-12 substr. MG1655 (acc. no. NP_415279) that was similarly obtained by gene synthesis, lgtA was inserted by transposition (SeqID2) using plasmid pEcomar-lgtA-galT. To enhance de novo synthesis of UDP-N-acetylglucosamine, genes encoding L-glutamine: D-fructose-6-phosphate aminotransferase (glmS), phosphoglucosamine mutase from *E. coli* K-12 substr. MG1655 (glmM) and N-acetylglucosamine-1-phosphate uridyltransferase/glucosamine-1-phosphate acetyltransferase (glmU) from *E. coli* K-12 substr. MG1655 (acc. no. NP_418185, NP_417643, NP_418186, respectively) were codon-optimized and obtained by gene synthesis. The operon glmUM was cloned under the control of constitutive tetracyclin promoter $P_{tet}$ while glmS was cloned under the constitutive $P_{T5}$ promoter. The transposon cassette $<P_{tet}$-glmUM-$P_{T5}$-glmS-FRT-dhfr-FRT>$ (SeqID3), flanked by the inverted terminal repeats specifically recognized by the mariner-like element Himar1 transposase was inserted from pEcomar-glmUM-glmS revealing a lacto-N-triose II production strain. Additionally, the expression fragment $<P_{tet}$-lacY(6HIS)-FRT-aadA-FRT>$ (SeqID4) was integrated by using the EZ-Tn5 transposase.

The gal-operon (galETKM) was amplified from *E. coli* K12 TG1 (SeqID6) using primer 605 and 606 and inserted into the galM ybhJ locus of *E. coli* BL21 (DE3) strain by homologous recombination facilitated by using the red recombinase helper plasmid pKD46 (Datsenko and Warner, Proc. Natl. Acad. Sci. 2000, USA 97:6640-6645). Sequences of the heterologous genes and gene clusters are deposit in appendix 1.

Example 2

Batch Fermentation of *E. coli* BL21 (DE3) 707 Screening Various β-1,3-N-Acetyl-Glycosaminyltransferases The gene for the β-1,3-N-acetyl-glucosaminyltransferase Pmnag T from *Pasteurella multocida* subsp. *multocida* str. HN06 (acc. no. PMCN06_0022) was codon-optimized and synthetically synthesized by GenScript Cooperation (Piscataway, USA). Cloning of the gene occurred by sequence and ligation-independent cloning into the plasmid pET-DUET (Merck KGaA, Darmstadt, Germany). All primer used for cloning are listed in table 3 below.

*E. coli* BL21(DE3) 707 (table 2 below) harbouring plasmid pET-PmnagT coding for a β-1,3-N-acetyl glucosaminyltransferase was grown at 30° C. in mineral salts medium (Samain et al., J. Biotech. 1999, 72:33-47) supplemented with 2% (wt/vol) glucose and ampicillin 100 μg ml$^{-1}$. When the cultures reached an OD660 nm of 0.1, gene expression was induced by addition of 0.3 mM IPTG. After four hours of incubation 1.5 mM lactose was added. After an additional incubation for 24 hours at 30° C. in shaking flasks cells were harvested. LNT-2 was detected by thin layer chromatography. Therefore, cells were mechanically disrupted in a defined volume using glass beads. Subsequently, samples were applied on TLC Silica Gel 60 $F_{254}$ (Merck KGaA, Darmstadt, Germany). The mobile phase was composed of acetone:butanol:acetic acid:water (35:35:7:23).

Figure 2:
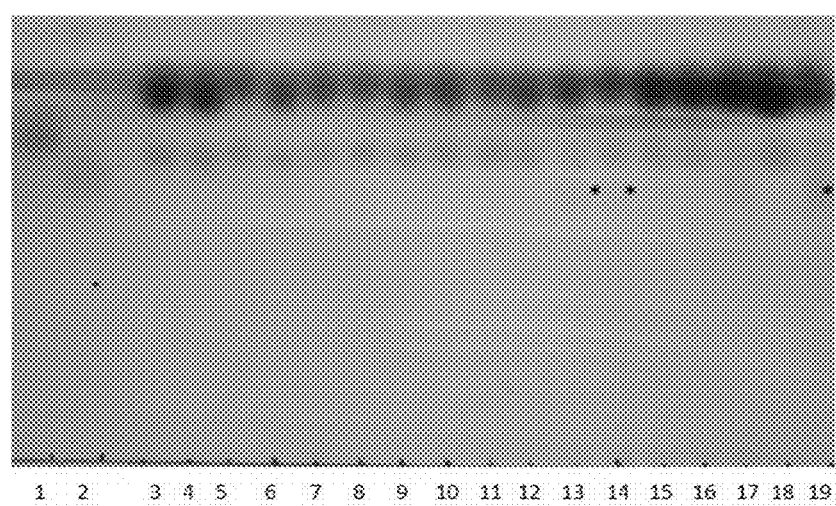
FIG. 2 shows the results of the TLC analysis of culture extracts of lacto-N-triose II (LNT II) producing *E. coli* BL21(DE3) strains overexpressing the β-1,3-N-acetyl glucosaminyltransferase gene PmnagT (13, 14)

The result of the TLC analysis is shown in FIG. 2. The formation of a compound showing the same migration rate as the trisaccharide standard LNT-II could be observed when the gene PmnagT was overexpressed. The LNT-II production strain 724 served as a control (19). Standards for lactose (1) and LNT-II (2) are depicted. LNT-II product formation in the samples is marked by asterisks.

Example 3

Generation of an *E. coli* Lacto-N-Triose II Production Strain Overexpressing a Homologous Sugar Efflux Transporter The export of oligosaccharides produced in *E. coli* was proven to be a limiting factor during the fermentation process. However, trisaccharides like 2'-fucosyllactose and LNT-2 are translocated into the culture supernatant to some extent, thus probably encoding a working sugar efflux transporter. In order to improve the efflux of lacto-N-triose II (LNT-II; GluNAc(β1-3)Gal(β1-4)Glc), the *E. coli* BL21 (DE3) strain 1326 (table 2 below) was used for the screening of a library of sugar efflux transporters (SET). Putative SET proteins from *E. coli* were amplified from genomic DNA of *E. coli* BL21 (DE3) and integrated into vector pINT by sequence and ligation-independent cloning. Using the example of the gene yjhB, the primer 2567, 2568, 2526 and 2443 were used, generating the plasmid pINT-yjhB. The primer sequences used for cloning are listed in table 3 below.

*E. coli* BL21(DE3) 1326 harbouring plasmids encoding for 20 different *E. coli* transporters were grown at 30° C. in mineral salts medium (Samain et al., J. Biotech. 1999, 72:33-47) supplemented with 2% (wt/vol) glucose, ampicillin 100 μg ml$^{-1}$ and zeocin 40 μg ml$^{-1}$. When the cultures reached an OD660 nm of 0.1, gene expression of the genes was induced by addition of 200 ng/ml anhydrotetracycline. After four hours of incubation 2.5 mM lactose was added. After an additional incubation for 24 and 48 hours at 30° C. in shaking flasks the LNT-II concentration in the supernatant was determined by LC-MS.

Mass analysis was performed by characteristic fragment ion detection using an LC Triple-Quadrupole MS detection system. Precursor ions are selected and analyzed in quadrupole 1, fragmentation takes place in the collision cell using nitrogen as CID gas, selection of fragment ions is performed in quadrupole 3.

Lacto-N-tetraose (LNT (Gal(β1-3)GlcNAc(β1-3)Gal(β1-4)Glc)), LNT-II and Maltotriose (internal standard for quantification) were analyzed in ESI positive ionization mode. LNT forms an ion of m/z 708.3 [M+H$^+$], LNT-II an ion of m/z 546.1 [M+H$^+$] and Maltotriose an ion of m/z 522.0 [M+NH$_4^+$]. Adduct formation of this carbohydrate [m/z 504.0] takes place with an ammonium ion (NH4$^+$), resulting in mass shift of +18. Thus for Maltotriose a precursor ion of m/z 522.0 was selected. The precursor ion was further fragmented in the collision cell into the characteristic fragment ions m/z 487.1, m/z 325.0 and m/z 163.2. The molecular ion of LNT (m/z 708.3) was fragmented into m/z 546.3, m/z 528.3, m/z 366.2 and m/z 204.0. LNT-II (m/z 546.1) was fragmented into m/z 204.2, 186.0, 138.0 and 126.0 (see method description).

Chromatographic separation of LNT and LNT-II was performed on a Luna NH$_2$ HPLC column (Phenomenex, Aschaffenburg, Germany). This was necessary due to partial fragmentation of LNT during ionization resulting in LNT-II signals affecting quantification results of the individual carbohydrates.

Only for the strain expressing the gene yjhB, an increased amount of LNT-2 in the culture supernatant was observed (see table 1 below).

TABLE 1

| Calculated concentrations of LNT-II in the culture supernatant of an *E. coli* BL21 (DE3) strain overexpressing yjhB and the reference strain. | | | |
| --- | --- | --- | --- |
| Sample | Calc. conc. after 24 h of incubation [μM] | Calc. conc. after 48 h of incubation [μM] | Analyte RT |
| 1326 | 751 | 1265 | 0.616 |
| 1326 pINT-yjhB | 413 | 1975 | 0.609 |

Example 4

Batch Fermentations of *E. coli* BL21(DE3) 724 Screening Various β-1,4-Galactosyltransferases The genes for the β-1,4-galactosyltransferases Iex1 from *Aggregatibacter aphrophilus* NJ8700 (acc. no. YP_003008647), PmgalT7 from *Pasteurella multocida* subsp. *multocida* str. HN06 (acc. No. PMCN06_0021), MsgalT8 from *Myxococcus stipitatus* DSM14675 (acc. no. MYSTI_04346), KdgalT10 from *Kingella denitrificans* ATCC 33394 (acc. no. HMPREF9098_2407), gatD from *Pasteurella multocida* M1404 (acc. no. GQ444331), BfgalT2 from *Bacterioidis fragilis* NCTC9343 (acc. no. BF9343_0585), IsgD from *Haemophilus influenza* (acc. no. AAA24981) and HpgalT from *Helicobacter pylori* (acc. no. AB035971) were codon-optimized and synthetically synthesized by GenScript Cooperation (Piscataway, USA). Cloning of the genes occurred by sequence and ligation-independent cloning (Li and Elledge, Nat Methods. 2007 March; 4(3):251-6.). Therefore, the plasmid pINT, harbouring the malE gene under control of an anhydrotetracycline-inducible promoter, was used, enabling the generation of a N-terminal fusion of the β-1,4-galactosyltransferase genes with malE. Solely, the β-1,4-galactosyltransferase encoding gene waaX from *Pectobacterium atrosepticum* JG10-08 (acc. no. ECA0154) was cloned into plasmid pACYC-Duet (Merck KGaA, Darmstadt, Germany). All primer used for cloning are listed in table 3 below.

*E. coli* BL21(DE3) 724 (table 2 below) harbouring plasmid pCDF-galE and a plasmid coding for the gene fusion of malE with a β-1,4-galactosyltransferase was grown at 30° C. in mineral salts medium (Samain et al., J. Biotech. 1999, 72:33-47) supplemented with 2% (wt/vol) glucose, ampicillin 100 μg ml$^{-1}$ and zeocin 40 μg ml$^{-1}$. When the cultures reached an OD660 nm of 0.1, gene expression of the galE gene and the β-1,4-galactosyltransferase was induced by addition of 0.3 mM IPTG and 200 ng/ml anhydrotetracycline. *E. coli* BL21(DE3) 534 (table 2 below) harbouring plasmids pET-lgtA, pCOLA-glmUM-glmS, pCDF-galT-galE and pACYC-waaX was grown at 30° C. in mineral salts medium supplemented with 2% (wt/vol) glucose, ampicillin 100 μg ml$^{-1}$, chloramphenicol 34 μg ml$^{-1}$, streptomycin 50 μg ml$^{-1}$ and kanamycin 30 μg ml$^{-1}$. When the cultures reached an OD660 nm of 0.1, gene expression was induced by addition of 0.3 mM IPTG. Four hours after induction of gene expression 2 mM lactose were added. After an additional incubation for 48 hours at 30° C. in shaking flasks, cells were harvested and mechanically disrupted. Lacto-N-neotetraose (LNnT (Gal(β1-4)GlcNAc(β1-3)Gal(β1-4)Glc)) was detected by thin layer chromatography. Therefore, cells were mechanically disrupted using glass beads. Subsequently, samples were applied on TLC Silica Gel 60 F$_{254}$ (Merck KGaA, Darmstadt, Germany). The mobile phase was composed of acetone:butanol:acetic acid:water (35:35: 7:23).

Figure 3:
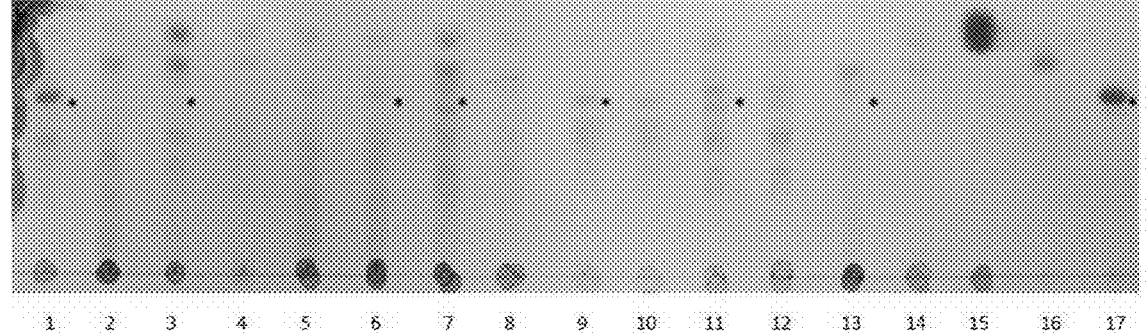
FIG. 3 shows the results of the TLC analysis of culture extracts of lacto-N-tetraose (LNT) producing *E. coli* BL21 (DE3) strains overexpressing the β-1,4-galactosyltransferase encoding genes BfgalT2 (1), PmgalT7 (3), MsgalT8 (6), gatD (7), lex1 (9), IgtB (11) or IsgD (13)
Figure 4:
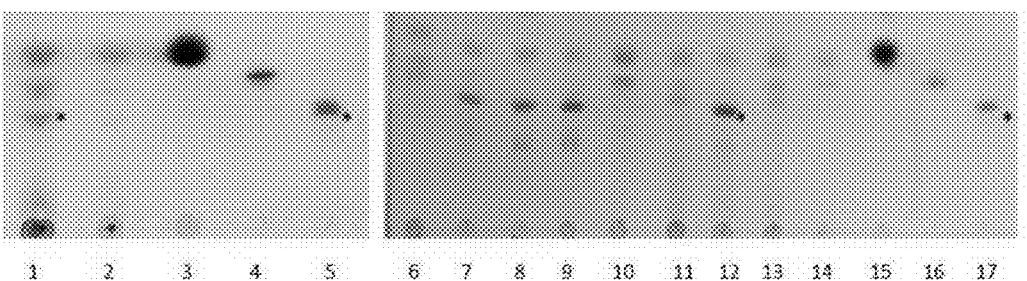
FIG. 4 shows the results of the TLC analysis of culture extracts of lacto-N-tetraose (LNT) producing *E. coli* BL21 (DE3) strains overexpressing the β-1,4-galactosyltransferase encoding genes KdgalT10 (1), cpsl14J (7), cpslaJ (8, 9), HpgalT (12)
Figure 5:
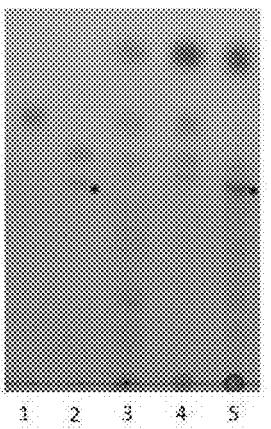
FIG. 5 shows the results of the TLC analysis of culture extracts of lacto-N-tetraose producing *E. coli* BL21(DE3) strains overexpressing the β-1,4-galactosyltransferase encoding gene waaX (5)

The results of the TLC analyses are shown in FIGS. 3-5. FIG. 3 shows the TLC analysis of culture extracts of lacto-N-tetraose (LNT) producing *E. coli* BL21(DE3) strains overexpressing the β-1,4-galactosyltransferase encoding genes BfgalT2 (1), PmgalT7 (3), MsgalT8 (6), gatD (7), Iex1 (9), IgtB (11) or IsgD (13). Standards for lactose (15), LNT-II (16) and LNnT (17) are depicted. LNnT product formation in the samples is marked by asterisks.

FIG. 4 shows the TLC analysis of culture extracts of lacto-N-tetraose (LNT) producing *E. coli* BL21(DE3) strains overexpressing the β-1,4-galactosyltransferase encoding genes KdgalT10 (1), cpsl14J (7), cpslaJ (8, 9), HpgalT (12). Standards for lactose (3, 15), LNT-II (4, 16) and LNnT (5, 17) are depicted. LNnT product formation in the samples is marked by asterisks.

FIG. 5 shows the TLC analysis of culture extracts of lacto-N-tetraose producing *E. coli* BL21(DE3) strains overexpressing the β-1,4-galactosyltransferase encoding gene waaX (5). Standards for lactose (1), LNT-II and LNnT (2) are depicted. Again, LNnT product formation in the samples is marked by asterisks.

The formation of a compound showing the same migration rate as the tetrasaccharide standard LNnT could be observed when the following genes were overexpressed: Iex1, PmgalT7, MsgalT8, BfgalT2, gatD, IsgD, KdgalT10, HpgalT, wax.

The β-1,4-galactosyltransferases cpslaJ and cpsl14J, known from literature to produce LNnT (Watanabe et al., J Biochem. 2002 February; 131(2):183-91; Kolkman et al., J Bacteriol. 1996 July; 178(13):3736-41), were also included in the activity screening and served as positive control. Using the described expression system, the formation of LNnT could be observed by CpslaJ and Cpsl14J (FIG. 3). In total, 11 out of 30 tested genes were observed to produce LNnT from LNT-II and UDP-galactose.

Example 5

Batch Fermentations of *E. coli* BL21(DE3) 534 Screening Different β-1,3-Galactosyltransferases Using genomic DNA of *E. coli* K12 DH5a as template, galE was amplified using primer 1163 and 1162. The PCR product was purified, restricted with restriction endonucleases NdeI and XhoI and ligated into the second multiple cloning site of vector pCDFDuet (Merck KGaA, Darmstadt, Germany), which was cut with the same enzymes. GalE is expressed from the IPTG inducible T7 promoter. The *E. coli* K12 gene galT was amplified from genomic DNA and integrated into plasmid pCDF-galE by sequence and ligation-independent cloning using primer 991-994, producing the plasmid pCDF-galT-galE.

Using the codon-optimized gene of lgtA as template, amplification occurred using primer 688 and 689. The PCR product was purified, restricted with restriction endonucleases NdeI and AatII and ligated into the multiple cloning site of vector pETDuet (Merck KGaA, Darmstadt, Germany), which was cut with the same enzymes, producing the plasmid pET-lgtA.

Cloning of the codon-optimized gene construct of glmUM occurred by sequence and ligation-independent cloning into the plasmid pCOLA-Duet (Merck KGaA, Darmstadt, Germany) using primer 848-851. The codon-optimized form of glmS was amplified using primer 852 and 853. The PCR product was purified, restricted with restriction endonucleases NdeI and AatII and ligated into the second multiple cloning site of vector pCOLA-glmUM, which was cut with the same enzymes, producing the plasmid pCOLA-glmUM-glmS.

The genes for the β-1,3-galactosyltransferases wbdO from *Salmonella enterica* subsp. salamae serovar Greenside (acc. no. AY730594) and furA from *Lutiella nitroferrum* 2002 (FuraDRAFT_0419) were also codon-optimized and synthetically synthesized by GenScript Cooperation (Piscataway, USA). Cloning of the genes occurred by sequence and ligation-independent cloning into the plasmid pACYC-Duet (Merck KGaA, Darmstadt, Germany). All primer used for cloning are listed in table 3 below.

*E. coli* BL21(DE3) 534 harbouring plasmids pET-lgtA, pCOLA-glmUM-glmS, pCDF-galT-galE and a plasmid coding for a β-1,3-galactosyltransferase pACYC-furA or pACYC-wbdO was grown at 30° C. in mineral salts medium (Samain et al., J. Biotech. 1999, 72:33-47) supplemented with 2% (w/v) glucose, ampicillin 100 μg ml$^{-1}$, chloramphenicol 34 μg ml$^{-1}$, streptomycin 50 μg ml$^{-1}$ and kanamycin 30 μg ml$^{-1}$. When the cultures reached an OD660 nm of 0.1, gene expression was induced by addition of 0.3 mM IPTG. After four hours of incubation 2 mM lactose was added. After an additional incubation for 48 hours at 30° C. in shaking flasks, cells were harvested. LNT was detected by thin layer chromatography. Therefore, cells were mechanically disrupted using glass beads. Subsequently, samples were applied on TLC Silica Gel 60 F$_{254}$ (Merck KGaA, Darmstadt, Germany). The mobile phase was composed of acetone:butanol:acetic acid:water (35:35:7:23).

Figure 6:
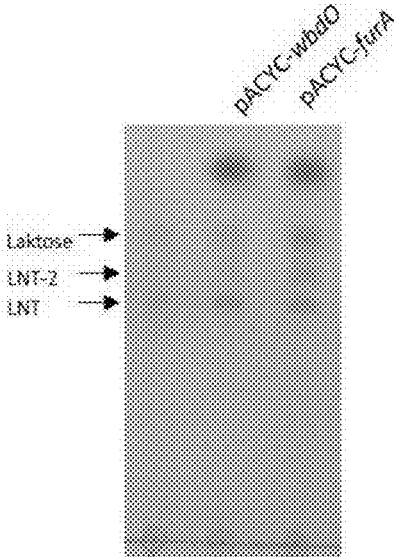
FIG. 6 shows the results of the TLC analysis of culture extracts of lacto-N-tetraose producing *E. coli* BL21(DE3) strains overexpressing the β-1,3-galactosyltransferase encoding genes wbdO or furA.

The results of the TLC analyses are shown in FIG. 6, showing TLC analysis of culture extracts of lacto-N-tetraose producing *E. coli* BL21(DE3) strains overexpressing the β-1,3-galactosyltransferase encoding genes wbdO or furA. LNT product formation in the samples is marked. Out of 12 tested putative β-1,3-galactosyltransferases, the formation of a compound showing the same migration rate as the tetrasaccharide standard LNT could only be observed when genes wbdO and furA were overexpressed.

Example 6

Development of an Improved Plasmid-Free *E. coli* Lacto-N-Tetraose Production Strain

*Escherichia* coli BL21(DE3) strain 724 was used to construct a lacto-N-tetraose (LNT) producing strain. Metabolic engineering included the genomic integration of the transposon cassettes <P$_{tet}$-wbdO-P$_{T5}$-galE-FRT-cat-FRT> (SeqID5), flanked by the inverted terminal repeats specifically recognized by the mariner-like element Himar1 transposase, which was inserted from pEcomar-wbdO-galE. The resulting strain 1353 was further metabolically engineered to exhibit an increased intracellular LNT-II pool resulting in the elevated production of LNT. Therefore, the mayor facilitator superfamily transporter yjhB (acc. no. YP_003001824) was deleted from the genome of the *E. coli* strain, generating strain 1431 (table 2 below).

Batch fermentation of the *E. coli* BL21(DE3) strains 1353 and 1431 was conducted for 48 hours at 30° C. in mineral salts medium (Samain et al., J. Biotech. 1999, 72:33-47) containing 2% (wt/vol) glucose as sole carbon and energy source. When the cultures reached an OD660 nm of 0.5, 2.5 mM lactose was added. The presence of LNT-II and LNT in the culture supernatant was detected by high performance liquid chromatography (HPLC).

Analysis by HPLC was performed using a refractive index detector (RID-10A) (Shimadzu, Duisburg, Germany) and a ReproSil Carbohydrate, 5 µm (250 mm×4.6 mm) (Dr. Maisch GmbH, Germany) connected to an HPLC system (Shimadzu, Duisburg, Germany). Elution was performed isocratically with acetonitril:H$_2$O (68/32 (v/v)) as eluent at 35° C. and a flow rate of 1.4 ml/min. 40 µl of the sample were applied to the column. Samples were filtered (0.22 µm pore size) and cleared by solid phase extraction on an ion exchange matrix (Strata ABW, Phenomenex, Aschaffenburg, Germany).

Figure 7:
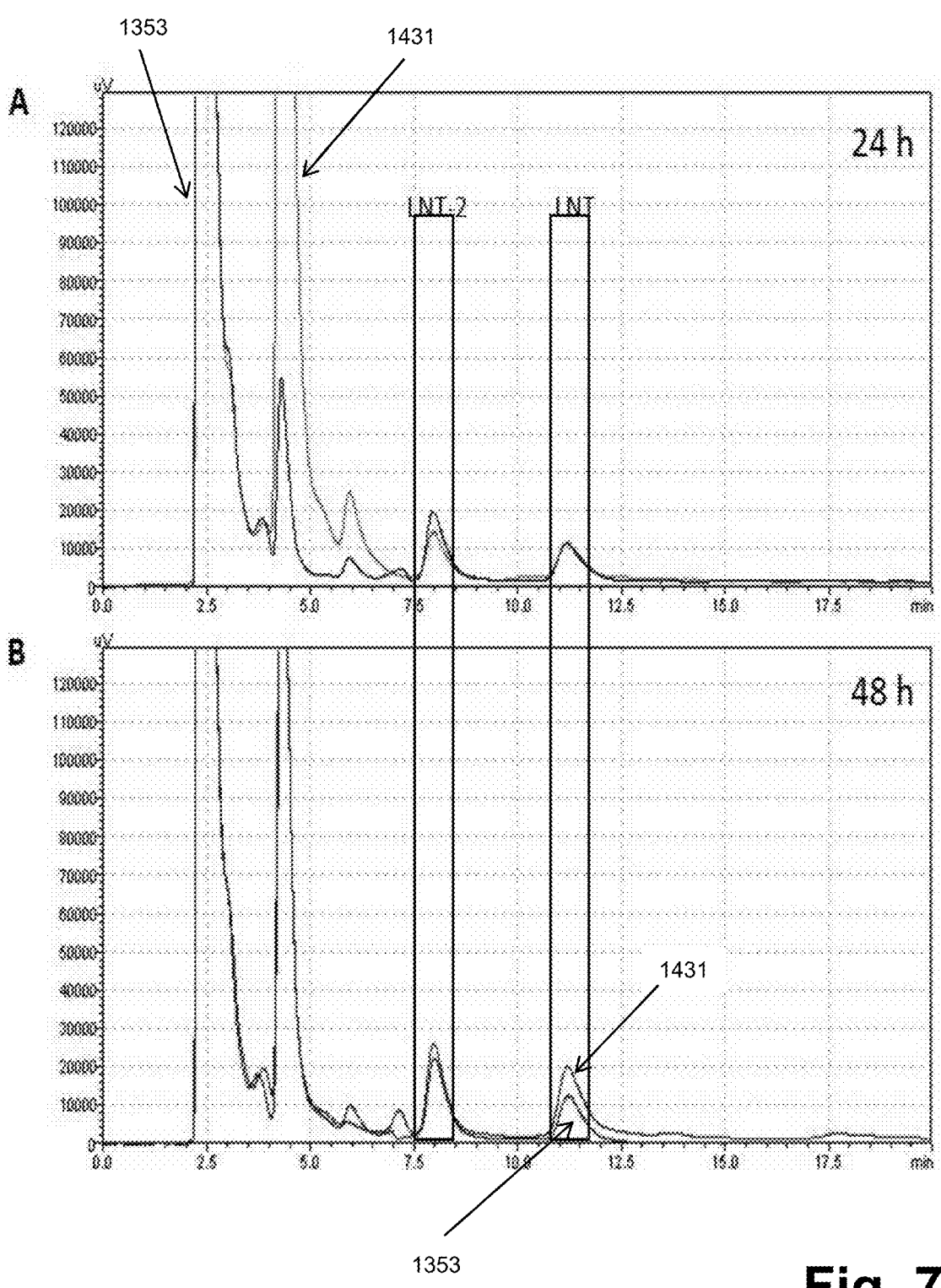
FIG. 7 shows the results of HPLC analyses of the culture supernatant of lacto-N-tetraose producing *E. coli* BL21 (DE3) strain. (A) Supernatant of *E. coli* BL21(DE3) 1353 and 1431 grown in the presence of glucose and lactose after 24 h of incubation. (B) Supernatant of *E. coli* BL21(DE3) 1353 and 1431 grown in the presence of glucose and lactose after 48 h of incubation.

The results of the HPLC analyses are shown in FIG. 7, showing HPLC analyses of the culture supernatant of lacto-N-tetraose producing E. coli BL21 (DE3) strain. (A) Supernatant of E. coli BL21(DE3) 1353 (black graph) and 1431 (pink graph) grown in the presence of glucose and lactose after 24 h of incubation. (B) Supernatant of E. coli BL21 (DE3) 1353 (blue graph) and 1431 (brown graph) grown in the presence of glucose and lactose after 48 h of incubation. As can be seen from the HPLC analyses, the deletion of yjhB in a LNT producing strain resulted in an elevated accumulation of LNT in the culture supernatant.

Example 7

Generation of an E. coli Lacto-N-Tetraose Production Strain Overexpressing a Sugar Efflux Transporter Since an export of lacto-N-tetraose into the medium is only moderate for production strains, a screening of a sugar efflux transporter library was conducted. In accordance to example 3 putative SET proteins were either amplified from E. coli genomic DNA or were codon-optimized and synthetically synthesized by GenScript Cooperation (Piscataway, USA). Following amplification genes were integrated into vector pINT by sequence and ligation-independent cloning. The primer design for the cloning of E. coli genes was in accordance to example 3. Synthetic genes were synthesized with standardized nucleotide overhangs and likewise integrated into the expression vector using the primer 2527, 2444, 2526 and 2443. The primer sequences used for cloning are listed in table 3 below.

E. coli BL21(DE3) 1353 (table 2 below) harbouring plasmids encoding for 66 different transporters were grown at 30° C. in mineral salts medium (Samain et al., J. Biotech. 1999, 72:33-47) supplemented with 3% (w/v) glucose, 5 g l$^{-1}$ NH$_4$Cl$_2$, ampicillin 100 µg ml$^{-1}$ and kanamycin 15 µg ml$^{-1}$. Precultivation appeared in 96-well plates harbouring a total volume of 200 µl. After 24 h of incubation at 30° C. by continuous shaking, 50 µl per well was transferred into 96-well deep well plates harbouring a total volume of 400 µl mineral salts medium additionally supplemented with 200 ng ml$^{-1}$ anhydrotetracycline and 10 mM lactose. After a sustained incubation for 24 to 48 hours the LNT concentrations in the supernatant were determined by LC-MS. Mass analysis was performed as described in example 3.

FIG. 8 shows the relative concentration of lacto-N-tetraose in the supernatant of E. coli BL21 (DE3) strains overexpressing sugar efflux transporters compared to the control strain 1353. The LNT titer of strain 1353 was set to 100%. As shown in FIG. 8, the overexpression of 11 out of 66 genes resulted in a doubled LNT production. Among these, also a protein encoded in the genome of E. coli BL21 (DE3) proved to enhance the LNT export (TP37, yebQ, acc. no. NC_012971). YebQ is a predicted MFS transporter, putatively involved in multi drug efflux, which might represent a responsible transporter protein that realizes the observed basal efflux of LNT during fermentation of strain 1353.

Furthermore, the exporters encoded by the genes spoVB of Bacillus amyloliquefaciens (TP1, acc. no. AFJ60154), yabM of Erwinia pyrilfoliae (TP2, acc. no. CAY73138), bcr of E. coli MG1655 (TP18, acc. no. AAC75243), ydeA of E. coli MG1655 (TP20, acc. no. AAC74601), proP2 of Haemophilus parainfluenzae (TP54, acc. no. EGC72107), setA of Pectobacterium carotovorum (TP55, acc. no. ZP_03829909), fucP of E. coli MG1655 (TP59, acc. no. AIZ90162), mdeA of Staphylococcus aureus Bmb9393 (TP61, acc. no. SABB_01261), ImrA of Lactococcus lactis (TP62, acc. no. L116532), setA of Pseudomonas sp. MT-1 (TP72, acc. no. BAP78849) and setA of Beauveria bassiana D1-5 (TP73, acc. no. KGQ13398) resulted in an increased LNT production when overexpressed in the E. coli production strain 1353.

Example 8

Generation of an E. coli Lacto-N-Triose II Production Strain by Overexpression of Heterologous Sugar Efflux Transporters The LNT exporter screening described in example 6 interestingly disclosed two proteins—TP11 from Mannheimia succiniciproducens MBEL55E (proP, acc. no. AAU37785) and TP70 from Cedecea neteri M006 (setA, acc. no. WP_039290253)—whose overexpression resulted in a significantly increased production of LNT-II and consequently in a decreased LNT production (data not shown). This observation was confirmed in an experimental setup as described in example 3. The overexpression of the sugar efflux transporter YjhB served as a positive control. The overexpression of TP11 as well as TP70 resulted in an approximately 4-fold increase in LNT-II production which was even slightly more than for YjhB: FIG. 9 shows a diagram displaying the concentrations of lacto-N-triose II in the supernatant of E. coli BL21 (DE3) strains overexpressing the sugar efflux transporters TP11 (2), YjhB (3) or TP70 (4). Strain 1326 harbouring an empty control plasmid served as a control (1). Thus, 3 sugar efflux transporters were identified which target LNT-II for export and whose overexpression might be useful to engineer a LNT-II production strain.

TABLE 2

| Strains and plasmids | | |
| --- | --- | --- |
| Strain | Genotype | Ref. |
| E. coli BL21(DE3) | F-ompT hsdSB(rB-, mB-) gal dcm (DE3) | Merck KGaA, Darmstadt, Germany |
| E. coli BL21(DE3) 534 | E. coli BL21(DE3) ΔlacZ Δara ΔwcaJ ΔfucIK ΔnagAB harbouring genomic integrations of: galETKM, lacy | This study |

TABLE 2-continued

| Strains and plasmids | | |
| --- | --- | --- |
| Strain | Genotype | Ref. |
| *E. coli* BL21(DE3) 724 | *E. coli* BL21(DE3) ΔlacZ Δara ΔwcaJ ΔfucIK ΔnagAB harbouring genomic integrations of: galETKM, lacY, lgtA-galT-kanR, glmUM-glmS-dhfr | This study |
| *E. coli* BL21(DE3) 1326 | *E. coli* BL21(DE3) ΔlacZ Δara ΔwcaJ ΔfucIK ΔnagAB harbouring genomic integrations of: galETKM, lacY, lgtA-galT-kanR, glmUM-glmS-dhfr, lacy(6HIS)-aadA | This study |
| *E. coli* BL21(DE3) 707 | *E. coli* BL21(DE3) ΔlacZ Δara ΔwcaJ ΔfucIK ΔnagAB harbouring genomic integrations of: galETKM, lacY, glmUM-glmS-dhfr | This study |
| *E. coli* BL21(DE3) 1353 | *E. coli* BL21(DE3) ΔlacZ Δara ΔwcaJ ΔfucIK ΔnagAB harbouring genomic integrations of: galETKM, lacY, lgtA-galT-kanR, glmUM-glmS-dhfr, wbdO-galE-cat | This study |
| *E. coli* BL21(DE3) 1431 | *E. coli* BL21(DE3) ΔlacZ Δara ΔwcaJ ΔfucIK ΔnagAB harbouring genomic integrations of: galETKM, lacY, lgtA-galT-kanR, glmUM-glmS-dhfr, wbdO-galE-cat, ΔyjhB-aacC1 | This study |
| pCDF-galE | galE of *E. coli* K12 integrated into vector pCDFDuet | EP 14 162 869.3 |
| pET-lgtA (SeqID7) | lgtA of *Neisseria meningitidis* integrated into vector pETDuet | This study |
| pCDF-galT-galE (SeqID8) | galT and galE of *Escherichia coli* K12 integrated into vector pCDFDuet | This study |
| pCOLA-glmUM-glmS (SeqID9) | glmU, glmM and glmS of *Escherichia coli* K12 integrated into vector pCOLADuet | This study |
| pINT-malE-lex1 | Gene fusion of malE with lex-1 of *Aggregatibacter aphrophilus* NJ8700 integrated into vector pINT | EP 14 162 869.3 |
| pINT-malE-PmgalT7 (SeqID10) | Gene fusion of PmgalT7 of *Pasteurella multocida* subsp. *multocida* str. HN06 integrated into vector pINT | This study |
| pINT-malE-MsgalT8 SeqID11) | Gene fusion of MsgalT8 of *Myxococcus stipitatus* DSM14675 integrated into vector pINT | This study |
| pINT-malE-KdgalT10 (SeqID12) | Gene fusion of KdgalT10 of *Kingella denitrificans* ATCC 33394 integrated into vector pINT | This study |
| pINT-malE-gatD (SeqID13) | Gene fusion of gatD of *Pasteurella multocida* M1404 integrated into vector pINT | This study |
| pINT-malE-BFgalT2 (SeqID14) | Gene fusion of BfgalT2 of *Bacterioidis fragilis* NCTC9343 integrated into vector pINT | This study |
| pINT-malE-IsgD (SeqID15) | Gene fusion of IsgD of *Haemophilus influenza* integrated into vector pINT | This study |
| pINT-malE-HPgalT (SeqID16) | Gene fusion of HpgalT of *Helicobacter pylori* integrated into vector pINT | This study |
| pACYC-waaX (SeqID17) | waaX of *Pectobacterium atrosepticum* JG10-08 integrated into vector pACYCDuet | This study |
| pACYC-wbdO (SeqID18) | wbdO of *Salmonella enterica* subsp. *salamae* serovar Greenside integrated into vector pACYCDuet | This study |
| pACYC-furA (SeqID19) | furA of *Lutiella nitroferrum* 2002 integrated into vector pACYCDuet | This study |
| pET-PmnagT (SeqID20) | PmnagT of *Pasteurella multocida* subsp. multocida str. HN06 integrated into vector pETDuet | This study |
| pINT-yjhB (SeqID21) | yjhB of *E. coli* BL21 DE3 integrated into vector pINT | This study |
| pINT-yebQ (SeqID22) | yebQ of *E. coli* BL21 DE3 integrated into vector pINT | This study |
| pINT-proP (SeqID23) | proP of Mannheimia succiniciproducens MBEL55E integrated into vector pINT | This study |
| pINT-Cn-setA (SeqID24) | setA of *Cedecea neteri* M006 integrated into vector pINT | This study |
| pINT-spoVB (SeqID25) | spoVB of *Bacillus amyloliquefaciens* integrated into vector pINT | This study |
| pINT-yabM (SeqID26) | yabM of *Erwinia pyrifoliae* integrated into vector pINT | This study |

TABLE 2-continued

| Strain | Genotype | Ref. |
|---|---|---|
| | Strains and plasmids | |
| pINT-ydeA (SeqID27) | ydeA of *E. coli* MG1655 integrated into vector pINT | This study |
| pINT-proP2 (SeqID28) | proP2 of *Haemophilus parainfluenzae* integrated into vector pINT | This study |
| pINT-Pc-setA (SeqID29) | setA of *Pectobacterium carotovorum* integrated into vector pINT | This study |
| pINT-fucP (SeqID30) | fucP of *Escherichia coli* BL21 (DE3) integrated into vector pINT | This study |
| pINT-mdeA (SeqID31) | mdeA of *Staphylococcus aureus* Bmb9393 integrated into vector pINT | This study |
| pINT-ImrA (SeqID32) | ImrA of *Lactococcus lactis* integrated into vector pINT | This study |
| pINT-Ps-setA (SeqID33) | setA of *Pseudomonas* sp. MT-1 integrated into vector pINT | This study |
| pINT-Bb-setA (SeqID34) | setA of Beauveria bassiana D1-5 integrated into vector pINT | This study |

TABLE 3

Oligonucleotides used for PCR

| Primer | Sequence 5'-3' |
|---|---|
| 605 KI gal fwd | TTACTCAGCAATAAACTGATATTCCGTCAGGCTGG (SeqID35) |
| 606 KI gal rev | TTGTAATCTCGCGCTCTTCACATCAGACTTTCCATATAGAGCGTAATTTC CGTTAACGTCGGTAGTGCTGACCTTGCCGGAGG (SeqID36) |
| 1119 ME-for | CTGTCTCTTATCACATCTCCTGAAATGGCCAGATGTAATTCCTAATTTTT GTTG (SeqID37) |
| 1120 ME rev | CTGTCTCTTATCACATCTCACATTACATCTGAGCGATTGTTAGG (SeqID38) |
| 1163 galE_NdeI-for | GATCACATATGAGAGTTCTGGTTACCGGTG (SeqID39) |
| 1164 galE_XhoI-rev | GATCACTCGAGTCATTAATCGGGATATCCCTGTGGATGGC (SeqID40) |
| 5176 lex1 pINT-f | GTCGATGAAGCCCTGAAAGACGCGCAGACTATGCACTTCATTGAAAAC AAAAACTTCGTC (SeqID41) |
| 5177 lex1 pINT-r | GATGGCCTTTTTGCGTGTCGACGCGGCCGCCTAGATAAACAGGATGAT ATTTTTGCCTIG (SeqID42) |
| 5178 pINT lexl-f | CAAGGCAAAAATATCATCCTGTTTATCTAGGCGGCCGCGTCGACACGC AAAAAGGCCATC (SeqID43) |
| 5179 pINT lexl-r | GACGAAGTTTTTGTTTTCAATGAAGTGCATAGTCTGCGCGTCTTTCAGG GCTTCATCGAC (SeqID44) |
| 5192 waaX pINT for | GTCGATGAAGCCCTGAAAGACGCGCAGACTATGATTGATAACCTGATTA AGCGTACCCCG (SeqID45) |
| 5193 waaX pINT rev | ATGGCCTTTTTGCGTGTCGACGCGGCCGCTTAATTCGAGCGGGTAAAG ATCTTCATCAGG (SeqID46) |
| 5194 pINT waaX for | CTGATGAAGATCTTTACCCGCTCGAATTAAGCGGCCGCGTCGACACGC AAAAAGGCCATC (SeqID47) |
| 5195 pINT waaX rev | CGGGGTACGCTTAATCAGGTTATCAATCATAGTCTGCGCGTCTTTCAGG GCTTCATCGAC (SeqID48) |
| 5164 PmgalT7 pINT for | GTCGATGAAGCCCTGAAAGACGCGCAGACTATGAGCGGTGAACACTAT GTCATTAGCCTG (SeqID49) |
| 5165 PmgalT7 pINT rev | GATGGCCTTTTTGCGTGTCGACGCGGCCGCTCATTTAAATTCGATGATC ATCTTGTCGTT (SeqID50) |
| 5166 pINT PmgalT7 for | AACGACAAGATGATCATCGAATTTAAATGAGCGGCCGCGTCGACACGC AAAAAGGCCATC (SeqID51) |
| 5167 pINT PmgalT7 rev | CAGGCTAATGACATAGTGTTCACCGCTCATAGTCTGCGCGTCTTTCAGG GCTTCATCGAC (SeqID52) |

TABLE 3-continued

| Oligonucleotides used for PCR | |
| --- | --- |
| Primer | Sequence 5'-3' |
| 5168 MsgalT8 pINT for | GTCGATGAAGCCCTGAAAGACGCGCAGACTATGGATGAAATCAAACTG TCGGTGGTTATG (SeqID53) |
| 5169 MsgalT8 pINT rev | GATGGCCTTTTTGCGTGTCGACGCGGCCGCTCATTGGCGACGCCAATC GAACGCAACGCG (SeqID54) |
| 5170 pINT MsgalT8 for | CGCGTTGCGTTCGATTGGCGTCGCCAATGAGCGGCCGCGTCGACACG CAAAAAGGCCATC (SeqID55) |
| 5171 pINT MsgalT8 rev | CATAACCACCGACAGTTTGATTTCATCCATAGTCTGCGCGTCTTTCAGG GCTTCATCGAC (SeqID56) |
| 5561 KdgalT10 pINT for | GTCGATGAAGCCCTGAAAGACGCGCAGACTATGGAAAACTATGTCGTC TCTATCCGCACC (SeqID57) |
| 5562 KdgalT10 pINT-rev | GATGGCCTTTTTGCGTGTCGACGCGGCCGCTCATTTGAACGGAACAAT CTTTTTGTCATC (SeqID58) |
| 5563 pINT-KdgalT10 for | GATGACAAAAAGATTGTTCCGTTCAAATGAGCGGCCGCGTCGACACGC AAAAAGGCCATC (SeqID59) |
| 5564 pINT-KdgalT10 rev | GGTGCGGATAGAGACGACATAGTTTTCCATAGTCTGCGCGTCTTTCAG GGCTTCATCGAC (SeqID60) |
| 5172 gatD pINT for | GTCGATGAAGCCCTGAAAGACGCGCAGACTATGTCCTCAGCTTTCCATT ACGTCATTAGC (SeqID61) |
| 5173 gatD pINT rev | GATGGCCTTTTTGCGTGTCGACGCGGCCGCTCATTCAAATTCGATAATC ATGGTGATTTT (SeqID62) |
| 5174 pINT gatD for | AAAATCACCATGATTATCGAATTTGAATGAGCGGCCGCGTCGACACGCA AAAAGGCCATC (SeqID63) |
| 5175 pINT gatD rev | GCTAATGACGTAATGGAAAGCTGAGGACATAGTCTGCGCGTCTTTCAG GGCTTCATCGAC (SeqID64) |
| 5160 BfglaT2 pINT for | GTCGATGAAGCCCTGAAAGACGCGCAGACTATGAACGTGAATAAGCCG ACCACCGAAAAG (SeqID65) |
| 5161 BfgalT2 pINT rev | GATGGCCTTTTTGCGTGTCGACGCGGCCGCTCAGTATTCTTCAATTTTG TCCAGTTGATA (SeqID66) |
| 5162 pINT BfgalT2 for | TATCAACTGGACAAAATTGAAGAATACTGAGCGGCCGCGTCGACACGC AAAAAGGCCATC (SeqID67) |
| 5163 pINT BfgalT2 rev | CTTTTCGGTGGTCGGCTTATTCACGTTCATAGTCTGCGCGTCTTTCAGG GCTTCATCGAC (SeqID68) |
| 5746 | GTGATCAACGCCGCCAGCGGTCGTCAGACTGTCGATGAAGCCCTGAAA GACGCGCAGACT (SeqID69) |
| 5747 | GCGGCCGCGTCGACACGCAAAAAGGCCATCCATCCGTCAGGATGGCC TTCTGCTTAATTT (SeqID70) |
| 5748 | AAATTAAGCAGAAGGCCATCCTGACGGATGGATGGCCTTTTTGCGTGT CGACGCGGCCGC (SeqID71) |
| 5749 | AGTCTGCGCGTCTTTCAGGGCTTCATCGACAGTCTGACGACCGCTGGC GGCGTTGATCAC (SeqID72) |
| 1886 SLIC wbdO pACYC for | GTTTAACTTTAATAAGGAGATATACCATGCTGACGGAAGTGCGCCCGGT CTCTACGACGAAACCGC (SeqID73) |
| 1887 SLIC wbdO pACYC rev | CGACCTGCAGGCGCGCCGAGCTCGAATTCATTTGATGTATTTGCAATA GAACACAGAAAAGACCGT (SeqID74) |
| 1888 SLIC pACYC wbdo rev | GTGTTCTATTGCAAATACATCAAATGAATTCGAGCTCGGCGCGCCTGCA GGTCGACAAGCTTGCGG (SeqID75) |
| 1889 SLIC pACYC Wbd0 For | GAGACCGGGCGCACTTCCGTCAGCATGGTATATCTCCTTATTAAAGTTA AACAAAATTATTTCTACAGG (SeqID76) |
| 1890 SLIC pACYC furA rev | GTATGGTGACCCTGTGGCGCAAATGAGAATTCGAGCTCGGCGCGCCTG CAGGTCGACAAGCT (SeqID77) |

TABLE 3-continued

Oligonucleotides used for PCR

| Primer | Sequence 5'-3' |
|---|---|
| 1891 SLIC pACYC furA for | GCGCTGCCCTGTTTGATTTTATCCATGGTATATCTCCTTATTAAAGTTAA ACAAAATTATTTCT (SeqID78) |
| 1892 SLIC furA pACYC rev | CCTGCAGGCGCGCCGAGCTCGAATTCTCATTTGCGCCACAGGGTCACC ATACGTGCCGGCAGG (SeqID79) |
| 1893 SLIC furA pACYC for | GITTAACTTTAATAAGGAGATATACCATGGATAAAATCAAACAGGGCAG CGCCTCTCTGGTTGTCG (SeqID80) |
| 3055 SLIC PmnagT pET rev | CAGACTCGAGGGTACCGACGTCCTAATAAGTAGATGAATATTTATCAGG ACGAAGAT (SeqID81) |
| 3056 SLIC pET PmnagT for | AACTAAAGGTTTATTTTCCATATGTATATCTCCTTCTTATACTTAACTAAT ATAC (SeqID82) |
| 3057 SLIC pET PmnagT rev | TAAATATTCATCTACTTATTAGGACGTCGGTACCCTCGAGTCTGGTAAA GAAACCGCTGCTGCG (SeqID83) |
| 3058 SLIC PmnagT pET for | GTATAAGAAGGAGATATACATATGGAAAATAAACCTTTAGTTTCAGTTTT GATTTGTGC (SeqID84) |
| 2567_SLIC_yjhB-for | TAACTTTAAGAAGGAGATATACAAGAGCTCGAGTCGAAGGAGATAGAAC CATGGCAACAGCATGGTATAAACAAG (SeqID85) |
| 2568_SLIC_yjhB-rev | GCGTGTCGACGCGTTTAGAGGCCCCAAGGGGTTATGCTAGTATCGATT TATCATTTAGCCACGGATAGTTTATAAATTTTAC (SeqID86) |
| 2526_SLIC_pINT_TP-rev | GGTTCTATCTCCTTCGACTCGAGCTCTTGTATATCTCCTTCTTAAAGTTA AACAAAATTATTTCTAGATTTTTGTCGAAC (SeqID87) |
| 2443_SLIC_pINT_TP-forw | TAAATCGATACTAGCATAACCCCTTGGGGCCTCTAAACGCGTCGACAC GCAAAAAGGCCATCC (SeqID88) |
| 2527_SLIC_TP_pINT-forw | GTTCGACAAAAATCTAGAAATAATTTTGTTTAACTTTAAGAAGGAGATAT ACAAGAGCTCGAGTCGAAGGAGATAGAACC (SeqID89) |
| 2444_SLIC_TP_pINT-rev | GGATGGCCTTTTTGCGTGTCGACGCGTTTAGAGGCCCCAAGGGGTTAT GCTAGTATCGATTTA (SeqID90) |
| 688 IgtA AatII rev | ATATGACGTCTCATTAGCGGTTTTTCAGGAGACG (SeqID91) |
| 689 IgtA NdeI for | ATATCATATGCCGTCCGAAGCATTCCGTCGTCACC (SeqID92) |
| 991 galT-pCDF for | TAACTTTAATAAGGAGATATACCATGACGCAATTTAATCCCGTTGATCAT CCACATCGCCGC (SeqID93) |
| 992 pCDF-galT for | ATTTTCGCGAATCCGGAGTGTAAAAGCTTGCGGCCGCATAATGCTTAAG TCGAACAGAAAGTAATCG (SeqID94) |
| 993 galT-pCDF rev | AAGCATTATGCGGCCGCAAGCTTTTACACTCCGGATTCGCGAAAATGG ATATCGCTGACTGCGCGCAAACGC (SeqID95) |
| 994 pCDF-galT rev | TCAACGGGATTAAATTGCGTCATGGTATATCTCCTTATTAAAGTTAAACA AAATTATTTCTACAGGGG (SeqID96) |
| 848 glmM pCOLA SLIC rev | ATGGTGATGGCTGCTGCCCATTTAAACCGCTTTGACTGCGTCGGCAATA CGGTGCGC (SeqID97) |
| 849 glmU pCOLA SLIC for | GTTTAACTTTAATAAGGAGATATACCATGCTGAACAACGCGATGTCTGTT GTTATCCTGG (SeqID98) |
| 850 pCOLA glmM SLIC rev | CGCAGTCAAAGCGGTTTAAATGGGCAGCAGCCATCACCATCATCACCA CAGCC (SeqID99) |
| 851 pCOLA glmU SLIC for | TCGCGTTGTTCAGCATGGTATATCTCCTTATTAAAGTTAAACAAAATTAT TTCTACAGG (SeqID100) |
| 852 glmSco pCOLA for NdeI | ATATATCATATGTGCGGTATCGTTGGTGCTATCGC (SeqID101) |
| 853 glmSco pCOLA rev AatII | ATATATGACGTCTTATTCCACGGTCACGGATTTCGC (SeqID102) |

The invention claimed is:

1. A method for the production of lacto-N-triose II by a genetically modified microbial host cell, comprising providing a genetically modified microbial host cell that comprises:

at least one recombinant β-1,3-N-acetylglucosaminyl-transferase, wherein the at least one recombinant β-1,3-N-acetylglucosaminyltransferase belongs to the class of lgtA of *Neisseria meningitidis*, and increased expression or activity of at least one sugar export protein capable of exporting the lacto-N-triose II, wherein the at least one sugar export protein is YjhB from *E. coli* or ProP from *Mannheimia succiniciproducens;* cultivating the microbial host cell in a medium under conditions permissive for the production of the lacto-N-triose II, whereby the lacto-N-triose II is exported into the medium at an increased level compared to the unmodified microbial host cell, and obtaining the lacto-N-triose II from the medium.

2. The method of claim 1, wherein, the endogenous β-galactosidase gene and the endogenous glucosamine-6-phosphate deaminase gene of the genetically modified microbial host cell are inactivated or deleted, and wherein said genetically modified microbial host cell comprises a nucleic acid sequence coding for a functional lactose permease protein.

3. The method of claim 1, wherein the genetically modified microbial host cell comprises an increased UDP-N-acetylglucosamine and UDP-galactose or GDP-fucose or CMP-N-acetylneuraminic acid production capability as compared to a genetically unmodified host cell, wherein optionally said increased UDP-N-acetylglucosamine and UDP-galactose production capability comprises the overexpression of one or more genes encoding for proteins comprising the following activities for a: L-glutamine:D-fructose-6-phosphate aminotransferase, N-acetyl glucosamine-1-phosphate uridyltransferase/glucosamine-1-phosphate acetyl transferase, phosphoglucosamine mutase, UDP-galactose-4-epimerase, phosphoglucomutase, glucose-1-phosphate uridylyltransferase.

4. The method of claim 1, wherein said genetically modified microbial host cell is cultivated in the presence of glucose, sucrose, glycerol or a combination thereof, but not by addition or in the presence of N-acetylglucosamine, galactose or combination thereof.

5. A genetically modified microbial host cell for the production of lacto-N-triose II, wherein the microbial host cell comprises:

a. at least one recombinant β-1,3-N-acetylglucosaminyl-transferase, wherein the at least one recombinant β-1,3-N-acetylglucosaminyltransferase belongs to the class of lgtA of *Neisseria meningitidis*, and b. increased expression or activity of at least one sugar export protein capable of exporting the lacto-N-triose II, wherein the at least one sugar export protein is YjhB from *E. coli* or ProP from *Mannheimia succiniciproducens.*

6. The genetically modified microbial host cell of claim 5, wherein the endogenous β-galactosidase gene and the endogenous glucosamine-6-phosphate deaminase gene in the genetically modified microbial host cell are inactivated or deleted, and wherein said genetically modified microbial host cell comprises a nucleic acid sequence coding for a functional lactose permease protein.

7. The genetically modified microbial host cell of claim 5, wherein the genetically modified microbial host cell comprises an increased UDP-N-acetylglucosamine and UDP-galactose or GDP-fucose or CMP-N-acetylneuraminic acid production capability as compared to a genetically unmodified host cell, wherein optionally said increased UDP-N-acetylglucosamine and UDP-galactose production capability comprises the overexpression of one or more genes encoding for proteins comprising the following activities for a: L-glutamine:D-fructose-6-phosphate aminotransferase, N-acetyl glucosamine-1-phosphate uridyltransferase/glucosamine-1-phosphate acetyl transferase, phosphoglucosamine mutase, UDP-galactose-4-epimerase, phosphoglucomutase, glucose-1-phosphate uridylyltransferase.

* * * * *

SEQUENCE LISTING

```
Sequence total quantity: 102
SEQ ID NO: 1           moltype = DNA   length = 2851
FEATURE                Location/Qualifiers
misc_feature           1..2851
                       note = construct Ptet-lacY-FRT-add1-FRT
source                 1..2851
                       mol_type = other DNA
                       organism = synthetic construct
SEQUENCE: 1
tggccagatg attaattcct aattttttgtt gacactctat cattgataga gttattttac   60
cactccctat cagtgataga gaaaagtgaa atgaatagtt cgacaaaaat ctagaaataa  120
ttttgtttaa ctttaagaag gagatataca aatgtactat ttaaaaaaca caaacttttg  180
gatgttcggt ttattctttt tcttttactt ttttatcatg ggagcctact tcccgttttt  240
cccgatttgg ctacatgaca tcaaccatat cagcaaaagt gatacgggta ttattttttgc  300
cgctatttct ctgttctcgc tattattcca accgctgttt ggtctgcttt ctgacaaact  360
cgggctcgc aaaatacctgc tgtggattat taccggcatg ttagtgatgt ttgcgccgtt  420
ctttattttt atcttcgggc cactgttaca atacaacatt ttagtaggat cgattgttgg  480
tggtatttat ctaggctttt gttttaacgc cggtgcgcca gcagtagagg catttattga  540
gaaagtcagc cgtcgcagta atttcgaatt tggtcgcgcg cggatgtttg gctgtgttgg  600
ctggcgcctg tgtgcctcga ttgtcggcat catgttcacc atcaataatc agtttgtttt  660
ctggctgggc tctggctgtg cactcatcct cgccgttta ctcttttttcg ccaaaacgga  720
tgcgccctct tctgccacgg ttgccaatgc ggtaggtgcc aaccattcgg catttagcct  780
taagctggca ctggaactgt tcagacagcc aaaactgtgg tttttgtcac tgtatgttat  840
tggcgtttcc tgcacctacg atgtttttga ccaacagttt gctaatttct ttacttcgtt  900
ctttgctacc ggtgaacagg gtacgcgggt atttggctac gtaacgacaa tgggcgaatt  960
acttaacgcc tcgattatgt tctttgcgcc actgatcatt aatcgcatcg gtgggaaaaa 1020
cgccctgctg ctggctggca ctattatgtc tgtacgtatt attggctcat cgttcgccac 1080
ctcagcgctg gaagtggtta ttctgaaaac gctgcatatg tttgaagtac cgttcctgct 1140
ggtgggctgc tttaaatata ttaccagcca gtttgaagtg cgtttttcag cgacgattta 1200
tctggtctgt ttctgcttct ttaagcaact ggcgatgatt tttatgtctg tactggcggg 1260
caatatgtat gaaagcatcg gtttccaggg cgcttatctg gtgctgggtc tggtggcgct 1320
gggcttcacc ttaatttccg tgttcacgct tagcggcccc ggccgcttt ccctgctgcg 1380
tcgtcaggtg aatgaagtcg ctgggagcta agcggccgcg tcgacacgca aaaaggccat 1440
ccgtcaggat ggccttctgc ttaatttgat gcctggcagt ttatggcggg cgtcctgccc 1500
gccaccctcc gggccgttgc ttcgcaacgt tcaaatccgc tcccgcgga tttgtcctac 1560
tcaggagagc gttcaccgac aaacaacaga taaaacgaaa ggcccagtct tccgactgag 1620
cctttcgttt tatttgatgc ctggcagttc cctactctcg catgggcaga ccccacacta 1680
ccatcatgta tgaatatcct ccttagttcc tattccgaag ttcctattct ctagaaagta 1740
taggaacttc ggcgcgtcct acctgtgaca cgcgtgccgc agtctcacgc ccggagcgta 1800
gcgaccgagt gagctagcta tttgtttatt tttctaaata cattcaaata tgtatccgct 1860
catgagacaa taaccctgat aaatgcttca ataatattga aaaaggaaga gtatgaggga 1920
agcggtgatc gccgaagtat cgactcaact atcagaggta gttggcgtca tcgagcgcca 1980
tctcgaaccg acgttgctgg ccgtacattt gtacggctcc gcagtggatg gcggcctgaa 2040
gccacacagt gatattgatt tgctggttac ggtgaccgta aggcttgatg aaacaacgcg 2100
gcgagctttg atcaacgacc ttttggaaac ttcggcttcc cctggagaga gcgagattct 2160
ccgcgctgta gaagtcacca ttgttgtgca cgacgacatc attccgtggc gttatccagc 2220
taagcgcgaa ctgcaatttg gagaatggca gcgcaatgac attcttgcag gtatcttcga 2280
gccagccacg atcgacattg atctggctat cttgctgaca aaagcaagag aacatagcgt 2340
tgccttggta ggtccagcgg cggaggaact ctttgatccg gttcctgaac aggatctatt 2400
tgaggcgcta aatgaaacct taacgctatg gaactcgccg cccgactggg ctggcgatga 2460
gcgaaatgta gtgcttacgt tgtcccgcat ttggtacagc gcagtaaccg gcaaaatcgc 2520
gccgaaggat gtcgctgccg actgggcaat ggagcgcctg ccggcccagt atcagcccgt 2580
catacttgaa gctagacagg cttatcttgg acaagaagaa gatcgcttgg cctcgcgcgc 2640
agatcagttg gaagaatttg tccactacgt gaaaggcgag atcaccaagg tagtcggcaa 2700
ataatgtcta caattcgtt caagccgagg ggccgcaaga tccggccacg atgacccggt 2760
cgtcgggtac cggcaggggcg gggcgtaagg cgcgccattt aaatgaagtt cctattccga 2820
agttcctatt ctctagaaag tataggaact t                                 2851

SEQ ID NO: 2           moltype = DNA   length = 4568
FEATURE                Location/Qualifiers
misc_feature           1..4568
                       note = construct Ptet-lgtA-PT5-galT-FRT-kanR-FRT
source                 1..4568
                       mol_type = other DNA
                       organism = synthetic construct
SEQUENCE: 2
acaggttggc tgataagtcc ccggtctagc ttgcatgcag attgcagcat tacacgtctt   60
gagcgattgt gtaggctgga gctgcttcga agttcctata ctttctagag aataggaact  120
tcggaatagg aacttcattt aaatggcgcg ccttacgccc cgccctgcg gtaccgagag  180
cgcttttgaa gctggggtgg gcgaagaact ccagcatgag atcccgcgc tggaggatca  240
tccagccggc gtcccggaaa acgattccga agcccaacct tcatagaag gcggcggtgg  300
aatcgaaatc tcgtgatggc aggttgggcg tcgcttggtc ggtcatttcg aaccccagag  360
tcccgctcag aagaactcgt caagaaggcg atagaaggcg atgcgctgcg aatcgggagc  420
ggcgataccg taaagcacga ggaagcggtc agcccattcg ccgccaagct cttcagcaat  480
atcacgggta gccaacgcta tgtcctgata gcggtccgcc acacccagcc ggccacagtc  540
gatgaatcca gaaaagcggc cattttccac catgatattc ggcaagcagg catcgccatg  600
ggtcacgacg agatcctcgc cgtcgggcat gcgcgccttg agcctggcga acagttcggc  660
tggcgcgagc ccctgatgct cttcgtccag atcatcctga tcgacaagac cggcttccat  720
```

-continued

```
ccgagtacgt gctcgctcga tgcgatgttt cgcttggtgg tcgaatgggc aggtagccgg    780
atcaagcgta tgcagccgcc gcattgcatc agccatgatg gatactttct cggcaggagc    840
aaggtgagat gacaggagat cctgccccgg cacttcgccc aatagcagcc agtcccttcc    900
cgcttcagtg acaacgtcga gcacagctgc gcaaggaacg cccgtcgtgg ccagccacga    960
tagccgcgct gcctcgtcct gcagttcatt cagggcaccg gacaggtcgg tcttgacaaa   1020
aagaaccggg cgcccctgcg ctgacagccg gaacacggcg gcatcagagc agccgattgc   1080
ctgttgtgcc cagtcatagc cgaatagcct ctccacccaa gcggccggag aacctgcgtg   1140
caatccatct tgttcaatca tgcgaaacga tcctcatcct gtctcttgat cagatcttga   1200
tcccctgcgc catcagatcc ttggcggcaa gaaagccatc cagtttactt tgcagggctt   1260
cccaacctta ccagagggcg ccccagctgg caattccggt tcgcttgctg tccataaaac   1320
cgcccagtct agctatcgcc atgtaagccc actgcaagct acctgctttc tctttgcgct   1380
tgcgttttcc cttgtccaga tagcccagta gctgacattc atccggggtc agcaccgttt   1440
ctgcggactg gctttctacg tgttccgctt cctttagcag cccttgcgcc ctgagtgctt   1500
gcggcagcgt gagggggatct tgacgcgtgt cacaggtagg acgcgccgaa gttcctatac   1560
tttctagaga ataggaactt cggaatagga actaaggagg atattcatac atgatggtag   1620
tgttcgaaat taatacgact cactataggg gaattgattc tggtaccaaa tgagtcgacc   1680
ggccagatga ttaattccta attttgttg acactctatc attgatagag ttattttacc   1740
actccctatc agtgatagag aaaagtgaaa tgaatagttc gacaaaaatc tagaaataat   1800
tttgtttaac tttaagaagg agatatacaa atgccgtccg aagcattccg tcgtcaccgt   1860
gcttatcgcg aaaacaaact gcagccactg gtctctgtcc tgatctcgcg atacaacgtt   1920
gagaaatact tcgcacagtc tctggcagct gtagttaacc agacctggcg taacctggat   1980
atcctgatcg tagatgacgg ctctacggat ggtacgctgg cgatcgcaca gcgtttccag   2040
gaacaggacg gtcgtatccg cattctcgct cagccgcgta actctggtct gatcccgtct   2100
ctgaacatcg gtctggacga actggccaaa tctggtggtg gtggcgaata catcgcccgt   2160
actgacgccg acgacattgc ggccccggat tggatcgaaa aaatcgtagg tgaaatggag   2220
aaagaccgct ctatcatcgc gatgggtgct tggctggaaa ttctgtccga agagaaagac   2280
ggtaaccgtc tggcccgtca ccatgaacac ggcaaaatct ggaaaaaacc gacccgtcac   2340
gaagatatcg cggacttctt cccgttcggt aacccgatcc ataacaacac catgatcatg   2400
cgtcgtagcg taatcgacgg tggtctgcgt tacaacaccg aacgtgattg ggcagaagac   2460
taccagtttt ggtatgacgt gtctaaactg ggtcgtctgg cttactaccg agaagcgctg   2520
gttaaatacc gtctgcacgc caaccaggtt agctccaaat actccatccg tcagcacgaa   2580
atcgcacagg gtatccagaa aacggctcgt aacgacttcc tgcagtccat gggtttcaaa   2640
acccgtttcg actctctgga gtaccgtcag atcaaagcgg ttgcgtatga gctgctggag   2700
aaacacctgc cggaagagga ctttgaacgt gcgcgtcgtt cctgtacca gtgcttcaaa   2760
cgtaccgaca ctctgccggc gggtgcatgg ctcgactttg cagcggatgg tcgtatgcgt   2820
cgtctgttta ccctgcgtca gtacttcggt atcctgcatc gtctcctgaa aaaccgctaa   2880
tgatttcgtc gacacacagg aaacatatta aaaattaaaa cctgcaggag tttaaacgcg   2940
gccgcgatat cgttgtaaaa cgacggccag tgcaagaatc ataaaaaatt tatttgcttt   3000
caggaaaatt tttctgtata atagattcat aaatttgaac gaggagtttt tgtgagcgga   3060
taacaattcc ccatcttagt atattagtta agtataaata cacaaggaga tataccatga   3120
cgcaatttaa tcccgttgat catccacatc gccgctacaa cccgctcacc gggcaatgga   3180
ttctggtttc accgcaccgc gctaagcgcc cctggcaggg ggcgcaggaa acgccagcca   3240
aacaggtgtt acctgcgcac gatccagatt gcttcctctg cgcaggtaat gtgcgggtga   3300
caggcgataa aaaccccgat tacaccggga cttacgtttt cactaatgac tttgcgcgtt   3360
tgatgtctga cacgccagat gcgccagaaa gtcacgatcc gctgatgcgt tgccagagcg   3420
cgcgcggcac cagccgggtg atctgctttt caccggatca cagtaaaacg ctgccagagc   3480
tcagcgttgc agcattgacg gaaatcgtca aaacctggca ggagcaaacc ggagaactga   3540
ggaaaacgta cccatgggtg caggtttttg aaaacaaagg cgcggcgatg ggctgctcta   3600
acccgcatcc gcacggtcag atttgggcaa atagcttcct gcctaacgaa gctgagcgcg   3660
aagaccgcct gcaaaaagaa tattttgccg aacagaaatc accaatgctg gtggattatg   3720
ttcagcgacg gctggcagac ggtagccgta ccgttgtcga aaccgaacac tggttagccg   3780
tcgtgcctta ctgggctgcc tggccgttcg aaacgctact gctgcccaaa gcccacgttt   3840
tacggatcac cgatttgacc gacgcccagc gcagcgatct ggcgctggcg ttgaaaaagc   3900
tgaccagtcg ttatgacaac ctcttccagt gctccttccc ctactctatg ggctggcacg   3960
gcgcgccatt taatggcgaa gagaatcaac actggcagct gcgcgcaa ttttatccgt   4020
ctctgctgcg ctccgccacc gtacgtaaat ttatggttgg ttatgaaatg ctggcagaga   4080
cccagcgaga cctgaccgca gaacaggcag cagagcgttt gcgcgcagtc agcgatatcc   4140
attttcgcga atcggagtg taacgcggag gcgcgccatt taaatcaacc tcagcggtca   4200
tagctgtttc ctgtgactga gcaataacta gcataacccc ttggggcctc taaacgggtc   4260
ttgaggggtt ttttgctgaa accaatttgc ctggcggcag tagcgcggtg gtcccacctg   4320
accccatgcc gaactcagaa gtgaaacgcc gtagcgccga tggtagtgtg gggtctcccc   4380
atgcgagagt agggaactgc caggcatcaa ataaaacgaa aggctcagtc gaaagactgg   4440
gcctttcggg atccaggccg gcctgttaac gaattaatct tccgcggcaa caaaaattag   4500
gaattaatca tctggccaat ttcaggtggc acttttcggg cagaccgggg acttatcagc   4560
caacctgt                                                           4568
```

```
SEQ ID NO: 3               moltype = DNA  length = 6521
FEATURE                    Location/Qualifiers
misc_feature              1..6521
                           note = construct Ptet-glmUM-PT5-glmS-FRT-dhfr-FRT
source                     1..6521
                           mol_type = other DNA
                           organism = synthetic construct
SEQUENCE: 3
acaggttggc tgataagtcc ccggtctagc ttgcatgcag attgcagcat tacacgtctt    60
gagcgattgt gtaggctgga gctgcttcga aattaatacg actcactata ggggaattga   120
ttctggtacc aaatgagtcg accggccaga tgattaattc ctaattttg ttgacactct   180
atcattgata gagttatttt accactccct atcagtgata gagaaaagtg aaatgaatag   240
ttcgacaaaa atctagaaat aattttgttt aactttaaga aggagatata caaatgctga   300
```

-continued

```
acaacgcgat gtctgttgtt atcctggcgg cgggtaaagg tacccgtatg tactctgacc   360
tgccgaaagt tctgcacacc ctggcgggta aagcgatggt tcagcacgtt atcgacgcgg   420
cgaacgaact gggtgcggcg cacgttcacc tggtttacgg tcacggtggt gacctgctga   480
aacaggcgct gaaagacgac aacctgaact gggttctgca ggcggaacag ctgggtaccg   540
gtcacgcgat gcagcaggcg gcgccgttct tcgcggacga cgaagacatc ctgatgctgt   600
acggtgacgt tccgctgatc tctgttgaaa ccctgcagcg tctgcgtgac gcgaaaccgc   660
agggtggtat cggtctgctg accgttaaac tggacgaccc gaccggttac ggtcgtatca   720
cccgtgaaaa cggtaaagta accggtatcg ttgaacacaa agacgcgacc gacgaacagc   780
gtcagatcca ggagatcaac accggtatcc tgatcgcgaa cggtgcagac atgaaacgtt   840
ggctggcgaa actgaccaac aacaacgcgc agggtgaata ctacatcacc gacatcatcg   900
cgctggcgta ccaggaaggt cgtgaaatcg ttgcggttca cccgcagcgt ctgtctgaag   960
ttgaaggtgt taacaaccgt ctgcagctgt ctcgtctgga acgtgtttac cagtctgaac  1020
aggcggaaaa actgctgctg cgcgggtgtta tgctgcgtga cccggcgcgt ttcgacctgc  1080
gtggtaccct gacccacggt cgtgacgttg aaatcgacac caacgttatc atcgaaggta  1140
acgttaccct gggtcaccgt gtaaaaatcg gcaccggttg cgttatcaaa aactctgtta  1200
tcggtacgga ctgcgaaatc tctccgtaca ccgttgttga agacgcgaac ctggcggcgg  1260
cgtgcaccat cggtccgttc gcgcgtctgc gtccgggtgc ggaactgctg gaaggtgcgc  1320
acgttggtaa cttcgttgaa atgaaaaaag cgcgtctggg taaaggttct aaagcgggtc  1380
acctgaccta cctgggtgac gcggaaatcg gtgacaacgt taacatcggt gcgggtacca  1440
tcacctgcaa ctacgacggt gcgaacaaat tcaaaaccat catcggtgac gacgttttcg  1500
ttggttctga cacccagctg gttgcgccgg ttaccgttgg taaaggtgcg accatcgcgg  1560
cgggtaccac cgttacccgt aacgttggtg aaaacgcgct ggcgatctct cgtgttccgc  1620
agacccagaa agaaggttgg cgtcgtccgg ttaaaaaaaa ataacgaagg agatagaacc  1680
atgtccaacc gtaaatactt cggtacggac ggtatccgtg gtcgtgtagg tgatgctccg  1740
attacgccgg atttcgtcct gaaactcggt tgggcagcgg gtaaagttct cgcacgtcac  1800
ggctctcgta aaatcatcat cggtaaagac acccgtatct ctggttacat gctcgaatct  1860
gcactggaag cgggtctggc tgcagctggt ctgtctgcac tgttcacggg tccgatgcca  1920
accccagctg tagcgtacct gactcgcact ttccgtgcag aagcaggtat cgtgatctct  1980
gcctctcaca acccgttcta cgacaacggt atcaaattct tcagcatcga tggtaccaaa  2040
ctcccagacg cggttgaaga ggctatcgaa gcggaaatgg agaaagaaat ctcttgtgta  2100
gactctgccg aactcggtaa agcgtctcgt atcgttgatg cagcgggtcg ttacatcgag  2160
ttctgcaaag ccacctttcc gaacgaactg agccgtgtctg agctgaaaat cgtcgtagac  2220
tgtgccaacg gtgcgactta ccacattgcc ccaaacgtac tgcgtgagct gggtgctaac  2280
gtcatcgcga tcggttgtga accgaacggt gtcaacatca acgcggaagt aggtgcgacc  2340
gatgttcgtg cactgcaggc tcgtgtactc gcggagaaag cggatctcgg tatcgccttt  2400
gacggtgatg gtgaccgtgt tatcatggtt gaccacgaag gtaacaaagt ggatggtgac  2460
cagatcatgt acatcattgc ccgtgaaggt ctgcgtcagg gtcagctgcg tggtggtgca  2520
gtaggtaccc tcatgagcaa catgggtctg gaactggccc tgaaacagct gggtatccca  2580
ttcgctcgtg ctaaagtagg cgaccgttac gttctggaga aaatgcagga gaaaggttgg  2640
cgtatcggtg ccgaaaactc tggtcacgtc atcctgctgg acaaaaccac taccggtgac  2700
ggtatcgtag caggtctgca ggtactcgcc gctatggccc gtaaccacat gtccctccat  2760
gacctctgct ctggtatgaa aatgttcccg cagatcctgg ttaacgttcg ttacaccgca  2820
ggttctggtg atccgctgga acacgagtct gtgaaagcg taccgcaga agtggaagcg  2880
gccctgggta accgtggtcg tgtactgctg cgtaaatccg gtactgagcc actgatccgt  2940
gttatggttg agggcgaaga tgaagcccag gtcaccgaat ttgcgcaccg tattgccgac  3000
gcagtcaaag cggtttaatt tcgtcgacac acaggaaaca tattaaaaat taaaacctgc  3060
aggagtttaa acgcggccgc gatatcgttg taaaacgacg gccagtgcaa gaatcataaa  3120
aaatttatttt gctttcagga aaatttttct gtataataga ttcataaatt tgagagagga  3180
gttttttgtga gcggataaca attccccatc ttagtatatt agttaagtat aaatacacaa  3240
ggagatatac atatgtgcgg tatcgttggt gctatcgcac agcgtgatgt agcggagatc  3300
ctcctggaag gtctgcgtcg tctcgaatac cgtggttacg actctgccgg tctggcagta  3360
gtggatgcag aaggtcacat gactcgtctg cgtcgtctgg gtaaagtgca gatgctcgcg  3420
caggcggcgg aagaacaccc actccacggt ggtacgggta tcgcacacac tcgttgggca  3480
acccacggtg aaccgtctga ggtcaacgca cacccgcatg ttagcgagca catcgtagtc  3540
gttcacaacg gtatcatcga gaaccacgaa ccactccgtg aggaactcaa agccccgtggt  3600
tacaccttcg taagcgaaac cgacacggaa gttatcgccc acctcgttaa ctgggaactc  3660
aaacagggtg gtactctgcg tgaagcagtt ctgcgtgcca ttccacagct gcgtggtgca  3720
tacggtaccg tgatcatgga ctctcgtcat ccggataccc tgctcgccgc acgttctggt  3780
tctccactcg ttatcggtct gggtatgggt gagaacttca tcgcctctga tcagctggcc  3840
ctgctcccag ttacccgtcg cttcatcttc ctggaagagg gtgcatcgc cgaaatcacc  3900
cgtcgttccg ttaacatctt cgacaaaacg ggtgcggaag ttaaacgtca ggacatcgag  3960
tctaacctgc agtatgacgc tggtgacaaa ggcatctacc gtcactacat gcagaaagag  4020
atctacgaac agccgaacgc gatcaaaaac accctgaccg gtcgtatctc tcacggtcag  4080
gttgacctgt ctgagctggg tccaaacgcg gacgaactcc tgtccaaagt cgagcacatc  4140
cagatcctgg cttgtggtac ctcttacaac tccggtatgg tttctcgtta ctggttcgaa  4200
tctctggcag gtatcccatg cgacgttgaa atcgcctccg aattccgtta tcgtaaatct  4260
gcggtacgtc gtaactccct catgatcacc ctgtctcagt ctggtgaaac cgctgatact  4320
ctggcaggtc tgcgtctcag caaagaactg ggttacctgg gttctctggc catctgcaac  4380
gttccgggtt ctagcctggt tcgtgagtct gacctggctc tgatgaccaa cgcgggtacg  4440
gagatcggtg ttgcctctac caaagcgttc actaccagc tcactgtcct gctgatgctg  4500
gttgccaaac tgtctcgtct caaaggcctc gacgctagca tcgaacacga catcgtacac  4560
ggtctgcagg ccctcccatc tcgtatcgag cagatgctgt ctcaggacaa acgtatcgaa  4620
gcactggcag aagacttcag cgacaaacac cacgcgctgt ttctgggtcg tggtgaccag  4680
tacccaattg cgtctggaagg tgccctgaaa ctgaaagaga tctacggtac ccatgcagaa  4740
gcatacgcag cgggtgagct gaaacatggt ccactggccc tgatcgacgc agatatgccg  4800
gttattgtgg ttgctccgaa caacgaactg ctggagaaac tgaaatccaa catcgaggaa  4860
gtacgtgcgc gtggtggtca gctgtacgtg tttgctgacc aggacgcggg tttcgtttcc  4920
agcgacaaca tgcacatcat cgaaatgccg catgttgaag aggtaatcgc gccaatcttc  4980
tacaccgtac cgctgcagct gctggcgtac catgtagccc tgatcaaagg tacggacgtt  5040
```

```
gaccagccgc gtaacctggc gaaatccgtg accgtggaat aacgcggagg cgcgccattt   5100
aaatcaacct cagcggtcat agctgtttcc tgtgactgag caataactag cataaccccct  5160
tggggcctct aaacgggtct tgaggggttt tttgctgaaa ccaatttgcc tggcggcagt   5220
agcgcggtgg tcccacctga ccccatgccg aactcagaag tgaaacgccg tagcgccgat   5280
ggtagtgtgg ggtctcccca tgcgagagta gggaactgcc aggcatcaaa taaaacgaaa   5340
ggctcagtcg aaagactggg cctttcggga tccaggccgg cctgttaacg aattaatctt   5400
ccgcggcggt atcgataagc ttgatatcga attccgaagt tcctattctc tagaaagtat   5460
aggaacttca ggtctgaaga ggagtttacg tccagccaag ctagcttggc tgcaggtcgt   5520
cgaaattcta ccgggtaggg gaggcgcttt tcccaaggca gtctggagca tgcgctttag   5580
cagccccgct gggcacttgg cgctacacaa gtggcctctg gcctcgcaca cattccacat   5640
ccaccggtag cgccaaccg gctccgttct ttggtggccc cttcgcgcca ccttctactc     5700
ctccctagt caggaagttc ccccccgccc cgcagctcgc gtcgtgcagg acgtgacaaa     5760
tggaagtagc acgtctcact agtctcgtgc agatggacag caccgctgag caatggaagc   5820
gggtaggcct ttgggcagc ggccaatagc agctttgctc cttcgctttc tgggctcaga     5880
ggctgggaag gggtgggtcc gggggcgggc tcagggcgg gctcagggc ggggcgggcg       5940
cccgaaggtc ctccggaggc ccggcattct gcacgcttca aaagcgcacg tctgccgcgc   6000
tgttctcctc ttcctcatct ccgggccttt cgacctgcag cctgttgaca attaatcatc   6060
ggcatagtat atcggcatag tataatacga caaggtgagg aactaaacca tgggtcaaag   6120
tagcgatgaa gccaacgctc ccgttgcagg gcagtttgcg cttcccctga gtgccacctt   6180
tggcttaggg gatcgcgtac gcaagaaatc tggtgccgct tggcagggtc aagtcgtcgg   6240
ttggtattgc acaaaactca ctcctgaagg ctatgcggtc gagtccgaat cccacccagg   6300
ctcagtgcaa atttatcctg tggctgcact tgaacgtgtc gcctaatgag gggatcaatt    6360
ctctagagct cgctgatcag aagttcctat tctctagaaa gtataggaac ttcgatggcc   6420
cctcatccct gaagccaata caacaaaaat taggaattaa tcatctggcc aatttcaggt   6480
ggcactttt gggcagaccg gggacttatc agccaacctg t                        6521
```

```
SEQ ID NO: 4           moltype = DNA  length = 2937
FEATURE                Location/Qualifiers
source                 1..2937
                       mol_type = other DNA
                       organism = synthetic construct
misc_feature           1..2937
                       note = construct
SEQUENCE: 4
ggccagatga ttaattccta atttttgttg acactctatc attgatagag ttattttacc   60
actccctatc agtgatagag aaaagtgaaa tgaatagttc gacaaaaatc tagaaataat   120
tttgtttaac tttaagaagg agatatacaa atgggctact atttaaaaaa cacaaacttt   180
tggatgttcg gttattcttt tttcttttac ttttttatca tgggagccta cttcccgttt   240
ttcccgattt ggctacatga catcaaccat atcagcaaca gtgatacggg tattatttt     300
gccgctattt ctctgttctc gctattattc caaccgctgt ttggtctgct ttctgacaaa   360
ctcgggctgc gcaaatacct gctgtggatt attaccggca tgttagtgat gtttgcgccg   420
ttctttattt ttatcttcgg gccactgtta caatacaaca ttttagtagg atcgattgtt    480
ggtggtattt atctaggctt ttgtttaac gccggtgagc cagcagtaga ggcatttatt     540
gagaaagtca gccgtcgcag taatttcgaa tttggtcgcg cgcggatgtt tggctgtgtt   600
ggctgggcgc tgtgtgcctc gattgtcggc atcatgttca ccatcaataa tcagtttgtt   660
ttctggctgg gctctggctg tgcactcatc ctcgccgttt tactcttttt cgccaaaacg   720
gatgcgcct cttctcatca ccatcaccat cacgccacgg ttgccaatgc ggtaggtgcc    780
aaccattcgg catttagcct taagctggca ctggaactgt tcagacagcc aaaactgtgg   840
tttttgtcac tgtatgttat tggcgtttcc tgcacctacg atgtttttga ccaacagttt   900
gctaatttct ttacttcgtt ctttgctacc ggtgaacagg gtacgcgggt atttggctac   960
gtaacgacaa tgggcgaatt acttaacgcc tcgattatgt tctttgcgcc actgatcatt   1020
aatcgcatcg gtgggaaaaa cgccctgctg ctggctggca ctattatgtc tgtacgtatt   1080
attggctcat cgttcgccac ctcagcgctg gaagtggtta ttctgaaaac gctgcatatg   1140
tttgaagtac cgttcctgct ggtgggctgc tttaaatata ttaccagcca gtttgaagtg   1200
cgttttttcag cgacgattta tctggtctgt ttctgtctct ttaagcaact ggcgatgatt   1260
tttatgtctg tactggcggg caatatgtat gaaagcatcg gtttccaggg cgcttatctg   1320
gtgctgggtc tggtggcgct gggcttcacc ttaatttccg tgttcacgct tagcggcccc   1380
ggcccgcttt ccctgctgcg tcgtcaggtg aatgaagtcg cttaagcggc cgcgtcgaca   1440
cgcaaaaagg ccatccgtca ggatggcctt ctgcttaatt tgatgcctgg cagtttatgg   1500
cgggcgtcct gcccgccacc ctccgggccg ttgcttcgca acgttcaaat ccgctcccgg   1560
cggatttgtc ctactcagga gagcgttcac cgacaaacaa cagataaaac gaaaggccca   1620
gtctttcgac tgagcctttc gttttatttg atgcctggca gttccctact ctcgcatggg   1680
gagaccccac actaccatca tgtatgaata tcctccttag ttcctattcc gaagttccta   1740
ttctctagaa agtataggaa cttcgggcg tcctacctgt gacacgcgtg ccgcagtctc   1800
acgcccggag cgtagcgacc gagtgagcta gctatttgtt tatttttcta aatacattca   1860
aatatgtatc cgctcatgag acaataaccc tgataaatgc ttcaataata ttgaaaaagg   1920
aagagtatga gggaagcggt gatcgccgaa gtatcgactc aactatcaga ggtagttggc   1980
gtcatcgagc gccatctcga accgacgttg ctggccgtac atttgtacgg ctccgcagtg   2040
gatggcggcc tgaagccaca cagtgatatt gatttgctgg ttacggtgac cgtaaggctt   2100
gatgaaacaa cgcggcgagc tttgatcaac gaccttttgg aaacttcggc ttcccctgga   2160
gagagcgaga ttctccgcgc tgtagaagtc accattgttg tgcacgacga catcattccg   2220
tggcgttatc cagctaagcg cgaactgcaa tttggagaat ggcagcgcaa tgacattctt   2280
gcaggtatct tcgagccagc cacgatcgac attgatctgg ctatcttgct gacaaaagca   2340
agagaacata gcgttgcctt ggtaggtcca gcggcggagg aactctttga tccggttcct   2400
gaacaggatc tatttgaggc gctaaatgaa accttaacgc tatggaactc gccgcccgac   2460
tgggctggcg atgagcgaaa tgtagtgctt acgttgtccc gcatttggta cagcgcagta   2520
accggcaaaa tcgcgccgaa ggatgtcgct gccgactggg caatggagcg cctgccggcc   2580
cagtatcagc ccgtcatact tgaagctaga caggcttatc ttgacaaga agaagatcgc     2640
ttggcctcgc gcgcagatca gttggaagaa tttgtccact acgtgaaagg cgagatcacc   2700
```

-continued

```
aaggtagtcg gcaaataatg tctaacaatt cgttcaagcc gagggggccgc aagatccggc   2760
cacgatgacc cggtcgtcgg gtaccggcag ggcggggcgt aaggcgcgcc atttaaatga   2820
agttcctatt ccgaagttcc tattctctag aaagtatagg aacttcgaag cagctccagc   2880
ctacacaatc gctcaagacg tgtaatgctg caatctgcat gcaagcttgg cactggc      2937
```

```
SEQ ID NO: 5              moltype = DNA   length = 3856
FEATURE                   Location/Qualifiers
source                    1..3856
                          mol_type = other DNA
                          organism = synthetic construct
misc_feature              1..3856
                          note = Ptet-wbdO-PT5-galE-FRT-cat-FRT
SEQUENCE: 5
acaggttggc tgataagtcc ccggtctgcc cgaaaagtgc cacctgaaat tggccagatg   60
attaattcct aattttttgtt gattctggta ccaaatgagt cgaccggcca gatgattaat   120
tcctaatttt tgttgacact ctatcattga tagagttatt ttaccactcc ctatcagtga   180
tagagaaaag tgaaatgaat agttcgacaa aaatctagaa ataattttgt ttaactttaa   240
gaaggagata tacaaatgct gacggaagtg cgcccggtct ctacgacgaa accgctggtg   300
tctgtgattc tgccggtgaa caaattcaac ccgtatctgg atcgtgcaat tcattcaatc   360
ctgagtcagt cctatccgtc gattgaactg attatcattg caaacaattg caccaatgac   420
tttttcgatg ctctgaaaaa acgtgaatgt gaaaccatta aagtgctgcg cacgaacatc   480
gcgtatctgc cgtactgcct gaataaaggc ctggatctgt gtaacggtga ctttgttgcc   540
cgcatggatt cagatgacat ttcgcacccg gaacgtatcg atcgccaggt cgacttcctg   600
attaacaatc cggacatcga tgtggttggc accaatgcag tctatattga tgaagatgac   660
atcgaactgg aaaaaagcaa cctgccggtg aacaataacg ctattcgtaa aatgctgccg   720
tataaatgct gtctggtgca tccgtctgtt atgtttcgca aaaatgtgt gatcaccagc   780
ggcggttaca tgttcgcgaa ttattctgaa gattacgaac tgtggaaccg tctggccgtt   840
gaaggccgca atttttataa cctgagcgaa tacctgctgt attaccgtct gcacaataac   900
caatcaacgt cgaaaaataa cctgtttatg gtgatggcga acgatgtcgc cattaaagtg   960
aaatatttcc tgctgaccaa gaaaattagc tacctgctgg gtatcattcg cacggtcttt   1020
tctgtgttct attgcaaata catcaaatga tttcgtcgac acacaggaaa catattaaaa   1080
attaaaacct gcaggagttt aaacgcggcc gcgatatcgt tgtaaaacga cggccagtgc   1140
aagaatcata aaaaatttat ttgctttcag gaaaattttt ctgtataata gattcataaa   1200
tttgagagag gagtttttgt gagcggataa caattcccca tcttagtata ttagttaagt   1260
ataaatacac cgcggaggcg tcgaaggaga tacaaccatg agagttctgg ttaccggtgg   1320
tagcggttac attggaagtc atacctgtgt gcaattactg caaaacggtc atgatgtcat   1380
cattcttgat aacctctgta acagtaagcg cagcgtactg cctgttatcg agcgtttagg   1440
cggcaaacat ccaacgtttg ttgaaggcga tattcgtaac gaagcgttga tgaccgagat   1500
cctgcacgat cacgctatcg acaccgtgat ccacttcgcc ggctgaaag ccgtgggcga   1560
atcggtacaa aaaccgctgg aatattacga caacaatgtc aacggcactc tgcgcctgat   1620
tagcgccatg cgcgccgcta acgtcaaaaa ctttattttt agctcctccg ccaccgttta   1680
tggcgatcag cccaaaattc catacgttga aagcttcccg accggcacac cgcaaagccc   1740
ttacgacaaa agcaagctga tggtggaaca gatcctcacc gatctgcaaa agcccagcc   1800
ggactggagc attgccctgc tgcgctactt caacccggtt ggcgcgcatc cgtcgggcga   1860
tatgggcgaa gatccgcaag gcattccgaa taacctgatg ccatacatcg cccaggttgc   1920
tgtaggccgt cgcgactcgc tggcgatttt tggtaacgat tatccgaccg aagatggtac   1980
tggcgtacgc gattacatcc acgtaatgga tctggccgac ggtcacgtcg ttggcgatgga   2040
aaaactggcg aacaagccag gcgtacacat ctacaacctc ggcgctggcg taggcaacag   2100
cgtgctggac gtggttaatg ccttcagcaa agcctgcggc aaaccggtta attatcattt   2160
tgcaccgcgt cgcgagggcg accttccggc ctactgggcg gacgccagca aagccgaccg   2220
tgaactgaac tggcgcgtaa cgcgcacact cgatgaaatg gcgcaggaca cctggcactg   2280
gcagtcacgc catccacagg gatatcccga ttaacgccat ttaaatcaac ctcagcggtc   2340
atagctgttt cctgtgactg agcaataact agcataaccc cttggggcct ctaaacgggt   2400
cttgagggg ttttttgctga aaccaatttg cctggcggca gtagcgcggt ggtcccacct   2460
gaccccatgc cgaactcaga agtgaaacgc cgtagcgccg atggtagtgt ggggtctccc   2520
catgcgagag tagggaactg ccaggcatca aataaaacga aaggctcagt cgaaagactg   2580
ggcctttcgg gatccaggcc ggctgttaa cgaattaatc ttccgcggcg gtatcgataa   2640
gcttgatatc gaggctgaca tgggaattag ccatggtcca tatgaatatc ctccttagtt   2700
cctattccga agttcctatt ctctagaaag tataggaact gcgcgccgcc tacctgtgac   2760
ggaagatcac ttcgcagaat aaataaatcc tggtgtccct gttgataccg ggaagccctg   2820
ggccaacttt tggcgaaaat gagacgttga tcggcacgta agaggttcca actttcacca   2880
taatgaaata agatcactac cgggcgtatt ttttgagttg tcgagatttt caggagctaa   2940
ggaagctaaa atggagaaaa aaatcactgg atataccacc gttgatatat cccaatggca   3000
tcgtaaagaa cattttgagg catttcagtc agttgctcaa tatacctata accagaccgt   3060
tcagctggat attacggcct ttttaaagac cgtaaagaaa aataagcaca gttttatcc   3120
ggcctttatt cacattcttg cccgcctgat gaatgctcat ccggaattac gtatggcaat   3180
gaaagacggt gagctggtga tatgggtag tgttcaccct tgttacaccg ttttccatga   3240
gcaaactgaa acgttttcat cgctctggag tgaataccac gacgatttcc ggcagtttct   3300
acacatatat tcgcaagatg tggcgtgtta cggtgaaaac ctggcctatt tccctaaagg   3360
gtttattgag aatatgtttt tcgtctcagc caatccctgg gtgagtttca ccagttttga   3420
tttaaacgtg gccaatatgg acaacttctt cgccccgtt ttcaccatgg gcaaatatta   3480
tacgcaaggc gacaaggtgc tgatgccgct ggcgattcag gttcatcatg ccgtttgtga   3540
tggcttccat gtcggcagat gcttaatgaa tacaacagta ctgcgatgag tggcagggcg   3600
gggcgtaagg cggcgcattt aaatgaagtt cctattccga gttcctatt ctctagaaag   3660
tataggaact tcgaagcagc tccagcctac acaatcgctc aagacgtgta atgctgcaat   3720
ctgcatgcaa gcttggcact ggcgatgcg cctcatccct gaagccaata gcagctcca   3780
gcctacacaa tcgctcaaga cgtgtaatgc tgcaatctgc atgcaagcta gaccgggggac   3840
ttatcagcca acctgt                                                   3856
```

```
SEQ ID NO: 6            moltype = DNA   length = 4259
FEATURE                Location/Qualifiers
misc_feature           1..4259
                       note = construct galMKTE
source                 1..4259
                       mol_type = other DNA
                       organism = synthetic construct
SEQUENCE: 6
ttactcagca ataaactgat attccgtcag gctggaatac tcttcgccag gacgcaggaa    60
gcagtccggt tgcggccatt cagggtggtt cgggctgtcc ggtagaaact cgctttccag   120
agccagccct tgccagtcgg cgtaaggttc ggttccccgc gacggtgtgc cgccgaggaa   180
gttgccggag tagaattgca gagccggagc ggtggtgtag accttcagct gcaatttttc   240
atctgctgac cagacatgcg ccgccacttt cttgccatcg cctttggcct gtaacaagaa   300
tgcgtgatcg taacctttca ctttgcgctg atcgtcgtcg gcaagaaact cactggcgat   360
gatttttggcg ctgcgaaat caaaagacgt tccggcgaca gatttcaggc cgtcgtgcgg   420
aatgccgcct tcatcaaccg gcagatattc gtccgccaga atctgcaact tgtgattgcg   480
cacgtcagac tgctcgccgt caagattgaa atagacgtga ttagtcatat tcaccgggca   540
aggtttatca actgtggcgc gataagtaat ggagatacgg ttatcgtcgg tcagacgata   600
ttgcaccgtc gcgccgagat tacccgggaa gccctgatca ccatcatctg aactcagggc   660
aaacagcacc tgacgatcgt tctggttcac aatctgccag cgacgtttgt cgaacccttc   720
cggcccgccg tgcagctggt taacgccctg acttggcgaa agcgtcacgg tttcaccgtc   780
aaaggtataa cggctattgg cgatacggtt ggcataacga ccaatagagg ccccccagaaa  840
cgcggcctga tcctgatagc attccggggct ggcacagccg agcagcgcct cgcggacgct   900
gccatcggaa agcggaatac gggcggaaag taaagtcgca ccccagtcca tcagcgtgac   960
taccatccct gcgttgttac gcaaagttaa cagtcggtac ggctgaccat cgggtgccag  1020
tgcggagtt tcgttcagca ctgtcctgct ccttgtgatg gtttacaaac gtaaaaagtc  1080
tctttaatac ctgttttttgc ttcatattgt tcagcgacag cttgctgtac ggcaggcacc  1140
agctcttccg ggatcagcgc gacgatacag ccgccaaatc cgccgccggt catgcgtacg  1200
ccaccttttgt cgccaatcac agctttgacg atttctacca gagtgtcaat ttgcggcacg  1260
gtgatttcga aatcatcgcg catagaggca tgagactccg ccatcaactc gcccatacgt  1320
ttcaggtcgc cttgctccag cgcgctggca gcttcaacgg tgcgggcgtt ttcagtcagt  1380
atatgacgca cgcgtttttgc cacgatcggg tccagttcat gcgcaacagc gttgaactct  1440
tcaatggtga catcacgcag ggctggctgc tggaagaaac gcgcaccggt ttcgcactgt  1500
tcacgacggg tgttgtattc gctgccaacc agggtacgtt tgaagttact gttgatgatg  1560
acgacagcca caccttttggg catggaaact gctttggtcc ccagtgagcg gcaatcgatc  1620
agcaaggcat gatctttctt gccgagcgcg gaaattagct gatccatgat cccgcagtta  1680
cagcctacaa actggttttttc tgcttcctga ccgttaagcg cgatttgtgc gccgtccagc  1740
ggcagatgat aaagctgctg caatacggtt ccgaccgcga cttccagtga agcggaagaa  1800
cttaaccggg caccctgcgg cacattgccg ctgatcacca tgtccacgcc gcgaagctg  1860
ttgttacgca gttgcagatg tttcaccacg ccacgaacgt agttagccca ttgatagttt  1920
tcatgtgcga caatgggcgc atcgagggaa aactcgtcga gctgattttt ataatcggct  1980
gccatcacgc gaactttacg gtcatcgcgt ggtgcacaac tgatcacggt ttgataatca  2040
atcgcgcagg gcagaacgaa accgtcgttg tagtcggtgt gttcaccaat caaattcacg  2100
cggccaggcg cctgaatggt gtgagtggca gggtagccaa atgcgttggc aaacagagat  2160
tgtgtttttt ctttcagact catttcttac actccggatt cgcgaaaatg gatatcgctg  2220
actgcgcgca aacgctctgc tgcctgttct gcggtcaggt ctcgctgggt ctctgccagc  2280
atttcataac caaccataaa tttacgtacg gtggcggagc gacgcagagg cggataaaag  2340
tgcgcgtgca gctgccagtg ttgattctct tcgccattaa atggcgcgcc gtgccagccc  2400
atagagtagg ggaaggagca ctggaagagg ttgtcataac gactggtcag ctttttcaac  2460
gccagcgcca gatcgctgcg ctgggcgtcg gtcaaatcgg tgatccgtaa aacgtgggct  2520
ttgggcagca gtagcgtttc gaacggccag gcagcccagt aaggcacgac ggctaaccag  2580
tgttcggttt cgacaacggt acggctaccg tctgccagct cgcgctgaac ataatccacc  2640
agcattggtg atttctgttc ggcaaaatat tcttttttgca ggcggtcttc gcgctcagct  2700
tcgttaggca ggaagctatt tgcccaaatc tgaccgtgcg gatgcgggtt agagcagccc  2760
atcgccgcgc ctttgttttc aaaaacctgc acccatgggt acgtttttccc cagttctgcg  2820
gtttgctcct gccaggtttt gacgatttcc gtcaatgctg caacgctgag ctctggcagc  2880
gttttactgt gatccggtga aaagcagatc acccggctgg tgccgcgcgc gctctggcaa  2940
cgcatcagcg gatcgtgact ttctggcgca tctggcgtgt cagacatcaa agccgcaaag  3000
tcattagtga aaacgtaagt cccggtgtaa tcggggtttt tatcgcctgt cacccgcaca  3060
ttacctgcgc agaggaagca atctggatcg tgcgcaggta acacctgttt ggctggcgtt  3120
tcctgcgccc cctgccaggg gcgcttagcg cggtgcggtg aaaccagaat ccattgcccg  3180
gtgagcgggt gtagcggcg atgtggatga tcaacgggat taaattcgt catggtcgtt  3240
ccttaatcgg gatatccctg tggatggcgt gactgccagt gccaggtgtc ctgcgccatt  3300
tcatcgagtg tgcgcgttac gcgccagttc agttcacggt ggcttttgac ggcttttccc  3360
cagtaggccg gaaggtcgcc ctcgcgacgc ggtgcaaaat gataattaac cggtttgccg  3420
caggctttgc tgaaggcatt aaccacgtcc agcacgctgt tgcctacgcc agcgccgagg  3480
ttgtagatgt gtacgcctgg cttgttcgcc agttttttcca tcgccacgac gtgaccgtcc  3540
gccagatcca ttacgtggat gtaatcgcgt acgccagtac catcttcggt cggataatgc  3600
ttaccaaaaa tcgccagcga gtcgcgacgg cctacagcaa cctgggcgat gtatggcatc  3660
aggttattcg gaatgccttg cggatcttcg cccatatcgc ccgacggatg cgcgccaacc  3720
gggttgaagt agcgcagcag ggcaatgctc agtccggct gggctttttg cagatcggtg  3780
aggatctgtt ccaccatcag cttgcttttg ccgtaagggc tttgcggtgt gccggtcggg  3840
aagctttcaa cgtatggaat tttgggctga tcgccataaa cggtggcgga ggagctaaaa  3900
ataaagtttt tgacgttagc ggcgcgcatg cgctaatca ggcgcagagt gccgttgacg  3960
ttgttgtcgt aatattccag cggttttttgt accgattcgc ccacggcttt cagcccggcg  4020
aagtggatca cggtgtcgat agcgtgatcg tgcaggatct cggtcatcaa cgcttcgtta  4080
cgaatatcgc cttcaacaaa cgttggatgt ttgccgccta aacgtcgat aacaggcagt  4140
acgctgcgct tactgttaca gaggttatca agaatgatga catcatgacc gttttgcagt  4200
aattgcacac aggtatgact tccaatgtaa ccgctaccac cggtaaccag aactctcat  4259
```

-continued

```
SEQ ID NO: 7            moltype = DNA  length = 6431
FEATURE                 Location/Qualifiers
misc_feature            1..6431
                        note = construct pET-lgtA
source                  1..6431
                        mol_type = other DNA
                        organism = synthetic construct
SEQUENCE: 7
ggggaattgt gagcggataa caattcccct ctagaaataa ttttgtttaa ctttaagaag   60
gagatatacc atgggcagca gccatcacca tcatcaccac agccaggatc cgaattcgag  120
ctcggcgcgc ctgcaggtcg acaagcttgc ggccgcataa tgcttaagtc gaacagaaag  180
taatcgtatt gtacacggcc gcataatcga aattaatacg actcactata ggggaattgt  240
gagcggataa caattcccca tcttagtata ttagttaagt ataagaagga gatatacata  300
tgccgtccga agcattccgt cgtcaccgtg cttatcgcga aaacaaactg cagccactgg  360
tctctgtcct gatctgcgca tacaacgttg agaaatactt cgcacagtct ctggcagctg  420
tagttaacca gacctggcgt aacctggata tcctgatcgt agatgacggc tctacggatg  480
gtacgctggc gatcgcacag cgtttccagg aacaggacgg tcgtatccgc attctcgctc  540
agccgcgtaa ctctggtctg atcccgtctc tgaacatcgg tctggacgaa ctggccaaat  600
ctggtcggtgg tggcgaatac atcgcccgta ctgacgccga cgacattgcg ccccggatt  660
ggatcgaaaa aatcgtaggt gaaatggaga aagaccgctc tatcatcgcg atgggtgctt  720
ggctggaagt tctgtccgaa gagaaagacg gtaaccgtct ggcccgtcac catgaacacg  780
gcaaaatctg gaaaaaaccg acccgtcacg aagatatcgc ggacttcttc ccgttcggta  840
acccgatcca taacaacacc atgatcatgc gtcgtagcgt aatcgacggt ggtctgcgtt  900
acaacaccga acgtgattgg gcagaagact accagttttg gtatgacgtg tctaaactgg  960
gtcgtctggc ttactaccca gaagcgctgg ttaaataccg tctgcacgcc aaccaggtta 1020
gctccaaata ctccatccgt cagcacgaaa tcgcacaggg tatccagaaa acggctcgta 1080
acgacttcct gcagtccatg ggtttcaaaa cccgtttcga ctctctggag taccgtcaga 1140
tcaaagcggt tgcgtatgag ctgctggaga acacctgcc ggaagaggac tttgaacgtg 1200
cgcgtcgttt cctgtaccag tgcttcaaac gtaccgacgc tctgccggcg ggtgcatggc 1260
tcgactttgc agcggatggt cgtatgcgtc gtctgtttac cctgcgtcag tacttcggta 1320
tcctgcatcg tctcctgaaa aaccgctaat gagacgtcgg taccctcgag tctggtaaag 1380
aaaccgctgc tgcgaaattt gaacgccagc acatggactc gtctactagc gcagcttaat 1440
taacctaggc tgctgccacc gctgagcaat aactagcata acccctttggg gcctctaaac 1500
gggtcttgag gggttttttg ctgaaaggag gaactatatc cggattggcg aatgggacgc 1560
gccctgtagc ggcgcattaa gcgcggcggg tgtggtggtt acgcgcagcg tgaccgctac 1620
acttgccagc gccctagcgc ccgctccttt cgctttcttc ccttcctttc tcgccacgtt 1680
cgccggcttt ccccgtcaag ctctaaatcg ggggctccct ttagggttcc gatttagtgc 1740
tttacggcac ctcgacccca aaaaacttga ttagggtgat ggttcacgta gtgggccatc 1800
gccctgatag acggtttttc gccctttgac gttggagtcc acgttcttta atagtggact 1860
cttgttccaa actggaacaa cactcaaccc tatctcggtc tattcttttg atttataagg 1920
gattttgccg atttcggcct attggttaaa aaatgagctg atttaacaaa aatttaacgc 1980
gaattttaac aaaatattaa cgtttacaat ttctggcggc acgatggcat gagattatca 2040
aaaaggatct tcacctagat cctttttaaat taaaaatgaa gttttaaatc aatctaaagt 2100
atatatgagt aaacttggtc tgacagttac caatgcttaa tcagtgaggc acctatctca 2160
gcgatctgtc tatttcgttc atccatagtt gcctgactcc ccgtcgtgta gataactacg 2220
atacggggagg gcttaccatc tggccccagt gctgcaatga taccgcgaga cccacgctca 2280
ccggctccag atttatcagc aataaaccag ccagccggaa gggccgagcg cagaagtggt 2340
cctgcaactt tatccgcctc catccagtct attaattgtt gccgggaagc tagagtaagt 2400
agttcgccag ttaatagttt cgcaacgtt gttgccattg ctacaggcat cgtggtgtca 2460
cgctcgtcgt ttggtatggc ttcattcagc tccggttccc aacgatcaag gcgagttaca 2520
tgatcccccca tgttgtgcaa aaaagcggtt agctccttcg gtcctccgat cgttgtcaga 2580
agtaagttgg ccgcagtgtt atcactcatg gttatggcag cactgcataa ttctcttact 2640
gtcatgccat ccgtaagatg cttttctgtg actggtgagt actcaaccaa gtcattctga 2700
gaatagtgta tgcggcgacc gagttgctct tgcccggcgt caatacggga taataccgta 2760
ccacatagca gaactttaaa agtgctcatc attggaaaac gttcttcggg gcgaaaactc 2820
tcaaggatct taccgctgtt gagatccagt tcgatgtaac ccactcgtgc acccaactga 2880
tcttcagcat cttttacttt caccagcgtt tctgggtgag caaaaacagg aaggcaaaat 2940
gccgcaaaaa agggaataag ggcgacacgg aaatgttgaa tactcatact cttcctttt  3000
caatcatgat tgaagcattt atcagggtta ttgtctcatg agcggataca tatttgaatg 3060
tatttagaaa aataaacaaa taggtcatga ccaaaatccc ttaacgtgag ttttcgttcc 3120
actgagcgtc agacccgta gaaaagatca aaggatcttc ttgagatcct tttttttctgc 3180
gcgtaatctg ctgcttgcaa acaaaaaaac caccgctacc agcggtggtt tgtttgccgg 3240
atcaagagct accaactctt tttccgaagg taactggctt cagcagagcg cagataccaa 3300
atactgtcct tctagtgtag ccgtagttag gccaccactt caagaactct gtagcaccgc 3360
ctacatacct cgctctgcta atcctgttac cagtggctgc tgccagtggc gataagtcgt 3420
gtcttaccgg gttggactca agacgatagt taccggataa ggcgcagcgg tcgggctgaa 3480
cggggggttc gtgcacacag cccagcttgg agcgaacgac ctacaccgaa ctgagatacc 3540
tacagcgtga gctatgagaa agcgccacgc ttcccgaagg gagaaaggcg gacaggtatc 3600
cggtaagcgg cagggtcgga acaggagagc gcacgaggga gcttccaggg gaaacgcct 3660
ggtatcttta tagtcctgtc gggtttcgcc acctctgact tgagcgtcga ttttgtgat 3720
gctcgtcagg gggcggagc ctatggaaaa acgccagcaa cgcggccttt ttacggttcc 3780
tggccttttg ctggcctttt gctcacatgt tctttcctgc gttatcccct gattctgtgg 3840
ataaccgtat taccgccttt gagtgagctg ataccgctcg ccgcagccga acgaccgagc 3900
gcagcgagtc agtgagcgag gaagcggaag agcgcctgat gcggtatttt ctccttacgc 3960
atctgtgcgg tatttcacac cgcatatatg gtgcactctc agtacaatct gctctgatgc 4020
cgcatagtta agccagtata cactccgcta tcgctacgtg actgggtcat ggctgcgccc 4080
cgacacccgc caacacccgc tgacgcgccc tgacgggctt gtctgctccc ggcatccgct 4140
tacagacaag ctgtgaccgt ctccgggagc tgcatgtgtc agaggttttc accgtcatca 4200
```

```
ccgaaacgcg cgaggcagct gcggtaaagc tcatcagcgt ggtcgtgaag cgattcacag   4260
atgtctgcct gttcatccgc gtccagctcg ttgagtttct ccagaagcgt taatgtctgg   4320
cttctgataa agcgggccat gttaagggcg gttttttcct gtttggtcac tgatgcctcc   4380
gtgtaagggg gatttctgtt catggggta atgataccga tgaaacgaga gaggatgctc    4440
acgatacggg ttactgatga tgaacatgcc cggttactgg aacgttgtga gggtaaacaa   4500
ctggcggtat ggatgcggcg ggaccagaga aaaatcactc agggtcaatg ccagcgcttc   4560
gttaatacag atgtaggtgt tccacagggt agccagcagc atcctgcgat gcagatccgg   4620
aacataatgg tgcagggcgc tgacttccgc gtttccagac tttacgaaac acggaaaccg   4680
aagaccattc atgttgttgc tcaggtcgca gacgttttgc agcagcagtc gcttcacgtt   4740
cgctcgcgta tcggtgattc attctgctaa ccagtaaggc aaccccgcca gcctagccgg   4800
gtcctcaacg acaggagcac gatcatgcta gtcatgcccc gcgcccaccg gaaggagctg   4860
actgggttga aggctctcaa gggcatcggt cgagatcccg gtgcctaatg agtgagctaa   4920
cttacattaa ttgcgttgcg ctcactgccc gctttccagt cgggaaacct gtcgtgccag   4980
ctgcattaat gaatcggcca acgcgcgggg agaggcggtt tgcgtattgg gcgccaggt    5040
ggtttttctt ttcaccagtg agacgggcaa cagctgattg cccttcaccg cctggccctg   5100
agagagttgc agcaagcggt ccacgctggt ttgcccagc aggcgaaaat cctgtttgat    5160
ggtggttaac ggcgggatat aacatgagct gtcttcggta tcgtcgtatc ccactaccga   5220
gatgtccgca ccaacgcgca gcccggactc ggtaatgagc cgcattgcgc ccagcgccat   5280
ctgatcgttg gcaaccagca tcgcagtggg aacgatgccc tcattcagca tttgcatggt   5340
ttgttgaaaa ccggacatgg cactccagtc gccttcccgt tccgctatcg gctgaatttg   5400
attgcgagtg agatatttat gccagccagc cagacgcaga cgcgccgaga cagaacttaa   5460
tgggcccgct aacagcgcga tttgctggtg acccaatgcg accagatgct ccacgcccag   5520
tcgcgtaccg tcttcatggg agaaaataat actgttgatg ggtgtctggt cagagacatc   5580
aagaaataac gccggaacat tagtgcaggc agcttccaca gcaatggcat cctggtcatc   5640
cagcggatag ttaatgatca gcccactgac gcgttgcgcg agaagattgt gcaccgccgc   5700
tttacaggct tcgacgccgc ttcgttctac catcgacacc accacgctgg cacccagttg   5760
atcggcgcga gatttaatcg ccgcgacaat ttgcgacggc gcgtgcaggg ccagactgga   5820
ggtggcaacg ccaatcagca acgactgttt gcccgccagt tgttgtgcca cgcggttggg   5880
aatgtaattc agctccgcca tcgccgcttc cactttttcc cgcgttttcg cagaaacgtg   5940
gctggcctgg ttcaccacgc gggaaacggt ctgataagag acaccggcat actctgcgac   6000
atcgtataac gttactggtt tcacattcac caccctgaat tgactctctt ccgggcgcta   6060
tcatgccata ccgcgaaagg ttttgcgcca ttcgatggtg tccgggatct cgacgctctc   6120
ccttatgcga ctcctgcatt aggaagcagc ccagtagtag gttgaggccg ttgagcaccg   6180
ccgccgcaag gaatggtgca tgcaaggaga tggcgcccaa cagtcccccg gccacggggc   6240
ctgccaccat acccacgccg aaacaagcgc tcatgagccc gaagtggcga gcccgatctt   6300
ccccatcggt gatgtcggcg atataggcgc cagcaaccgc acctgtggcg ccggtgatgc   6360
cggccacgat gcgtccggcg tagaggatcg agatcgatct cgatcccgcg aaattaatac   6420
gactcactat a                                                       6431
```

```
SEQ ID NO: 8           moltype = DNA  length = 5739
FEATURE                Location/Qualifiers
misc_feature           1..5739
                       note = construct pCDF-galT-galE
source                 1..5739
                       mol_type = other DNA
                       organism = synthetic construct
SEQUENCE: 8
ggggaattgt gagcggataa caattcccct gtagaaataa ttttgtttaa ctttaataag   60
gagatatacc atgacgcaat ttaatcccgt tgatcatcca catcgccgct acaacccgct   120
caccgggcaa tggattctgg tttcaccgca ccgcgctaag cgccctggc aggggggcgca  180
ggaaacgcca gccaaacagg tgttacctgc gcacgatcca gattgcttcc tctgcgcagg   240
taatgtgcgg gtgacaggcg ataaaaaccc cgattacacc gggacttacg ttttcactaa   300
tgactttgcg gctttgatgt ctgacacgcc agatgcgcca gaaagtcacg atccgctgat   360
gcgttgccag agcgcgcgcg gcaccagccg ggtgatctgc ttttcaccgg atcacagtaa   420
aacgctgcca gagctcaacg ttgcagcatt gacggaaatc gtcaaaacct ggcaggagca   480
aaccgcagaa ctggggaaaa cgtacccatg ggtgcaggtt tttgaaaaca aaggcgcggc   540
gatgggctgc tctaacccgc atccgcacgt tcagatttgg gcaaatagct cctgcctaa    600
cgaagctgag cgcgaagacc gcctgcaaaa agaatatttt gccgaacaga aatcaccaat   660
gctggtggat tatgttcagc gcgagctggc agacggtagc cgtaccgttg tcgaaaccga   720
acactggtta gccgtcgtgc cttactgggc tgcctggccg ttcgaaacgc tactgctgcc   780
caaagcccac gttttacgga tcaccggattc gaccgacgcc cagcgcagcg atctggcgct   840
ggcgttgaaa aagctgacca gtcgttatga caacctcttc cagtgctcct tccctactc    900
tatgggctgg cacggcgcgc catttaatgg cgaagagaat caacactggc agctgcacgc   960
gcacttttat ccgcctctgc tgcgctccgc caccgtacgt aaatttatgg ttggttatga   1020
aatgctggca gagacccagc gagacctgac cgcagaacag gcagcagagc gtttgcgcgc   1080
agtcagcgat atccatttc gcgaatccgg agtgtaaaag cttgcggccg cataatgctt   1140
aagtcgaaca gaaagtaatc gtattgtaca cggccgcata atcgaaatta atacgactca   1200
ctataggg a attgtgagcg gataacaatt cccatcttag tatattagt taagtataag    1260
aaggagatat acagatcaca tgagagtt ctggttaccg gtggtagcgg ttacattgga     1320
agtcatacct gtgtgcaatt actgcaaaac ggtcatgatg tcatcattct tgataacctc   1380
tgtaacagta agcgcagcgt actgcctgtt atcgagcgtt taggcggcaa acatccaacg   1440
tttgttgaag gcgatattcg taacgaagcg ttgatgaccg atcctgca cgatcacgct     1500
atcgacaccg tgatccactt cgccgggctg aaagccgtgg gcgaatcggt acaaaaaccg   1560
ctggaatatt acgacaacaa tgtcaacggc actctgcgc tgatagccg catgcgcgcc     1620
gctaacgtca aaaactttat ttttagctcc tccgccaccg tttatggcga tcagcccaaa   1680
attccatacg ttgaaagctt cccgaccggc acaccgcaaa gccttacgg caaaagcaag    1740
ctgatggtgg aacagatcct caccgatctg caaaaagccc agccggactg gagcattgcc   1800
ctgctgcgct acttcaaccc ggttggcgcg catccgtcgg gcgatatggg cgaagatccg   1860
caaggcattc cgaataacct gatgccatac atcgcccagg ttgctgtagg ccgtcgcgac   1920
```

-continued

```
tcgctggcga tttttggtaa cgattatccg accgaagatg gtactggcgt acgcgattac  1980
atccacgtaa tggatctggc ggacggtcac gtcgtggcga tggaaaaact ggcgaacaag  2040
ccaggcgtac acatctacaa cctcggcgct ggcgtaggca acagcgtgct ggacgtggtt  2100
aatgccttca gcaaagcctg cggcaaaccg gttaattatc attttgcacc gcgtcgcgag  2160
ggcgaccttc cggcctactg ggcggacgcc agcaaagccg accgtgaact gaactggcgc  2220
gtaacgcgca cactcgatga aatggcgcag gacacctggc actggcagtc acgccatcca  2280
cagggatatc ccgattaatg actcgagtga tctcgagtct ggtaaagaaa ccgctgctgc  2340
gaaatttgaa cgccagcaca tggactcgtc tactagcgca gcttaattaa cctaggctgc  2400
tgccaccgct gagcaataac tagcataacc ccttggggc tctaaacggg tcttgagggg  2460
ttttttgctg aaacctcagg catttgagaa gcacacggtc acactgcttc cggtagtcaa  2520
taaaccggta aaccagcaat agacataagc ggctatttaa cgaccctgcc ctgaaccgac  2580
gaccgggtca tcgtggccgg atcttgcggc ccctcggctt gaacgaattg ttagacatta  2640
tttgccgact accttggtga tctcgccttt cacgtagtgg acaaattctt ccaactgatc  2700
tgcgcgcgag gccaagcgat cttcttcttg tccaagataa gcctgtctag cttcaagtat  2760
gacgggctga tactgggccg gcaggcgctc cattgcccag tcggcagcga catccttcgg  2820
cgcgattttg ccggttactg cgctgtacca aatgcgggac aacgtaagca ctacatttcg  2880
ctcatcgcca gcccagtcgg gcggcgagtt ccatagcgtt aaggtttcat ttagcgcctc  2940
aaatagatcc tgttcaggaa ccggatcaaa gagttcctcc gccgctggac ctaccaaggc  3000
aacgctatgt tctcttgctt ttgtcagcaa gatagccaga tcaatgtcga tcgtggctgg  3060
ctcgaagata cctgcaagaa tgtcattgcg ctgccattct ccaaattgca gttcgcgctt  3120
agctggataa cgccacggaa tgatgtcgtc gtgcacaaca atggtgactt ctacagcgcg  3180
gagaatctcg ctctctccag gggaagccga agtttccgaa aggtcgttga tcaaagctcg  3240
ccgcgttgtt tcatcaagcc ttacggtcac cgtaaccagc aaatcaatat cactgtgtgg  3300
cttcaggccg ccatccactg cggagccgta caaatgtacg gccagcaacg tcggttcgag  3360
atggcgctcg atgacgccaa ctacctctga tagttgagtc gatacttcgg cgatcaccgc  3420
ttccctcata ctcttccttt ttcaatatta ttgaagcatt tatcagggtt attgtctcat  3480
gagcggatac atatttgaat gtatttagaa aaataaacaa atagctagct cactcggtcg  3540
ctacgctccg ggcgtgagac tgcggcgggc gctgcggaca catacaaagt tacccacaga  3600
ttccgtggat aagcagggga ctaacatgtg aggcaaaaca gcagggccgc gccggtggcg  3660
tttttccata ggctccgccc tcctgccaga gttcacataa acagacgctt ttccggtgca  3720
tctgtgggag ccgtgaggct caaccatgaa tctgacagta cgggcgaaac ccgacaggac  3780
ttaaagatcc ccaccgtttc cggcgggtcg ctccctcttg cgctctcctg ttccgaccct  3840
gccgtttacc ggatacctgt tccgcctttc tcccttacgg gaagtgtggc gctttctcat  3900
agctcacaca ctggtatctc ggctcggtgt aggtcgttcg ctccaagctg ggctgtaagc  3960
aagaactccc cgttcagccc gactgctgcg ccttatccgg taactgttca cttgagtcca  4020
acccggaaaa gcacggtaaa acgccactgg cagcagccat tggtaactgg gagttcgcag  4080
aggatttgtt tagctaaaca cgcggttgct cttgaagtgt gcgccaaagt ccggctacac  4140
tggaaggaca gatttggttg ctgtgctctg cgaaagccag ttaccacggt taagcagttc  4200
cccaactgac ttaaccttcg atcaaaccac ctccccaggt ggttttttcg tttacaggac  4260
aaaagattac gcgcagaaaa aaaggatctc aagaagatcc tttgatcttt tctactgaac  4320
cgctctagat ttcagtgcaa tttatctctt caaatgtagc acctgaagtc agccccatac  4380
gatataagtt gtaattctca tgttagtcat gccccgcgcc caccggaagg agctgactgg  4440
gttgaaggct ctcaagggct cggtcgaga tcccggtgcc taatgagtga gctaacttac  4500
attaattgcg ttgcgctcac tgcccgcttt ccagtcggga aacctgtcgt gccagctgca  4560
ttaatgaatc ggccaacgcg cggggagagg cggtttgcgt attgggcgcc agggtggttt  4620
ttcttttcac cagtgagacg ggcaacagct gattgccctt caccgcctgg ccctgagaga  4680
gttgcagcaa gcggtccacg ctggtttgcc ccagcaggcg aaaatcctgt ttgatggtgg  4740
ttaacggcgg gatataacat gagctgtctt cggtatcgtc gtatcccact accgagatgt  4800
ccgcaccaac gcgcagcccg gactcggtaa tggcgcgcat tgcgcccagc gccatctgat  4860
cgttggcaac cagcatcgca gtgggaacga tgccctcatt cagcatttgc atggtttgtt  4920
gaaaaccgga catggcactc cagtcgcctt cccgttccgc tatcggctga atttgattgc  4980
gagtgagata tttatgccag ccagccagac gcagacgcgc cgagacagaa cttaatgggc  5040
ccgctaacag cgcgatttgc tggtgaccca atgcgaccag atgctccacg cccagtcgcg  5100
taccgtcttc atgggagaaa ataatactgt tgatgggtgt ctggtcagag acatcaagaa  5160
ataacgccgg aacattagtg caggcagctt ccacagcaat ggcatcctgg tcatccagcg  5220
gatagttaat gatcagccca ctgacgcgtt gcgcgagaag attgtgcacc gccgctttac  5280
aggcttcgac gccgcttcgt tctaccatcg acaccaccac gctggcaccc agttgatcgg  5340
cgcgagattt aatcgccgcg acaatttgcg acggcgcgtg cagggccaga ctggaggtgg  5400
caacgccaat cagcaacgac tgtttgcccg ccagttgttg tgccacgcgg ttgggaatgt  5460
aattcagctc cgccatcgcc gcttccactt tttcccgcgt tttcgcagaa acgtggctgg  5520
cctggttcac cacgcgggaa acggtctgat aagagacacc ggcatactct gcgacatcgt  5580
ataacgttac tggtttcaca ttcaccaccc tgaattgact ctcttccggg cgctatcatg  5640
ccataccgcg aaaggttttg cgccattcga tggtgtccgg gatctcgacg ctctccctta  5700
tgcgactcct gcattaggaa attaatacga ctcactata                          5739
```

SEQ ID NO: 9          moltype = DNA  length = 8232
FEATURE               Location/Qualifiers
misc_feature         1..8232
                      note = construct pCOLA-glmUM-glmS
source               1..8232
                      mol_type = other DNA
                      organism = synthetic construct SEQUENCE: 9
```
cagcccactg acgcgttgcg cgagaagatt gtgcaccgcc gctttacagg cttcgacgcc  60
gcttcgttct accatcgaca ccaccacgct ggcacccagt tgatcggcgc gagatttaat  120
cgccgcgaca atttgcgacg gcgcgtgcag ggcagactg gaggtggcaa cgccaatcag  180
caacgactgt ttgcccgcca gttgttgtgc cacgcggttg ggaatgtaat tcagctccgc  240
catcgccgct tccactttt cccgcgtttt cgcagaaacg tggctggcct ggttcaccac  300
gcgggaaacg gtctgataag agacaccggc atactctgcg acatcgtata cgttactggg  360
```

```
tttcacattc accaccctga attgactctc ttccgggcgc tatcatgcca taccgcgaaa    420
ggttttgcgc cattcgatgg tgtccgggat ctcgacgctc tcccttatgc gactcctgca    480
ttaggaaatt aatacgactc actatagggg aattgtgagc ggataacaat tcccctgtag    540
aaataatttt gtttaacttt aataaggaga tataccatgc tgaacaacgc gatgtctgtt    600
gttatcctgg cggcgggtaa aggtacccgt atgtactctg acctgccgaa agttctgcac    660
accctggcgg gtaaagcgat ggttcagcac gttatcgacg cggcgaacga actgggtgcg    720
gcgcacgttc acctggttta cggtcacggt ggtgacctgc tgaaacaggc gctgaaagac    780
gacaacctga actgggttct gcaggcggaa cagctgggta ccggtcacgc gatgcagcag    840
gcggcgccgt tcttcgcgga cgacgaagac atcctgatgc tgtacggtga cgttccgctg    900
atctctgttg aaaccctgca gcgtctgcgt gacgcgaaac cgcagggtgg tatcggtctg    960
ctgaccgtta aactggacga cccgaccggt tacggtcgta tcacccgtga aaacggtaaa   1020
gtaaccggta tcgttgaaca caaagacgcg accgacgaac agcgtcagat ccaggagatc   1080
aacaccggta tcctgatcgc gaacggtgca gacatgaca gttggctggc gaaactgacc   1140
aacaacaacg cgcagggtga atactacatc accgacatca tcgcgctgac gtaccaggaa   1200
ggtcgtgaaa tcgttgcggt tcacccgcag cgtctgtctg aagttgaagg tgttaacaac   1260
cgtctgcagc tgtctcgtct ggaacgtgtt taccagtctg aacaggcgga aaaactgctg   1320
ctggcgggtg ttatgctgcg tgaccgccg cgtttcgacc tgcgtggtac cctgacccac   1380
ggtcgtgacg ttgaaatcga caccaacgtt atcatcgaag gtaacgttac cctgggtcac   1440
cgtgtaaaaa tcggcaccgg ttgcgttatc aaaaactctg ttatcggtga cgactgcgaa   1500
atctctccgt acaccgttgt tgaagacgcg aacctggcgg cggcgtgcac catcggtccg   1560
ttcgcgcgtc tgcgtccggg tgcggaactg ctggaaggtg cgcacgttgg taacttcgtt   1620
gaaatgaaaa aagcgcgtct gggtaaaggt tctaaagcgg gtcacctgac ctacctgggt   1680
gacgcggaaa tcggtgacaa cgttaacatc ggtgcgggta ccatcacctg caactacgac   1740
ggtgcgaaca aattcaaaac catcatcggt gacgacgttt cgttggttc tgacacccag   1800
ctggttgcgc cggttaccgt tggtaaaggt gcgaccatcg cggcgggtac caccgttacc   1860
cgtaacgttg gtgaaaacgc gctggcgatc tctcgtgttc cgcagaccca gaaagaaggt   1920
tggcgtcgtc cggttaaaaa aaaataacga aggagataga accatgtcca accgtaaata   1980
cttcggtacg gacggtatcc gtggtcgtgt aggtgatgct ccgattacgc cggatttcgt   2040
cctgaaactc ggttgggcag cgggtaaagt tctcgcacgt cacggctctc gtaaaatcat   2100
catcggtaaa gacacccgta tctctggtta catgctcgaa tctgcactgg aagcgggtct   2160
ggctgcagct ggtctgtctg cactgttcac gggtccgatg ccaacccag ctgtagcgta   2220
cctgactcgc actttccgtg cagaagcagg tatcgtgatc tctgcctctc acaacccgtt   2280
ctacgacaac ggtatcaaat tcttcagcat cgatggtacc aaactcccag acgcggttga   2340
agaggctatc gaagcggaaa tggagaaaga aatctcttgt gtagactctg ccgaactcga   2400
taaagcgtct cgtatcgttg atgcagcggg tcgttacatc gagttctgca aagccacctt   2460
tccgaacgaa ctgagcctgt ctgagctgaa aatcgtcgta gactgtgcca acggtgcgac   2520
ttaccacatt gccccaaacg tactgcgtga gctgggtgct aacgtcatcg cgatcggttg   2580
tgaaccgaac ggtgtcaaca tcaacgcgga agtaggtgcg accgatgttc gtgcactgca   2640
ggctcgtgta ctcgcggaga aagcggatct cggtatcgcc tttgacggtg atggtgaccg   2700
tgttatcatg gttgaccacg aaggtaacaa agtggatggt gaccagatca tgtacatcat   2760
tgcccgtgaa ggtctgcgtc agggtcagct gcgtggtggt gcagtaggta ccctcatgag   2820
caacatgggt ctggaactgg ccctgaaaca gctgggtatc ccattcgctc gtgctaaagt   2880
aggcgaccgt tacgttctgg agaaaatgca ggagaaaggt tggcgtatcg gtgccgaaca   2940
ctctggtcac gtcatcctgc tggacaaaac cactaccggt gacggtatcg tagcaggtct   3000
gcaggtactc gccgctatgg cccgtaacca catgtccctc catgacctct gctctggtat   3060
gaaaatgttc ccgcagatcc tggttaacgt tcgttcacc gcaggttctg gtgatccgct   3120
ggaacacgag tctgtgaaag ccgttaccgc agaagtgaa ccgcctgac gtaaccgtgg   3180
tcgtgtactg ctgcgtaaat ccggtactga gccactgatc cgtgttatgg ttgagggcga   3240
agatgaagcc caggtcaccg aatttgcgca ccgtattgcc gacgcagtca aagcggttta   3300
aatgggcagc agccatcacc atcatcacca cagccaggat ccgaattcga gctcggcgcg   3360
cctgcaggtc gacaagcttg cggccgcata atgcttaagt cgaacagaaa gtaatcgtat   3420
tgtacacggc cgcataatcg aaattaatac gactcactat aggggaattg tgagcggata   3480
acaattcccc atcttagtat attagttaag tataagaagg agatatacat atgtgcggta   3540
tcgttggtgc tatcgcacag cgtgatgtag cggagatcct cctggaaggt ctgcgtcgtc   3600
tcgaataccg tggttacgac tctgccggtc tggcagtagt gatgcagaa ggtcacatga   3660
ctcgtctgcg tcgtctgggt aaagtgcaga tgctgcgcca ggcggcggaa gaacacccac   3720
tccacggtgg tacgggtatc gcacacactc gttgggcaac ccacggtgaa ccgtctgagg   3780
tcaacgcaca cccgcatgtt agcgagcaca tcgtagtcgt tcacaacggt atcatcgaga   3840
accacgaacc actccgtgag gaactcaaag cccgtggtta caccttcgta agcgaaaccg   3900
acacggaagt tatcgcccac ctcgttaact gggaactcaa acaggtggt actctgcgtg   3960
aagcagttct gcgtgccatt ccacagctgc gtggtcata cggtaccgtg atcatggact   4020
ctcgtcatcc ggataccctg ctcgccgcac gttctggttc tccactcgtt atcggtctgg   4080
gtatgggtga aacttcatc gcctctgatc agctggccct gctcccagtt accgtcgct   4140
tcatcttcct ggaagagggt gacatcgccg aaatcaccg tcgttccgt aacatcttcg   4200
acaaaacggg tgcggaagtt aaacgtcagg acatcgagtc taacctgcag tatgacgctg   4260
gtgacaaagg catctaccgt cactacatgc agaaagagat ctacgaacag ccgaacgcga   4320
tcaaaaacac cctgaccggt cgtatctctc acggtcaggt tgacctgtct gagctgggtc   4380
caaacgcgga cgaactcctg tccaaagtcg agcacatcca gatcctggct tgtgtggacc   4440
cttacaactc cggtatggtt tctcgttact ggttcgaatc tctggccaggt atcccatgcg   4500
acgttgaaat cgcctccgaa ttccgttatc gtaaatctgc ggtacgtcgt aactccctca   4560
tgatcaccct gtctcagtct ggtgaaaccg ctgatactct ggcaggtctg cgtctcagca   4620
aagaactggg ttacctgggt tctctggcca tctgcaacgt tccgggttct agcctggttc   4680
gtgagtctga cctggctctg atgaccaacg cgggtacgga gatcggtgtt gcctctacca   4740
aagcgttcac tacccagctc actgtcctgc tgatgctggt tgcccaaactg tctcgtctca   4800
aaggcctcga cgctagcatc gaacacgaca tcgtacacgg tctgcaggcc ctcccatctc   4860
gtatcgagca gatgctgtct caggacaaac gtatcgaagc actggcagaa gacttcagcg   4920
acaaacacca cgcgctgttt ctgggtcgtg tgaccagta cccaattgcg ctggaaggtg   4980
ccctgaaact gaaagagatc agctacatcc atgcagaggc atacgcagcg ggtgagctga   5040
aacatggtcc actggccctg atcgacgcag atatgccggt tattgtggtt gctccgaaca   5100
```

```
acgaactgct ggagaaactg aaatccaaca tcgaggaagt acgtgcgcgt ggtggtcagc   5160
tgtacgtgtt tgctgaccag gacgcgggtt tcgtttccag cgacaacatg cacatcatcg   5220
aaatgccgca tgttgaagag gtaatcgcgc caatcttcta caccgtaccg ctgcagctgc   5280
tggcgtacca tgtagccctg atcaaaggta cggacgttga ccagccgcgt aacctggcga   5340
aatccgtgac cgtggaataa gacgtccggta ccctcgagtc tggtaaagaa accgctgctg   5400
cgaaatttga acgccagcac atggactcgt ctactagcgc agcttaatta acctaggctg   5460
ctgccaccgc tgagcaataa ctagcataac cccttggggc ctctaaacgg gtcttgaggg   5520
gttttttgct gaaacctcag gcatttgaga agcacacggt cacactgctt ccggtagtca   5580
ataaaccggt aaaccagcaa tagacataag cggctattta cgaccctgc cctgaaccga   5640
cgacaagctg acgaccgggt ctccgcaagt ggcacttttc ggggaaatgt gcgcggaacc   5700
cctatttgtt tattttttcta aatacattca aatatgtatc cgctcatgaa ttaattctta   5760
gaaaaactca tcgagcatca aatgaaactg caatttattc atatcaggat tatcaatacc   5820
atattttgga aaaagccgtt tctgtaatga aggagaaaac tcaccgaggc agttccatag   5880
gatggcaaga tcctggtatc ggtctgcgat tccgactcgt ccaacatcaa tacaacctat   5940
taatttcccc tcgtcaaaaa taaggttatc aagtgagaaa tcaccatgag tgacgactga   6000
atccggtgag aatggcaaaa gtttatgcat ttctttccag acttgttcaa caggccagcc   6060
attacgctcg tcatcaaaat cactcgcatc aaccaaaccg ttattcattc gtgattgcgc   6120
ctgagcgaga cgaaatacgc ggtcgcgtt aaaaggacaa ttacaaacag gaatcgaatg   6180
caaccggcgc aggaacactg ccagcgcatc aacaatattt tcacctgaat caggatattc   6240
ttctaatacc tggaatgctg ttttcccggg gatcgcagtg gtgagtaacc atgcatcatc   6300
aggagtacgg ataaaatgct tgatggtcgg aagaggcata aattccgtca gccagtttag   6360
tctgaccatc tcatctgtaa catcattggc aacgctacct ttgccatgtt tcagaaacaa   6420
ctctggcgca tcgggcttcc catacaatcg atagattgtc gcacctgatt gcccgacatt   6480
atcgcgagcc catttatacc catataaatc agcatccatg ttggaattta atcgcggcct   6540
agagcaagac gtttcccgtt gaatatggct catactcttc ctttttcaat attattgaag   6600
catttatcag ggttattgtc tcatgagcgg atacatattt gaatgtattt agaaaaataa   6660
acaaataggc atgctagcgc agaaacgtcc tagaagatgc caggaggata cttagcagag   6720
agacaataag gccggagcga agccgttttt ccataggctc cgcccccctg acgaacatca   6780
cgaaatctga cgctcaaatc agtggtggcg aaacccgaca ggactataaa gataccaggc   6840
gtttcccct gatggctccc tcttgcgctc tcctgttccc gtcctgcggc gtccgtgttg   6900
tggtggaggc tttacccaaa tcaccacgtc ccgttccgtg tagacagttc gctccaagct   6960
gggctgtgtg caagaacccc ccgttcagcc cgactgctgc gccttatccg gtaactatca   7020
tcttgagtcc aacccggaaa gacacgacaa aacgccactg gcagcagcca ttggtaactg   7080
agaattagtg gatttagata tcgagagtct tgaagtggtg gcctaacaga ggctacactg   7140
aaaggacagt atttggtatc tgcgctccac taaagccagt taccaggtta agcagttccc   7200
caactgactt aaccttcgat caaaccgcct ccccaggcgg tttttttcgtt tacagagcag   7260
gagattacga cgatcgtaaa aggatctcaa gaagatcctt tacggattcc cgacaccatc   7320
actctagatt tcagtgcaat ttatctcttc aaatgtagca cctgaagtca gccccatacg   7380
atataagttg taattctcat gttagtcatg ccccgcgccc accggaagga gctgactggg   7440
ttgaaggctc tcaagggcat cggtcgagat cccggtgcct aatgagtgag ctaacttaca   7500
ttaattgcgt tgcgctcact gcccgctttc cagtcgggaa acctgtcgtg ccagctgcat   7560
taatgaatcg gccaacgcgc ggggagaggc ggtttgcgta ttgggcgcca gggtggtttt   7620
tcttttcacc agtgagacgg gcaacagctg attgcccttc accgcctggc cctgagagag   7680
ttgcagcaag cggtccacgc tggtttgccc cagcaggcga aaatcctgtt tgatggtggt   7740
taacggcggg atataacatg agctgtcttc ggtatcgtcg tatcccacta ccgagatgtc   7800
cgcaccaacg cgcagcccgg actcggtaat ggcgcgcatt gcgcccagcg ccatctgatc   7860
gttggcaacc agcatcgcag tgggaacgat gccctcattc agcatttgca tggtttgttg   7920
aaaaccggac atggcactcc agtcgccttc ccgttccgct atcggctgaa tttgattgcg   7980
agtgagatat ttatgccagc cagccagacg cagacgcgcc gagacagaac ttaatgggcc   8040
cgctaacagc gcgatttgct ggtgacccaa tgcgaccaga tgctccacgc ccagtcgcgt   8100
accgtcttca tgggagaaaa taatactgtt gatgggtgtc tggtcagaga tcatcaagaaa  8160
taacgccgga acattagtgc aggcagcttc cacagcaatg gcatcctggt catccagcgg   8220
atagttaatg at                                                        8232

SEQ ID NO: 10          moltype = DNA  length = 6792
FEATURE                Location/Qualifiers
misc_feature           1..6792
                       note = construct pINT-malE-PmgalT7
source                 1..6792
                       mol_type = other DNA
                       organism = synthetic construct
SEQUENCE: 10
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aaggggatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgaagatcct ttgatctttt   420
ctacggggtc tgacgctcag tggaacgaaa actcacgtta agggattttg gtcatgagat   480
tatcaaaaag gatcttcacc tagatccttt taaactagtg aagttaccat cacggaaaaa   540
ggttatgctg cttttaagac ccactttcac atttaagttg tttttctaat ccgcatatga   600
tcaattcaag gccgaataag aaggctggct ctgcaccttg gtgatcaaat aattcgatag   660
cttgtcgtaa taatggcggc atactatcag tagtaggtgt ttccctttct ctttagcga   720
cttgatgctc ttgatcttcc aatacgcaac ctaaagtaaa atgccccact cgctgagtg   780
catataatgc attctctagt gaaaaacctt gttggcataa aaaggctaat tgattttcga   840
gagtttcata ctgtttttct gtaggccgtg tacctaaatg tacttttgct ccatcgcgat   900
gacttagtaa agcacatcta aaactttag cgttattacg taaaaaatct tgccagcttt   960
cccccttctaa agggcaaaag tgagtatggt gcctatctaa catctcaatg gctaaggcgt   1020
```

-continued

```
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttccttttt caatattatt   1200
gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaattttttg ttgcacactct atcattgata gagttatttt accactccct   1380
atcagtgata gagaaaagtg aaatgaatag ttcgacaaaa atctagaaat aattttgttt   1440
aactttaaga aggagatata caaatgaaaa tcgaagaagg taaactggta atctggatta   1500
acggcgataa aggctataac ggtctcgctg aagtcggtaa gaaattcgag aaagataccg   1560
gaattaaagt caccgttgag catccggata aactggaaga gaaattccca caggttgcgg   1620
caactggcga tggccctgac attatcttct gggcacacga ccgctttggt ggctacgctc   1680
aatctgcct gttggctgaa atcaccccgg acaaagcgtt ccaggacaag ctgtatccgt   1740
ttacctggga tgccgtacgt tacaacggca agctgattgc ttacccgatc gctgttgaag   1800
cgttatcgct gatttataac aaagatctgc tgccgaaccc gccaaaaacc tgggaagaga   1860
tccccggcgct ggataaagaa ctgaaagcga aaggtaagag cgcgctgatg ttcaacctgc   1920
aagaaccgta cttcacctgg ccgctgattg ctgctgacgg gggttatgcg ttcaagtatg   1980
aaaacggcaa gtacgacatt aaagacgtgg gcgtggataa cgctggcgcg aaagcgggtc   2040
tgaccttcct ggttgacctg attaaaaaca aacacatgaa tgcagacacc gattactcca   2100
tcgcagaagc tgcctttaat aaaggcgaaa cagcgatgac catcaacggc ccgtgggcat   2160
ggtccaacat cgacaccagc aaagtgaatt atggtgtaac ggtactgccg accttcaagg   2220
gtcaaccatc caaaccgttc gttggcgtgc tgagcgcagg tattaacgcc gccagtccga   2280
acaaagagct ggcaaaagag ttcctcgaaa actatctgct gactgatgaa ggtctggaag   2340
cggttaataa agacaaaccg ctgggtgccg tagcgctgaa gtcttacgag gaagagttgg   2400
cgaaagatcc acgtattgcc gccaccatgg aaaacgccca gaaaggtgaa atcatgccga   2460
acatcccgca gatgtccgct ttctggtatg ccgtgcgtac tgcggtgatc aacgccgcca   2520
gcggtcgtca gactgtcgat gaagccctga aagacgcgca gactatgagc ggtgaacact   2580
atgtcattag cctgtcgtcg gcagttgaac gtcgccagca cattcgtaac cagttttcgc   2640
agaagaacat cccgtttcag ttttttcgatg caatttcacc gtcgccgctg ctggaccagc   2700
tggtgctgca atttttcccg cgtctggcgg atagctctct gaccggcggt gaaaaagcct   2760
gctttatgag ccatctgtct ctgtggcaca aatgtgtgga agaaaacctg ccgtatattg   2820
tggttttttga agatgacatc gttctgggca aagatgcgga caagttcctg attggtgatg   2880
aatggctgtt ttctcgtttc gacccggaag aaatctttat tatccgcctg gaaaccttcc   2940
tgcagaaagt cgtgtgcgaa agcacccata ttgccccgta tacgcaccgc gatttttctga   3000
gtctgaaatc cgcacatttc ggcacggctg gttacgtcat cagtcagggc gcggccaaat   3060
ttctgctgga tattttcaag aacatctcca atgaacacat tgcgccgatc gacgaactga   3120
tttttaacca gttcctggtt aagaactcat tcaacgtcta ccaactgtcg ccggcaatct   3180
gtgttcagga actgcaactg aacaatgaaa gttccgctct gcagagccaa ctggaactgg   3240
aacgtaacaa attccgcaat aaaaagtctg aagaactgaa gcgtaaccgc aagaacttca   3300
tcgaaaagtt catctacatc ctgaaaaagc cgaagcgtat gctggataac aataagcgta   3360
agcgcgaaga gagtaagatc gaaaacgaca agatgatcat cgaatttaaa tgagcggccg   3420
cgtcgacacg caaaaaggcc atccgtcagg atggccttct gcttaattat ctagatgcct   3480
ggcagtttat ggcgggcgtc ctgcccgcca ccctccgggc cgttgcttcg caacgttcaa   3540
atccgctccc ggcggatttg tcctactcag gagagcgttc accgacaaac aacagataaa   3600
acgaaaggcc cagtctttcg actgagcctt tcgttttatt tgatgcctgg cagttccta   3660
ctctcgcatg gggagacccc acactaccat catgtatgaa tatcctcctt agttcctatt   3720
ccgaagggta atggcatcag ggaatggcga acgcgctccc cacactacca tcatgtatga   3780
atatcctcct tagttcctat tccgaagttc ctattctcta gaaagtatag gaacttcggt   3840
ggaacgacgc gtaactcacg ttaagggatt ttggtcatga tcagcacgtg ttgacaatta   3900
atcatcggca tagtatatcg gcatagtata atacgacaag gtgaggaact aaaccatggc   3960
caagttgacc agtgccgttc cggtgctcac cgcgcgcgac gtcgccggag cggtcgagtt   4020
ctggaccgac cggctcgggt tctcccggga cttcgtggag gacgacttcg ccggtgtggt   4080
ccgggacgac gtgaccctgt tcatcagcgc ggtccaggac caggtggtgc cggacaacac   4140
cctggcctgg gtgtgggtgc gcggcctgga cgagctgtac gccgagtggt cggaggtcgt   4200
gtccacgaac ttccgggacg cctccgggcc ggccatgacc gagatcggcg agcagccgtg   4260
ggggcgggag ttcgccctgc gcgacccggc cggcaactgc gtgcacttcg tggccgagga   4320
gcaggactga gtggcagggc ggggcgtaag cgcgccatt taaatgaagt tcctattccg   4380
aagttcctat tctctagaaa gtataggaac ttcgaagcag ctccagccta cacaatcgct   4440
caagacggaa cccgcgcttg gcaggaaagt aatagggata gcagtccag cctacacaat   4500
cgctcaagac gtgtaatgct gcacaataac cctgctgcag aggcctgcat gcaagcttgg   4560
cgtaatcatg gtcatagctg tttcctgtgt gaaattgtta tccgctcaca attccacaca   4620
acatacgagc cggaagcata aagtgtaaag cctggggtgc ctaatgagtg agctaactca   4680
cattaattgc gttgcgctca ctgcccgctt tccagtcggg aaacctgtcg tgccagctgc   4740
attaatgaat cggccaacgc gcggggagag gcggtttgcg tattgggcgc tcttccgctt   4800
cctcgctcac tgactcgctg cgctcggtcg ttcggctgcg gcgagcggta tcagctcact   4860
caaaggcggt aatacggtta tccacagaat caggggataa cgcaggaaag aacatgtgag   4920
caaaaggcca gcaaaaggcc aggaaccgta aaaaggccgc gttgctggcg tttttccata   4980
ggctccgccc cctgacgag catcacaaaa atcgacgctc aagtcagagg tggcgaaacc   5040
cgacaggact ataaagatac caggcgtttc ccctggaag ctccctcgtg cgctctcctg   5100
ttccgaccct gccgcttacc ggatacctgt ccgcctttct ccttcgggaa gcgtggcgc   5160
tttctcatag ctcacgctgt aggtatctca gttcggtgta ggtcgttcgc tccaagctgg   5220
gctgtgtgca cgaacccccc gttcagcccg accgctgcgc cttatccggt aactatcgtc   5280
ttgagtccaa cccggtaaga cacgacttat cgccactggc agcagccact ggtaacagga   5340
ttagcagagc gaggtatgta ggcggtgcta cagagttctt gaagtggtgg cctaactacg   5400
gctacactag aagaacagta tttggtatct gcgctctgct gaagccagtt accttcggaa   5460
aaagagttgg tagctcttga tccggcaaac aaaccaccgc tggtagcggt ggtttttttg   5520
tttgcaagca gcagattacg cgcagaaaaa aaggatctca agaagatcct ttgatctttt   5580
ctacggggtc tgacgctcag tggaacgaaa actcacgtta agggattttg gtcatgagat   5640
tatcaaaaag gatcttcacc tagatccttt taaattaaaa atgaagtttt aaatcaatct   5700
aaagtatata tgagtaaact tggtctgaca gttaccaatg cttaatcagt gaggcaccta   5760
```

```
tctcagcgat ctgtctattt cgttcatcca tagttgcctg actccccgtc gtgtagataa    5820
ctacgatacg ggagggctta ccatctggcc ccagtgctgc aatgataccg cgagacccac    5880
gctcaccggc tccagattta tcagcaataa accagccagc cggaagggcc gagcgcagaa    5940
gtggtcctgc aactttatcc gcctccatcc agtctattaa ttgttgccgg gaagctagag    6000
taagtagttc gccagttaat agtttgcgca acgttgttgc cattgctaca ggcatcgtgg    6060
tgtcacgctc gtcgtttggt atggcttcat tcagctccgg ttcccaacga tcaaggcgag    6120
ttacatgatc ccccatgttg tgcaaaaaag cggttagctc cttcggtcct ccgatcgttg    6180
tcagaagtaa gttggccgca gtgttatcac tcatggttat ggcagcactg cataattctc    6240
ttactgtcat gccatccgta agatgctttt ctgtgactgg tgagtactca accaagtcat    6300
tctgagaata gtgtatgcgg cgaccgagtt gctcttgccc ggcgtcaata cgggataata    6360
ccgcgccaca tagcagaact ttaaaagtgc tcatcattgg aaaacgttct cggggcgaa    6420
aactctcaag gatcttaccg ctgttgagat ccagttcgat gtaacccact cgtgcaccca    6480
actgatcttc agcatctttt actttcacca gcgtttctgt gtgagcaaaa acaggaaggc    6540
aaaatgccgc aaaaaaggga ataagggcga cacggaaatg ttgaatactc atactcttcc    6600
tttttcaata ttattgaagc atttatcagg gttattgtct catgagcgga tacatatttg    6660
aatgtattta gaaaaataaa caaatagggg ttccgcgcac atttccccga aaagtgccac    6720
ctgacgtcta agaaaccatt attatcatga cattaaccta taaaaatagg cgtatcacga    6780
ggcccttttcg tc                                                       6792
```

SEQ ID NO: 11        moltype = DNA   length = 6702
FEATURE              Location/Qualifiers
misc_feature        1..6702
                     note = construct pINT-malE-MsgalT8
source              1..6702
                     mol_type = other DNA
                     organism = synthetic construct
SEQUENCE: 11

```
tcgcgcgttt cggtgatgac ggtgaaaacc tctgacacat gcagctcccg gagacggtca    60
cagcttgtct gtaagcggat gccgggagca gacaagcccg tcaggcgcg tcagcggggtg     120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct ttgatctttt    420
ctacggggtc tgacgctcag tggaacgaaa actcacgtta agggatttttg gtcatgagat    480
tatcaaaaag gatcttcacc tagatccttt taaactagtg aagttaccat cacggaaaaa    540
ggttatgctg ctttttaagac ccactttcac atttaagttg ttttttctaat ccgcatatga    600
tcaattcaag gccgaataag aaggctggct ctgcaccttg gtgatcaaat aattcgatag    660
cttgtcgtaa taatggcggc atactatcag tagtaggttg ttccctttct tctttagcga    720
cttgatgctc ttgatcttcc aatacgcaac ctaaagtaaa atgccccact cgctgagtg    780
catataatgc attctctagt gaaaaacctt gttggcataa aaaggctaat tgattttcga    840
gagtttcata ctgtttttct gtaggccgtg tacctaaatg tacttttgct ccatcgcgat    900
gacttagtaa agcacatcta aaactttttag cgttattacg taaaaaatct tgccagcttt    960
ccccttctaa agggcaaaag tgagtatggt gcctatctaa catctcaatg gctaaggcgt    1020
cgagcaaagc ccgcttattt tttacatgcc aatacaatgt aggctgctct acacctagct    1080
tctgggcgag tttacgggtt gttaaacctt cgattccgac ctcattaagc agctctaatg    1140
cgctgttaat cactttactt ttatctaaac gagacatact cttccttttt caatattatt    1200
gaagcatttta tcaggttat tgtctcatga gcggatacat atttgaatgt atttagaaaa    1260
ataaacaaat aggggttccg cgcacatttc ccgaaaagt gccacctgaa attggccaga    1320
tgattaattc ctaatttttg ttgacactct atcattgata gagttatttt accactccct    1380
atcagtgata gagaaaagtg aaatgaatag ttcgacaaaa atctagaaat aattttgtt    1440
aactttaaga aggagatata caaatgaaa tcgaagaagg taaactggta atctggatta    1500
acggcgataa aggctataac ggtctcgctg aagtcggtaa gaaattcgag aaagataccg    1560
gaattaaagt caccgttgag catccggata aactggaaga gaaattccca caggttgcgg    1620
caactggcga tggccctgac attatcttct gggcacacga ccgctttggt ggctacgctg    1680
aatctggcct gttggctgaa atcacccgg acaaagcgtt ccaggacaag ctgtatccgt    1740
ttacctggga tgccgtacgt tacaacggca agctgattgc ttaccgatc gctgttgaag    1800
cgttatcgcg gatttataac aaagatctgc tgccgaaccc gccaaaaacc tgggaagaga    1860
tcccggcgct ggataaagaa ctgaaagcga aaggtaagag cgcgctgatg ttcaacctgc    1920
aagaaccgta cttcacctgg ccgctgatcg ctgctgacgg gggttatgcg ttcaagtatg    1980
aaaacggcaa gtacgacatt aaagacgtgg gcgtggataa cgctggcgcg aaagcgggtc    2040
tgaccttcct ggttgacctg attaaaaaca aacacatgaa tgcagacacc gattactcca    2100
tcgcagaagc tgcctttaat aaaggcgaaa cagcgatgac catcaacggc ccgtgggcat    2160
ggtccaacat cgacaccagc aaagtgaatt atggtgtaac ggttctcaagg    2220
gtcaaccatc caaaccgttc gttggcgtgc tgagcgcagg tattaacgcc gccagtccga    2280
acaaagagct ggcaaaagag ttcctcgaaa actatctgct gactgatgaa ggtctggaag    2340
cggttaataa agacaaaccg ctgggtgccg tagcgctgaa gtcttacgag gaagagttgg    2400
cgaaagatcc acgtattgcc gccaccatgg aaaacgccca gaaaggtgaa atcatgccga    2460
acatcccgca gatgtccgct ttctggtatg ccgtgcgtac tgcggtgatc aacgccgcca    2520
gcggtcgtca gactgtcgat gaagccctga aagacgcgca gactatggat gaaatcaaac    2580
tgtcggtggt tatgccgtat tacaaacgtc tgcgtgaatt tatgcgtgtc ctgccgctga    2640
atgcccgctt ctttagccgt catgaatatg aagtggttct gagtctggac gaaccgtccg    2700
aagaagccga tctgctgcgt gtcctgcgcg acttcccgtc tattcgttgg cgcgttctgg    2760
tcaatgacct ggatcacccg tggcgtccgc gtgccgtac actgaacgtt ggcatccgta    2820
atgctctggg tgaaaacgtc ctggtcgtga gccggaatc tgcgtttgtg accgatgttc    2880
cggcacgcgc tctggatcat attgcagcaa acccgggtac cgcagctctg ggtcacgttt    2940
gttttgcaac gttcgatgcg ctggaagccc gtcaggcag cctggaaaaa acgtgcgctc    3000
cgccgtggaa tctgtatggt tctatctgtg tcccgcgtga acgtctggca cgtgtgcatg    3060
gctacgacga aagcttcgat cgctgggcg gtgatgacga taacctgcgt attcgcctga    3120
```

```
tgcagaccga aacgtatctg catccgctgg acgatatgcg catcctgcac ctgagttttg   3180
aagcccgtaa agtgcgtcaa gcagcagaac cgccgtcccc ggaatacgca gaacgtattt   3240
tccagccggt gtcaccgcaa gcaaatccgg gcggttgggg tgaatcgttt cagcgcgttg   3300
cgttcgattg gcgtcgccaa tgagcggccg cgtcgacacg caaaaaggcc atccgtcagg   3360
atggccttct gcttaattat ctagatgcct ggcagtttat ggcggggcgtc ctgcccgcca   3420
ccctccgggc cgttgcttcg caacgttcaa atccgctccc ggcggatttg tcctactcag   3480
gagagcgttc accgacaaac aacagataaa acgaaaggcc cagtcttccg actgagcctt   3540
tcgttttatt tgatgcctgg cagttcccta ctctcgcatg gggagacccc acactaccat   3600
catgtatgaa tatcctcctt agttcctatt ccgaagggta atggcatcag ggaatggcga   3660
acgcgctccc cacactacca tcatgtatga atatcctcct tagttcctat tccgaagttc   3720
ctattctcta gaaagtatag gaacttcggt ggaacgacgc gtaactcacg ttaagggatt   3780
ttggtcatga tcagcacgtg ttgacaatta atcatcggca tagtatatcg gcatagtata   3840
atacgacaag gtgaggaact aaaccatggc caagttgacc agtgccgttc cggtgctcac   3900
cgcgcgcgac gtcgccggag cggtcgagtt ctggaccgac cggctcgggt tctcccggga   3960
cttcgtggag gacgacttcg ccggtgtggt ccgggacgac gtgaccctgt tcatcagcgc   4020
ggtccaggac caggtggtgc cggacaacac cctggcctgg gtgtgggtgc gcggcctgga   4080
cgagctgtac gccgagtggt cggaggtcgt gtccacgaac ttccgggacg cctccgggcc   4140
ggccatgacc gagatcggcg agcagccgtg ggggcgggag ttcgccctgc gcgacccggc   4200
cggcaactgc gtgcacttcg tggccgagga gcaggactga gtggcagggc ggggcgtaag   4260
gcgcgccatt taaatgaagt tcctattccg aagttcctat tctctagaaa gtataggaac   4320
ttcgaagcag ctccagccta cacaatcgct caagacggaa cccgcgcttg caggaaagt   4380
aataggggata gcagctccag cctacacaat cgctcaagac gtgtaatgct gcacaataac   4440
cctgctgcag aggcctgcat gcaagcttgg cgtaatcatg gtcatagctg tttcctgtgt   4500
gaaattgtta tccgctcaca attccacaca acatacgagc cggaagcata aagtgtaaag   4560
cctggggtgc ctaatgagtg agctaactca cattaattgc gttgcgctca ctgcccgctt   4620
tccagtcggg aaacctgtcg tgccagctgc attaatgaat cggccaacgc gcggggagag   4680
gcggtttgcg tattgggcgc tcttccgctt cctcgctcac tgactcgctg cgctcggtcg   4740
ttcggctgcg gcgagcggta tcagctcact caaaggcggt aatacggtta tccacagaat   4800
caggggataa gcaggaaag aacatgtgag caaaaggcca gcaaaaggcc aggaaccgta   4860
aaaaggccgc gttgctggcg tttttccata ggctccgccc cctgacgag catcacaaaa   4920
atcgacgctc aagtcagagg tggcgaaacc cgacaggact ataaagatac caggcgtttc   4980
ccctggaag ctccctcgtg cgctctcctg ttccgaccct gccgcttacc ggatacctgt   5040
ccgcctttct cccttcggga agcgtggcgc tttctcatag ctcacgctgt aggtatctca   5100
gttcggtgta ggtcgttcgc tccaagctgg gctgtgtgca cgaaccccc gttcagcccg   5160
accgctgcgc cttatccggt aactatcgtc ttgagtccaa cccggtaaga cacgacttat   5220
cgccactggc agcagccact ggtaacagga ttagcagagc gaggtatgta ggcggtgcta   5280
cagagttctt gaagtggtgg cctaactacg gctacactag aagaacagta tttggtatct   5340
gcgctctgct gaagccagtt accttcggaa aaagagttgg tagctcttga tccggcaaac   5400
aaaccaccgc tggtagcggt ggtttttttg tttgcaagca gcagattacg cgcagaaaaa   5460
aaggatctca agaagatcct ttgatctttt ctacggggtc tgacgctcag tggaacgaaa   5520
actcacgtta agggattttg gtcatgagat tatcaaaaag gatcttcacc tagatccttt   5580
taaattaaaa atgaagtttt aaatcaatct aaagtatata tgagtaaact tggtctgaca   5640
gttaccaatg cttaatcagt gaggcaccta tctcagcgat ctgtctattt cgttcatcca   5700
tagttgcctg actccccgtc gtgtagataa ctacgatacg ggagggctta ccatctggcc   5760
ccagtgctgc aatgataccg cgagacccac gctcaccggc tccagattta tcagcaataa   5820
accagccagc cggaagggcc gagcgcagaa gtggtcctgc aactttatcc gcctccatcc   5880
agtctattaa ttgttgccgg gaagctagag taagtagttc gccagttaat agtttgcgca   5940
acgttgttgc cattgctaca ggcatcgtgg tgtcacgctc gtcgtttggt atggcttcat   6000
tcagctccgg ttcccaacga tcaaggcgag ttacatgatc ccccatgttg tgcaaaaaag   6060
cggttagctc cttcggtcct ccgatcgttg tcagaagtaa gttggccgca gtgttatcac   6120
tcatggttat ggcagcactg cataattctc ttactgtcat gccatccgta agatgcttt   6180
ctgtgactgg tgagtactca accaagtcat tctgagaata gtgtatgcgg cgaccgagtt   6240
gctcttgccc ggcgtcaata cgggataata ccgcgccaca tagcagaact ttaaaagtgc   6300
tcatcattgg aaaacgttct cggggcgaa aactctcaag gatcttaccg ctgttgagat   6360
ccagttcgat gtaacccact cgtgcaccca actgatcttc agcatctttt actttcacca   6420
gcgtttctgg gtgagcaaaa acaggaaggc aaaatgccgc aaaaaaggga ataagggcga   6480
cacgaaaatg ttgaatactc atactcttcc tttttcaata ttattgaagc atttatcagg   6540
gttattgtct catgagcgga tacatatttg aatgtatttg aaaaataaa caaataggggg   6600
ttccgcgcac atttccccga aaagtgccac ctgacgtcta agaaaccatt attatcatga   6660
cattaaccta taaaaatagg cgtatcacga ggccctttcg tc                      6702
```

```
SEQ ID NO: 12             moltype = DNA   length = 6777
FEATURE                   Location/Qualifiers
misc_feature             1..6777
                          note = construct pINT-malE-KdgalT10
source                    1..6777
                          mol_type = other DNA
                          organism = synthetic construct
SEQUENCE: 12
tcgcgcgttt cggtgatgac ggtgaaaacc tctgacacat gcagctcccg gagacggtca   60
cagcttgtct gtaagcggat gccgggagca gacaagcccg tcaggcgcg tcagcgggtg   120
ttggcgggtg tcgggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgaagatcct ttgatctttt   420
ctacggggtc tgacgctcag tggaacgaaa actcacgtta agggattttg gtcatgagat   480
tatcaaaaag gatcttcacc tagatccttt taaactagta agttaccat cacggaaaaa   540
ggttatgctg cttttaagac ccactttcac atttaagttg tttttctaat ccgcatatga   600
```

```
tcaattcaag gccgaataag aaggctggct ctgcaccttg gtgatcaaat aattcgatag   660
cttgtcgtaa taatggcggc atactatcag tagtaggtgt ttccctttct tctttagcga   720
cttgatgctc ttgatcttcc aatacgcaac ctaaagtaaa atgccccact gcgctgagtg   780
catataatgc attctctagt gaaaaacctt gttggcataa aaaggctaat tgattttcga   840
gagtttcata ctgttttttct gtaggccgtg tacctaaatg tacttttgct ccatcgcgat   900
gacttagtaa agcacatcta aaactttttag cgttattacg taaaaaaatct tgccagcttt   960
cccttctaa agggcaaaag tgagtatggt gcctatctaa catctcaatg gctaaggcgt  1020
cgagcaaagc ccgcttattt tttacatgcc aatacaatgt aggctgctct acacctagct  1080
tctgggcgag tttacgggtt gttaaacctt cgattccgac ctcattaagc agctctaatg  1140
cgctgttaat cactttactt ttatctaaac gagacatact cttccttttt caatattatt  1200
gaagcattta tcagggttat tgtctcatga gcggatacat atttgaatgt atttagaaaa  1260
ataaacaaat aggggttccg cgcacatttc cccgaaaagt gccacctgaa attggccaga  1320
tgattaattc ctaattttttg ttgacactct atcattgata gagttatttt accactccct  1380
atcagtgata gagaaaagtg aaatgaatag ttcgacaaaa atctagaaat aattttgttt  1440
aactttaaga aggagatata caaatgaaaa tcgaagaagg taaactggta atctggatta  1500
acggcgataa aggctataac ggtctcgctg aagtcggtaa gaaattcgag aaagataccg  1560
gaattaaagt caccgttgag catccggata aactggaaga gaaattccca caggttgcgg  1620
caactggcga tggccctgac attatcttct gggcacacga ccgctttggt ggctacgctc  1680
aatctggcct gttggctgaa atcacccccg acaaagcgtt ccaggacaag ctgtatccgt  1740
ttacctggga tgccgtacgt tacaacggca agctgattgc ttacccgatc gctgttgaag  1800
cgttatcgct gatttataac aaagatctgc tgccgaaccc gccaaaaacc tgggaagaga  1860
tcccggcgct ggataaagaa ctgaaagcga aaggtaagag cgcgctgatg ttcaacctgg  1920
aagaaccgta cttcacctgg ccgctgattg ctgctgacgg gggttatgcg ttcaagtatg  1980
aaaacggcaa gtacgacatt aaagacgtgg gcgtggataa cgctggcgcg aaagcgggtc  2040
tgaccttcct ggttgacctg attaaaaaca aacacatgaa tgcagacacc gattactcca  2100
tcgcagaagc tgcctttaat aaaggcgaaa cagcgatgac catcaacggc ccgtgggcat  2160
ggtccaacat cgacaccagc aaagtgaatt atggtgtaac ggtactgccg accttcaagg  2220
gtcaaccatc caaaccgttc gttggcgtgc tgagcgcagg tattaacgcc gccagtccga  2280
acaaagagct ggcaaaagag ttcctcgaaa actatctgct gactgatgaa ggtctggaag  2340
cggttaataa agacaaaccg ctgggtgccg tagcgctgaa gtcttacgag gaagagttgg  2400
cgaaagatcc acgtattgcc gccaccatgg aaaacgccca gaaaggtgaa atcatgccga  2460
acatcccgca gatgtccgct ttctggtatg ccgtgcgtac tgcggtgatc aacgccgcca  2520
gcggtcgtca gactgtcgat gaagccctga agacgcgca gactatggaa aactatgtcg  2580
tctctatccg caccgcagcc caacgccgcc agcatgtcgc cgcgaattc aataagcacc  2640
aaatcgcctt tcatttcttt gatgcggtga ccccggaaac gctggcggaa agcatcgcag  2700
aacactgccc gaacctggca gacgcctttc tgaccggcgg tgaaaagggc tgtttcatgt  2760
ctcatgtctg cctgtgggca aaatgtgtgg ctgatgacct gccgtatatt ggcatctttg  2820
aagatgacgt tattttcggt cagaacagct ctcgtttttct gaatgatacc aaatggctgg  2880
acgaacgttt tcagaaccaa tcattcatta tccgcatgga aacgtttctg aaggcgaacc  2940
cggttgccct gagcaaatct ggcgtccgtc cgttcaatgg tcgtaagatc ctgcgcctgc  3000
agagtttttgg cttcggtacc gcggcctatc tgatttccca gcaaaccgca atcacgctgc  3060
tgaattggat tcgcgaagtc gctccggaaa aactggaacc gattgataac atgctgttta  3120
atgcagcttc agaaattccg gaaatccaga tgtaccaaat ctcgccgcc ctgtgcattc  3180
aggaactgca actgaaccgc gcagatagtt ccctgtcatc gaccctggaa gacggtcgtc  3240
tggcacgtca ccagcaactg gatggcggta aaacccagcc ggaacagacg caagaaaacc  3300
gtaacatctt cgcatgggct aagaacaaga tcgtgaagga atacaagcgc gttaaacgtc  3360
gctggacgga tgacaaaaag attgttccgt tcaaatgagc ggccgcgtcg acacgcaaaa  3420
aggccatccg tcaggatggc cttctgctta attatctaga tgcctggcag tttatggcgg  3480
gcgtcctgcc cgccacctc cgggcgttg cttcgcaacg ttcaaatccg ctcccggcgg  3540
atttgtccta ctcaggagag cgttcaccga caaacaacag ataaaacgaa aggcccagtc  3600
tttcgactga gcctttcgtt ttatttgatg cctggcagt ccctactctc gcatggggag  3660
accccacact accatcatgt atgaatatcc tccttagttc ctattccgaa gggtaatggc  3720
atcagggaat ggcgaacgcg ctccccacac taccatcatg tatgaatatc ctccttagtt  3780
cctattccga agttcctatt ctctagaaag tataggaact tcggtggaac gacgcgtaac  3840
tcacgttaag ggattttggt catgatcagc acgtgttgac aattaatcat cggcatagta  3900
tatcggcata gtataatacg acaaggtgag gaactaaacc atggccagt tgaccagtg  3960
cgttccggtg ctcaccgcgc gcgacgtcgc cggagcggtc gagttctgga ccgaccggct  4020
cgggttctcc cgggacttcg tggaggacga cttcgccggt gtggtccggg acgacgtgac  4080
cctgttcatc agcgcggtcc aggaccaggt ggtgccggac aacaccctgg cctgggtgtg  4140
ggtgcgcggc ctgtacgagc tgtacgccga gtggtcggac gtcgtgtcca cgaacttccg  4200
ggacgcctcc gggccggcca tgaccgagat cggcgagcag ccgtggggc gggagttcgc  4260
cctgcgcgac ccggccggca actgcgtgca cttcgtggcc gaggagcagg actgagtggc  4320
agggcggggc gtaaggcgcg ccatttaaat gaagttccta ttccgaagtt cctattctct  4380
agaaagtata ggaacttcga agcagctcca gcctacacaa tctcaaga cggaacccgc  4440
gcttggcagg aaagtaatag ggatagcagc tccagcctac acaatcgctc aagacgtgta  4500
atgctgcaca ataaccctgc tgcagaggcc tgcatgcaag cttggcgtaa tcatggtcat  4560
agctgtttcc tgtgtgaaat tgttatccgc tcacaattcc acacaacata cgagccggaa  4620
gcataaagtg taaagcctgg ggtgcctaat gagtgagcta actcacatta ttgcgttgc  4680
gctcactgcc cgctttccag tcgggaaacc tgtcgtgcca gctgcattaa tgaatcggcc  4740
aacgcgcggg gagaggcggt ttgcgtattg ggcgctcttc cgcttcctcg ctcactgact  4800
cgctgcgctc ggtcgttcgg ctgcggcgag cggtatcagc tcactcaaag gcggtaatac  4860
ggttatccac agaatcaggg gataacgcag gaaagaacat gtgagcaaaa ggccagcaaa  4920
aggccaggaa ccgtaaaaag gccgcgttgc tggcgttttt ccataggctc cgcccccctg  4980
acgagcatca caaaaatcga cgctcaagtc agaggtggcg aaacccgaca ggactataaa  5040
gataccaggc gtttccccct ggaagctccc tcgtgcgctc tcctgttccg acctgccgc  5100
ttaccggata cctgtccgcc tttctccctt cgggaagcgt ggcgctttct catagctcac  5160
gctgtaggta tctcagttcg gtgtaggtcg ttcgctccaa gctgggctgt gtgcacgaac  5220
ccccgttca gcccgaccgc tgcgccttat ccggtaacta tcgtcttgag tccaacccgg  5280
taagacacga cttatcgcca ctggcagcag ccactggtaa caggattagc agagcgaggt  5340
```

-continued

```
atgtaggcgg tgctacagag ttcttgaagt ggtggcctaa ctacggctac actagaagaa  5400
cagtatttgg tatctgcgct ctgctgaagc cagttacctt cggaaaaaga gttggtagct  5460
cttgatccgg caaacaaacc accgctggta gcggtggttt ttttgtttgc aagcagcaga  5520
ttacgcgcag aaaaaaagga tctcaagaag atcctttgat cttttctacg gggtctgacg  5580
ctcagtggaa cgaaaactca cgttaaggga ttttggtcat gagattatca aaaaggatct  5640
tcacctagat cctttttaaat taaaaatgaa gttttaaatc aatctaaagt atatatgagt  5700
aaacttggtc tgacagttac caatgcttaa tcagtgaggc acctatctca gcgatctgtc  5760
tatttcgttc atccatagtt gcctgactcc ccgtcgtgta gataactacg atacgggagg  5820
gcttaccatc tggccccagt gctgcaatga taccgcgaga cccacgctca ccggctccag  5880
atttatcagc aataaaccag ccagccggaa gggccgagcg cagaagtggt cctgcaactt  5940
tatccgcctc catccagtct attaattgtt gccgggaagc tagagtaagt agttcgccag  6000
ttaatagttt gcgcaacgtt gttgccattg ctacaggcat cgtggtgtca cgctcgtcgt  6060
ttggtatggc ttcattcagc tccggttccc aacgatcaag gcgagttaca tgatcccca  6120
tgttgtgcaa aaaagcggtt agctccttcg gtcctccgat cgttgtcaga agtaagttgg  6180
ccgcagtgtt atcactcatg gttatggcag cactgcataa ttctcttact gtcatgccat  6240
ccgtaagatg cttttctgtg actggtgagt actcaaccaa gtcattctga gaatagtgta  6300
tgcggcgacc gagttgctct tgcccggcgt caatacggga taataccgcg ccacatagca  6360
gaactttaaa agtgctcatc attggaaaac gttcttcggg gcgaaaactc tcaaggatct  6420
taccgctgtt gagatccagt tcgatgtaac ccactcgtgc acccaactga tcttcagcat  6480
cttttacttt caccagcgtt tctgggtgag caaaaacagg aaggcaaaat gccgcaaaaa  6540
agggaataag ggcgacacgg aaatgttgaa tactcatact cttccttttt caatattatt  6600
gaagcattta tcagggttat tgtctcatga gcggatacat atttgaatgt atttagaaaa  6660
ataaacaaat aggggttccg cgcacatttc cccgaaaagt gccacctgac gtctaagaaa  6720
ccattattat catgacatta acctataaaa ataggcgtat cacgaggccc tttcgtc     6777
```

```
SEQ ID NO: 13            moltype = DNA  length = 6786
FEATURE                  Location/Qualifiers
misc_feature            1..6786
                        note = construct pINT-malE-gatD
source                  1..6786
                        mol_type = other DNA
                        organism = synthetic construct
SEQUENCE: 13
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcgggctgg cttaactatg cggcatcaga gcagattgta ctgagagtgc  180
accatatgcg gtgtgaaata ccgcacagat gcgtaaggag aaaataccgc atcaggcgcc  240
attcgccatt caggctgcgc aactgttggg aagggcgatc ggtgcgggcc tcttcgctat  300
tacgccagct ggcgaaaggg ggatgtgctg caaggcgatt aagttgggta acgccaggt  360
tttcccagtc acgacgttgt aaaacgacgg ccagtgaatt cgaagatcct ttgatctttt  420
ctacggggtc tgacgctcag tggaacgaaa actcacgtta agggattttg gtcatgagat  480
tatcaaaaag gatcttcacc tagatccttt aaaactagt aagttaccat cacggaaaaa  540
ggttatgctg cttttaagac ccactttcac atttaagttg ttttctaat ccgcatatga  600
tcaattcaag gccgaataag aaggctggct ctgcaccttg gtgatcaaat aattcgatag  660
cttgtcgtaa taatggcggc atactatcag tagtaggtgt ttccctttct tctttagcga  720
cttgatgctc ttgatcttcc aatacgcaac ctaaagtaaa atgccccact gcgctgagtg  780
catataaatgc attctctagt gaaaaacctt gttggcataa aaaggctaat tgatttttcga  840
gagtttcata ctgtttttct gtaggccgtg tacctaaatg tacttttgct ccatcgcgat  900
gacttagtaa agcacatcta aaactttag cgttattacg taaaaaatct tgccagcttt  960
ccccttctaa agggcaaaag tgagtatggt gcctatctaa catctcaatg gctaaggcgt  1020
cgagcaaagc ccgcttattt tttacatgcc aatacaatgt aggctgctct acacctagct  1080
tctgggcgag tttacggggtt gttaaacctt cgattccgac ctcattaagc agctctaatg  1140
cgctgttaat cactttactt ttatctaaac gagacatact cttcctttttt caatattatt  1200
gaagcattta tcagggttat tgtctcatga gcggatacat atttgaatgt atttagaaaa  1260
ataaacaaat aggggttccg cgcacatttc cccgaaaagt gccacctgaa attggccaga  1320
tgattaattc ctaattttttg ttgacactct atcattgata gagttatttt accactccct  1380
atcagtgata gagaaaagtg aaatgaatag ttcgacaaaa atctagaaat aattttgttt  1440
aactttaaga aggagatata caaatgaaaa tcgaagaagg taaactggta atctggatta  1500
acggcgataa aggctataac ggtctcgctg aagtcggtaa gaaattcgag aaagataccg  1560
gaattaaagt caccgttgag catccggata aactggaaga gaaattccca caggttgcgg  1620
caactggcga tggccctgac attatcttct gggcacacga ccgctttggt ggctacgctc  1680
aatctggcct gttggctgaa atcaccccgg acaaagcgtt ccaggacaag ctgtatccgt  1740
ttacctggga tgccgtacgt tacaacggca agctgattgc ttacccgatc gctgttgaag  1800
cgttatcgct gatttataac aaagatctgc tgccgaaccc gccaaaaacc tgggaagaga  1860
tcccggcgct ggataaagaa ctgaaagcga aaggtaagag cgcgctgatg ttcaacctgc  1920
aagaaccgta cttcacctgg ccgctgattg ctgctgacgg gggttatgcg ttcaagtatg  1980
aaaacggcaa gtacgacatt aaagacgtgg gcgtggataa cgctggcgcg aaagcgggtc  2040
tgaccttcct ggttgacctg attaaaaaca aacacatgaa tgcagacacc gattactcca  2100
tcgcagaagc tgcctttaat aaaggcgaaa cagcgatgac catcaacggc ccgtgggcat  2160
ggtccaacat cgacaccagc aaagtgaatt atggtgtaac ggtactgccg accttcaagg  2220
gtcaaccatc caaaccgttc gttggcgtgc tgagcgcagg tattaacgcc gccagtccga  2280
acaaagagct ggcaaaagag ttcctcgaaa actatctgct gactgatgaa ggtctggaag  2340
cggttaataa agacaaaccg ctgggtgccg tagcgctgaa gtcttacgag gaagagttgg  2400
cgaaagatcc acgtattgcc gccaccatgg aaaacgccca gaaaggtgaa atcatgccga  2460
acatcccgca gatgtccgct ttctggtatg ccgtgcgtac tgcggtgatc aacgccgcca  2520
gcggtcgtca gactgtcgat gaagccctga aagacgcgca gactatgtcc tcagctttcc  2580
attacgtcat tagcctggca tcggcagttg aacgccgtca gcacattagc gaacagtttt  2640
cccaatacga cattccgttt cagttttttcg atgcgatcag tccgtccccg ctgctgaacc  2700
agctggtgtc tcaatttttc ccgtccctgg ccgatagctc tctgaccgac ggcgaaaaag  2760
```

```
gttgctttat ttcacatctg tcgctgtggc acaagtgtgt tgaaaagaac ctgccgtata    2820
ttgtggtttt tgaagatgac atcctgctgg gcaagaatgc agataaattc ctgattgaag    2880
acgaatggtt tttctctcgt tttaacacga atgatgtctt catcgtgcgc ctggaaacct    2940
ttctgcagaa agtgtattgc caaccgagct acatcaagtc ttactacaac cgtgaactgc    3000
tgaccctgaa aagcacgcat ttcggcaccg caggttatat tatcagtctg ggtgcggcca    3060
agtttctgct gtccctgttc aacaaaatgc acattgaaga agttgctccg atcgatgaac    3120
tgctgtttaa taagttcctg gaacgcaaag actttacggt ctaccagttc agtccggcac    3180
tgtgcattca ggaactgcaa ctgaacaaat cagatgctgt cctgctgtcg caactggaac    3240
tggaacgtag caaatgtcgc attatgaccg aatctcgtat cggccgcgaa aagaaaaaac    3300
tgaaggataa gatcatccat gttctgacga agccgaaacg tatgctggaa aagaaacgtc    3360
agcgcaatga agacaagaaa atcaccatga ttatcgaatt tgaatgagcg gccgcgtcga    3420
cacgcaaaaa ggccatccgt caggatggcc ttctgcttaa ttatctagat gcctggcagt    3480
ttatggcggg cgtcctgccc gccaccctcc gggccgttgc ttcgcaacgt tcaaatccgc    3540
tcccgcggga tttgtcctac tcaggagagc gttcaccgac aaacaacaga taaaacgaaa    3600
ggcccagtct ttcgactgag cctttcgttt tatttgatgc ctggcagttc cctactctcg    3660
catgggggaga ccccacacta ccatcatgta tgaatatcct ccttagttcc tattccgaag    3720
ggtaatggca tcagggaatg gcgaacgcgc tccccacact accatcatgt atgaatatcc    3780
tccttagttc ctattccgaa gttcctattc tctagaaagt ataggaactt cggtggaacg    3840
acgcgtaact cacgttaagg gattttggtc atgatcagca cgtgttgaca attaatcatc    3900
ggcatagtat atcggcatag tataatacga caaggtgagg aactaaacca tggccaagtt    3960
gaccagtgcc gttccggtgc tcaccgcgcg cgacgtcgcc ggagcggtcg agttctggac    4020
cgaccggctc gggttctccc gggacttcgt ggaggacgac ttcgccggtg ttgtccggga    4080
cgacgtgacc ctgttcatca gcgcggtcca ggaccaggtg gtgccggaca acaccctggc    4140
ctgggtgtgg gtgcgcggcc tggacgagct gtacgccgag tggtcggagg tcgtgtccac    4200
gaacttccgg gacgcctccg ggccggccat gaccgagatc ggcgagcagc cgtgggggcg    4260
ggagttcgcc ctgcgcgacc cggccggcaa ctgcgtgcac ttcgtggccg aggagcagga    4320
ctgagtggca gggcggggcg taaggcgcgc catttaaatg aagttcctat tccgaagttc    4380
ctattctcta gaaagtatag gaacttcgaa gcagctccag cctacacaat cgctcaagac    4440
ggaacccgcg cttggcagga aagtaatagg gatagcagct ccagcctaca caatcgctca    4500
agacgtgtaa tgctgcacaa taaccctgct gcagaggcct gcatgcaagc ttggcgtaat    4560
catggtcata gctgtttcct gtgtgaaatt gttatccgct cacaattcca cacaacatac    4620
gagccggaag cataaagtgt aaagcctggg gtgcctaatg agtgagctaa ctcacattaa    4680
ttgcgttgcg ctcactgccc gctttccagt cgggaaacct gtcgtgccag ctgcattaat    4740
gaatcggcca acgcgcgggg agaggcggtt tgcgtattgg gcgctcttcc gcttcctcgc    4800
tcactgactc gctgcgctcg gtcgttcggc tgcggcgagc ggtatcagct cactcaaagg    4860
cggtaatacg gttatccaca gaatcagggg ataacgcagg aaagaacatg tgagcaaaag    4920
gccagcaaaa ggccaggaac cgtaaaaagg ccgcgttgct ggcgtttttc cataggctcc    4980
gcccccctga cgagcatcac aaaaatcgac gctcaagtca gaggtggcga aacccgacag    5040
gactataaag ataccaggcg tttccccctg gaagctccct cgtgcgctct cctgttccga    5100
ccctgccgct taccggatac ctgtccgcct ttctcccttc gggaagcgtg gcgctttctc    5160
atagctcacg ctgtaggtat ctcagttcgg tgtaggtcgt tcgctccaag ctgggctgtg    5220
tgcacgaacc ccccgttcag cccgaccgct gcgccttatc cggtaactat cgtcttgagt    5280
ccaacccggt aagacacgac ttatcgccac tggcagcagc cactggtaac aggattagca    5340
gagcgaggta tgtaggcggt gctacagagt tcttgaagtg gtggcctaac tacggctaca    5400
ctagaagaac agtatttggt atctgcgctc tgctgaagcc agttaccttc ggaaaaagag    5460
ttggtagctc ttgatccggc aaacaaacca ccgctggtag cggtggtttt tttgtttgca    5520
agcagcagat tacgcgcaga aaaaaaggat ctcaagaaga tcctttgatc ttttctacgg    5580
ggtctgacgc tcagtggaac gaaaactcac gttaagggat tttggtcatg agattatcaa    5640
aaaggatctt cacctagatc cttttaaatt aaaaatgaag ttttaaatca atctaaagta    5700
tatatgagta aacttggtct gacagttacc aatgcttaat cagtgaggca cctatctcag    5760
cgatctgtct atttcgttca tccatagttg cctgactccc cgtcgtgtag ataactacga    5820
tacgggaggg cttaccatct ggccccagtg ctgcaatgat accgcgagac ccacgctcac    5880
cggctccaga tttatcagca ataaaccagc cagccggaag ggccgagcgc agaagtggtc    5940
ctgcaacttt atccgcctcc atccagtcta ttaattgttg ccgggaagct agagtaagta    6000
gttcgccagt taatagtttg cgcaacgttg ttgccattgc tacaggcatc gtggtgtcac    6060
gctcgtcgtt tggtatggct tcattcagct ccggttccca acgatcaagg cgagttacat    6120
gatcccccat gttgtgcaaa aaagcggtta gctccttcgg tcctccgatc gttgtcagaa    6180
gtaagttggc cgcagtgtta tcactcatgg ttatggcagc actgcataat tctcttactg    6240
tcatgccatc cgtaagatgc ttttctgtga ctggtgagta ctcaaccaag tcattctgag    6300
aatagtgtat gcggcgaccg agttgctctt gcccggcgtc aatacgggat aataccgcgc    6360
cacatagcag aactttaaaa gtgctcatca ttggaaaacg ttcttcgggg cgaaaactct    6420
caaggatctt accgctgttg agatccagtt cgatgtaacc cactcgtgca cccaactgat    6480
cttcagcatc ttttactttc accagcgttt ctgggtgagc aaaaacagga aggcaaaatg    6540
ccgcaaaaaa gggaataagg cgacacggaa aatgttgaat actcatactc ttcctttttc    6600
aatattattg aagcatttat cagggttatt gtctcatgag cggatacata tttgaatgta    6660
tttagaaaaa taaacaaata ggggttccgc gcacatttcc ccgaaaagtg ccacctgacg    6720
tctaagaaac cattattatc atgacattaa cctataaaaa taggcgtatc acgaggccct    6780
ttcgtc                                                                6786
```

```
SEQ ID NO: 14          moltype = DNA   length = 7506
FEATURE                Location/Qualifiers
misc_feature           1..7506
                       note = construct pINT-malE-BFgalT2
source                 1..7506
                       mol_type = other DNA
                       organism = synthetic construct
SEQUENCE: 14
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg    120
```

-continued

```
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct ttgatctttt    420
ctacggggtc tgacgctcag tggaacgaaa actcacgtta agggattttg gtcatgagat    480
tatcaaaaag gatcttcacc tagatccttt taaactagtg aagttaccat cacggaaaaa    540
ggttatgctg cttttaagac ccactttcac atttaagttg ttttctaat ccgcatatga    600
tcaattcaag gccgaataag aaggctggct ctgcaccttg gtgatcaaat aattcgatag    660
cttgtcgtaa taatggcggc atactatcag tagtaggtgt ttcccttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgtttttct gtaggccgtg tacctaaatg tactttttgct ccatcgcgat    900
gacttagtaa agcacatcta aaactttag cgttattacg taaaaaatct tgccagcttt    960
ccccttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttcctttt caatattatt   1200
gaagcattta tcaggggttat tgtctctcatga gcggatacat atttgaatgt atttagaaaa   1260
ataaacaaat aggggttccg cgcacatttc cccgaaaagt gccacctgaa attggccaga   1320
tgattaattc ctaatttttg ttgacactct atcattgata gagttatttt accactccct   1380
atcagtgata gagaaaagtg aaatgaatag ttcgacaaaa atctagaaat aattttgttt   1440
aactttaaga aggagatata caaatgaaaa tcgaagaagg taaactggta atctggatta   1500
acggcgataa aggctataac ggtctcgctg aagtcggtaa gaaattcgag aaagataccg   1560
gaattaaagt caccgttgag catccggata aactggaaga gaaattccca caggttgcgg   1620
caactggcga tggccctgac attatcttct gggcacacga ccgctttgct ggctacgctc   1680
aatctggcct gttggctgaa atcacccccg acaaagcgtt ccaggacaag ctgtatccgt   1740
ttacctggga tgccgtacgt tacaacggca agctgattgc ttacccgatc gctgttgaag   1800
cgttatcgct gatttataac aaagatctgc tgccgaaccc gccaaaaacc tgggaagaga   1860
tcccggccgt ggataaagaa ctgaaagcga aaggtaagag cgcgctgatg ttcaacctgc   1920
aagaaccgta cttcacctgg ccgctgattg ctgctgacgg gggttatgcg ttcaagtatg   1980
aaaacggcaa gtacgacatt aaagacgtgg gcgtggataa cgctggcgcg aaagcgggtc   2040
tgaccttcct ggttgacctg attaaaaaca aacacatgaa tgcagacacc gattactcca   2100
tcgcagaagc tgcctttaat aaaggcgaaa cagcgatgac catcaacggc ccgtgggcat   2160
ggtccaacat cgacaccagc aaagtgaatt atggtgtaac ggtactgccg accttcaagg   2220
gtcaaccatc caaaccgttc gttggcgtgc tgagcgcagg tattaacgcc gccagtccga   2280
acaaagagct ggcaaaagag ttcctcgaaa actatctgct gactgatgaa ggtctggaag   2340
cggttaataa agacaaaccg ctgggtgccg tagcgctgaa gtcttacgag gaagagttgg   2400
cgaaagatcc acgtattgcc gccaccatgg aaaacgccca gaaaggtgaa atcatgccga   2460
acatcccgca gatgtccgct ttctggtatg ccgtgcgtac tgcggtgatc aacgccgcca   2520
gcggtcgtca gactgtcgat gaagccctga aagacgcgca gactatgaac gtgaataagc   2580
cgaccaccga aaagaaactg attgacctga caacgacgat tatccataac tttgatgtga   2640
gcattgtgat gagcttctat aagcgttaca ccgaatttcg caaagtgctg aataacg   2700
cgccgtatct gcagcgtaat ggcattgaag tcattatcgt gctggatgac ccggatgaaa   2760
aaagcgaact gctgatgctg ctgcaaaact atccgttcat caattggaag ctgattatca   2820
acgaacgtaa acatgcaccg cgcaaccacg cttctgttct gaatgtcggt ctgaaacatg   2880
cgaccaaaaa gtatattctg cagatcgatc cggaagttga atttctgacg gatattatct   2940
ggcaaatgcg tgacgccatt gaaaaatatc cgatgcacta catcctgccg atgatggcct   3000
atgtcccgta cgaacaggaa ctgaccgaaa caaacatcaa ggaactggat ttcatcccgt   3060
ggggcaacct gatggtggaa cgcaatcatc tgtataaact gcacggttac gatgaaacct   3120
tcattacgtg gggcggtgaa gataacaata tgcgtgcgcg cctggacatg tcaggcatta   3180
aaaagtttat cctgccggaa gccaagacca tccatcgtga aaagaactat gatccgaatg   3240
aacgttcgaa gcgcattaat aaacacagta tctccgactg gcgcaaaatg aactacccgt   3300
cagaagcaat tgctaataag gatatctggg gctcggaatt caacaaagtt atttatgatt   3360
ggcaggacaa tcaatacgcc aaagatctgt gctataccta cctgcagcaa tttattggtt   3420
tcgaaatccg tcatccggcg gcctttcgta aacgccacaa aaagattgtc ctgtgtcagg   3480
catataacga agaaaaactg atcgaaggct tcctgacgaa catggctaat tactttgatg   3540
gtattatcct gctggatgac gaaagtaccg atcgcacgtg ggacctggca atccatgata   3600
agatcatcct gaaggtgaaa aagaaacgtt ccggttttaa tgatctggaa aaccgcaata   3660
ttctgctgga cctgtcagcg ttttttccagt cggaatggtt ttgcttcatg gatatcgacg   3720
aacgtttcga tgaacgcttt accaacttca gcgaattcga aaacaacaag gaaatccacg   3780
tggtttcttt tcgtggcgtg tatctgtgga atgatgaaca gagctacaag ggcgacattc   3840
cgaactctaa taaaggtatc ctgaccgttt atcgtatgtt ccgcccgatt ggtcataccc   3900
acatcaacac gcataagaaa ctgcacttca ttgcgacgcc gtattttacc aacacgtggc   3960
agagtaatat cctgtttaag gattacggct ccatgaaaga aaatgaccgt attcgcaagt   4020
atgaacgcta catccaggaa gatcagcaaa aagacatgag ctctggttat gattacctgc   4080
tgaacagcga aaatctgtat caactggaca aaattgaaga atactgagcg gccgcgtcga   4140
cacgcaaaaa ggccatccgt caggatggcc ttctgcttaa ttatctagat gcctggcagt   4200
ttatggcggg cgtcctgccc gccaccctcc gggccgttgc ttcgcaacgt tcaaatccgc   4260
tcccggcgga tttgtcctac tcaggagagc gttcaccgac aaacaacaga taaaacgaaa   4320
ggcccagtct ttcgactgag cctttcgttt tatttgatgc ctggcagttc cctactctcg   4380
catggggaga ccccacacta ccatcatgta tgaatatcct ccttagttcc tattccgaag   4440
ggtaatggca tcagggaatg cgaacgcgc tccccacact accatcatgt atgaatatcc   4500
tccttagttc ctattccgaa gttcctattc tctagaaagt ataggaactt cggtggaacg   4560
acgcgtaact cacgttaagg gattttggtc atgatcagca cgtgttgaca attaatcatc   4620
ggcatagtat atcggcatag tataatacga caaggtgagg aactaaacca tggccaagtt   4680
gaccagtgcc gttccggtgc tcaccgcgcg cgacgtcgcc ggagcggtcg agttctggac   4740
cgaccggctc gggttctccc gggacttcgt ggaggacgac ttcgccggtg tggtccggga   4800
cgacgtgacc ctgttcatca gcgcggtcca ggaccaggtg gtgccggaca caccctggc    4860
```

```
ctgggtgtgg gtgcgcggcc tggacgagct gtacgccgag tggtcggagg tcgtgtccac   4920
gaacttccgg gacgcctccg ggccggccat gaccgagatc ggcgagcagc cgtgggggcg   4980
ggagttcgcc ctgcgcgacc cggccggcaa ctgcgtgcac ttcgtggccg aggagcagga   5040
ctgagtggca gggcggggcg taaggcgcgc catttaaatg aagttcctat tccgaagttc   5100
ctattctcta gaaagtatag gaacttcgaa gcagctccag cctacacaat cgctcaagac   5160
ggaacccgcg cttggcagga aagtaatagg gatagcagct ccagcctaca caatcgctca   5220
agacgtgtaa tgctgcacaa taaccctgct gcagaggcct gcatgcaagc ttggcgtaat   5280
catggtcata gctgtttcct gtgtgaaatt gttatccgct cacaattcca cacaacatac   5340
gagccggaag cataaagtgt aaagcctggg gtgcctaatg agtgagctaa ctcacattaa   5400
ttgcgttgcg ctcactgccc gctttccagt cgggaaacct gtcgtgccag ctgcattaat   5460
gaatcggcca acgcgcgggg agaggcggtt tgcgtattgg gcgctcttcc gcttcctcgc   5520
tcactgactc gctgcgctcg gtcgttcggc tgcggcgagc ggtatcagct cactcaaagg   5580
cggtaatacg gttatccaca gaatcagggg ataacgcagg aaagaacatg tgagcaaaag   5640
gccagcaaaa ggccaggaac cgtaaaaagg ccgcgttgct ggcgtttttc cataggctcc   5700
gcccccctga cgagcatcac aaaaatcgac gctcaagtca gaggtggcga aacccgacag   5760
gactataaag ataccaggcg tttccccctg gaagctccct cgtgcgctct cctgttccga   5820
ccctgccgct taccggatac ctgtccgcct ttctcccttc gggaagcgtg gcgctttctc   5880
atagctcacg ctgtaggtat ctcagttcgg tgtaggtcgt tcgctccaag ctgggctgtg   5940
tgcacgaacc ccccgttcag cccgaccgct gcgccttatc cggtaactat cgtcttgagt   6000
ccaacccggt aagacacgac ttatcgccac tggcagcagc cactggtaac aggattagca   6060
gagcgaggta tgtaggcggt gctacagagt tcttgaagtg gtggcctaac tacggctaca   6120
ctagaagaac agtatttggt atctgcgctc tgctgaagcc agttaccttc ggaaaaagag   6180
ttggtagctc ttgatccggc aaacaaacca ccgctggtag cggtggtttt tttgtttgca   6240
agcagcagat tacgcgcaga aaaaaaggat ctcaagaaga tcctttgatc ttttctacgg   6300
ggtctgacgc tcagtggaac gaaaactcac gttaagggat tttggtcatg agattatcaa   6360
aaaggatctt cacctagatc ctttaaatt aaaaatgaag ttttaaatca atctaaagta   6420
tatatgagta aacttggtct gacagttacc aatgcttaat cagtgaggca cctatctcag   6480
cgatctgtct atttcgttca tccatagttg cctgactccc cgtcgtgtag ataactacga   6540
tacgggaggg cttaccatct ggccccagtg ctgcaatgat accgcgagac ccacgctcac   6600
cggctccaga tttatcagca ataaaccagc cagccggaag ggccgagcgc agaagtggtc   6660
ctgcaacttt atccgcctcc atccagtcta ttaattgttg ccgggaagct agagtaagta   6720
gttcgccagt taatagtttg cgcaacgttg ttgccattgc tacaggcatc gtggtgtcac   6780
gctcgtcgtt tggtatggct tcattcagct ccggttccca acgatcaagg cgagttacat   6840
gatccccat gttgtgcaaa aaagcggtta gctccttcgg tcctccgatc gttgtcagaa   6900
gtaagttggc cgcagtgtta tcactcatgg ttatggcagc actgcataat tctcttactg   6960
tcatgccatc cgtaagatgc ttttctgtga ctggtgagta ctcaaccaag tcattctgag   7020
aatagtgtat gcggcgaccg agttgctctt gcccggcgtc aatacgggat aataccgcgc   7080
cacatagcag aactttaaaa gtgctcatca ttggaaaacg ttcttcgggg cgaaaactct   7140
caaggatctt accgctgttg agatccagtt cgatgtaacc cactcgtgca cccaactgat   7200
cttcagcatc ttttactttc accagcgttt ctgggtgagc aaaaacagga aggcaaaatg   7260
ccgcaaaaaa gggaataagg gcgacacgga aatgttgaat actcatactc ttcctttttc   7320
aatattattg aagcatttat cagggttatt gtctcatgag cggatacata tttgaatgta   7380
tttagaaaaa taaacaaata ggggttccgc gcacatttcc ccgaaaagtg ccacctgacg   7440
tctaagaaac cattattatc atgacattaa cctataaaaa taggcgtatc acgaggccct   7500
ttcgtc                                                              7506
```

```
SEQ ID NO: 15            moltype = DNA  length = 6717
FEATURE                  Location/Qualifiers
misc_feature            1..6717
                        note = construct pINT-malE-lsgD
source                  1..6717
                        mol_type = other DNA
                        organism = synthetic construct
SEQUENCE: 15
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgaagatcct ttgatctttt   420
ctacggggtc tgacgctcag tggaacgaaa actcacgtta agggattttg gtcatgagat   480
tatcaaaaag gatcttcacc tagatccttt aaactagta aagttaccat cacggaaaaa   540
ggttatgctg cttttaagac ccactttcac atttaagttg ttttctaat ccgcatatga   600
tcaattcaag gccgaataag aaggctggct ctgcaccttg gtgatcaaat aattcgatag   660
cttgtcgtaa taatggcggc atactatcag tagtaggtgt ttccctttct tctttagcga   720
cttgatgctc ttgatcttcc aatacgcaac ctaaagtaaa atgccccact gcgctgagtg   780
catataatgc attctctagt gaaaaacctt gttggcataa aaaggctaat tgattttcga   840
gagtttcata ctgtttttct gtaggccgtg tacctaaatg tacttttgct ccatcgcgat   900
gacttagtaa agcacatcta aaactttag cgttattacg taaaaaatct tgccagcttt   960
cccctttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttcctttt caatattatt   1200
gaagcattta tcagggttat tgtctcatga gcggatacat atttgaatgt atttagaaaa   1260
ataaacaaat aggggttccg cgcacatttc ccgaaaagt gccacctgaa attggccaga   1320
tgattaattc ctaattttg ttgacactct atcattgata gagttatttt accactccct   1380
atcagtgata gagaaaagtg aaatgaatag ttcgacaaaa atctagaaat aattttgttt   1440
aactttaaga aggagatata caaatgaaaa tcgaagaagg taaactggta atctggatta   1500
```

-continued

```
acggcgataa aggctataac ggtctcgctg aagtcggtaa gaaattcgag aaagataccg   1560
gaattaaagt caccgttgag catccggata aactggaaga gaaattccca caggttgcgg   1620
caactggcga tggccctgac attatcttct gggcacacga ccgctttggt ggctacgctc   1680
aatctggcct gttggctgaa atcaccccgg acaaagcgtt ccaggacaag ctgtatccgt   1740
ttacctggga tgccgtacgt tacaacggca agctgattgc ttacccgatc gctgttgaag   1800
cgttatcgct gatttataac aaagatctgc tgccgaaccc gccaaaaacc tgggaagaga   1860
tcccggcgct ggataaagaa ctgaaagcga aaggtaagag cgcgctgatg ttcaacctgc   1920
aagaaccgta cttcacctgg ccgctgattg ctgctgacgg gggttatgcg ttcaagtatg   1980
aaaacggcaa gtacgacatt aaagacgtgg gcgtggataa cgctggcgcg aaagcgggtc   2040
tgaccttcct ggttgacctg attaaaaaca aacacatgaa tgcagacacc gattactcca   2100
tcgcagaagc tgcctttaat aaaggcgaaa cagcgatgac catcaacggc ccgtgggcat   2160
ggtccaacat cgacaccagc aaagtgaatt atggtgtaac ggtactgccg accttcaagg   2220
gtcaaccatc caaaccgttc gttggcgtgc tgagcgcagg tattaacgcc gccagtccga   2280
acaaagagct ggcaaaagag ttcctcgaaa actatctgct gactgatgaa ggtctggaag   2340
cggttaataa agacaaaccg ctgggtgccg tagcgctgaa gtcttacgag gaagagttgg   2400
cgaaagatcc acgtattgcc gccaccatgg aaaacgccca gaaaggtgaa atcatgccga   2460
acatcccgca gatgtccgct ttctggtatg ccgtgcgtac tgccggtgatc aacgccgcca   2520
gcggtcgtca gactgtcgat gaagccctga aagacgcgca gactatgctg aagaagtacc   2580
tgattagcct ggataaggac attcaacgcc gcaagctgtt tttctcgcag aagaacacgg   2640
aagattttca aattttctca gcgatcaaca ccatgcagaa agattgggac gaactggcat   2700
cgatcttcaa catcgaacaa ttcaaggctc attacttccg taacgtcacc aagggcgaaa   2760
ttggttgcac gctgagtcac ctgtccgtct atcagaaaat tgtggaagat aacgacatcg   2820
cagaagattc atacgctctg gtttgtgaag atgacgccct gtttcatctg gatttccagc   2880
aaaatctgac cgcactgctg agtgaaaaac tggaagctga aattatcctg ctgggccagt   2940
ccaacattaa caattttaat gatacggacc tggaaatcaa ttacccgacc acgtttagct   3000
tcctgtgcaa aaagaccggt aacgtgaatt atgcgttccc gtataaatct tactttgccg   3060
gcacggttgg ttacctgatt aaaaagagcg cggcccgtcg cttcattcag caaatctctc   3120
agaacaaacc gttttggctg gcggatgact ttctgctgtt cgaacaaaac ttcaatatcc   3180
gtaataaggt ggttcgcccg ctgatggtta ttgaaaaccc ggtcctgatc tcaaatctgg   3240
aatcggtgcg cggcagcctg tctaacaatc tgctgaaaaa gctgatgaaa tatccgctga   3300
aaaagatttt tgcgatcaaa aagaacctgg ccaattaagc ggccgcgtcg acacgcaaaa   3360
aggccatccg tcaggatggc cttctgctta attatctaga tgcctggcag tttatggcgg   3420
gcgtcctgcc cgccaccctc cgggccgttg cttcgcaacg ttcaaatccg ctcccggcgg   3480
atttgtccta ctcaggagag cgttcaccga caaacacgaa ataaaacgaa aggcccagtc   3540
tttcgactga gcctttcgtt ttatttgatg cctggcagtt ccctactctc gcatggggag   3600
accccacact accatcatgt atgaatatcc tccttagttc ctattccgaa gggtaatggc   3660
atcagggaat ggcgaacgcg ctccccacac taccatcatg tatgaatatc ctccttagtt   3720
cctattccga agttcctatt ctctagaaag tataggaact tcggtggaac gacgcgtaac   3780
tcacgttaag ggattttggt catgatcagc acgtgttgac aattaatcat cggcatagta   3840
tatcggcata gtataatacg acaaggtgag gaactaaacc atggccaagt tgaccagtgt   3900
cgttccggtc ctcaccgcgc gcgacgtcgc cggagcggtc gagttctgga ccgaccggct   3960
cgggttctcc cgggacttcg tggaggacga cttcgccggt gtggtccggg acgacgtgac   4020
cctgttcatc agcgcggtcc aggaccaggt ggtgccggac aacaccctgg cctgggtgac   4080
ggtgcgcggc ctggacgagc tgtacgccga gtggtcggag gtcgtgtcca cgaacttccg   4140
ggacgcctcc gggccggcca tgaccgagat cggcgagcag ccgtggggggc gggagttcgc   4200
cctgcgcgac ccggccggca actgcgtgca cttcgtggcc gaggagcagg actgagtggc   4260
agggcgggac gtaaggcgcg ccatttaaat gaagttccta ttccgaagtt cctattctct   4320
agaaagtata ggaacttcga agcagctcca gcctacacaa tcgctcaaga cggaacccgc   4380
gcttggcagg aaagtaatag ggatagcagc tccagcctac acaatcgctc aagacgtgta   4440
atgctgcaca ataaccctgc tgcagaggcc tgcatgcaag cttggcgtaa tcatggtcat   4500
agctgtttcc tgtgtgaaat tgttatccgc tcacaattcc acacaacata cgagccggaa   4560
gcataaagtg taaagcctgg ggtgcctaat gagtgagcta actcacatta attgcgttgc   4620
gctcactgcc cgctttccag tcgggaaacc tgtcgtgcca gctgcattaa tgaatcggcc   4680
aacgcgcggg gagaggcggt ttgcgtattg ggcgctcttc cgcttcctcg ctcactgact   4740
cgctgcgctc ggtcgttcgg ctgcggcgag cggtatcagc tcactcaaag gcggtaaatac   4800
ggttatccac agaatcaggg gataacgcag gaaagaacat gtgagcaaaa ggccagcaaa   4860
aggccaggaa ccgtaaaaag gccgcgttgc tggcgttttt ccataggctc cgcccccctg   4920
acgagcatca caaaaatcga cgctcaagtc agaggtggcg aaacccgaca ggactataaa   4980
gataccaggc gtttccccct ggaagctccc tcgtgcgctc tcctgttccg accctgccgc   5040
ttaccggata cctgtccgcc tttctccctt cgggaagcgt ggcgctttct catagctcac   5100
gctgtaggta tctcagttcg gtgtaggtcg ttcgctccaa gctgggctgt gtgcacgaac   5160
ccccgttca gcccgaccgc tgcgccttat ccggtaacta tcgtcttgag tccaacccgg   5220
taagacacga cttatcgcca ctggcagcag ccactggtaa caggattagc agagcgaggt   5280
atgtagaggc tgctacagag ttcttgaagt ggtggcctaa ctacggctac actagaagaa   5340
cagtatttgg tatctgcgct ctgctgaagc cagttacctt cggaaaaaga gttggtagct   5400
cttgatccgg caaacaaacc accgctggta gcggtggttt ttttgtttgc aagcagcaga   5460
ttacgcgcag aaaaaaagga tctcaagaag atcctttgat cttttctacg gggtctgacg   5520
ctcagtggaa cgaaaactca cgttaaggga ttttggtcat gagattatca aaaaggatct   5580
tcacctagat ccttttaaat taaaaatgaa gttttaaatc aatctaaagt atatatgagt   5640
aaacttggtc tgacagttac caatgcttaa tcagtgaggc acctatctca gcgatcgtgtc   5700
tatttcgttc atccatagtt gcctgactcc ccgtcgtgta gataactacg atacgggagg   5760
gcttaccatc tggccccagt gctgcaatga taccgcgaga cccacgctca ccggctccag   5820
atttatcagc aataaaccag ccagccggaa gggccgagcg cagaagtggt cctgcaactt   5880
tatccgcctc catccagtct attaattgtt gccgggaagc tagagtaagt agttcgccag   5940
ttaatagttt gcgcaacgtt gttgccattg ctacaggcat cgtggtgtca cgctcgtcgt   6000
ttggtatggc ttcattcagc tccggttccc aacgatcaag gcgagttaca tgatccccca   6060
tgttgtgcaa aaaagcggtt agctccttcg gtcctccgat cgttgtcaga agtaagttgg   6120
ccgcagtgtt atcactcatg gttatggcag cactgcataa ttctcttact gtcatgccat   6180
ccgtaagatg cttttctgtg actggtgagt actcaaccaa gtcattctga gaatagtgta   6240
```

-continued

```
tgcggcgacc gagttgctct tgcccggcgt caatacggga taataccgcg ccacatagca    6300
gaactttaaa agtgctcatc attggaaaac gttcttcggg gcgaaaactc tcaaggatct    6360
taccgctgtt gagatccagt tcgatgtaac ccactcgtgc acccaactga tcttcagcat    6420
cttttacttt caccagcgtt tctgggtgag caaaaacagg aaggcaaaat gccgcaaaaa    6480
agggaataag ggcgacacgg aaatgttgaa tactcatact cttccttttt caatattatt    6540
gaagcattta tcagggttat tgtctcatga gcggatacat atttgaatgt atttagaaaa    6600
ataaacaaat aggggttccg cgcacatttc cccgaaaagt gccacctgac gtctaagaaa    6660
ccattattat catgacatta acctataaaa ataggcgtat cacgaggccc tttcgtc      6717
```

```
SEQ ID NO: 16           moltype = DNA  length = 6769
FEATURE                 Location/Qualifiers
misc_feature            1..6769
                        note = construct pINT-malE-HPgalT
source                  1..6769
                        mol_type = other DNA
                        organism = synthetic construct
SEQUENCE: 16
tcgcgcgttt cggtgatgac ggtgaaaacc tctgacacat gcagctcccg gagacggtca    60
cagcttgtct gtaagcggat gccgggagca gacaagcccg tcagggcgcg tcagcggggtg   120
ttggcgggtg tcgggctgg  cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct ttgatctttt    420
ctacggggtc tgacgctcag tggaacgaaa actcacgtta agggattttg gtcatgagat    480
tatcaaaaag gatcttcacc tagatccttt taaactagtg aagttaccat cacggaaaaa    540
ggttatgctg cttttaagac ccactttcac atttaagttg tttttctaat ccgcatatga    600
tcaattcaag gccgaataag aaggctggct ctgcaccttg gtgatcaaat aattcgatag    660
cttgtcgtaa taatgcggc  atactatcag tagtaggtgt ttccctttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgtttttct gtaggccgtg tacctaaatg tactttgct  ccatcgcgat    900
gacttagtaa agcacatcta aaactttag  cgttattacg taaaaaatct tgccagcttt    960
cccctctaa  agggcaaag  tgagtatggt gcctatctaa catctcaatg gctaaggcgt    1020
cgagcaaagc ccgcttattt tttacatgcc aatacaatgt aggctgctct acacctagct    1080
tctgggcgag tttacgggtt gttaaacctt cgattccgac ctcattaagc agctctaatg    1140
cgctgttaat cactttactt ttatctaaac gagacatact cttccttttt caatattatt    1200
gaagcattta tcagggttat tgtctcatga gcggatacat atttgaatgt atttagaaaa    1260
ataaacaaat aggggttccg cgcacatttc cccgaaaagt gccacctgaa attggccaga    1320
tgattaattc ctaattttg  ttgacactct atcattgata gagttatttt accactccct    1380
atcagtgata gagaaaagtg aaatgaatag ttcgacaaaa atctagaaat aattttgttt    1440
aactttaaga aggagatata caaatgaaaa tcgaagaagg taaactggta atctggatta    1500
acggcgataa aggctataac ggtctcgctg aagtcggaag gaaattccca caggttgcgg    1560
gaattaaagt caccgttgag catccggata aactggaaga gaaattccca caggttgcgg    1620
caactggcga tggccctgac attatcttct gggcacacga ccgctttggt ggctacgctc    1680
aatctggcct gttggctgaa atcacccggg acaaagcgtt ccaggacaag ctgtatccgt    1740
ttacctggga tgccgtacgt tacaacggca agctgattgc ttacccgatc gctgttgaag    1800
cgttatcgct gatttataac aaagatctgc tgccgaaccc gccaaaaacc tgggaagaga    1860
tccccggcgct ggataaagaa ctgaaagcga aaggtaagag cgcgctgatg ttcaacctgc    1920
aagaaccgta cttcacctgg ccgctgattg ctgctgacgg gggttatgcg ttcaagtatg    1980
aaaacgcaa  gtacgacatt aaagacgtgg gcgtggataa cgctggcgcg aaagcgggtc    2040
tgacettcct ggttgacctg attaaaaaca aacacatgaa tgcagacacc gattactcca    2100
tcgcagaagc tgcctttaat aaaggcgaaa cagcgatgac catcaacggc ccgtgggcat    2160
ggtccaacat cgacaccagc aaagtgaatt atggtgtaac ggtactgccg accttcaagg    2220
gtcaaccatc caaaccgttc gttggcgtgc tgagcgcagg tattaacgcc gccagtccga    2280
acaaagagct ggcaaagag  ttcctcgaaa actatctgct gactgatgaa ggtctggaag    2340
cggttaataa agacaaaccg ctgggtgccg tagcgctgaa gtcttacgag gaagagttgg    2400
cgaaagatcc acgtattgcc gccaccatgg aaaacgccca gaaaggtgaa atcatgccga    2460
acatcccgca gatgtccgct ttctggtatg ccgtgcgtac tgcggtgatc aacgccgcca    2520
gcggtcgtca gactgtcgat gaagccctga aagacgcgca gactatgcgt gtgtttatta    2580
tttccctgaa tcaaaagtg  tgtgatacct tcggtctggt gttccgtgat acgacgaccc    2640
tgctgaacaa cattaacgcg acccatcacc aggcccaaat ttttgatgca atctactcca    2700
aaacgttcga aggcggtctg catccgctgg ttaaaaaaca tctgcacccg tactttatta    2760
cccagaacat caaagacatg ggcattacca cgaattcgat cagcgaagtc tctaaatttc    2820
actacgctct gaaataccat gcgaaattcc tgacctgggg cgaactgggt tgctatgcta    2880
gtcactactc cctgtgggaa aaatgcattg aactgaacga agcgatttgt atcctggaag    2940
atgacatcac gctgaaagaa gatttttaag aaggcctgga cttcctggaa aaacatattc    3000
aggaactggg ttatgtgcgt ctgatgcacc tgctgtacga tccgaatgtt aaaagcgaac    3060
cgctgaacca taaaatcac  gaaatccagg aacgcgtggg cattatcaaa gcctattctc    3120
atggcgttgg cacccaaggt tacgtcatta cgccgaaaat cgcaaaagtc ttcaaaaaac    3180
atagtcgtaa atgggtggtt ccggtggata ccattatgga cgcgacgttt atccacggtg    3240
tcaaaaatct ggtgctgcaa ccgttcgtta ttgccgatga cgaacaaatt caaccatcg    3300
cacgcaaaga agaaccgtat tcgccgaaaa tcgccctgat gcgtgaactg cacttcaaat    3360
acctggaaat actggcaattc gtctaagcgg ccgcgcacct acgcaacaaag gccatccatc    3420
cgtcaggatg gccttctgct taattatcta gatgcctggc agtttatggc gggcgtcctg    3480
cccgccaccc tccgggccgt tgcttcgcaa cgttcaaatc cgctcccggc ggatttgtcc    3540
tactcaggag agcgttcacc gacaaacaac agataaaacg aaaggcccag tctttcgact    3600
gagcctttcg ttttatttga tgcctggcag ttccctactc tcgcatgggg agaccccaca    3660
ctaccatcat gtatgaatat cctccttagt tcctattccg aagggtaatg gcatcaggga    3720
```

-continued

```
atggcgaacg cgctccccac actaccatca tgtatgaata tcctccttag ttcctattcc   3780
gaagttccta ttctctagaa agtataggaa cttcggtgga acgacgcgta actcacgtta   3840
agggattttg gtcatgatca gcacgtgttg acaattaatc atcggcatag tatatcggca   3900
tagtataata cgacaaggtg aggaactaaa ccatggccaa gttgaccagt gccgttccgg   3960
tgctcaccgc gcgcgacgtc gccggagcgg tcgagttctg gaccgaccgg ctcgggttct   4020
cccgggactt cgtggaggac gacttcgccg gtgtggtccg ggacgacgtg accctgttca   4080
tcagcgcggt ccaggaccag gtggtgccgg acaacaccct ggcctgggtg tgggtgcgcg   4140
gcctggacga gctgtacgcc gagtggtcgg aggtcgtgtc cacgaacttc cgggacgcct   4200
ccgggccggc catgaccgag atcggcgagc agccgtgggg gcgggagttc gccctgcgcg   4260
acccggccgg caactgcgtg cacttcgtgg ccgaggagca ggactgagtg gcagggcgag   4320
gcgtaaggcg cgccatttaa atgaagttcc tattccgaag ttcctattct ctagaaagta   4380
taggaacttc gaagcagctc cagcctacac aatcgctcaa gacggaaccc gcgcttggca   4440
ggaaagtaat agggatagca gctccagcct acacaatcgc tcaagacgtg taatgctgca   4500
caataaccct gctgcagagg cctgcagtca agcttggcgt aatcatggtc atagctgttt   4560
cctgtgtgaa attgttatcc gctcacaatt ccacacaaca tacgagccgg aagcataaag   4620
tgtaaagcct ggggtgccta atgagtgagc taactcacat taattgcgtt gcgctcactg   4680
cccgctttcc agtcgggaaa cctgtcgtgc cagctgcatt aatgaatcgg ccaacgcgcg   4740
gggagaggcg gtttgcgtat tgggcgctct tccgcttcct cgctcactga ctcgctgcgc   4800
tcggtcgttc ggctgcggcg agcggtatca gctcactcaa aggcggtaat acggttatcc   4860
acagaatcag gggataacgc aggaaagaac atgtgagcaa aaggccagca aaaggccagg   4920
aaccgtaaaa aggccgcgtt gctggcgttt ttccataggc tccgcccccc tgacgagcat   4980
cacaaaaatc gacgctcaag tcagaggtgg cgaaacccga caggactata aagataccag   5040
gcgtttcccc ctggaagctc cctcgtgcgc tctcctgttc cgaccctgcc gcttaccgga   5100
tacctgtccg cctttctccc ttcgggaagc gtggcgcttt ctcatagctc acgctgtagg   5160
tatctcagtt cggtgtaggt cgttcgctcc aagctgggct gtgtgcacga accccccgtt   5220
cagcccgacc gctgcgcctt atccggtaac tatcgtcttg agtccaaccc ggtaagacac   5280
gacttatcgc cactggcagc agccactggt aacaggatta gcagagcgag gtatgtaggc   5340
ggtgctacag agttcttgaa gtggtggcct aactacggct acactagaag aacagtattt   5400
ggtatctgcg ctctgctgaa gccagttacc ttcggaaaaa gagttggtag ctcttgatcc   5460
ggcaaacaaa ccaccgctgg tagcggtggt ttttttgttt gcaagcagca gattacgcgc   5520
agaaaaaaag gatctcaaga agatcctttg atcttttcta cggggtctga cgctcagtgg   5580
aacgaaaact cacgttaagg gattttggtc atgagattat caaaaaggat cttcacctag   5640
atccttttaa attaaaaatg aagttttaaa tcaatctaaa gtatatatga gtaaacttgg   5700
tctgacagtt accaatgctt aatcagtgag gcacctatct caccgatctg tctatttcgt   5760
tcatccatag ttgcctgact ccccgtcgtg tagataacta cgatacggga gggcttacca   5820
tctggcccca gtgctgcaat gataccgcga gacccacgct caccggctcc agatttatca   5880
gcaataaacc agccagccgg aagggccgag cgcagaagtg gtcctgcaac tttatccgcc   5940
tccatccagt ctattaattg ttgccgggaa gctagagtaa gtagttcgcc agttaatagt   6000
ttgcgcaacg ttgttgccat tgctacaggc atcgtggtgt cacgctcgtc gtttggtatg   6060
gcttcattca gctccggttc ccaacgatca aggcgagtta catgatcccc catgttgtgc   6120
aaaaaagcgg ttagctcctt cggtcctccg atcgttgtca gaagtaagtt ggccgcagtg   6180
ttatcactca tggttatggc agcactgcat aattctctta ctgtcatgcc atccgtaaga   6240
tgcttttctg tgactggtga gtactcaacc aagtcattct gagaatagtg tatgcggcga   6300
ccgagttgct cttgcccggc gtcaatacgg gataataccg cgccacatag cagaacttta   6360
aaagtgctca tcattggaaa acgttcttcg gggcgaaaac tctcaaggat cttaccgctg   6420
ttgagatcca gttcgatgta acccactcgt gcacccaact gatcttcagc atcttttact   6480
ttcaccagcg tttctgggtg agcaaaaaca ggaaggcaaa atgccgcaaa aaagggaata   6540
agggcgacac ggaaatgttg aatactcata ctcttccttt tcaatatta ttgaagcatt   6600
tatcagggtt attgtctcat gagcggatac atatttgaat gtatttagaa aaataaacaa   6660
ataggggttc cgcgcacatt ccccgaaaa gtgccacctg acgtctaaga aaccattatt   6720
atcatgacat taacctataa aaataggcgt atcacgaggc cctttcgtc              6769
```

```
SEQ ID NO: 17          moltype = DNA   length = 4714
FEATURE                Location/Qualifiers
misc_feature           1..4714
                       note = construct pACYC-waaX
source                 1..4714
                       mol_type = other DNA
                       organism = synthetic construct
SEQUENCE: 17
ggggaattgt gagcggataa caattcccct gtagaaataa ttttgtttaa ctttaataag   60
gagatatacc atgaaagtgt ttgtggtcaa cctggataag gataaggata aaaaagaaa   120
aatcaagaat gaatgccgca acgcagaact ggactatgaa attatctcag cagttgatgg   180
ccgtgaactg agctacaacg aactgaaatc taaggtccat ccggtgtcac tgaattatct   240
gtcgaaaggc gaaattggtt gcgtcctgtc ccaccagcgt atttacaaac gcatcctgga   300
tgacgatatt gactatgctc tgatcctgga agacgatgtg gaactgagtc aagatatcaa   360
ggttttctg aaggaattcc tgtccgtcaa agacaagaac aaaggcgatg tgtttctgct   420
gtacccgtca ggtctgcgtt tcctgaaccg tcgcatcaac gtgtcgcatg attatttctt   480
ttatgaagcg tacaacagct cttgtgccca cggttatatt atcagcaaca aagcggccaa   540
aaagctgatt cgcatcaata ccccgattat cctggttgca gatgcttggc tgtggttta   600
ccagatttct ctgctgaaag tgtatgttct gaacaaagaa ctggttcgtg catatgacgt   660
cgataaaagt ctgtccacca tcgaaacgga acgcagcctg ctgctggacg aaaaggaaa   720
gcatcagatg caaatcatca aaaagcaacc gctgtactac ctgatcaagt actaccacaa   780
gtacatccgt cgcctgttca tcaataagga taaataagaa ttcgagctcg gcgcgcctgc   840
aggtcgacaa gcttgcggcc gcataatgct taagtcgaac agaaagtaat cgtattgtac   900
acggccgcat aatcgaaatt aatacgactc actataggg aattgtgagc ggataacaat   960
tccccatctt agtatattag ttaagtataa gaaggagata tacatatggc agatctcaat   1020
tggatatcgg ccggccacgc gatcgctgac gtcggtaccc tcgagtctgg taaagaaacc   1080
gctgctgcga aatttgaacg ccagcacatg gactcgtcta ctagcgcagc ttaattaacc   1140
```

-continued

```
taggctgctg ccaccgctga gcaataacta gcataacccc ttggggcctc taaacgggtc    1200
ttgaggggtt ttttgctgaa acctcaggca tttgagaagc acacggtcac actgcttccg    1260
gtagtcaata aaccggtaaa ccagcaatag acataagcgg ctatttaacg accctgccct    1320
gaaccgacga ccgggtcgaa tttgctttcg aatttctgcc attcatccgc ttattatcac    1380
ttattcaggc gtagcaccag gcgtttaagg gcaccaataa ctgccttaaa aaaattacgc    1440
cccgccctgc cactcatcgc agtactgttg taattcatta agcattctgc cgacatggaa    1500
gccatcacag acggcatgat gaacctgaat cgccagcggc atcagcacct tgtcgccttg    1560
cgtataatat ttgcccatag tgaaacgggg ggcgaagaag ttgtccatat tggccacgtt    1620
taaatcaaaa ctggtgaaac tcacccaggg attggctgag acgaaaaaca tattctcaat    1680
aaacccttta gggaaatagg ccaggttttc accgtaacac gccacatctt gcgaatatat    1740
gtgtagaaac tgccggaaat cgtcgtggta ttcactccag agcgatgaaa acgtttcagt    1800
ttgctcatgg aaaacggtgt aacaagggtg aacactatcc catatcacca gctcaccgtc    1860
tttcattgcc atacggaact ccggatgagc attcatcagg cgggcaagaa tgtgaataaa    1920
ggccggataa aacttgtgct tattttctt tacggtcttt aaaaaggccg taatatccag     1980
ctgaacggtc tggttatagg tacattgagc aactgactga aatgcctcaa aatgttcttt    2040
acgatgccat tgggatatat caacggtggt atatccagtg attttttct ccattttagc     2100
ttccttagct cctgaaaatc tcgataactc aaaaaatacg cccggtagtg atcttatttc     2160
attatggtga aagttggaac ctcttacgtg ccgatcaacg tctcattttc gccaaaagtt    2220
ggcccagggc ttcccggtat caacagggac accaggattt atttattctg cgaagtgatc    2280
ttccgtcaca ggtatttatt cggcgcaaag tgcgtcgggt gatgctgcca acttactgat    2340
ttagtgtatg atggtgtttt tgaggtgctc cagtggcttc tgtttctatc agctgtccct    2400
cctgttcagc tactgacggg gtggtgcgta acggcaaaag caccgccgga catcagcgct    2460
agcggagtgt atactggctt actatgttgg cactgatgag ggtgtcagtg aagtgcttca    2520
tgtggcagga gaaaaaaggc tgcaccggtg cgtcagcaga atatgtgata caggatatat    2580
tccgcttcct cgctcactga ctcgctacgc tcggtcgttc gactgcggcg agcggaaatg    2640
gcttacgaac ggggcggaga tttcctggaa gatgccagga agatacttaa cagggaagtg    2700
agagggccgc ggcaaagccg ttttccata ggctccgccc ccctgacaag catcacgaaa     2760
tctgacgctc aaatcagtgg tggcgaaacc cgacaggact ataaagatac caggcgtttc    2820
ccctggcggc tccctcgtgc gctctcctgt tcctgccttt cggtttaccg gtgtcattcc    2880
gctgttatgg ccgcgtttgt ctcattccac gcctgacact cagttccggg taggcagttc    2940
gctccaagct ggactgtatg cacgaacccc ccgttcagtc cgaccgctgc gccttatccg    3000
gtaactatcg tcttgagtcc aacccggaaa gacatgcaaa agcaccactg gcagcagcca    3060
ctggtaattg atttagagga gttagtcttg aagtcatgcg ccggttaagg ctaaactgaa    3120
aggacaagtt ttggtgactg cgctcctcca agccagttac ctcggttcaa agagttggta    3180
gctcagagaa ccttcgaaaa accgccctgc aaggcggttt tttcgttttc agagcaagag    3240
attacgcgca gaccaaaacg atctcaagaa gatcatctta ttaatcagat aaaatatttc    3300
tagatttcag tgcaatttat ctcttcaaat gtagcacctg aagtcagccc catacgatat    3360
aagttgtaat tctcatgtta gtcatgcccc gcgcccaccg gaaggagctg actgggttga    3420
aggctctcaa gggcatcggt cgagatcccg gtgcctaatg agtgagctaa cttacattaa    3480
ttgcgttgcg ctcactgccc gctttccagt cgggaaacct gtcgtgccag ctgcattaat    3540
gaatcggcca acgcgcgggg agaggcggtt tgcgtattgg gcgccagggt ggtttttctt    3600
ttcaccagtg agacgggcaa cagctgattg cccttcaccg cctggccctg agagagttgc    3660
agcaagcggt ccacgctggt ttgccccagc aggcgaaaat cctgtttgat ggtggttaac    3720
ggcgggatat aacatgagct gtcttcggta tcgtcgtatc ccactaccga gatgtccgca    3780
ccaacgcgca gcccggactc ggtaatggcg cgcattgcgc ccagcgccat ctgatcgttg    3840
gcaaccagca tcgcagtggg aacgatgccc tcattcagca tttgcatggt ttgttgaaaa    3900
ccggacatgg cactccagtc gccttcccgt tccgctatcg gctgaatttg attgcgagtg    3960
agatatttat gccagccagc cagacgcaga cgcgccgaga cagaacttaa tgggcccgct    4020
aacagcgcga tttgctggtg acccaatgcg accagatgct ccacgcccag tcgcgtaccg    4080
tcttcatggg agaaaataat actgttgatg ggtgtctggt cagagacatc aagaaataac    4140
gccggaacat tagtgcaggc agcttccaca gcaatgacat cctggtcatc cagcggataa    4200
ttaatgatca gcccactgac gcgttgcgcg agaagattga tgcaccgccg tttacaggct    4260
tcgacgccgc ttcgttctac catcgacacc accacgctgg cacccagttg atcggcgcga    4320
gatttaatcc ccgcgacaat ttgcgacggc gcgtgcaggg ccagactgga ggtggcaacg    4380
ccaatcagca acgactgttt gcccgccagt tgttgtgcca cgcggttgga aatgtaattc    4440
agctccgcca tcgccgcttc cacttttttcc cgcgttttcg cagaaacgtg gctggcctgg    4500
ttcaccacgc gggaaacggt ctgataagag acaccggcat actctgcgac atcgtataac    4560
gttactggtt tcacattcac caccctgaat tgactctctt ccgggcgcta tcatgccata    4620
ccgcgaaagg ttttgcgcca ttcgatggtg tccgggatct cgacgctctc ccttatgcga    4680
ctcctgcatt aggaaattaa tacgactcac tata                                4714
```

```
SEQ ID NO: 18        moltype = DNA   length = 4760
FEATURE              Location/Qualifiers
misc_feature         1..4760
                     note = construct pACYC-wbdO
source               1..4760
                     mol_type = other DNA
                     organism = synthetic construct
SEQUENCE: 18
ggggaattgt gagcggataa caattcccct gtagaaataa ttttgtttaa ctttaataag     60
gagatatacc atgctgacgg aagtgcgccc ggtctctacg acgaaaccgc tggtgtctgt    120
gattctgccg gtgaacaaat tcaacccgta tctggatcgt gcaattcatt caatcctgag    180
tcagtcctat ccgtcgattg aactgattat cattgcaaac aattgcacca atgacttttt    240
cgatgctctg aaaaaacgtg aatgtgaaac cattaaagtg ctgcgcacga acatcgcgta    300
tctgccgtac tgcctgaata aaggcctgga tctgtgtaac ggtgactttg ttgcccgcat    360
ggattcagat gacatttcgc acccggaacg tatcgatcgc caggtcgact tcctgattaa    420
caatccggac atcgatgtgg ttggcaccaa tgcagtctat attgatgaag atgacatcga    480
actggaaaaa agcaacctgc cggtgaacaa taacgctatt cgtaaaatgc tgccgtataa    540
atgctgtctg gtgcatccgt ctgttatgtt tcgcaaaaat gtcgtgatca ccagcggcgg    600
```

```
ttacatgttc gcgaattatt ctgaagatta cgaactgtgg aaccgtctgg ccgttgaagg   660
ccgcaatttt tataacctga gcgaatacct gctgtattac cgtctgcaca ataaccaatc   720
aacgtcgaaa aataacctgt ttatggtgat ggcgaacgat gtcgccatta aagtgaaata   780
tttcctgctg accaagaaaa ttagctacct gctgggtatc attcgcacgg tctttctgt   840
gttctattgc aaatacatca aatgaattcg agctcggcgc gcctgcaggt cgacaagctt   900
gcggccgcat aatgcttaag tcgaacagaa agtaatcgta ttgtacacgg ccgcataatc   960
gaaattaata cgactcacta taggggaatt gtgagcggat aacaattccc catcttagta  1020
tattagttaa gtataagaag gagatataca tatggcagat ctcaattgga tatcggccgg  1080
ccacgcgatc gctgacgtcg gtaccctcga gtctggtaaa gaaaccgctg ctgcgaaatt  1140
tgaacgccag cacatggact cgtctactag cgcagcttaa ttaacctagg ctgctgccac  1200
cgctgagcaa taactagcat aacccctgg ggcctctaaa cgggtcttga ggggttttt  1260
gctgaaacct caggcatttg agaagcacac ggtcacactg cttccggtag tcaataaacc  1320
ggtaaaccag caatagacat aagcggctat ttaacgaccc tgccctgaac cgacgaccgg  1380
gtcgaatttg ctttcgaatt tctgccattc atccgcttat tatcacttat tcaggcgtag  1440
caccaggcgt ttaagggcac caataactgc cttaaaaaaa ttacgccccg ccctgccact  1500
catcgcagta ctgttgtaat tcattaagca ttctgccgac atggaagcca tcacagacgg  1560
catgatgaac ctgaatcgcc agcggcatca gcaccttgtc gccttgcgta taatatttgc  1620
ccatagtgaa aacggggggcg aagaagttgt ccatattggc cacgtttaaa tcaaaactgg  1680
tgaaactcac ccaggggattg gctgagacga aaaacatatt ctcaataaac cctttaggga  1740
aataggccag gttttcaccg taacacgcca catcttgcga atatatgtgt agaaactgcc  1800
ggaaatcgtc gtggtattca ctccagagcg atgaaaacgt ttcagtttgc tcatggaaaa  1860
cggtgtaaca agggtgaaca ctatcccata tcaccagctc accgtctttc attgccatac  1920
ggaactccgg atgagcattc atcaggcggg caagaatgtg aataaaggcc ggataaaact  1980
tgtgcttatt tttctttacg gtctttaaaa aggccgtaat atccagctga acggtctggt  2040
tataggtaca ttgagcaact gactgaaatg cctcaaaatg ttctttacga tgccattggg  2100
atatatcaac ggtggtatat ccagtgattt ttttctccat tttagcttcc ttagctcctg  2160
aaaatctcga taactcaaaa aatacgcccg gtagtgatct tatttcatta tggtgaaagt  2220
tggaacctct tacgtgccga tcaacgtctc attttcgcca aaagttggcc cagggcttcc  2280
cggtatcaac agggacacca ggatttattt attctgcgaa gtgatcttcc gtcacaggta  2340
tttattcggc gcaaagtgcg tcgggtgatg ctgccaactt actgatttag tgtatgatgg  2400
tgtttttgag gtgctccagt ggcttctgtt tctatcagct gtccctcctg ttcagctact  2460
gacggggtgg tgcgtaacgg caaaagcacc gccggacatc agcgctagcg gagtgtatac  2520
tggcttacta tgttggcact gatgagggtg tcagtgaagt gcttcatgtg gcaggagaaa  2580
aaaggctgca ccggtgcgtc agcagaatat gtgatacagg atatattccg cttcctcggt  2640
cactgactcg ctacgctcgg tcgttcgact gcggcgagcg gaaatggctt acgaacgggt  2700
cggagatttc ctggaagatg ccaggaagat acttaacagg gaagtgagag ggccgcggca  2760
aagccgtttt tccataggct ccgccccct gacaagcatc acgaaatctg acgctcaaat  2820
cagtggtggc gaaacccgac aggactataa agataccagg cgtttcccct ggcggctccc  2880
tcgtgcgctc tcctgttcct gcctttcggt ttaccggtgt cattccgctg ttatggccgc  2940
gtttgtctca ttccacgcct gacactcagt tccgggtagg cagttcgctc caagctggac  3000
tgtatgcacg aacccccgt tcagtccgac cgctgcgcct atccggtaa ctatcgtctt  3060
gagtccaacc cggaaagaca tgcaaaagca ccactggcag cagccactgg taattgattt  3120
agaggagtta gtcttgaagt catgcgccgg ttaaggctaa actgaaagga caagttttgg  3180
tgactgcgct cctccaagcc agttacctcg gttcaaagag ttggtagctc agagaacctt  3240
cgaaaaaccg ccctgcaagg cggttttttc gttttcagag caagagatta cgcgcagacc  3300
aaaacgatct caagaagatc atcttattaa tcagataaaa tatttctaga tttcagtgca  3360
atttatctct tcaaatgtag cacctgaagt cagccccata cgatataagt tgtaattctc  3420
atgttagtca tgccccgcgc ccaccggaag gagctgactg ggttgaaggc tctcaagggc  3480
atcggtcgag atcccggtgc ctaatgagtg agctaactta cattaattgc gttgcgctca  3540
ctgcccgctt tccagtcggg aaacctgtcg tgccagctgc attaatgaat cggccaacgc  3600
gcggggagag gcggtttgcg tattgggcgc caggtggt tttcttttca ccagtgagac  3660
gggcaacagc tgattgccct tcaccgcctg gccctgagag agttgcagca agcggtccac  3720
gctggtttgc cccagcaggc gaaaatcctg tttgatggtg gttaacggcg ggatataaca  3780
tgagctgtct tcggtatcgt cgtatcccac taccgagatg tccgcaccaa cgcgcagccc  3840
ggactcggta atggcgcgca ttgcgcccag cgccatctga tcgttggcaa ccagcatcgc  3900
agtgggaacg atgccctcat tcagcatttg catggtttgt tgaaaaccgg acatggcact  3960
ccagtcgcct tcccgttccg ctatcggctg aatttgattg cgagtgagat atttatgcca  4020
gccagccaga cgcagacgcg ccgagacaga acttaatggg cccgctaaca gcgcgatttg  4080
ctggtgaccc aatgcgacca gatgctccac gcccagtcgc gtaccgtctt catgggagaa  4140
aataatactg ttgatgggtg tctggtcaga gacatcaaga aataacgccg gaacattagt  4200
gcaggcagct tccacagcaa tggcatcctg gtcatccagc ggatagttaa tgatcagccc  4260
actgacgcgt tgcgcgagaa gattgtgcac cgccgcttta caggcttcga cgccgcttcg  4320
ttctaccatc gacaccacca cgctggcacc cagttgatcg gcgcgagatt taatcgccgc  4380
gacaatttgc gacggcgcgt gcagggccag actggaggtg gcaacgccaa tcagcaacga  4440
ctgtttgccc gccagttgtt gtgccacgcg gttgggaatg taattcagct ccgccatcgc  4500
cgcttccact ttttcccgcg ttttcgcaga aacgtggctg gcctggttca ccacgcggga  4560
aacggtctga taagagacac cggcatactc tgcgacatcg tataacgtta ctggtttcac  4620
attcaccacc ctgaattgac tctcttccgg cgctatcat gccataccgc gaaaggtttt  4680
gcgccattcg atggtgtccg gatctcgac gctctccctt atgcgactcc tgcattagga  4740
aattaatacg actcactata                                               4760
```

SEQ ID NO: 19          moltype = DNA  length = 4795
FEATURE                Location/Qualifiers
misc_feature           1..4795
                       note = construct pACYC-furA
source                 1..4795
                       mol_type = other DNA
                       organism = synthetic construct

SEQUENCE: 19

```
ggggaattgt gagcggataa caattcccct gtagaaataa ttttgtttaa ctttaataag   60
gagatatacc atggataaaa tcaaacaggg cagcgcctct ctggttgtcg gtgaccagca  120
agaaaaacat ccggtggttt cagtgctgct gccggttaat cgtgtcgatc gcttttttcat  180
tccggcagtt gaatcgatcc tgacccaaac gctgcaggat tttgaactga tcattatcgc  240
taatgcgtgt agcaccgaac atctgaacaa aattcgtctg acgtatggtg atcacaatcg  300
tgttcgcatt ctgaacaccg aaatcaaagg cctgccgttt gcgctgaatc tgggcgtgca  360
caacgcccgt ggtctgtata ttgcacgcat ggatgctgat gacatttcta tcccggaacg  420
cctggaaaaa caactgaata cgctggaaca gaacaagaaa attggcgtcg tgagctctgg  480
tgtggacttt attgatgaaa atgaccaggc gatccgtgag ggtaaattcc cggaactgac  540
cgacaaagat catcgtcgcc tgctgccgct gatttgctgt atcgcccacc cgacggttat  600
ggtccgcaaa gaaattatca acaaactggg cggttatagt tttggtagtt tctccgaaga  660
ctacgatctg tggctgcgta ttatgcgcga actgccggaa gttgaatttt atcgtatccc  720
ggaatccctg ctgaaatacc gtcgccatgg caatcaggcc accagttcca aaaacattaa  780
gaaaattcgc gcgtacaact cagccctgaa aattcgtgaa ctgtttctgt cgcgcaaact  840
gaaattcatt atcggtatta tcctgccggc acgtatggtg accctgtggc gcaaatgaga  900
attcgagctc ggcgcgcctg caggtcgaca agcttgcggc cgcataatgc ttaagtcgaa  960
cagaaagtaa tcgtattgta cacggccgca taatcgaaat taatacgact cactataggg 1020
gaattgtgag cggataacaa ttccccatct tagtatatta gttaagtata agaaggagat 1080
atacatatgg cagatctcaa ttggatatcg gccggccacg cgatcgctga cgtcggtacc 1140
ctcgagtctg gtaaagaaac cgctgctgcg aaatttgaac gccagcacat ggactcgtct 1200
actagcgcag cttaattaac ctaggctgct gccaccgctg agcaataact agcataaccc 1260
cttggggcct ctaaacgggt cttgagggt tttttgctga aacctcaggc atttgagaag 1320
cacacggtca cactgcttcc ggtagtcaat aaaccggtaa accagcaata gacataagcg 1380
gctatttaac gaccctgccc tgaaccgacg accgggtcga atttgctttc gaatttctgc 1440
cattcatccg cttattatca cttattcagg cgtagcacca ggcgtttaag ggcaccaata 1500
actgccttaa aaaaattacg ccccgccctg ccactcatcg cagtactgtt gtaattcatt 1560
aagcattctg ccgacatgga agccatcaca gacggcatga tgaacctgaa tcgccagcgg 1620
catcagcacc ttgtcgcctt gcgtataata tttgcccata gtgaaaacgg gggcgaagaa 1680
gttgtccata ttggccacgt ttaaatcaaa actggtgaaa ctcacccagg gattggctga 1740
gacgaaaaac atattctcaa taaacccttt agggaaatag gccaggtttt caccgtaaca 1800
cgccacatct tgcgaatata tgtgtagaaa ctgccggaaa tcgtcgtggt attcactcca 1860
gagcgatgaa aacgtttcag tttgctcatg gaaaacggtg taacaagggt gaacactatc 1920
ccatatcacc agctcaccgt ctttcattgc catacggaac tccggatgag cattcatcag 1980
gcgggcaaga atgtgaataa aggccggata aaacttgtgc ttattttct ttacggtctt 2040
taaaaaggcc gtaatatcca gctgaacggt ctggttgtat gtacattgag caactgactg 2100
aaatgcctca aaatgttctt tacgatgcca ttgggatata tcaacggtgg tatatccagt 2160
gatttttttc tccattttag cttccttagc tcctgaaaat ctcgataact caaaaaatac 2220
gcccggtagt gatcttattt cattatggtg aaagttggaa cctcttacgt gccgatcaac 2280
gtctcatttt cgccaaaagt tggcccaggg cttcccggta tcaacaggga caccaggatt 2340
tatttattct gcgaagtgat cttccgtcac aggtatttat tcggcgcaaa gtgcgtcggg 2400
tgatgctgcc aacttactga tttagtgtat gatggtgttt ttgaggtgct ccagtggctt 2460
ctgtttctat cagctgtccc tcctgttcag ctactgacgg ggtggtgcgt aacggcaaaa 2520
gcaccgccgg acatcagcgc tagcggagtg tatactgact tactatgttg gcactgatga 2580
gggtgtcagt gaagtgcttc atgtggcagg agaaaaaagg ctgcaccggt gcgtcagcag 2640
aatatgtgat acaggatata ttccgcttcc tcgctcactg actcgctacg ctcggtcgtt 2700
cgactgcggc gagcggaaat ggcttacgaa cggggcggag atttcctgga agatgccagg 2760
aagatactta acagggaagt gagagggccg cggcaaagcc gtttttccat aggctccgcc 2820
cccctgacaa gcatcacgaa atctgacgct caaatcagtg gtggcgaaac ccgacaggac 2880
tataaagata ccaggcgttt cccctggcgg ctccctcgtg cgctctcctg ttcctgcctt 2940
tcggtttacc ggtgtcattc cgctgttatg ccgcgtttg tctcattcca cgcctgacac 3000
tcagttccgg gtaggcagtt cgctccaagc tggactgtat gcacgaaccc cccgttcagt 3060
ccgaccgctg cgccttatcc ggtaactatc gtcttgagtc caacccggaa agacatgcaa 3120
aagcaccact ggcagcagcc actggtaatt gatttagagg agttagtctt gaagtcatgc 3180
gccggttaag gctaaactga aaggacaagt tttggtgact gcgctcctcc aagccagtta 3240
cctcggttca aagagttggt agctcagaga accttcgaaa aaccgccctg caaggcggtt 3300
ttttcgtttt cagagcaaga gattacgcgc agaccaaaac gatctcaaga agatcatctt 3360
attaatcaga taaaatattt ctagatttca gtgcaattta tctcttcaaa tgtagcacct 3420
gaagtcagcc ccatacgata taagttgtaa ttctcatgtt agtcatgccc cgcgcccacc 3480
ggaaggagct gactgggttg aaggctctca agggctccgg tcgagatccc ggtgcctaat 3540
gagtgagcta acttacatta attgcgttgc gctcactgcc cgctttccag tcgggaaacc 3600
tgtcgtgcca gctgcattaa tgaatcggcc aacgcgcggg gagaggcggt ttgcgtattg 3660
ggcgccaggc tggtttttct tttcaccagt gagacgggca acagctgatt gcccttcacc 3720
gcctggccct gagagagttg cagcaagcgg tccacgctgg tttgcccag caggcgaaaa 3780
tcctgtttga tggtggttaa cggcgggata acatgcggtg tgtcttcggt atcgtcgtat 3840
cccactaccg agatgtccgc accaacgcgc agcccggact cggtaatggc gcgcattgcg 3900
cccagcgcca tctgatcgtt ggcaaccagc atcgcagtgg gaacgatgcc ctcattcagc 3960
atttgcatgg tttgttgaaa accggacatg gcactccagt cgccttcccg ttccgctatc 4020
ggctgaattt gattgcgagt gagatattta tgccagccag ccagacgcag acgcgccgag 4080
acagaactta atgggcccgc taacagcgcg atttgctggt gacccaatgc gaccagatgc 4140
tccacgccca gtcgcgtacc gtcttcatgg gagaaaataa tactgttgat gggtgtctgg 4200
tcagagacat caagaaataa cgccggaaca ttagtgcagg cagcttccac agcaatggca 4260
tcctggtcat ccagcggata gttaatgatc agcccactga cgcgttgcgc gagaagattg 4320
tgcaccgccg ctttacaggc ttcgacgccg cttcgttcta ccatcgacac caccacgctg 4380
gcacccagtt gatcggcgcg agatttaatc gccgcgacaa tttgcgacgg cgcgtgcagg 4440
gccagactgg aggtggcaac gccaatcagc aacgactgtt tgcccgccag ttgttgtgcc 4500
acgcggttgg gaatgtaatt cagctccgcc atcgccgctt ccactttttc ccgcgttttc 4560
gcagaaacgg ggctggcctg gttcaccacg cgggaaacgg tctgataaga gacaccggca 4620
tactctgcga catcgtataa cgttactggt ttcacattca ccaccctgaa ttgactctct 4680
tccgggcgct atcatgccat accgcgaaag gttttgcgc attcgatggt gtccgggatc 4740
```

-continued

```
tcgacgctct cccttatgcg actcctgcat taggaaatta atacgactca ctata         4795

SEQ ID NO: 20          moltype = DNA   length = 6383
FEATURE                Location/Qualifiers
misc_feature           1..6383
                       note = construct pET-PmnagT
source                 1..6383
                       mol_type = other DNA
                       organism = synthetic construct
SEQUENCE: 20
ggggaattgt gagcggataa caattcccct ctagaaataa ttttgtttaa ctttaagaag      60
gagatatacc atgggcagca gccatcacca tcatcaccac agccaggatc cgaattcgag     120
ctcggcgcgc ctgcaggtcg acaagcttgc ggccgcataa tgcttaagtc gaacagaaag     180
taatcgtatt gtacacggcc gcataatcga aattaatacg actcactata ggggaattgt     240
gagcggataa caattcccca tcttagtata ttagttaagt ataagaagga gatacatata     300
tggaaaataa acctttagtt tcagttttga tttgtgctta taatgtcgag aaatatattg     360
aagaatgtat taatgcagtg attaatcaga catataagaa cttagaaatt attattgtga     420
atgatggttc ttctgataat acttattttc ttttaaaaaa gttagctgaa aaagataatc     480
gtataaaaat attaaatttc aataatcata ttggaataat ttctgcttta aatgaaggtt     540
taaaagagat agctggagaa tatattgctc gaacagattc tgatgatata actaagccag     600
attggattga gaaaatatta acttgtatgc aaaatgatcc taaaatcatc gctatgggat     660
cttatcttac tgtcttgtca gaagaaaata atggtagtgt gcttgctaat catcataaaa     720
ataaagttga atggaaaaat ccattagagc acaaagatat tgttgagaaa atgttatttg     780
gtaatcctat tcataataat tcaatggtta tgagaagtga gatatataca aagtatcact     840
taatttatga tccagattat cattatgctg aagattataa attttggctg gaagttagtc     900
gaattgggaa attagcaaat tatcctgagt cactcgttata ttatagactt caccgaaatc     960
aaacatcttc tattcataat agccaacaag aaatataatgg taaaaaatta cgtttacaag    1020
ctcttaatta ttatttaaaa gatcttggta ttgattatca gttacctgaa aaattttat     1080
tcaaagatat agcgttattg caagaaatat tttatgaacg aggtatgttt agagaaaata    1140
taataaggcg tatcatctac gaatgttatc tttccttggg agagtataat tataaagata    1200
tttattattt tttaataaat aaaaataact ttctttctat aaaagacaaa tttaaaataa    1260
taaaaaaata tcttcgtcct gataaatatt catctactta ttaggacgtc ggtaccctcg    1320
agtctggtaa agaaaccgct gctgcgaaat ttgaacgcca gcacatggac tcgtctacta    1380
gcgcagctta attaacctag gctgctgcca ccgctgagca ataactagca taacccttg     1440
gggcctctaa acgggtcttg aggggttttt tgctgaaagg aggaactata tccggattgg    1500
cgaatgggac gcgccctgta gcggcgcatt aagcgcggcg ggtgtggtgg ttacgcgcag    1560
cgtgaccgct acacttgcca gcgccctagc gcccgctcct ttcgctttct tcccttcctt    1620
tctcgccacg ttcgccggct ttccccgtca agctctaaat cgggggctcc ctttagggtt    1680
ccgatttagt gctttacggc acctcgaccc caaaaaactt gattagggtg atggttcacg    1740
tagtgggcca tcgccctgat agacggtttt tcgccctttg acgttggagt ccacgttctt    1800
taatagtgga ctcttgttcc aaactggaac aacactcaac cctatctcgg tctattcttt    1860
tgatttataa gggattttgc cgatttcggc ctattggtta aaaaatgagc tgatttaaca    1920
aaaatttaac gcgaatttta acaaaatatt aacgtttaca atttctggcg cacgatggc     1980
atgagattat caaaaaggat cttcacctag atcctttaa attaaaaatg aagtttttaaa    2040
tcaatctaaa gtatatatga gtaaacttgg tctgacagtt accaatgctt aatcagtgag    2100
gcacctatct cagcgatctg tctatttcgt tcatccatag ttgcctgact ccccgtcgtg    2160
tagataacta cgatacggga gggcttacca tctggcccca gtgctgcaat gataccgcga    2220
gacccacgct caccggctcc agatttatca gcaataaacc agccagccgg aagggccgag    2280
cgcagaagtg gtcctgcaac tttatccgcc tccatccagt ctattaattg ttgccgggaa    2340
gctagagtaa gtagttcgcc agttaatagt ttgcgcaacg ttgttgccat tgctacaggc    2400
atcgtggtgt cacgctcgtc gtttggtatg gcttcattca gctccggttc ccaacgatca    2460
aggcgagtta catgatcccc catgttgtgc aaaaaagcgg ttagctcctt cggtcctccg    2520
atcgttgtca gaagtaagtt ggccgcagtg ttatcactca tggttatggc agcactgcat    2580
aattctctta ctgtcatgcc atccgtaaga tgcttttctg tgactggtga gtactcaacc    2640
aagtcattct gagaatagtg tatgcggcga ccgagttgct cttgcccggc gtcaatacgg    2700
gataataccg cgccacatag cagaacttta aaagtgctca tcattggaaa acgttcttcg    2760
gggcgaaaac tctcaaggat cttaccgctg ttgagatcca gttcgatgta acccactcgt    2820
gcacccaact gatcttcagc atcttttact ttcaccagcg tttctgggtg agcaaaaaca    2880
ggaaggcaaa atgccgcaaa aaagggaata agggcgacac ggaaatgttg aatactcata    2940
ctcttccttt ttcaatcatg attgaagcat ttatctgggt tattgtctca tgagcggata    3000
catatttgaa tgtatttaga aaaataaaca ataggtcat gaccaaaatc ccttaacgtg    3060
agttttcgtt ccactgagcg tcagacccg tagaaaagat caaaggatct cttgagatc     3120
cttttttct gcgcgtaatc tgctgcttgc aaacaaaaaa accaccgcta ccagcggtgg    3180
tttgtttgcc ggatcaagag ctaccaactc tttttccgaa ggtaactggc ttcagcagga    3240
cgcagatacc aaatactgtc cttctagtgt agccgtagtt aggccaccac ttcaagaact    3300
ctgtagcacc gcctacatac ctcgctctgc taatcctgtt accagtggct gctgccagtg    3360
gcgataagtc gtgtcttacc gggttggact caagacgata gttaccggat aaggcgcagc    3420
ggtcgggctg aacggggggt tcgtgcacac agcccagctt ggagcgaacg acctacaccg    3480
aactgagata cctacagcgt gagctatgag aaagcgccac gcttcccgaa gggagaaagg    3540
cggacaggta tccggtaagc ggcagggtcg aacaggagag cgcacgagg gagcttccag     3600
ggggaaacgc ctggtatctt tatagtcctg tcgggtttcg ccacctctga cttgagcgtc    3660
gatttttgtg atgctcgtca ggggggcgga gcctatggaa aaacgccagc aacgcggcct    3720
ttttacggtt cctggccttt tgctggcctt ttgctcacat gttctttcct gcgttatccc    3780
ctgattctgt ggataaccgt attaccgcct ttgagtgagc tgataccgct cgccgcagcc    3840
gaacgaccga gcgcagcgag tcagtgagcg aggaagcgga agagcgcctg atgcggtatt    3900
ttctccttac gcatctgtgc ggtatttcac accgcatata tggtgcactc tcagtacaat    3960
ctgctctgat gccgcatagt taagccagta tacactccgc tatcgctacg tgactgggtc    4020
atggctgcgc cccgacaccc gccaacaccc gctgacgcgc cctgacgggc ttgtctgctc    4080
ccggcatccg cttacagaca agctgtgacc gtctccggga gctgcatgtg tcagaggttt    4140
```

```
tcaccgtcat caccgaaacg cgcgaggcag ctgcggtaaa gctcatcagc gtggtcgtga   4200
agcgattcac agatgtctgc ctgttcatcc gcgtccagct cgttgagttt ctccagaagc   4260
gttaatgtct ggcttctgat aaagcgggcc atgttaaggg cggttttttc ctgtttggtc   4320
actgatgcct ccgtgtaagg gggatttctg ttcatggggg taatgatacc gatgaaacga   4380
gagaggatgc tcacgatacg ggttactgat gatgaacagc cccggttact ggaacgttgt   4440
gagggtaaac aactggccgt atggatgcgg cgggaccaga gaaaaatcac tcagggtcaa   4500
tgccagcgct tcgttaatac agatgtaggt gttccacagg gtagccagca gcatcctgcg   4560
atgcagatcc ggaacataat ggtgcagggc gctgacttcc gcgtttccag actttacgaa   4620
acacggaaac cgaagaccat tcatgttgtt gctcaggtcg cagacgtttt gcagcagcag   4680
tcgcttcacg ttcgctcgcg tatcggtgat tcattctgct aaccagtaag gcaaccccgc   4740
cagcctagcc gggtcctcaa cgacaggagc acgatcatgc tagtcatgcc ccgcgcccac   4800
cggaaggagc tgactgggtt gaaggctctc aagggcatcg gtcgagatcc cggtgcctaa   4860
tgagtgagct aacttacatt aattgcgttg cgctcactgc ccgctttcca gtcgggaaac   4920
ctgtcgtgcc agctgcatta atgaatcggc caacgcgcgg ggagaggcgg tttgcgtatt   4980
gggcgccagg gtggtttttc ttttcaccag tgagacgggc aacagctgat tgcccttcac   5040
cgcctggccc tgagagagtt gcagcaagcg gtccacgctg gtttgcccca gcaggcgaaa   5100
atcctgtttg atggtggtta acggcgggat ataacatgag ctgtcttcgg tatcgtcgta   5160
tcccactacc gagatgtccg caccaacgcg cagcccggac tcggtaatgg cgcgcattgc   5220
gcccagcgcc atctgatcgt tggcaaccag catcgcagtg ggaacgatgc cctcattcag   5280
catttgcatg gtttgttgaa aaccggacat ggcactccag tcgccttccc gttccgctat   5340
cggctgaatt tgattgcgag tgagatattt atgccagcca gccagacgca gacgcgccga   5400
gacagaactt aatgggcccg ctaacagcgc gatttgctgg taaccccaatg cgaccagatg   5460
ctccacgccc agtcgcgtac cgtcttcatg ggagaaaata atactgttga tgggtgtctg   5520
gtcagagaca tcaagaaata acgccggaac attagtgcag gcagcttcca cagcaatggc   5580
atcctggtca tccagcggat agttaatgat cagcccactg acgcgttgcg cgagaagatt   5640
gtgcaccgcc gctttacagg cttcgacgcc gcttcgttct accatcgaca ccaccacgct   5700
ggcacccagt tgatcggcgc gagatttaat cgccgcgaca atttgcgacg gcgcgtgcag   5760
ggccagactg gaggtggcaa cgccaatcag caacgactgt ttgcccgcca gttgttgtgc   5820
cacgcggttg ggaatgtaat tcagctccgc catcgccgct tccactttttt cccgcgtttt   5880
cgcagaaacg tggctggcct ggttcaccac gcgggaaacg gtctgataag agacaccggc   5940
atactctgcg acatcgtata acgttactgg tttcacattc accaccctga attgactctc   6000
ttccgggcgc tatcatgcca taccgcgaaa ggttttgcgc cattcgatgg tgtccgggat   6060
ctcgacgctc tcccttatgc gactcctgca ttaggaagca gcccagtagt aggttgaggc   6120
cgttgagcac cgccgccgca aggaatggtg catgcaagga gatggcgccc aacagtcccc   6180
cggccacggg gcctgccacc atacccacgc cgaaacaagc gctcatgagc ccgaagtggc   6240
gagcccgatc ttccccatcg gtgatgtcgg cgatataggc gccagcaacc gcacctgtgg   6300
cgccggtgat gccggccacg atgcgtccgg cgtagaggat cgagatcgat ctcgatcccg   6360
cgaaattaat acgactcact ata                                         6383
```

```
SEQ ID NO: 21        moltype = DNA  length = 6711
FEATURE              Location/Qualifiers
misc_feature        1..6711
                     note = construct pINT-yjhB
source              1..6711
                     mol_type = other DNA
                     organism = synthetic construct
SEQUENCE: 21
tcgcgcgttt cggtgatgac ggtgaaaacc tctgacacat gcagctcccg gagacggtca   60
cagcttgtct gtaagcggat gccgggagca gacaagcccg tcaggcgcg tcagcgggtg   120
ttggcgggtg tcgggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgaagatcct ttgatctttt   420
ctacggggtc tgacgctcag tggaacgaaa actcacgtta gtcatgagat   480
tatcaaaaag gatcttcacc tagatccttt taaactagtg aagttaccat cacggaaaaa   540
ggttatgctg cttttaagac ccactttcac atttaagttg ttttttctaat ccgcatatga   600
tcaattcaag gccgaataag aaggctggct ctgcaccttg gtgatcaaat aattcgatag   660
cttgtcgtaa taatggcggc atactatcag tagtaggtgt ttcccttttct tctttagcga   720
cttgatgctc ttgatcttcc aatacgcaac ctaaagtaaa atgccccact gcgctgagtg   780
catataatgc attctctagt gaaaaacctt gttggcataa aaaggctaat tgattttttcga   840
gagtttcata ctgttttttct gtaggccgtg tacctaaatg tacttttgct ccatcgcgat   900
gacttagtaa agcacatcta aaactttttag cgttattacg taaaaaatct tgccagcttt   960
cccttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttcctttttt caatattatt   1200
gaagcatttta tcagggttat tgtctcatga gcggatacat atttgaatgt atttagaaaa   1260
ataaacaaat aggggttccg cgcacatttc cccgaaaagt gccacctgaa attggcccaga   1320
tgattaattc ctaattttttg ttgacactct atcattgata gagttattttt accactccct   1380
atcagtgata gagaaaagtg aaatgaatag ttcgacaaaa atctagaaat aattttgttt   1440
aactttaaga aggagatata caagagctcg agtcgaagga gatagaacca tggcaacagc   1500
atggtataaa caagttaatc caccacaacg gaaagctctt ttttccgcat ggcttggata   1560
tgtatttgat cgctttgatt ttattttacat cttcatatta taaaagcaga   1620
tcttggcatt acgatattc aggctacttt aatagggaca gtggccttca tagccagacc   1680
tattggaggg ggtttttttg gtgccatggc tgataaatat ggtcgtaagc caatgatgat   1740
gtgggcaatt ttcatttact cagtcggaac aggccttagc ggtattgcta caaacttata   1800
tatgctcgca gtttgccgtt ttattgttgg cttaggatg tctggtgaat atgcatgtgc   1860
ttcaacttat gcggtagaaa gttggcctaa aaatcttcaa tctaaagcta gtgctttttt   1920
```

-continued

```
ggtaagtggt ttttctgttg gaaatattat tgcggcacaa ataatccctc agtttgctga    1980
agtatatgga tggagaaact cttttttttat aggcctgtta ccagttttac tagttctttg   2040
gatcagaaaa agtgctccag aaagtcagga gtggattgaa gataaatata aggataaatc    2100
aacatttttg tctgtcttca gaaaaccaca tctttcaatc tctatgatcg ttttcctcgt    2160
ctgtttttgt ctatttggtg caaactggcc gataaacgga ctacttcctt cctacctggc    2220
agataatgga gttaatacag tggtcatttc aactctgatg acaatagcag gtttaggaac    2280
actgacaggt acaatatttt ttggtttttgt tggtgataag attggtgtaa aaaaagcctt    2340
tgtagtcggt ctaataactt catttatttt cctttgtcct ctttttttta tttctgtgaa     2400
aaactcttct cttataggat tatgtctctt tggattaatg tttacaaatt taggtattgc     2460
agggttggtt ccaaaattta tatatgatta ctttccaaca aaattaagag gattagggac     2520
cggtcttatt tataacttag gggcaactgg aggaatggcc gcacctgtat tagctacata     2580
catttcagga tattatggct taggtgtttc attattcatt gttacggttg cattctctgc     2640
cttattaatt ttgttagttg gttttgatat tccaggtaaa atttataaac tatccgtggc     2700
taaatgataa atcgatacta gcataacccc ttggggcctc taaacgcgtc gacacgcaaa     2760
aaggccatcc gtcaggatgg ccttctgctt aatttgatgc ctggcagttt atggcgggcg     2820
tcctgcccgc caccctccgg gccgttgctt cgcaacgttc aaatccgctc ccggcggatt     2880
tgtcctactc aggagagcgt tcaccgacaa acaacagata aaacgaaagg cccagtcttt     2940
cgactgagcc tttcgtttta tttgatgcct ggcagttccc tactctcgca tggggagacc     3000
ccacactacc atcatgtatg aatatcctcc ttagttccta ttccgaagtt cctattctct     3060
agaaagtata ggaacttcgg cgcgtcctac ctgtgacgga agatcacttc gcagaataaa     3120
taaatcctgg tgtccctgtt gataccggga agccctgggc caacttttgg cgaaaatgag     3180
acgttgatcg gcacgtaaga ggtccaact ttcaccataa tgaaataaga tcactaccgg      3240
gcgtattttt tgagttgtcg agattttcag gagctaagga agctaaaatg gagaaaaaaa     3300
tcactggata taccaccgtt gatatatccc aatggcatcg taaagaacat tttgaggcat     3360
ttcagtcagt tgctcaatgt acctataacc agaccgttca gctggatatt acggcctttt     3420
taaagaccgt aaagaaaaat aagcacaagt tttatccggc ctttattcac attcttgccc     3480
gcctgatgaa tgctcatccg gaattacgta tggcaatgaa agacggtgag ctggtgatat     3540
gggatagtgt tcacccttgt tacaccgttt tccatgagca aactgaaacg ttttcatcgc      3600
tctggagtga ataccacgac gatttccggc agtttctaca catatattcg caagatgtgg      3660
cgtgttacgg tgaaaacctg gcctatttcc ctaaagggtt tattgagaat atgtttttcg      3720
tctcagccaa tccctgggtg agtttcacca gttttgattt aaacgtggcc aatatggaca     3780
acttcttcgc ccccgttttc accatgggca aatattatac gcaaggcgac aaggtgctga     3840
tgccgctggc gattcaggtt catcatgccg tttgtgatgg cttccatgtc ggcagatgct     3900
taatgaatac aacagtactg cgatgagtgg cagggcgggg cgtaaggcgc gccatttaaa     3960
tgaagttcct attccgaagt tcctattctc tagaaagtat aggaacttcg aagcagctcc     4020
agcctacaca atcgctcaag acgtgtaatg ctgcaatctg catgcaagct tggcactggc     4080
cacgcaaaaa ggccatccgt caggatggcc ttctgcttaa tttgatgcct ggcagtttat     4140
ggcgggcgtc ctgcccgcca ccctccgggc cgttgcttcg caacgttcaa atccgctccc      4200
ggcggatttg tcctactcag gagagcgttc accgacaaac aacagataaa acgaaaggcc      4260
cagtctttcg actgagcctt tcgttttatt tgatgcctgg cagttcccta ctctcgcatg      4320
gggagacccc acactaccat cggggggcca tcgatgcagg tggcactttt cggggaaatg     4380
tgcgcggaac ccctatttgt ttatttttct aaatacattc aaatatgtat ccgctcatga     4440
gacaataacc ctgctgcaga ggcctgcatg caagcttggc gtaatcatgg tcatagctgt     4500
ttcctgtgtg aaattgttat ccgctcacaa ttccacacaa catacgagcc ggaagcataa     4560
agtgtaaagc ctggggtgcc taatgagtga gctaactcac attaattgcg ttgcgctcac     4620
tgcccgcttt ccagtcggga aacctgtcgt gccagctgca ttaatgaatc ggccaacgcg     4680
cggggagagg cggtttgcgt attgggcgct cttccgcttc ctcgctcact gactcgctgc     4740
gctcggtcgt tcggctgcgg cgagcggtat cagctcactc aaaggcggta atacggttat     4800
ccacagaatc aggggataac gcaggaaaga acatgtgagc aaaaggccag caaaaggcca     4860
ggaaccgtaa aaaggccgcg ttgctggcgt ttttccatag gctccgcccc cctgacgagc     4920
atcacaaaaa tcgacgctca agtcagaggt ggcgaaaccc gacaggacta taaagatacc     4980
aggcgtttcc ccctggaagc tccctcgtgc gctctcctgt tccgaccctg ccgcttaccg     5040
gatacctgtc cgcctttctc ccttcgggaa gcgtggcgct ttctcatagc tcacgctgta     5100
ggtatctcag ttcggtgtag gtcgttcgct ccaagctggg ctgtgtgcac gaaccccccg     5160
ttcagcccga ccgctgcgcc ttatccggta actatcgtct tgagtccaac ccggtaagac     5220
acgacttatc gccactggca gcagccactg gtaacaggat tagcagagcg aggtatgtag      5280
gcggtgctac agagttcttg aagtggtggc ctaactacgg ctacactaga agaacagtat     5340
ttggtatctg cgctctgctg aagccagtta ccttcggaaa aagagttggt agctcttgat     5400
ccggcaaaca aaccaccgct ggtagcggtg gtttttttgt ttgcaagcag cagattacgc      5460
gcagaaaaaa aggatctcaa gaagatcctt tgatcttttc tacggggtct gacgctcagt     5520
ggaacgaaaa ctcacgttaa gggattttgg tcatgagatt atcaaaaagg atcttcacct     5580
agatcctttt aaattaaaaa tgaagtttta aatcaatcta agtatatat gagtaaactt      5640
ggtctgacag ttaccaatgc ttaatcagtg aggcacctat ctcagcgatc tgtctatttc     5700
gttcatccat agttgcctga ctccccgtcg tgtagataac tacgatacgg gagggcttac     5760
catctggccc cagtgctgca atgataccgc gagacccacg ctcaccggct ccagatttat      5820
cagcaataaa ccagccagcc ggaagggccg agcgcagaag tggtcctgca actttatccg      5880
cctccatcca gtctattaat tgttgccggg aagctagagt aagtagttcg ccagttaata      5940
gtttgcgcaa cgttgttgcc attgctacag gcatcgtggt gtcacgctcg tcgtttggta     6000
tggcttcatt cagctccggt tcccaacgat caaggcgagt tacatgatcc cccatgttgt     6060
gcaaaaaagc ggttagctcc ttcggtcctc cgatcgttgt cagaagtaag ttggccgcag     6120
tgttatcact catggttatg gcagcactgc ataattctct tactgtcatg ccatccgtaa     6180
gatgcttttc tgtgactggt gagtactcaa ccaagtcatt ctgagaatag tgtatgcggc     6240
gaccgagttg ctcttgcccg gcgtcaatac gggataatac cgcgccacat agcagaactt     6300
taaaagtgct catcattgga aaacgttctt cggggcgaaa actctcaagg atcttaccgc      6360
tgttgagatc cagttcgatg taacccactc gtgcacccaa ctgatcttca gcatctttta     6420
ctttcaccag cgtttctggg tgagcaaaaa caggaaggca aaatgccgca aaaaagggaa     6480
taagggcgac acggaaatgt tgaatactca tactcttcct ttttcaatat tattgaagca     6540
tttatcaggg ttattgtctc atgagcggat acatatttga atgtatttag aaaaataaac     6600
aaataggggt tccgcgcaca tttccccgaa aagtgccacc tgacgtctaa gaaaccatta     6660
```

-continued

```
ttatcatgac attaacctat aaaaataggc gtatcacgag gcccttttcgt c          6711

SEQ ID NO: 22          moltype = DNA   length = 6867
FEATURE                Location/Qualifiers
misc_feature           1..6867
                       note = construct pINT-yebQ
source                 1..6867
                       mol_type = other DNA
                       organism = synthetic construct
SEQUENCE: 22
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg  120
ttggcgggtg tcgggctgg cttaactatg cggcatcaga gcagattgta ctgagagtgc  180
accatatgcg gtgtgaaata ccgcacagat gcgtaaggag aaaataccgc atcaggcgcc  240
attcgccatt caggctgcgc aactgttggg aagggcgatc ggtgcgggcc tcttcgctat  300
tacgccagct ggcgaaaggg ggatgtgctg caaggcgatt aagttgggta acgccagggt  360
tttcccagtc acgacgttgt aaaacgacgg ccagtgaatt cgagatcct ttgatctttt  420
ctacggggtc tgacgctcag tggaacgaaa actcacgtta agggattttg gtcatgagat  480
tatcaaaaag gatcttcacc tagatccttt taaactagtg aagttaccat cacggaaaaa  540
ggttatgctg cttttaagac ccactttcac atttaagttg tttttctaat ccgcatatga  600
tcaattcaag gccgaataag aaggctggct ctgcaccttg gtgatcaaat aattcgatag  660
cttgtcgtaa taatggcggc atactatcag tagtaggtgt ttccctttct tctttagcga  720
cttgatgctc ttgatcttcc aatacgcaac ctaaagtaaa atgccccact gcgctgagtg  780
catataatgc attctctagt gaaaaacctt gttggcataa aaaggctaat tgattttcga  840
gagtttcata ctgtttttct gtaggccgtg tacctaaatg tacttttgct ccatcgcgat  900
gacttagtaa agcacatcta aaactttttag cgttattacg taaaaaatct tgccagcttt  960
cccttctaa agggcaaaag tgagtatggt gcctatctaa catctcaatg gctaaggcgt 1020
cgagcaaagc ccgcttattt tttacatgcc aatacaatgt aggctgctct acacctagct 1080
tctgggcgag tttacgggtt gttaaacctt cgattccgac ctcattaagc agctctaatg 1140
cgctgttaat cactttactt ttatctaaac gagacatact cttcctttt caatattatt 1200
gaagcattta tcaggttat tgtctcatga gcggatacat atttgaatgt atttagaaaa 1260
ataaacaaat aggggttccg cgcacatttc cccgaaaagt gccacctgaa attggccaga 1320
tgattaattc ctaattttttg ttgacactct atcattgata gagttatttt accactccct 1380
atcagtgata gagaaaagtg aaatgaatag ttcgacaaaa atctagaaat aattttgttt 1440
aactttaaga aggagatata caagagctcg agtcgaagga gatagaacca tgccaaaagt 1500
tcaggccgac ggcctgccat tgcccagcg atacggtgcg atattaacca ttgtgattgg 1560
tatttcgatg gccgtccttg acggcgcaat cgccaacgtc gccctgccaa caatcgccac 1620
ggaccttcat gccacgccag ccagttccat ctgggtagtg aacgcctatc aaatcgccat 1680
tgtcatctcc ctgctctcgt tttcgttcct gggcgatatg tttggctatc gacgtattta 1740
taaatgcggt ctggtcgttt ttctgttgtc ttcactgttc tgcgcccttt ctgattcgct 1800
gcaaatgctc accccttgcgc gtgtcataca aggtttcggc ggtgcagcgt tgatgagcgt 1860
taataccgca cttatccgcc tgatctatcc acaacgtttt ctgggtagag ggatgggcat 1920
aaactcgttt attgttgccg tctcttctgc tgccgggccg acaattgctg cagcaatcct 1980
ctccatcgca tcctgaaat ggttattttt aatcaacgta ccgttaggta ttatcgccct 2040
gcttctggcg atgcgttttc tgccacccaa tggttctcgc gccagtaaac cccgtttcga 2100
cctgcccagc gccgtgatga acgcgttaac cttcggcctg cttatcactg cgttgagtgg 2160
tttcgctcag gggcaatcgc tgacgttaat tgctgcggaa atggtggtaa tggttgttgt 2220
tggtattttc tttattcgcc gccagctttc tcttcccgta ccgctgctac cggtggattt 2280
actgcgtatc ccgctgtttt cactttctat ttgcacatct gtttgctctt tctgcgcaca 2340
aatgctggca atggtttccc tgccctttta cctgcaaacc gtgctcgggc gtagtgaagt 2400
cgaaacaggt ttacttctga caccgtggcc gttagcaacg atggtgatgg ctccgctggc 2460
aggctatttg attgaacgcg tacatgcagg attgctgggg gctttagggt tgttcatcat 2520
ggctgcgggg ctttttttccc tggttctgct gcccgcgtca cctgcggata tcaatattat 2580
ctggccgatg atcttatgtg gtgctggatt tggcttattc cagtcaccca ataaccacac 2640
cattattacc tccgcgcctc gcgaacgtag cggtggagcc agtggcatgt taggaacggc 2700
tcgtctactg ggtcagagta gcggcgcggc gctggtggcg ctgatgctaa atcagtttgg 2760
agataatggt acacacgtct cgctgatggc tgcggctatt ctggcagtga ttgctgcctg 2820
tgtcagtggt ttacgtatca ctcagccacg atccagggca taataaatcg atactagcat 2880
aaccccttgg ggcctctaaa cgcgtcgaca cgcaaaaagg ccatccgtca ggatggcctt 2940
ctgcttaatt tgatgcctgg cagtttatgg cgggcgtcct gcccgccacc ctccgggccg 3000
ttgcttcgca acgttcaaat ccgctcccgg cggatttgtc ctactcagga gagcgttcac 3060
cgacaaacaa cagataaaac gaaaggccca gtctttcgac tgagcctttc gttttatttg 3120
atgcctggca gttccctact ctcgcatggg gagaccccac actaccatca tgtatgaata 3180
tcctccttag ttcctattcc gaagttccta tctctagaa agtataggaa cttcgacgcg 3240
tcctacctgt gacggaagat cacttcgcag aataaataaa tcctggtgtc cctgttgata 3300
ccgggaagcc ctgggccaac ttttggcgaa aatgagacgt tgatcggcac gtaagaggtt 3360
ccaactttca ccataatgaa ataagatcac taccgggcgt attttttgag ttgtcgagat 3420
tttcaggagc taaggaagct aaaatggaga aaaaaatcac tggatatacc accgttgata 3480
tatcccaatg gcatcgtaaa gaacattttg aggcatttca gtcagttgct caatgtacct 3540
ataaccagac cgttcagctg gatattacgg cctttttaaa gaccgtaaag aaaaataagc 3600
acaagtttta tccggccttt attcacattc ttgcccgcct gatgaatgct catccggaat 3660
tacgtatggc aatgaaagac ggtgagctgg tgatatggga tagtgttcac ccttgttaca 3720
ccgttttcca tgagcaaact gaaacgtttt catcgctctg gagtgaatac cacgacgatt 3780
tccggcagtt tctacacata ttcgcaag atgtggcgtg ttacggtgaa aacctggcct 3840
atttccctaa agggtttatt gagaatatgt ttttcgtctc agccaatccc tgggtgagtt 3900
tcaccagttt tgatttaaac gtggccaata tggacaactt cttcgccccc gttttcacca 3960
tgggcaaata ttatacgcaa ggcgacaagg tgctgatgcc gctggcgatt caggttcatc 4020
atgccgtttg tgatggcttc catgtcggca gatgcttaat gaatacaaca gtactgcgat 4080
gagtggcagg gcggggcgta aggcgcgcca tttaaatgaa gttcctattc cgaagttcct 4140
```

-continued

```
attctctaga aagtatagga acttcgaagc agctccagcc tacacaatcg ctcaagacgt 4200
gtaatgctgc aatctgcatg caagcttggc actggccacg caaaaaggcc atccgtcagg 4260
atggccttct gcttaatttg atgcctggca gtttatggcg ggcgtcctgc ccgccaccct 4320
ccgggccgtt gcttcgcaac gttcaaatcc gctcccggcg gatttgtcct actcaggaga 4380
gcgttcaccg acaaacaaca gataaaacga aaggcccagt ctttcgactg agcctttcgt 4440
tttatttgat gcctggcagt tccctactct cgcatgggga gaccccacac taccatcggg 4500
gggccatcga tgcaggtggc acttttcggg gaaatgtgcg cggaacccct atttgtttat 4560
ttttctaaat acattcaaat atgtatccgc tcatgagaca ataaccctgc tgcagaggcc 4620
tgcatgcaag cttggcgtaa tcatggtcat agctgtttcc tgtgtgaaat tgttatccgc 4680
tcacaattcc acacaacata cgagccggaa gcataaagtg taaagcctgg ggtgcctaat 4740
gagtgagcta actcacatta attgcgttgc gctcactgcc cgctttccag tcgggaaacc 4800
tgtcgtgcca gctgcattaa tgaatcggcc aacgcgcggg gagaggcggt ttgcgtattg 4860
ggcgctcttc cgcttcctcg ctcactgact cgctgcgctc ggtcgttcgg ctgcggcgag 4920
cggtatcagc tcactcaaag gcggtaatac ggttatccac agaatcaggg gataacgcag 4980
gaaagaacat gtgagcaaaa ggccagcaaa aggccaggaa ccgtaaaaag gccgcgttgc 5040
tggcgttttt ccataggctc cgcccccctg acgagcatca caaaaatcga cgctcaagtc 5100
agaggtggcg aaacccgaca ggactataaa gataccaggc gtttccccct ggaagctccc 5160
tcgtgcgctc tcctgttccg accctgccgc ttaccggata cctgtccgcc tttctccctt 5220
cgggaagcgt ggcgctttct catagctcac gctgtaggta tctcagttcg gtgtaggtcg 5280
ttcgctccaa gctgggctgt gtgcacgaac cccccgttca gcccgaccgc tgcgccttat 5340
ccggtaacta tcgtcttgag tccaacccgg taagacacga cttatcgcca ctggcagcag 5400
ccactggtaa caggattagc agagcgaggt atgtaggcgg tgctacagag ttcttgaagt 5460
ggtggcctaa ctacggctac actagaagaa cagtatttgg tatctgcgct ctgctgaagc 5520
cagttacctt cggaaaaaga gttggtagct cttgatccgg caaacaaacc accgctggta 5580
gcggtggttt ttttgtttgc aagcagcaga ttacgcgcag aaaaaaagga tctcaagaag 5640
atcctttgat cttttctacg gggtctgacg ctcagtggaa cgaaaactca cgttaaggga 5700
ttttggtcat gagattatca aaaaggatct tcacctagat cctttaaat taaaaatgaa 5760
gttttaaatc aatctaaagt atatatgagt aaacttggtc tgacagttac caatgcttaa 5820
tcagtgaggc acctatctca gcgatctgtc tatttcgttc atccatagtt gcctgactcc 5880
ccgtcgtgta gataactacg atacgggagg gcttaccatc tggccccagt gctgcaatga 5940
taccgcgaga cccacgctca ccggctccag atttatcagc aataaaccag ccagccggaa 6000
gggccgagcg cagaagtggt cctgcaactt tatccgcctc catccagtct attaattgtt 6060
gccgggaagc tagagtaagt agttcgccag ttaatagttt gcgcaacgtt gttgccattg 6120
ctacaggcat cgtggtgtca cgctcgtcgt ttggtatggc ttcattcagc tccggttccc 6180
aacgatcaag gcgagttaca tgatccccca tgttgtgcaa aaaagcggtt agctccttcg 6240
gtcctccgat cgttgtcaga agtaagttgg ccgcagtgtt atcactcatg gttatggcag 6300
cactgcataa ttctcttact gtcatgccat ccgtaagatg cttttctgtg actggtgagt 6360
actcaaccaa gtcattctga atagtgta tgcggcgacc gagttgctct gcccggcgt 6420
caatacggga taataccgcg ccacatagca gaactttaaa agtgctcatc attggaaaac 6480
gttcttcggg gcgaaaactc tcaaggatct taccgctgtt gagatccagt tcgatgtaac 6540
ccactcgtgc acccaactga tcttcagcat cttttacttt caccagcgtt tctgggtgag 6600
caaaaacagg aaggcaaaat gccgcaaaaa agggaataag ggcgacacgg aaatgttgaa 6660
tactcatact cttcctttt caatattatt gaagcattta tcagggttat tgtctcatga 6720
gcggatacat atttgaatgt atttagaaaa ataaacaaat aggggttccg cgcacatttc 6780
cccgaaaagt gccacctgac gtctaagaaa ccattattat catgacatta acctataaaa 6840
ataggcgtat cacgaggccc tttcgtc 6867
```

```
SEQ ID NO: 23           moltype = DNA   length = 6768
FEATURE                 Location/Qualifiers
misc_feature            1..6768
                        note = construct pINT-proP
source                  1..6768
                        mol_type = other DNA
                        organism = synthetic construct
SEQUENCE: 23
tcgcgcgttt cggtgatgac ggtgaaaacc tctgacacat gcagctcccg gagacggtca 60
cagcttgtct gtaagcggat gccgggagca gacaagcccg tcaggcgcg tcagcgggtg 120
ttggcgggtg tcgggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgaagatcct ttgatctttt 420
ctacggggtc tgacgctcag tggaacgaaa actcacgtta agggattttg gtcatgagat 480
tatcaaaaag gatcttcacc tagatccttt taaactagtg aagttaccat cacggaaaaa 540
ggttatgctg ctttttaagac ccactttcac atttaagttg tttttctaat ccgcatatga 600
tcaattcaag gccgaataag aaggctggct ctgcaccttg gtgatcaaat aattcgatag 660
cttgtcgtaa taatggcggc atactatcag tagtaggtgt ttccctttct tctttagcga 720
cttgatcgctc ttgatcttcc aatacgcaac ctaaagtaaa atgccccact gcgctgagtg 780
catataatgc attctctagt gaaaaacctt gttgcataa aaaggctaat tgattttcga 840
gagtttcata ctgttttct gtaggccgtg tacctaaatg tacttttgct ccatcgcgat 900
gacttagtaa agcacatcta aaactttag cgttattacg taaaaaatct tgccagcttt 960
ccccttctaa agggcaaaag tgagtatggt gcctatctaa catctcaatg gctaaggcgt 1020
cgagcaaagc ccgcttattt tttacatgcc aatacaatgt aggctgctct acacctagct 1080
tctgggcgag tttacgggtt gttaaacctt cgattccgac ctcattaagc agctctaatg 1140
cgctgttaat cactttactt ttatctaaac gagacatact cttcctttt caatattatt 1200
gaagcattta tcagggttat tgtctcatga gcggatacat atttgaatgt atttagaaaa 1260
ataaacaaat aggggttccg cgcacatttc cccgaaaagt gccacctgaa attggccaga 1320
tgattaattc ctaattttg ttgacactct atcattgata gagttatttt accactccct 1380
atcagtgata gagaaaagtg aaatgaatag ttcgacaaaa atctagaaat aattttgttt 1440
```

```
aactttaaga aggagatata caagagctcg agtcgaagga gatagaacca tgccgaacaa   1500
agctgaaacc tccccggcga aactgcgtct gaaagccttc ctgaaacgta tcaagattat   1560
gaacaccacc gaaaacagca aacagaagcc ggttaacgtg gttgcatttg ctttcctgct   1620
gaccgcgttt ctgacgggta tcgccagctc tttccaaacc ccgacgctga gcctgtttct   1680
ggcgcaggaa attcaagtct ctccgtttat ggtgggcatg ttctatacct caaatgcagt   1740
gctgggcatc gttctgtcgc agattctggc taaatacagt gattcccaag atgaccgtcg   1800
caagattatc attttctgca gtctgctggc gatcggcggt tgtatcacct tcgcctacaa   1860
ccgtaactac tacgtgctga tgttttttcgc gacgttcctg ctgtccctgg gtagttccgc   1920
aaacccgcag gcatttgcac tggcacgtga atatgcagac tacaccaaac gcgaagctat   1980
catgtttacc acgattatgc gcacgcagat cagcctggca tggattgttg gcccgccgct   2040
gtcattctcg attgcgctgg gctgggggttt tgaatatatg tacatggtcg cggcctcagc   2100
atttctgctg tgcgctatca ttgctaaagc gctgctgccg tatgtgccgc gtaaagccgt   2160
cgtgccgctg accaagccgg atgaagttgc gggtctgccg gccaaaaata aaaagcagag   2220
tgacaagcaa tccatccgcc tgctgtttat tacgtgcttc ctgatgtgga gttgtaacgg   2280
catgtatctg atctccatgc cgctgcatgt tattaatgaa ctgcacctga gtgaacgtct   2340
ggcgggcatt ctgatgggta ccgcagctgg cctggaaatc ccggtgatgc tgattgccgg   2400
ctatctgacc aaatacctga cgaaaaagtc tctgatcctg accgccctgt tcatgggtct   2460
gtttttctat attggcatgc tgtttgcaga acagacgtgg caactggtcg ccctgcaggc   2520
atttaacgct atcttcattg gtatcattgc gaccctgggc atggtgtact ttcaagatct   2580
gatgccgggc aaaatgggtt cagccaccac gctgttctcg aacgcggcca aatcatcgtg   2640
gatcgttgca ggtccgtttg tcggcatcat tgctcagatt tggaattata gctctgtgtt   2700
ctacatcagc attgttctgg tcgcggtgtc tctgtttagc atgtctaaag ttaagagcgt   2760
ctaataaaatc gatactagca taaccccttg gggcctctaa acgcgtcgac acgcaaaaag   2820
gccatccgtc aggatggcct tctgcttaat ttgatgcctg gcagtttatg gcgggcgtcc   2880
tgcccgccac cctccgggcc gttgcttcgc aacgttcaaa tccgctcccg gcggatttgt   2940
cctactcagg agagcgttca ccgacaaaca acagataaaa cgaaaggccc agtcttttcga   3000
ctgagccttt cgttttattt gatgcctggc agttccctac tctcgcatgg ggagacccca   3060
cactaccatc atgtatgaat atcctcctta gttcctattc cgaagttcct attctctaga   3120
aagtatagga acttcggcgc gtcctacctg tgacggaaga tcacttcgca gaataaataa   3180
atcctggtgt ccctgttgat accgggaagc cctgggccaa cttttggcga aaatgagacg   3240
ttgatcggca cgtaagaggt tccaactttc accataatga aataagatca ctaccgggcg   3300
tatttttttga gttgtcgaga ttttcaggag ctaaggaagc taaaatggag aaaaaaatca   3360
ctggatatac caccgttgat atatcccaat ggcatcgtaa agaacatttt gaggcatttc   3420
agtcagttgc tcaatgtacc tataaccaga ccgttcagct ggatattacg gcctttttaa   3480
agaccgtaaa gaaaaataag cacaagtttt atccggcctt tattcacatt cttgcccgcc   3540
tgatgaatgc tcatccggaa ttacgtatgg caatgaaaga cggtgagctg gtgatatggg   3600
atagtgttca cccttgttac accgttttcc atgagcaaac tgaaacgttt tcatcgctct   3660
ggagtgaata ccacgacgat ttccggcagt ttctacacat atattcgcaa gatgtggcgt   3720
gttacggtga aaacctggcc tatttcccta aagggtttat tgagaatatg tttttcgtct   3780
cagccaatcc ctgggtgagt ttcaccagtt ttgatttaaa cgtggccaat atggacaact   3840
tcttcgcccc cgtttttcacc atgggcaaat attatacgca aggcgacaag gtgctgatgc   3900
cgctggcgat tcaggttcat catgccgttt gtgatggctt ccatgtcggc agatgcttaa   3960
tgaatacaac agtactgcga tgagtggcag ggcggggcgt aaggcgcgcc atttaaatga   4020
agttcctatt ccgaagttcc tattctctag aaagtatagg aacttcgaag cagctccagc   4080
ctacacaatc gctcaagacg tgtaatgctg caatctgcat gcaagcttgg cactggccac   4140
gcaaaaaggc catccgtcag gatggccttc tgcttaattt gatgcctggc agtttatggc   4200
gggcgtcctg cccgccaccc tccgggccgt tgcttcgcaa cgttcaaatc cgctcccggc   4260
ggatttgtcc tactcaggag agcgttcacc gacaaacaac agataaaacg aaaggcccag   4320
tctttcgact gagcctttcg ttttatttga tgcctggcag ttccctactc tcgcatgggg   4380
agaccccaca ctaccatcgg ggggccatcg atgcaggtgg cacttttcgg ggaaatgtgc   4440
gcggaacccc tatttgttta tttttctaaa tacattcaaa tatgtatccg ctcatgagac   4500
aataacccctg ctgcagaggc ctgcatgcaa gcttggcgta atcatggtca tagctgtttc   4560
ctgtgtgaaa ttgttatccg ctcacaattc cacacaacat acgagccgga agcataaagt   4620
gtaaagcctg gggtgcctaa tgagtgagct aactcacatt aattgcgttg cgctcactgc   4680
ccgctttcca gtcgggaaac ctgtcgtgcc agctgcatta atgaatcggc caacgcgcgg   4740
ggagaggcgg tttgcgtatt gggcgctctt ccgcttcctc gctcactgac tcgctgcgct   4800
cggtcgttcg gctgcggcga gcggtatcag ctcactcaaa ggcggtaata cggttatcca   4860
cagaatcagg ggataacgca ggaaagaaca tgtgagcaaa aggccagcaa aaggccagga   4920
accgtaaaaa ggccgcgttg ctggcgtttt tccataggct ccgcccccct gacgagcatc   4980
acaaaaatcg acgctcaagt cagaggtggc gaaacccgac aggactataa agataccagg   5040
cgtttccccc tggaagctcc ctcgtgcgct ctcctgttcc gaccctgccg cttaccggat   5100
acctgtccgc ctttctccct tcgggaagcg tggcgctttc tcatagctca cgctgtaggt   5160
atctcagttc ggtgtaggtc gttcgctcca agctgggctg tgtgcacgaa ccccccgttc   5220
agcccgaccg ctgcgcctta tccggtaact atcgtcttga gtccaacccg gtaagacacg   5280
acttatcgcc actggcagca gccactggta acaggattag cagagcgagg tatgtaggcg   5340
gtgctacaga gttcttgaag tggtggccta actacggcta cactagaaga acagtatttg   5400
gtatctgcgc tctgctgaag ccagttacct tcggaaaaag agttggtagc tcttgatccg   5460
gcaaacaaac caccgctggt agcggtggtt tttttgtttg caagcagcag attacgcgca   5520
gaaaaaaagg atctcaagaa gatcctttga tcttttctac ggggtctgac gctcagtgga   5580
acgaaaactc acgttaaggg attttggtca tgagattatc aaaaaggatc ttcacctaga   5640
tccttttaaa ttaaaaatga agttttaaat caatctaaag tatatatgag taaacttggt   5700
ctgacagtta ccaatgctta atcagtgagg cacctatctc agcgatctgt ctatttcgtt   5760
catccatagt tgcctgactc cccgtcgtgt agataactac gatacgggag ggcttaccat   5820
ctggccccag tgctgcaatg ataccgcgag acccacgctc accggctcca gatttatcag   5880
caataaacca gccagccgga agggccgagc gcagaagtgg tcctgcaact ttatccgcct   5940
ccatccagtc tattaattgt tgccgggaag ctagagtaag tagttcgcca gttaatagtt   6000
tgcgcaacgt tgttgccatt gctacaggca tcgtggtgtc acgctcgtcg tttggtatgg   6060
cttcattcag ctccggttcc caacgatcaa ggcgagttac atgatccccc atgttgtgca   6120
aaaaagcggt tagctccttc ggtcctccga tcgttgtcag aagtaagttg gccgcagtgt   6180
```

```
tatcactcat ggttatggca gcactgcata attctcttac tgtcatgcca tccgtaagat    6240
gcttttctgt gactggtgag tactcaacca agtcattctg agaatagtgt atgcggcgac    6300
cgagttgctc ttgcccggcg tcaatacggg ataataccgc gccacatagc agaactttaa    6360
aagtgctcat cattggaaaa cgttcttcgg ggcgaaaact ctcaaggatc ttaccgctgt    6420
tgagatccag ttcgatgtaa cccactcgtg cacccaactg atcttcagca tcttttactt    6480
tcaccagcgt ttctgggtga gcaaaaacag gaaggcaaaa tgccgcaaaa aagggaataa    6540
gggcgacacg gaaatgttga atactcatac tcttcctttt tcaatattat tgaagcattt    6600
atcagggtta ttgtctcatg agcggataca tatttgaatg tatttagaaa aataaacaaa    6660
tagggggttcc gcgcacattt ccccgaaaag tgccacctga cgtctaagaa accattatta    6720
tcatgacatt aacctataaa aataggcgta tcacgaggcc ctttcgtc                  6768
```

```
SEQ ID NO: 24                moltype = DNA   length = 6672
FEATURE                      Location/Qualifiers
misc_feature                 1..6672
                             note = construct pINT-Cn-setA
source                       1..6672
                             mol_type = other DNA
                             organism = synthetic construct
SEQUENCE: 24
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg     120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct ttgatctttt    420
ctacggggtc tgacgctcag tggaacgaaa actcacgtta agggattttg gtcatgagat    480
tatcaaaaag gatcttcacc tagatccttt taaactagtg aagttaccat cacggaaaaa    540
ggttatgctg ctttttaagac ccactttcac atttaagttg tttttctaat ccgcatatga    600
tcaattcaag gccgaataag aaggctggct ctgcaccttg gtgatcaaat aattcgatag    660
cttgtcgtaa taatggcggc atactatcag tagtaggtgt ttccctttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgtttttct gtaggccgtg tacctaaatg tactttttgct ccatcgcgat    900
gacttagtaa agcacatcta aaactttag cgttattacg taaaaaatct tgccagcttt     960
cccctctaa agggcaaaag tgagtatggt gcctatctaa catctcaatg gctaaggcgt     1020
cgagcaaagc ccgcttattt tttacatgcc aatacaatgt aggctgctct acacctagct    1080
tctgggcgag tttacgggtt gttaaaactt cgattccgac ctcattaagc agctctaatg    1140
cgctgttaat cactttactt ttatctaaac gagacatact cttcctttt caatattatt     1200
gaagcattta tcaggttat tgtctcatga gcggatacat atttgaatgt atttagaaaa     1260
ataaacaaat aggggttccg cgcacatttc ccgaaaagt gccacctgaa attggccaga     1320
tgattaattc ctaattttg ttgacactct atcattgata gagttattt accactccct       1380
atcagtgata gagaaaagtg aaatgaatag ttcgacaaaa atctagaaat aattttgttt    1440
aactttaaga aggagatata caagagctcg agtcgaagga gatagaacca tgctgtggtt    1500
tctgacccgt gctcgtcgct tcaatccggt ttatgcggcc tttatggccg tcagcttcat    1560
gattggtgtg gccggtgcac tgcaggcacc gaccctgtct ctgtttctga cgcgtgaagt    1620
tgaagtcgcc ccgtttggg ttggtctgtt ctacacggtc aacgcaattg ctggcatcga    1680
tgtgagtctg ctgctggcca aacgtagtga ttcccaaggc gaccgtcgca aactgattat    1740
ggtgtgctgt gttatggcgg tcgccaactg cgtcctgttt gcattcaatc gccattatct    1800
gaccctgatc acgctgggtg tgatgtttgc aagcattgct aataccgcga tgccgcagat    1860
cttcgcactg gctcgtgaat acgccgatcg ttctgcacgc gaagtggtta tgtttagctc    1920
tattatgcgc gcccaactga gtctggcatg ggttattggc ccgccgctgt ccttcatgct    1980
ggccctgaaa tatggtttta ccacgatgtt cctgattgca gctggcattt ttgtgatctc    2040
actggctctg attatcttcg cgctgccgtc ggtgccgcgt gttgaacagc cggccgaagt    2100
ggcaattacc caagttagcg gttggaaaga ttctaacgtt cgcatgctgt ttatcgcctc    2160
aatgctgatg tggacctgta atacgatgta tattatcgac atgccgctgt ggatttcgca    2220
ggatctgggt ctgccggatg aactggccgg tctgctgatg ggtaccgccg caggcattga    2280
aatcccggct atgatcctgg cgggttatta cgtgaaacgt tttggcaaac gcaacatgat    2340
ggtcgcagct gtggcggccg gtattctgtt ttacgttggc ctgatcctgt tccatagcaa    2400
aacggcgcgtg gtcgtgctgc agctgtttaa tgccgtcttc attggtatta tcgcaggcat    2460
cggtatgctg tggtttcaag atctgatgcc gggtcgtccg ggtagcgcaa ccaccctgtt    2520
caccaactca atttcgacgg gcgtgattct ggccggtatt ctgcagggtg ccctggcaga    2580
aggttttggt cactatagtg tgtactggct gatggcagct ctggctgtta tcgcgctgtt    2640
cctgaccagc cgcgttaaaa acgtctaata aatcgatact agcataaccc cttggggcct    2700
ctaaacgcgt cgacacgcaa aaaggccatc cgtcaggatg gccttctgct taatttgatg    2760
cctggcagtt tatggcgggc gtcctgcccg ccacccctccg ggcgttgct tcgcaacgtt    2820
caaatccgct cccggcggat ttgtcctact caggagagcg ttcaccgaca acaacagat     2880
aaacgaaag gcccagtctt cgactgagc ctttcgtttt atttgatgcc tggcagttcc      2940
ctactctcgc atggggagac cccacactac catcatgtat gaatatctc cttagttcct     3000
attccgaagt tcctattctc tagaaagtat aggaacttcg gcgcgtccta cctgtgacgg    3060
aagatcactt cgcagaataa ataaatcctg gtgtccctgt tgataccggg aagccctggg    3120
ccaacttttg gcgaaaatga cgttgatc ggcacgtaag aggttccaac tttcaccata       3180
atgaaataag atcactaccg ggcgtatttt ttgagttgtg gagattttca ggagctaagg    3240
aagctaaaat ggagaaaaaa atcactggat ataccaccgt tgatatatcc caatggcatc    3300
gtaaagaaca ttttgaggca tttcagtcag ttgctcaatg tacctataac cagaccgttc    3360
agctggatat tacggccttt ttaaagaccg taaagaaaaa taagcacaag ttttatccgg    3420
cctttattca cattcttgcc cgcctgatga atgctcatcc ggaattacgt atggcaatga    3480
aagacgtgga gctggtgata tgggatagtg ttcacccttg ttacaccgtt ttccatgagc    3540
aaactgaaac gttttcatcg ctctggagtg aataccacga cgatttccgg cagtttctac    3600
```

-continued

```
acatatattc gcaagatgtg gcgtgttacg gtgaaaacct ggcctatttc cctaaagggt  3660
ttattgagaa tatgtttttc gtctcagcca atccctgggt gagtttcacc agttttgatt  3720
taaacgtggc caatatggac aacttcttcg ccccgtttt caccatgggc aaatattata  3780
cgcaaggcga caaggtgctg atgccgctgg cgattcaggt tcatcatgcc gtttgtgatg  3840
gcttccatgt cggcagatgc ttaatgaata caacagtact gcgatgagtg gcagggcggg  3900
gcgtaaggcg cgccatttaa atgaagttcc tattccgaag ttcctattct ctagaaagta  3960
taggaacttc gaagcagctc cagcctacac aatcgctcaa gacgtgtaat gctgcaatct  4020
gcatgcaagc ttggcactgg ccacgcaaaa aggccatccg tcaggatggc cttctgctta  4080
atttgatgcc tggcagttta tggcgggcgt cctgcccgcc accctccggg ccgttgcttc  4140
gcaacgttca aatccgctcc cggcggattt gtcctactca ggagagcgtt caccgacaaa  4200
caacagataa aacgaaaggc ccagtctttc gactgagcct ttcgtttat ttgatgcctg  4260
gcagttccct actctcgcat ggggagaccc cacactacca tcgggggggcc atcgatgcag  4320
gtggcacttt tcggggaaat gtgcgcggaa cccctatttg tttattttc taaatacatt  4380
caaatatgta tccgctcatg agacaataac cctgtgcgag aggcctgcat gcaagcttgg  4440
cgtaatcatg gtcatagctg tttcctgtgt gaaattgtta tccgctcaca attccacaca  4500
acatacgagc cggaagcata aagtgtaaag cctggggtgc ctaatgagtg agctaactca  4560
cattaattgc gttgcgctca ctgcccgctt tccagtcggg aaacctgtcg tgccagctgc  4620
attaatgaat cggccaacgc gcggggagag gcggtttgcg tattgggcgc tcttccgctt  4680
cctcgctcac tgactcgctg cgctcggtcg ttcggctgcg gcgagcggta tcagctcact  4740
caaaggcggt aatacggtta tccacagaat caggggataa cgcaggaaag aacatgtgag  4800
caaaaggcca gcaaaaggcc aggaaccgta aaaaggccgc gttgctggcg tttttccata  4860
ggctccgccc ccctgacgag catcacaaaa atcgacgctc aagtcagagg tggcgaaacc  4920
cgacaggact ataaagatac caggcgtttc ccccctggaag ctccctcgtg cgctctcctg  4980
ttccgaccct gccgcttacc ggatacctgt ccgcctttct cccttcggga agcgtggcgc  5040
tttctcatag ctcacgctgt aggtatctca gttcggtgta ggtcgttcgc tccaagctgg  5100
gctgtgtgca cgaacccccc gttcagcccg accgctgcgc cttatccggt aactatcgtc  5160
ttgagtccaa cccggtaaga cacgacttat cgccactggc agcagccact ggtaacagga  5220
ttagcagagc gaggtatgta ggcggtgcta cagagttctt gaagtggtgg cctaactacg  5280
gctacactag aagaacagta tttggtatct gcgctctgct gaagccagtt accttcggaa  5340
aaagagttgg tagctcttga tccggcaaac aaaccaccgc tggtagcggt ggtttttttg  5400
tttgcaagca gcagattacg cgcagaaaaa aaggatctca agaagatcct ttgatctttt  5460
ctacggggtc tgacgctcag tggaacgaaa actcacgtta agggattttg gtcatgagat  5520
tatcaaaaag gatcttcacc tagatccttt taaattaaaa atgaagtttt aaatcaatct  5580
aaagtatata tgagtaaact tggtctgaca gttaccaatg cttaatcagt gaggcaccta  5640
tctcagcgat ctgtctattt cgttcatcca tagttgcctg actccccgtc gtgtagataa  5700
ctacgatacg ggagggctta ccatctggcc ccagtgctgc aatgataccg cgagaccac   5760
gctcaccggc tccagattta tcagcaataa accagccagc cggaagggcc gagcgcagaa  5820
gtggtcctgc aactttatcc gcctccatcc agtctattaa ttgttgccgg gaagctagag  5880
taagtagttc gccagttaat agtttgcgca acgttgttgc cattgctaca ggcatcgtgg  5940
tgtcacgctc gtcgtttggt atggcttcat tcagctccgg ttcccaacga tcaaggcgag  6000
ttacatgatc ccccatgttg tgcaaaaaag cggttagctc cttcggtcct ccgatcgttg  6060
tcagaagtaa gttggccgca gtgttatcac tcatggttat ggcagcactg cataattctc  6120
ttactgtcat gccatccgta agatgctttt ctgtgactgg tgagtactca accaagtcat  6180
tctgagaata gtgtatgcgg cgaccgagtt gctcttgccc ggcgtcaata cgggataata  6240
ccgcgccaca tagcagaact ttaaaagtgc tcatcattgg aaaacgttct cgggggcgaa  6300
aactctcaag gatcttaccg ctgttgagat ccagttcgat gtaacccact cgtgcaccca  6360
actgatcttc agcatctttt actttcacca gcgtttctgg gtgagcaaaa acaggaaggc  6420
aaaatgccgc aaaaaaggga ataagggcga cacggaaatg ttgaatactc atactcttcc  6480
tttttcaata ttattgaagc atttatcagg gttattgtct catgagcgga tacatatttg  6540
aatgtattta gaaaaataaa caaatagggg ttccgcgcac atttccccga aaagtgccac  6600
ctgacgtcta agaaaccatt attatcatga cattaaccta taaaaatagg cgtatcacga  6660
ggccctttcg tc                                                      6672
```

```
SEQ ID NO: 25            moltype = DNA  length = 7074
FEATURE                  Location/Qualifiers
misc_feature             1..7074
                         note = construct pINT-spoVB
source                   1..7074
                         mol_type = other DNA
                         organism = synthetic construct
SEQUENCE: 25
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga cagattgta ctgagagtgc    180
accatatgcg gtgtgaaata ccgcacagat gcgtaaggag aaaataccgc atcaggcgc    240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgaagatcct ttgatctttt   420
ctacggggtc tgacgctcag tggaacgaaa actcacgtta agggattttg gtcatgagat   480
tatcaaaaag gatcttcacc tagatccttt taaactagtg aagttaccat cacgaaaaa    540
ggttatgctg ctttttaagac ccactttcac atttaagttg tttttctaat ccgcatatga   600
tcaattcaag gccgaataag aaggctggc ctgcaccttg gtgatcaaat aattcgatag    660
cttgtcgtaa taatggcggc atactatcag tagtaggtgt ttcccttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga   840
gagtttcata ctgtttttct gtaggccgtg tacctaaatg tacttttgct ccatcgcgat   900
gacttagtaa agcacatcta aaactttag cgttattacg taaaaaatct tgccagcttt    960
ccccttctaa agggcaaaag tgagtatggt gcctatctaa catctcaatg gctaaggcgt  1020
cgagcaaagc ccgcttattt tttacatgcc aatacaatgt aggctgctct acacctagct  1080
```

```
tctgggcgag tttacgggtt gttaaacctt cgattccgac ctcattaagc agctctaatg   1140
cgctgttaat cacttcactt ttatctaaac gagacatact cttccttttt caatattatt   1200
gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaatttttg ttgacactct atcattgata gagttatttt accactccct   1380
atcagtgata gagaaaagtg aaatgaatag ttcgacaaaa atctagaaat aattttgttt   1440
aactttaaga aggagatata caagagctcg agtcgaagga gatagaacca tgaatgactc   1500
ggtcggtgct aagcgtcaaa gtgcgtggaa gggtgcgttc gtcctggtcg ttgcgggcat   1560
cgttaccaag atcctgtctg ccgtgtatcg tgttccgttt cagaacattg tcggcgatgt   1620
gggtttctat atctaccagc aagtttaccc gtttctgggc attgcggtca tgctgagtac   1680
ctccggtttt ccggtgatca tctcgaagct gatgaacgat tacagcgacc ataaacagaa   1740
gattatgaag atcagtgcac tgtatgtgac ggcagcaggt ctggttctgt ttgccctgat   1800
gtacgcaggt gcagctccgc tggcgggctt catgggtgat gaccgtctgg tcatgctgat   1860
tcgcgtggcg gcctttgctt tcatcctgtt tccgttcacc gcggttttc gcggctattt   1920
ccagggtgtg cacgacatga tgccgtctgc tctgagtcag attacggaac aactgctgcg   1980
tgtggcagtt ctgctgggcc tgtctttttg gctgctgaaa tccggtcgtt cactgtacgc   2040
agctggtgca ggtgcagcat caggttcgat tgcaggtagt ctggcagctc tgtgcgttct   2100
ggcagtcttc tggtataaac gtgaagaaac caaaaaggat ggcgtcata tcgaaacggc   2160
ggttattatc aaaaagctgc tgctgtactc cgtgaccatt tgtatcagct ctgttctgat   2220
gctgctgctg cagctggttg atgcgctgaa cctgtattcg ctgctgagcg acggcaccga   2280
atcacatgcg gccaaacaac tgaagggcat ttacgaccgt ggtcagccgc tgctgcaact   2340
gggtacggtg tttgcggttt ccattgcagc ttcactggtc ccgagcatct ctaaagccgt   2400
gcacgaaaat aagccgttca ttatcaaaga aaaggctacc tctgcggtca aactgtgcct   2460
ggcggtgggc attggtgcta gtgcgggcct gttttgtatt ctggaaccgg ttaacatcat   2520
gctgttccag aattccgaag gtacccagac gctgcaaatc tttagtctgt ccattttctt   2580
tgcctcaatc gcactgaccg cagcagcaat cctgcaaggt gcaggtcata cggtgttccc   2640
ggcagtcagc gtgctggctg gcggtgcgct gaaatgggtc ctgaacgtgt ggctggttcc   2700
gggttggggt attaccggtg ctgcactggc tacggttctg gcatttgcag cagtcgcatg   2760
cctgaacctg cgtcgcatct ggtcgaaagg ttggctgacc aatattggcg gtgtgatcgc   2820
acgtctgtgc tggtgtagcc tgctgatggt gtttttcctg ctggtctata tgaaactgtg   2880
gcagctgttt gttccggtca gccgtgccgg cgcagtttgc gaatcactgt cggccagcgt   2940
gattggcggt ctgctgttca tctactgtat gatccgcatg aagatcttca ccgatgaaga   3000
actgagcggc ctgccgttcg gttctgcgct gagtaaactg aaaaagcgtc gcgaaaagca   3060
cggtcgctaa taaatcgata ctagcataac cccttgggc ctctaaacgc gtcgacacgc   3120
aaaaaggcca tccgtcagga tggccttctg cttaatttga tgcctggcag tttatgcggt   3180
gcgtcctgcc cgccaccctc cgggccgttg cttcgcaacg ttcaaatccg ctcccggcgg   3240
atttgtccta ctcaggagag cgttcaccga caaacaacag ataaaacgaa aggcccagtc   3300
tttcgactga gcctttcgtt ttatttgatg cctggcagtt ccctactctc gcatggggag   3360
accccacact accatcatgt atgaatatcc tccttagttc ctattccgaa gttcctattc   3420
tctagaaagt ataggaactt cggcgcgtcc tacctgtgac ggaagatcac ttcgcagaat   3480
aaataaatcc tggtgtccct gttgataccg ggaagccctg ggccaacttt tggcgaaaat   3540
gagacgttga tcggcacgta agaggttcca actttcacca taatgaaata agatcactac   3600
cgggcgtatt ttttgagttg tcgagatttt caggagctaa gatggagaaa   3660
aaatcactgg atataccacc gttgatatat cccaatggca tcgtaaagaa catttttgagg   3720
catttcagtc agttgctcaa tgtacctata accagaccgt tcagctggat attacggcct   3780
tttttaaagac cgtaaagaaa aataagcaca agttttatcc ggcctttatt cacattcttg   3840
cccgcctgat gaatgctcat ccggaattac gtatggcaat gaaagacggt gagctggtga   3900
tatgggatag tgttcaccct tgttacaccg ttttccatga gcaaactgaa acgttttcat   3960
cgctctggag tgaataccac gacgatttcc ggcagtttct acacatatat tcgcaagatg   4020
tggcgtgtta cggtgaaaac ctggcctatt tccctaaagg gtttattgag aatatgtttt   4080
tcgtctcagc caatccctgg gtgagtttca ccagttttga tttaaacgtg gccaatatgg   4140
acaacttctt cgcccccgtt ttcaccatgg gcaaatatta tacgcaaggc gacaaggtgc   4200
tgatgccgct ggcgattcag gttcatcatg ccgtttgtga tggcttccat gtcggcagat   4260
gcttaatgaa tacaacagta ctgcgatgag tggcagggcg gggcgtaagg cgcgccattt   4320
aaatgaagtt cctattccga agttcctatt ctctagaaat gataggaact tcgaagcagc   4380
tccagcctac acaatcgctc aagacgtgta atgctgcaat ctgcatgcaa gcttggcact   4440
ggccacgcaa aaaggccatc cgtcaggatg gccttctgct taatttgatg cctggcagtt   4500
tatggcgggc gtcctgcccg ccaccctccg gcccgttgct tcgcaacgtt caaatccgct   4560
cccggcggat ttgtcctact caggagagcg ttcaccgaca aacaacagat aaaacgaaag   4620
gcccagtctt tcgactgagc ctttcgtttt atttgatgcc tggcagtcc ctactctcgc   4680
atggggagac cccacactac catcgggggg ccatcgatgc aggtggcact tttcgggga   4740
atgtgcgcgg aaccccta tt tgtttatttt tctaaataca ttcaaatatg tatccgctca   4800
tgagacaata accctgctgc agaggcctgc atgcaagctt ggcgtaatca tggtcatagc   4860
tgtttcctgt gtgaaattgt tatccgctca caattccaca caacatacga gccggaagca   4920
taaagtgtaa agcctggggt gcctaatgag tgagctaact cacattaatt gcgttgcgct   4980
cactgcccgc tttccagtcg ggaaacctgt cgtgccagct gcattaatga atcggccaac   5040
gcgcggggag aggcggtttg cgtattgggc gctcttccgc ttcctcgctc actgactcgc   5100
tgcgctcggt cgttcggctg cggcgagcgg tatcagctca ctcaaaggcg gtaatacggt   5160
tatccacaga atcaggggat aacgcaggaa agaacatgtg agcaaaaggc cagcaaaagg   5220
ccaggaaccg taaaaaggcc gcgttgctgg cgtttttcca taggctccgc cccctgacg   5280
agcatcacaa aaatcgacgc tcaagtcaga ggtggcgaaa cccgacagga ctataaagat   5340
accaggcgtt tccccctgga agctccctcg tgcgctctcc tgttccgacc ctgccgctta   5400
ccggatacct gtccgccttt ctcccttcgg gaagcgtggc gctttctcat agctcacgct   5460
gtaggtatct cagttcggtg taggtcgttc gctccaagct gggctgtgtg cacgaacccc   5520
ccgttcagcc cgaccgctgc gccttatccg gtaactatcg tcttgagtcc aacccggtaa   5580
gacacgactt atcgccactg gcagcagcca ctggtaacag gattagcaga gcgaggtatg   5640
taggcggtgc tacagagttc ttgaagtggt ggcctaacta cggctacact agaagaacag   5700
tatttggtat ctgcgctctg ctgaagccag ttaccttcgg aaaaagagtt ggtagctctt   5760
gatccggcaa acaaaccacc gctggtagcg gtggtttttt tgtttgcaag cagcagatta   5820
```

```
cgcgcagaaa aaaaggatct caagaagatc ctttgatctt ttctacgggg tctgacgctc   5880
agtggaacga aaactcacgt taagggattt tggtcatgag attatcaaaa aggatcttca   5940
cctagatcct tttaaattaa aaatgaagtt ttaaatcaat ctaaagtata tatgagtaaa   6000
cttggtctga cagttaccaa tgcttaatca gtgaggcacc tatctcagcg atctgtctat   6060
ttcgttcatc catagttgcc tgactccccg tcgtgtagat aactacgata cgggagggct   6120
taccatctgg ccccagtgct gcaatgatac cgcgagaccc acgctcaccg gctccagatt   6180
tatcagcaat aaaccagcca gccggaaggg ccgagcgcag aagtggtcct gcaacttttat   6240
ccgcctccat ccagtctatt aattgttgcc gggaagctag agtaagtagt tcgccagtta   6300
atagtttgcg caacgttgtt gccattgcta caggcatcgt ggtgtcacgc tcgtcgtttg   6360
gtatggcttc attcagctcc ggttcccaac gatcaaggcg agttacatga tcccccatgt   6420
tgtgcaaaaa agcggttagc tccttcggtc ctccgatcgt tgtcagaagt aagttggccg   6480
cagtgttatc actcatggtt atggcagcac tgcataattc tcttactgtc atgccatccg   6540
taagatgctt ttctgtgact ggtgagtact caaccaagtc attctgagaa tagtgtatgc   6600
ggcgaccgag ttgctcttgc ccggcgtcaa tacgggataa taccgcgcca catagcagaa   6660
ctttaaaagt gctcatcatt ggaaaacgtt cttcggggcg aaaactctca aggatcttac   6720
cgctgttgag atccagttcg atgtaaccca ctcgtgcacc caactgatct tcagcatctt   6780
ttactttcac cagcgtttct gggtgagcaa aaacaggaag gcaaaatgcc gcaaaaaagg   6840
gaataagggc gacacggaaa tgttgaatac tcatactctt cctttttcaa tattattgaa   6900
gcatttatca gggttattgt ctcatgagcg gatacatatt tgaatgtatt tagaaaaata   6960
aacaaatagg ggttccgcgc acatttcccc gaaaagtgcc acctgacgtc taagaaacca   7020
ttattatcat gacattaacc tataaaaata ggcgtatcac gaggcccttt cgtc          7074
```

```
SEQ ID NO: 26          moltype = DNA   length = 6699
FEATURE                Location/Qualifiers
misc_feature           1..6699
                       note = construct pINT-yabM
source                 1..6699
                       mol_type = other DNA
                       organism = synthetic construct
SEQUENCE: 26
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg   120
ttggcgggtg tcgggctggc cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgaagatcct ttgatctttt   420
ctacggggtc tgacgctcag tggaacgaaa actcacgtta agggattttg gtcatgagat   480
tatcaaaaag gatcttcacc tagatccttt aaactagtga agttaccat cacggaaaaa   540
ggttatgctg cttttaagac ccactttcac atttaagttg tttttctaat ccgcatatga   600
tcaattcaag gccgaataag aaggctggct ctgcaccttg gtgatcaaat aattcgatag   660
cttgtcgtaa taatggcggc atactatcag tagtaggtgt ttccctttct tctttagcga   720
cttgatgctc ttgatcttcc aatacgcaac ctaaagtaaa atgccccact gcgctgagtg   780
catataatgc attctctagt gaaaaacctt gttggcataa aaaggctaat tgattttcga   840
gagtttcata ctgttttttct gtaggccgtg tacctaaatg tactttgct ccatcgcgat   900
gacttagtaa agcacatcta aaactttttag cgttattacg taaaaaatct tgccagcttt   960
cccccttctaa agggcaaaag tgagtatggt gcctatctaa catctcaatg gctaaggcgt   1020
cgagcaaagc ccgcttattt tttacatgcc aatacaatgt aggctgctct cacctagct   1080
tctgggcgag tttacgggtt gttaaacctt cgattccgac ctcattaagc agctctaatg   1140
cgctgttaat cactttactt ttatctaaac gagacatact cttccttttt caatattatt   1200
gaagcattta tcaggggttat tgtctcatga gcggatacat atttgaatgt atttagaaata   1260
ataaacaaat aggggggttccg cgcacatttc cccgaaaagt gccacctgaa attggccaga   1320
tgattaattc ctaatttttg ttgacactct atcattgata gagttattt accactccct   1380
atcagtgata gagaaaagtg aaatgaatag ttcgacaaaa atctagaaat aattttgttt   1440
aactttaaga aggagatata caagagctcg agtcgaagga gatagaacca tgaaggctct   1500
gtggtcgcgt cgccgtcgta tccacccggt ctatctggct tttatggcag tttcgtttat   1560
ggttggcatc gcaggtgcgc tgcagtcacc gaccctgtcg ctgttctga gccgtgaagt   1620
gggtgttcgc ccgttttggg tgggcctgtt ctatacggtt aacgcagtcg ctggtattat   1680
cgtttccctg ctgctggcca aacgttcaga taatcagggc gaccgtcgca tgctgattct   1740
gttctgctgt gttatggcga tcgccaacgc agtcctgttt gccttcaatc gccattatct   1800
gaccctggtc attgcaggtg tgctgctgag ctctatcgct agcgtggcga tgccgcagat   1860
ttttgctctg gcgcgtgaat acgcagatag ttccgcccgc gaagcagtca tgttctcatc   1920
ggtgatgcgt gcccaactgt cgctggcatg ggttatcggt ccgccgctga gctttgccat   1980
tgcactgaac tacggcttta ccgcgactgt cctggtcgcg gcctgctgt ttttgctctg   2040
cgtggctctg atttggttca ccctgccgag cgttccgcgt gcagaaaaca cggcagctga   2100
accgctgagt gatatctccg gttggaaaca ccgtgacgtg cgcatgctgt ttattgcctc   2160
tgttttcatg tggacctgta atacgatgta tgttatcgat atgccgctgt acattagtat   2220
cgtcctgggc ctgccggaca agctggcagg tctgctgatg ggtaccgcag caggcctgga   2280
aattccggtc atgctgctgg ctgtcacatt tgtgaaacgt tttggcaagc gcccgatgat   2340
gctgctggcg gttggctgcg gtgtcctgtt ttacctgggt ctggtgctgt ccacggccg   2400
tacggaactg atgctgctgc agctgctgaa cgctctgttt atcggcatta tcgcgcggcat   2460
tggtatgatc tggttccaag atctgatgcc gggtcgtccg ggtctgcaa ccacgctgtt   2520
taccaatagc atttctacgg gtgtgatcct ggcaggtgtg ctgcagggcg ttatggccga   2580
aaccttggc catcacgcag tctattggct ggcttccctg ctggcgctga tttctcttgc   2640
tctgagttgg caagttcgtg aagcgcgcac ggtgaagagt gttccgctgg cctaataaat   2700
cgatactagc ataaccccTt ggggcctcta aacgcgtcga cacgcaaaaa ggccatccgt   2760
caggatggcc ttctgcttaa tttgatgcct ggcagtttat ggcgggcgtc ctgcccgcca   2820
ccctccgggc cgttgcttcg caacgttcaa atccgctccc ggcggatttg tcctactcag   2880
gagagcgttc accgacaaac aacagataaa acgaaaggcc cagtctttcg actgagcctt   2940
```

-continued

```
tcgtttattt tgatgcctgg cagttcccta ctctcgcatg gggagacccc acactaccat   3000
catgtatgaa tatcctcctt agttcctatt ccgaagttcc tattctctag aaagtatagg   3060
aacttcggcg cgtcctacct gtgacggaag atcacttcgc agaataaata aatcctggtg   3120
tccctgttga taccgggaag ccctgggcca acttttggcg aaaatgagac gttgatcggc   3180
acgtaagagg ttccaacttt caccataatg aaataagatc actaccgggc gtatttttg   3240
agttgtcgag attttcagga gctaaggaag ctaaaatgga gaaaaaaatc actggatata   3300
ccaccgttga tatatcccaa tggcatcgta aagaacattt tgaggcattt cagtcagttg   3360
ctcaatgtac ctataaccag accgttcagc tggatattac ggcctttta aagaccgtaa   3420
agaaaaataa gcacaagttt tatccggcct ttattcacat tcttgcccgc ctgatgaatg   3480
ctcatccgga attacgtatg gcaatgaaag acggtgagct ggtgatatgg gatagtgttc   3540
acccttgtta caccgtttc catgagcaaa ctgaaacgtt ttcatcgctc tggagtgaat   3600
accacgacga tttccggcag tttctacaca tatattcgca agatgtggcg tgttacggtg   3660
aaaacctggc ctatttccct aaagggttta ttgagaatat gtttttcgtc tcagccaatc   3720
cctgggtgag tttcaccagt tttgatttaa acgtggccaa tatggacaac ttcttcgccc   3780
ccgtttcac catgggcaaa tattatacgc aaggcgacaa ggtgctgatg ccgctggcga   3840
ttcaggttca tcatgccgtt tgtgatggct tccatgtcgg cagatgctta atgaatacaa   3900
cagtactgcg atgagtggca gggcggggcg taaggcgcgc catttaaatg aagttcctat   3960
tccgaagttc ctattctcta gaaagtatag gaacttcgaa gcagctccag cctacacaat   4020
cgctcaagac gtgtaatgct gcaatctgca tgcaagcttg gcactggcca cgcaaaaagg   4080
ccatccgtca ggatggcctt ctgcttaatt tgatgcctgg cagtttatgg cgggcgtcct   4140
gcccgccacc ctccgggccg ttgcttcgca acgttcaaat ccgctcccgg cggatttgtc   4200
ctactcagga gagcgttcac cgacaaacaa cagataaaac gaaaggccca gtctttcgac   4260
tgagcctttc gttttatttg atgcctggca gttccctact ctcgcatggg gagacccac   4320
actaccatcg gggggccatc gatgcaggtg gcacttttcg gggaaatgtg cgcggaaccc   4380
ctatttgttt attttctaa atacattcaa atatgtatcc gctcatgaga caataaccct   4440
gctgcagagg cctgcatgca agcttggcgt aatcatggtc atagctgttt cctgtgtgaa   4500
attgttatcc gctcacaatt ccacacaaca tacgagccgg aagcataaag tgtaaagcct   4560
ggggtgccta atgagtgagc taactcacat taattgcgtt gcgctcactg cccgctttcc   4620
agtcgggaaa cctgtcgtgc cagctgcatt aatgaatcgg ccaacgcgcg gggagaggcg   4680
gtttgcgtat tgggcgctct tccgcttcct cgctcactga ctcgctgcgc tcggtcgttc   4740
ggctgcggcg agcggtatca gctcactcaa aggcggtaat acggttatcc acagaatcag   4800
gggataacgc aggaaagaac atgtgagcaa aaggccagca aaaggccagg aaccgtaaaa   4860
aggccgcgtt gctggcgttt ttccataggc tccgcccccc tgacgagcat cacaaaaatc   4920
gacgctcaag tcagaggtgg cgaaacccga caggactata aagataccag gcgtttcccc   4980
ctggaagctc cctcgtgcgc tctcctgttc cgaccctgcc gcttaccgga tacctgtccg   5040
cctttctccc ttcgggaagc gtggcgcttt ctcatagctc acgctgtagg tatctcagtt   5100
cggtgtaggt cgttcgctcc aagctgggct gtgtgcacga accccccgtt cagcccgacc   5160
gctgcgcctt atccggtaac tatcgtcttg agtccaaccc ggtaagacac gacttatcgc   5220
cactggcagc agccactggt aacaggatta gcagagcgag gtatgtaggc ggtgctacag   5280
agttcttgaa gtggtggcct aactacggct acactagaag aacagtattt ggtatctgcg   5340
ctctgctgaa gccagttacc ttcggaaaaa gagttggtag ctcttgatcc ggcaaacaaa   5400
ccaccgctgg tagcggtggt ttttttgttt gcaagcagca gattacgcgc agaaaaaaag   5460
gatctcaaga agatcctttg atcttttcta cggggtctga cgctcagtgg aacgaaaact   5520
cacgttaagg gattttggtc atgagattat caaaaaggat cttcacctag atccttttaa   5580
attaaaaatg aagttttaaa tcaatctaaa gtatatatga gtaaacttgg tctgacagtt   5640
accaatgctt aatcagtgag gcacctatct cagcgatctg tctatttcgt tcatccatag   5700
ttgcctgact ccccgtcgtg tagataacta cgatacggga gggcttacca tctggcccca   5760
gtgctgcaat gataccgcga gacccacgct caccggctcc agatttatca gcaataaacc   5820
agccagccgg aagggccgag cgcagaagtg gtcctgcaac tttatccgcc tccatccagt   5880
ctattaattg ttgccgggaa gctagagtaa gtagttcgcc agttaatagt ttgcgcaacg   5940
ttgttgccat tgctacaggc atcgtggtgt cacgctcgtc gtttggtatg gcttcattca   6000
gctccggttc ccaacgatca aggcgagtta catgatcccc catgttgtgc aaaaaagcgg   6060
ttagctcctt cggtcctccg atcgttgtca gaagtaagtt ggccgcagtg ttatcactca   6120
tggttatggc agcactgcat aattctctta ctgtcatgcc atccgtaaga tgcttttctg   6180
tgactggtga gtactcaacc aagtcattct gagaatagtg tatgcggcga ccgagttgct   6240
cttgcccggc gtcaatacgg gataataccg cgccacatag cagaacttta aaagtgctca   6300
tcattggaaa acgttcttcg gggcgaaaac tctcaaggat cttaccgctg ttgagatcca   6360
gttcgatgta acccactcgt gcacccaact gatcttcagc atcttttact ttcaccagcg   6420
tttctgggtg agcaaaaaca ggaaggcaaa atgccgcaaa aaagggaata agggcgacac   6480
ggaaatgttg aatactcata ctcttccttt ttcaatatta ttgaagcatt tatcagggtt   6540
attgtctcat gagcggatac atatttgaat gtatttagaa aaataaacaa ataggggttc   6600
cgcgcacatt tccccgaaaa gtgccacctg acgtctaaga aaccattatt atcatgacat   6660
taacctataa aaataggcgt atcacgaggc cctttcgtc                          6699
```

```
SEQ ID NO: 27           moltype = DNA   length = 6684
FEATURE                 Location/Qualifiers
misc_feature            1..6684
                        note = construct pINT-ydeA
source                  1..6684
                        mol_type = other DNA
                        organism = synthetic construct
SEQUENCE: 27
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc   240
attcgccatt caggctgcgc aactgttggg aaggcgatc ggtgcgggcc tcttcgctat    300
tacgccagct ggcgaaaggg ggatgtgctg caaggcgatt aagttgggta acgccagggt   360
tttcccagtc acgacgttgt aaaacgacgg ccagtgaatt cgaagatcct ttgatctttt   420
```

-continued

```
ctacggggtc tgacgctcag tggaacgaaa actcacgtta aggggattttg gtcatgagat   480
tatcaaaaag gatcttcacc tagatccttt taaactagtg aagttaccat cacggaaaaa   540
ggttatgctg cttttaagac ccactttcac atttaagttg ttttttctaat ccgcatatga   600
tcaattcaag gccgaataag aaggctggct ctgcaccttg gtgatcaaat aattcgatag   660
cttgtcgtaa taatggcggc atactatcag tagtaggtgt ttcccttttct tctttagcga   720
cttgatgctc ttgatcttcc aatacgcaac ctaaagtaaa atgccccact gcgctgagtg   780
catataatgc attctctagt gaaaaacctt gttggcataa aaaggctaat tgattttcga   840
gagtttcata ctgtttttct gtaggccgtg tacctaaatg tacttttgct ccatcgcgat   900
gacttagtaa agcacatcta aaactttttag cgttattacg taaaaaatct tgccagcttt   960
ccccttctaa agggcaaaag tgagtatggt gcctatctca catctcaatg gctaaggcgt  1020
cgagcaaagc ccgcttattt tttacatgcc aatacaatgt aggctgctct acacctagct  1080
tctgggcgag tttacgggtt gttaaaacctt cgattccgac ctcattaagc agctctaatg  1140
cgctgttaat cactttactt ttatctaaac gagacatact cttcctttttt caatattatt  1200
gaagcattta tcagggttat tgtctcatga gcggatacat atttgaatgt atttagaaaa  1260
ataaacaaat aggggttccg cgcacatttc cccgaaaagt gccacctgaa attggccaga  1320
tgattaattc ctaatttttg ttgacactct atcattgata gagttatttt accactccct  1380
atcagtgata gagaaaagtg aaatgaatag ttcgacaaaa atctagaaat aattttgttt  1440
aactttaaga aggagatata caagagctcg agtcgaagga gatagaacca tgacaacaaa  1500
cactgtttcc cgcaaagtgg cgtggctacg ggtcgttacg ctggcagtcg ccgccttcat  1560
cttcaacacc accgaatttg tccctgttgg cctgctctct gacattgcgc aaagtttttca  1620
catgcaaacc gctcaggtcg gcatcatgtt gaccatttac gcatgggtag tagcgctaat  1680
gtcattgcct tttatgttaa tgaccagtca ggttgaacgg cgcaaattac tgatctgcct  1740
gtttgtggtg tttattgcca gccacgtact gtcgttttttg tcgtggagct ttaccgttct  1800
ggtgatcagt cgcattggtg tggctttttgc acatgcgatt ttctggtcga ttacggcgtc  1860
tctggcgatc cgtatggctc cggccgggaa gcgagcacag gcattgagtt taattgccac  1920
cggtacagca ctggcgatgg tcttaggttt acctctcggg cgcattgtgg gccagtattt  1980
cggttggcga atgaccttct tcgcgattgg tattggggcg cttatcaccc ttttgtgcct  2040
gattaagtta cttcccttac tgcccagtga gcattccggt tcactgaaaa gcctcccgct  2100
attgttccgc cgcccggcat tgatgagcat ttatttgtta actgtggtgg ttgtcaccgc  2160
ccattacacg gcatacagct atatcgagcc ttttgtacaa aacattgcgg gattcagcgc  2220
caactttgcc acggcattac tgttattact cggtggtgcg ggcattattg gcagcgtgat  2280
tttcggtaaa ctgggtaatc agtatgcgtc tgcgttggtg agtacggcga ttgcgctgtt  2340
gctggtgtgc ctggcattgc tgttacctgc ggcgaacagt gaaatacacc tcgggggtgct  2400
gagtatttttc tgggggatcg cgatgatgat catcgggctt ggtatgcagg ttaaagtgct  2460
ggcgctggca ccagatgcta ccgacgtcgc gatggcgcta ttctccggca tatttaatat  2520
tggaatcggg gcgggtgcgt tggtaggtaa tcaggtgagt ttgcactggt caatgtcgat  2580
gattggttat gtgggcgcgg tgcctgcttt tgccgcgtta atttggtcaa tcattatatt  2640
tcgccgctgg ccagtgacac tcgaagaaca gacgcaatag taaatcgata ctagcataac  2700
cccttgggc ctctaaacgc gtcgacacgc aaaaaggcca tccgtcagga tggccttctg  2760
cttaatttga tgcctggcag tttatggcgg gcgtcctgcc cgccaccctc cgggccgttg  2820
cttcgcaacg ttcaaatccg ctcccggcgg atttgtccta ctcaggagag cgttcaccga  2880
caaacaacag ataaaacgaa aggcccagtc tttcgactga gcctttcgtt ttatttgatg  2940
cctggcagtt ccctactctc gcatggggag acccccacact accatcatgt atgaatatcc  3000
tccttagttc ctattccgaa gttcctattc tctagaaagt ataggaactt cggcgcgtcc  3060
tacctgtgac ggaagatcac ttcgcagaat aaataaatcc tggtgtccct gttgataccg  3120
ggaagccctg ggccaacttt tggcgaaaat gagacgttga tcggcacgta agaggttcca  3180
actttcacca taatgaaata agatcactac cgggcgtatt ttttgagttg tcgagatttt  3240
caggagctaa ggaagctaaa atggagaaaa aaatcactgg atataccacc gttgatatat  3300
cccaatggca tcgtaaagaa cattttgagg catttcagtc agttgctcaa tgtacctata  3360
accagaccgt tcagctggat attacggcct ttttaaagac cgtaaagaaa aataagcaca  3420
agttttatcc ggcctttatt cacattcttg cccgcctgat gaatgctcat ccggaattac  3480
gtatggcaat gaaagacggt gagctggtga tatgggatag tgttcaccct tgttacaccg  3540
ttttccatga gcaaactgaa acgttttcat cgctctggag tgaataccac gacgatttcc  3600
ggcagtttct acacatatat tcgcaagatg tggcgtgtta cggtgaaaac ctggcctatt  3660
tccctaaagg gtttattgag aatatgtttt tcgtctcagc caatccctgg gtgagtttca  3720
ccagttttga tttaaacgtg gccaatatgg acaacttctt cgcccccgtt ttcaccatgg  3780
gcaaatatta tacgcaaggc gacaaggtgc tgatgccgct ggcgattcag gttcatcatg  3840
ccgtttgtga tggcttccat gtcggcagat gcttaatgaa tacaacagta ctgcgatgag  3900
tggcaggggc gggcgtaagg cgcgccattt aaatgaagtt cctattccga agttcctatt  3960
ctctagaaag tataggaact tcgaagcagc tccagcctac acaatcgctc aagacgtgta  4020
atgctgcaat ctgcatgcaa gcttggcact ggccacgcaa aaaggccatc cgtcaggatg  4080
gccttctgct taatttgatg cctggcagtt atggcgggc gtcctgcccg ccaccctccg  4140
ggccgttgct tcgcaacgtt caaatccgct cccggcggat ttgtcctact caggagagcg  4200
ttcaccgaca aacaacagat aaaacgaaag gcccagtctt tcgactgagc ctttcgtttt  4260
atttgatgcc tggcagttcc ctactctcgc atggggagac ccacactac catcgggggg  4320
ccatcgatgc aggtggcact tttcggggaa atgtgcgcgg aacccctatt tgtttattt  4380
tctaaataca ttcaaatatg tatccgctca tgagacaata accctgctgc agaggcctgc  4440
atgcaagctt ggcgtaatca tggtcatagc tgtttcctgt gtgaaattgt tatccgctca  4500
caattccaca acatacga gccggaagca taaagtgtaa agcctggggt gcctaatgag  4560
tgagctaact cacattaatt gcgttgcgct cactgcccgc tttccagtcg ggaaacctgt  4620
cgtgccagct gcattaatga atcggccaac gcgcggggag aggcggtttg cgtattgggc  4680
gctcttccgc ttcctcgctc actgactcgc tgcgctcggt cgttcggctg cggcgagcgg  4740
tatcagctca ctcaaaggcg gtaatacggt tatccacaga atcaggggat aacgcaggaa  4800
agaacatgtg agcaaaaggc cagcaaaagg ccaggaaccg taaaaaggcc gcgttgctgg  4860
cgtttttcca taggctccgc cccctgacg agcatcacaa aaatcgacgc tcaagtcaga  4920
ggtggcgaaa cccgacagga ctataaagat accaggcgtt tccccctgga agctccctcg  4980
tgcgctctcc tgttccgacc ctgccgctta ccggatacct gtccgccttt ctcccttcgg  5040
gaagcgtggc gctttctcat agctcacgct gtaggtatct cagttcggtg taggtcgttc  5100
gctccaagct gggctgtgtg cacgaacccc ccgttcagcc cgaccgctgc gccttatccg  5160
```

```
gtaactatcg tcttgagtcc aacccggtaa gacacgactt atcgccactg gcagcagcca   5220
ctggtaacag gattagcaga gcgaggtatg taggcggtgc tacagagttc ttgaagtggt   5280
ggcctaacta cggctacact agaagaacag tatttggtat ctgcgctctg ctgaagccag   5340
ttaccttcgg aaaaagagtt ggtagctctt gatccggcaa acaaaccacc gctggtagcg   5400
gtggtttttt tgtttgcaag cagcagatta cgcgcagaaa aaaaggatct caagaagatc   5460
ctttgatctt ttctacgggg tctgacgctc agtggaacga aaactcacgt taagggattt   5520
tggtcatgag attatcaaaa aggatcttca cctagatcct tttaaattaa aaatgaagtt   5580
ttaaatcaat ctaaagtata tatgagtaaa cttggtctga cagttaccaa tgcttaatca   5640
gtgaggcacc tatctcagcg atctgtctat ttcgttcatc catagttgcc tgactccccg   5700
tcgtgtagat aactacgata cgggagggct taccatctgg ccccagtgct gcaatgatac   5760
cgcgagaccc acgctcaccg gctccagatt tatcagcaat aaaccagcca gccggaaggg   5820
ccgagcgcag aagtggtcct gcaactttat ccgcctccat ccagtctatt aattgttgcc   5880
gggaagctag agtaagtagt tcgccagtta atagtttgcg caacgttgtt gccattgcta   5940
caggcatcgt ggtgtcacgc tcgtcgtttg gtatggcttc attcagctcc ggttcccaac   6000
gatcaaggcg agttacatga tcccccatgt tgtgcaaaaa agcggttagc tccttcggtc   6060
ctccgatcgt tgtcagaagt aagttggccg cagtgttatc actcatggtt atggcagcac   6120
tgcataattc tcttactgtc atgccatccg taagatgctt ttctgtgact ggtgagtact   6180
caaccaagtc attctgagaa tagtgtatgc ggcgaccgag ttgctcttgc ccggcgtcaa   6240
tacgggataa taccgcgcca catagcagaa ctttaaaagt gctcatcatt ggaaaacgtt   6300
cttcggggcg aaaactctca aggatcttac cgctgttgag atccagttcg atgtaaccca   6360
ctcgtgcacc caactgatct tcagcatctt ttactttcac cagcgtttct gggtgagcaa   6420
aaacaggaag gcaaaatgcc gcaaaaaagg gaataagggc gacacggaaa tgttgaatac   6480
tcatactctt cctttttcaa tattattgaa gcatttatca gggttattgt ctcatgagcg   6540
gatacatatt tgaatgtatt tagaaaaata aacaaatagg ggttccgcgc acatttcccc   6600
gaaaagtgcc acctgacgtc taagaaacca ttattatcat gacattaacc tataaaaata   6660
ggcgtatcac gaggcccttt cgtc                                         6684

SEQ ID NO: 28          moltype = DNA  length = 6738
FEATURE                Location/Qualifiers
misc_feature           1..6738
                       note = construct pINT-propP2
source                 1..6738
                       mol_type = other DNA
                       organism = synthetic construct
SEQUENCE: 28
tcgcgcgttt cggtgatgac ggtgaaaacc tctgacacat gcagctcccg gagacggtca   60
cagcttgtct gtaagcggat gccgggagca gacaagcccg tcaggcgcg tcagcgggtg   120
ttggcgggtg tcggggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgaagatcct ttgatctttt   420
ctacggggtc tgacgctcag tggaacgaaa actcacgtta agggattttg gtcatgagat   480
tatcaaaaag gatcttcacc tagatccttt taaactagtg aagttaccat cacgggaaaa   540
ggttatgctg ctttttaagac ccactttcac atttaagttg ttttttctaat ccgcatatga   600
tcaattcaag gccgaataag aaggctggct ctgcaccttg gtgatcaaat aattcgatag   660
cttgtcgtaa taatggcggc atactatcag tagtaggtgt ttcccttttct tctttagcga   720
cttgatgctc ttgatcttcc aatacgcaac ctaaagtaaa atgccccact cgctgagtg   780
catataatgc attctctagt gaaaaacctt gttggcataa aaaggctaat tgattttcga   840
gagtttcata ctgttttct gtaggccgtg tacctaaatg tactttgct ccatcgcgat   900
gacttagtaa agcacatcta aaactttag cgttattacg taaaaaatct tgccagcttt   960
ccccttctaa agggcaaaag tgagtatggt gcctatctaa catctcaatg gctaaggcgt   1020
cgagcaaagc ccgcttattt tttacatgcc aatacaatgt aggctgctct cacctagct   1080
tctgggcgag tttacgggtt gttaaacctt cgattccgac ctcattaagc agctctaatg   1140
cgctgttaat cactttactt ttatctaaac gagacatact cttctttttt caatattatt   1200
gaagcatttta tcaggttat tgtctcatga gcggatacat atttgaatgt atttagaaaa   1260
ataaacaaat aggggttccg cgcacatttc ccgaaaagt gccacctgaa attgccaga   1320
tgattaattc ctaattttttg ttgacactct atcattgata gagttatttt accactccct   1380
atcagtgata gagaaaagtg aaatgaatag ttcgacaaa atctagaaat aattttgttt   1440
aactttaaga aggagatata caagagctcg agtcgaagga gatagaacca tgaatgaatc   1500
cgccgtgaaa atcaaccgca cctttatctc ccactatgct ctgctgctga aactgatgac   1560
catgttcgtc caacaacaga acagtacccc gtccaatatt gtggcgttta acttcctgct   1620
gatcgccttt ctgacgggta ttgcgagcgc cttccagacc ccgacgctgt cactgtatct   1680
gtcgcaagaa atcaatgtta gtccgttttt cgttggtcctg ttttactccg ttaacgcgat   1740
tatcggcatt atcctgagcc agattctggc caaatattct gataagcaag atgaccgtcg   1800
caaagtcatg attgtgtgct gtctgatcgc agtgctgggt tgcctgatct ttgcttacag   1860
ccgtaattat tacgttctga ttatcattgg caccacgctg ctgggcctgg gtagctctgc   1920
aaacccgcag tcatttgcac tggctcgtga atatgcagaa agttcccatc gcgaagctgt   1980
tatgttcacc acgattatgc gcaccagat cagtctggca tggattgtcg gtccgcgcat   2040
gtccttttc attgctctga attggggctt tgattatatg tacctggtcg caggttcagc   2100
tttcctgctg tgcgccggcg tgtcgaaact gctgccgaag atcccgcgtc agtctgcagt   2160
caaaaatcaa gaaattctgg acaacacccc gccgcgtcgc agtgtgattt acctgtttat   2220
cgccaatctg ctgctgtgga cgtgtaattc catgtacctg atcaacatgc cgctgttcgt   2280
gattaacgaa ctgcacctgg gtaaagaact ggcaggtagc ctgatcagcg cggagcagg   2340
cctggaaatt ccggtgatga tctttgccgg ctatctgacc aaatacttct caaaaaagcg   2400
cctgatgatg attgcactgg tttcgggtct ggctttttat tcatcgctgc tgttcagcga   2460
tcagacctgg caactgatcg gcctgcagat gctgaacgcg atctttattg gtatcaccgc   2520
cacgattggc atggtttatt ccaagacct gatgccgacc aaaatgggta cggcgaccac   2580
gctgtttagt aatgcagcta agagctcttg gatcattggc ggtccgatcg cgggcatcat   2640
```

```
tgccgaaatc tggcattaca actctgtgtt ttatgtggcg gttgccctga ttttcatcag  2700
cgtcggctgt atgtggaagg ttaagtctgt ctaataaatc gatactagca taaccccttg  2760
gggcctctaa acgcgtcgac acgcaaaaag gccatccgtc aggatggcct tctgcttaat  2820
ttgatgcctg gcagtttatg gcgggcgtcc tgcccgccac cctccgggcc gttgcttcgc  2880
aacgttcaaa tccgctcccg gcggatttgt cctactcagg agagcgttca ccgacaaaca  2940
acagataaaa cgaaaggccc agtctttcga ctgagccttt cgttttattt gatgcctggc  3000
agttccctac tctcgcatgg ggagacccca cactaccatc atgtatgaat atcctcctta  3060
gttcctattc cgaagttcct attctctaga aagtatagga acttcggcgc gtcctacctg  3120
tgacggaaga tcacttcgca gaataaataa atcctggtgt ccctgttgat accgggaagc  3180
cctgggccaa cttttggcga aaatgagacg ttgatcgacca cgtaagaggt tccaactttc  3240
accataatga aataagatca ctaccgggcg tattttttga gttgtcgaga ttttcaggag  3300
ctaaggaagc taaaatggag aaaaaaatca ctggatatac caccgttgat atatcccaat  3360
ggcatcgtaa agaacatttt gaggcatttc agtcagttgc tcaatgtacc tataaccaga  3420
ccgttcagct ggatattacg gcctttttaa agaccgtaaa gaaaaataag cacaagtttt  3480
atccggcctt tattcacatt cttgcccgcc tgatgaatgc tcatccggaa ttacgtatgg  3540
caatgaaaga cggtgagctg gtgatatggg atagtgttca cccttgttac accgttttcc  3600
atgagcaaac tgaaacgttt tcatcgctct ggagtgaata ccacgacgat ttccggcagt  3660
ttctacacat atattcgcaa gatgtggcgt gttacggtga aaacctggcc tatttcccta  3720
aagggtttat tgagaatatg tttttcgtct cagccaatcc ctgggtgagt ttcaccagtt  3780
ttgatttaaa cgtggccaat atggacaact tcttcgcccc cgttttcacc atgggcaaat  3840
attatacgca aggcgacaag gtgctgatgc cgctggcgat tcaggttcat catgccgttt  3900
gtgatggctt ccatgtcggc agatgcttaa tgaatacaac agtactgcga tgagtggcag  3960
ggcggggcgt aaggcgcgcc atttaaatga agttcctatt ccgaagttcc tattctctag  4020
aaagtatagg aacttcgaag cagctccagc ctacacaatc gctcaagacg tgtaatgctg  4080
caatctgcat gcaagcttgg cactggccac gcaaaaaggc catccgtcag gatggccttc  4140
tgcttaattt gatgcctggc agtttatggc gggcgtcctg cccgccaccc tccgggccgt  4200
tgcttcgcaa cgttcaaatc cgctcccggc ggatttgtcc tactcaggag agcgttcacc  4260
gacaaacaac agataaaacg aaaggcccag tctttcgact gagcctttcg ttttatttga  4320
tgcctggcag ttccctactc tcgcatgggg agaccccaca ctaccatcgg gggccatcg  4380
atgcaggtgg cacttttcgg ggaaatgtgc gcggaacccc tatttgttta tttttctaaa  4440
tacattcaaa tatgtatccg ctcatgagac aataaccctg ctgcagaggc ctgcatgcaa  4500
gcttggcgta atcatggtca tagctgtttc ctgtgtgaaa ttgttatccg ctcacaattc  4560
cacacaacat acgagccgga agcataaagt gtaaagcctg gggtgcctaa tgagtgagct  4620
aactcacatt aattgcgttg cgctcactgc ccgctttcca gtcgggaaac ctgtcgtgcc  4680
agctgcatta atgaatcggc caacgcgcgg gagaggcggt ttgcgtatt ggcgctctt  4740
ccgcttcctc gctcactgac tcgctgcgct cggtcgttcg gctgcggcga gcggtatcag  4800
ctcactcaaa ggcggtaata cggttatcca cagaatcagg ggataacgca ggaaagaaca  4860
tgtgagcaaa aggccagcaa aaggccagga accgtaaaaa ggccgcgttg ctggcgtttt  4920
tccataggct ccgcccccct gacgagcatc acaaaaatcg acgctcaagt cagaggtggc  4980
gaaacccgac aggactataa agataccagg cgtttccccc tggaagctcc ctcgtgcgct  5040
ctcctgttcc gaccctgccg cttaccggat acctgtccgc ctttctccct tcgggaagcg  5100
tggcgctttc tcatagctca cgctgtaggt atctcagttc ggtgtaggtc gttcgctcca  5160
agctgggctg tgtgcacgaa ccccccgttc agcccgaccg ctgcgcctta tccggtaact  5220
atcgtcttga gtccaacccg gtaagacacg acttatcgcc actggcagca gccactggta  5280
acaggattag cagagcgagg tatgtaggcg gtgctacaga gttcttgaag tggtggccta  5340
actacggcta cactagaaga acagtatttg gtatctgcgc tctgctgaag ccagttacct  5400
tcggaaaaag agttggtagc tcttgatccg gcaaacaaac caccgctggt agcggtggtt  5460
tttttgtttg caagcagcag attacgcgca gaaaaaaagg atctcaagaa gatcctttga  5520
tcttttctac ggggtctgac gctcagtgga acgaaaactc acgttaaggg attttggtca  5580
tgagattatc aaaaaggatc ttcacctaga tccttttaaa ttaaaaatga agttttaaat  5640
caatctaaag tatatatgag taaacttggt ctgacagtta ccaatgctta atcagtgagg  5700
cacctatctc agcgatctgt ctatttcgtt catccatagt tgcctgactc cccgtcgtgt  5760
agataactac gatacgggag ggcttaccat ctggccccag tgctgcaatg ataccgcgag  5820
acccacgctc accggctcca gatttatcag caataaacca gccagccgga agggccgagc  5880
gcagaagtgg tcctgcaact ttatccgcct ccatccagtc tattaattgt tgccgggaag  5940
ctagagtaag tagttcgcca gttaatagtt tgcgcaacgt tgttgccatt gctacaggca  6000
tcgtggtgtc acgctcgtcg tttggtatgg cttcattcag ctccggttcc caacgatcaa  6060
ggcgagttac atgatccccc atgttgtgca aaaaagcggt tagctccttc ggtcctccga  6120
tcgttgtcag aagtaagttg gccgcagtgt tatcactcat ggttatggca gcactgcata  6180
attctcttac tgtcatgcca tccgtaagat gcttttctgt gactggtgag tactcaacca  6240
agtcattctg agaatagtgt atgcggcgac cgagttgctc ttgcccggcg tcaatacggg  6300
ataataccgc gccacatagc agaactttaa aagtgctcat cattggaaaa cgttcttcgg  6360
ggcgaaaact ctcaaggatc ttaccgctgt tgagatccag ttcgatgtaa cccactcgtg  6420
cacccaactg atcttcagca tcttttactt tcaccagcgt ttctgggtga gcaaaaacag  6480
gaaggcaaaa tgccgcaaaa aagggaataa gggcgacacg aaatgttga atactcatac  6540
tcttcctttt tcaatattat tgaagcattt atcaggytta ttgtctcatg agcggataca  6600
tatttgaatg tatttagaaa aataaacaaa taggggttcc gcgcacattt ccccgaaaag  6660
tgccacctga cgtctaagaa accattatta tcatgacatt aacctataaa aataggcgta  6720
tcacgaggcc ctttcgtc                                                 6738
```

```
SEQ ID NO: 29        moltype = DNA  length = 6513
FEATURE              Location/Qualifiers
misc_feature        1..6513
                     note = construct pINT-Pc-setA
source              1..6513
                     mol_type = other DNA
                     organism = synthetic construct
SEQUENCE: 29
tcgcgcgttt cggtgatgac ggtgaaaacc tctgacacat gcagctcccg gagacggtca  60
```

-continued

```
cagcttgtct gtaagcggat gccgggagca gacaagcccg tcagggcgcg tcagcgggtg    120
ttggcgggtg tcgggctggg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct ttgatctttt    420
ctacggggtc tgacgctcag tggaacgaaa actcacgtta agggattttg gtcatgagat    480
tatcaaaaag gatcttcacc tagatccttt taaactagtg aagttaccat cacggaaaaa    540
ggttatgctg cttttaagac ccactttcac atttaagttg tttttctaat ccgcatatga    600
tcaattcaag gccgaataag aaggctggct ctgcaccttg gtgatcaaat aattcgatag    660
cttgtcgtaa taatggcggc atactatcag tagtaggtgt ttcccttttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgtttttct gtaggccgtg tacctaaatg tacttttgct ccatcgcgat    900
gacttagtaa agcacatcta aaactttttag cgttattacg taaaaaatct tgccagcttt    960
cccctctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttccttttt caatattatt   1200
gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaattttttg ttgacactct atcattgata gagttatttt accactccct   1380
atcagtgata gagaaaagtg aaatgaatag ttcgacaaaa atctagaaat aattttgttt   1440
aactttaaga aggagatata caagagctcg agtcgaagga gatagaacca tgttctacac   1500
gggctcggca gttattggta tcgtcgtctc gcagatgctg gctacgcgct cggatcgtca   1560
gggtgaccgc aagtcgctga tcttcgtttg ctgtctgctg ggtgcgctgg cctgcatgct   1620
gtttgcgtgg aaccgcaatt atttcatcct gctgtttatt ggtgtgctgc tgagctcttt   1680
cggcagtacc gccaacccgc agctgtttgc actggctcgc gaacatgcag ataaaacggg   1740
tcgtgaagcg gccatgttca gttccatcct gcgtgcccaa atttccctgg catgggtggt   1800
tggtccgccg attgcgtttg ccctggcact gggcttcggt tttaccacga tgtacctgac   1860
cgcagctgtc gtgttcatcc tgtgtggtat tctggtgaag ctgtttctgc cgagcatgcc   1920
gaaagccgtt gaaaagacca cgagcaccct ggaatctccg cgtcgcaatc gtcgcgacac   1980
gctgctgctg tttgttgcgt gcaccctgat gtggacgtgt aacggcatct atctgattaa   2040
tatgccgctg tacctggttc atgaactgca cctgccggaa aaactggcag gtatcatgat   2100
gggtgtcgca gcaggtctgg aaatcccggt tatgctgatt gccggttatg tcgcaaaacg   2160
tttcggcaag cgctttctga tgcgtctggc tgtcgcgagc ggtctgctgt ttttcggcgg   2220
tctgctggtg ctggatggcg aaatcgccct gctggcactg caggctctga acgcgatttt   2280
catcggcatt ctggctggca ttggtatgct gtactttcag gacctgatgc cgggccaagc   2340
aggtgcagct accacgctgt ttaccaacac cacgcgcgtg ggttggatta tctcaggttc   2400
gctggctggc atcgtggcgg aaatttggaa ttatcacgct gtgttttttct ttgcgctgct   2460
gatgatcgtc ggctctattt actgcatgtg gcgtattaaa gatgcgtaat aaatcgatac   2520
tagcataacc ccttgggggcc tctaaacgcg tcgacacga aaaaggccat ccgtcaggat   2580
ggccttctgc ttaatttgat gcctggcagt ttatggcggg cgtcctgccc gccaccctcc   2640
gggccgttgc ttcgcaacgt tcaaatccgc tcccggcgga tttgtcctac tcaggagagc   2700
gttcaccgac aaacaacaga taaaacgaaa ggcccagtct ttcgactgag cctttcgttt   2760
tatttgatgc ctggcagttc cctactctcg catgggggaga ccccacacta ccatcatgta   2820
tgaatatcct ccttagttcc tattccgaag ttcctattct ctagaaagta taggaacttc   2880
ggcgcgtcct acctgtgacg gaagatcact tcgcagaata aataaatcct ggtgtccctg   2940
ttgataccgg gaagccctgg gccaactttt ggcgaaaatg agacgttgat cggcacgtaa   3000
gaggttccaa ctttcaccat aatgaaataa gatcactacc gggcgtattt tttgagttgt   3060
cgagatttttc aggagctaag gaagctaaaa tggagaaaaa aatcactgga tataccaccg   3120
ttgatatatc ccaatggcat cgtaaagaac attttgaggc atttcagtca gttgctcaat   3180
gtacctataa ccagaccgtt cagctggata ttacggcctt tttaaagacc gtaaagaaaa   3240
ataagcacaa gttttatccg gcctttattc acattcttgc ccgcctgatg aatgctcatc   3300
cggaattacg tatggcaatg aaagacggtg agctggtgat atgggatagt gttcaccctt   3360
gttacaccgt tttccatgag caaactgaaa cgttttcatc gctctggagt gaataccacg   3420
acgatttccg gcagtttcta cacatatatt cgcaagatgt ggcgtgttac ggtgaaaacc   3480
tggcctattt ccctaaaggg tttattgaga atatgttttt cgtctcagcc aatccctggg   3540
tgagtttcac cagttttgat ttaaacgtgg ccaatatgga caacttcttc gcccccgttt   3600
tcaccatggg caaatattat acgcaaggcg acaaggtgct gatgccgctg gcgattcagg   3660
ttcatcatgc cgtttgtgat ggcttccatg tcggcagatg cttaatgaat acaacagtac   3720
tgcgatgagt ggcagggcgg ggcgtaaggc gcgccattta aatgaagttc ctattccgaa   3780
gttcctattc tctagaaagt ataggaactt cgaagcagct ccagcctaca caatcgctca   3840
agacgtgtaa tgctgcaatc tgcatgcaag cttggcactg gccacgcaaa aaggccatcc   3900
gtcaggatgg ccttctgctt aatttgatgc ctggcagttt atggcgggcg tcctgcccgc   3960
caccctccgg gccgttgctt cgcaacgttc aaatccgctc ccggcggatt tgtcctactc   4020
aggagagcgt tcaccgacaa acaacagata aaacgaaagg cccagtcttt cgactgagcc   4080
tttcgtttta tttgatgcct ggcagttccc tactctcgca tggggagacc ccacactacc   4140
atcggggggc catcgatgca ggtggcactt ttcggggaaa tgtgcgcgga acccctattt   4200
gtttatttttt ctaaatacat tcaaatatgt atccgctcat gagacaataa ccctgctgca   4260
gaggcctgca tgcaagcttg gcgtaatcat ggtcatagct gtttcctgtg tgaaattgtt   4320
atccgctcac aattccacac aacatacgag ccggaagcat aaagtgtaaa gcctggggtg   4380
cctaatgagt gagctaactc acattaattg cgttgcgctc actgcccgct ttccagtcgg   4440
gaaacctgtc gtgccagctg cattaatgaa tcggccaacg cgcggggaga ggcggtttgc   4500
gtattgggcg ctcttccgct tcctcgctca ctgactcgct gcgctcggtc gttcggctgc   4560
ggcgagcggt atcagctcac tcaaaggcgg taatacggtt atccacagaa tcaggggata   4620
acgcaggaaa gaacatgtga gcaaaaggcc agcaaaaggc caggaaccgt aaaaaggccg   4680
cgttgctggc gtttttccat aggctccgcc cccctgacga gcatcacaaa aatcgacgct   4740
caagtcagag gtggcgaaac ccgacaggac tataaagata ccaggcgttt ccccctggaa   4800
```

```
gctccctcgt gcgctctcct gttccgaccc tgccgcttac cggatacctg tccgcctttc  4860
tcccttcggg aagcgtggcg ctttctcata gctcacgctg taggtatctc agttcggtgt  4920
aggtcgttcg ctccaagctg ggctgtgtgc acgaacccccc cgttcagccc gaccgctgcg  4980
ccttatccgg taactatcgt cttgagtcca acccggtaag acacgactta tcgccactgg  5040
cagcagccac tggtaacagg attagcagag cgaggtatgt aggcggtgct acagagttct  5100
tgaagtggtg gcctaactac ggctacacta gaagaacagt atttggtatc tgcgctctgc  5160
tgaagccagt taccttcgga aaaagagttg gtagctcttg atccggcaaa caaaccaccg  5220
ctggtagcgg tggttttttt gtttgcaagc agcagattac gcgcagaaaa aaaggatctc  5280
aagaagatcc tttgatcttt tctacggggt ctgacgctca gtggaacgaa aactcacgtt  5340
aagggatttt ggtcatgaga ttatcaaaaa ggatcttcac ctagatcctt ttaaattaaa  5400
aatgaagttt taaatcaatc taaagtatat atgagtaaac ttggtctgac agttaccaat  5460
gcttaatcag tgaggcacct atctcagcga tctgtctatt tcgttcatcc atagttgcct  5520
gactcccccgt cgtgtagata actacgatac gggagggctt accatctggc cccagtgctg  5580
caatgatacc gcgagaccca cgctcaccgg ctccagattt atcagcaata aaccagccag  5640
ccggaagggc cgagcgcaga agtggtcctg caacttttatc cgcctccatc cagtctatta  5700
attgttgccg ggaagctaga gtaagtagtt cgccagttaa tagtttgcgc aacgttgttg  5760
ccattgctac aggcatcgtg gtgtcacgct cgtcgtttgg tatggcttca ttcagctccg  5820
gttcccaacg atcaaggcga gttacatgat ccccccatgtt gtgcaaaaaa gcggttagct  5880
ccttcggtcc tccgatcgtt gtcagaagta agttggccgc agtgttatca ctcatggtta  5940
tggcagcact gcataattct cttactgtca tgccatccgt aagatgcttt tctgtgactg  6000
gtgagtactc aaccaagtca ttctgagaat agtgtatgcg cgaccgagt tgctcttgcc  6060
cggcgtcaat acgggataat accgcgccac atagcagaac tttaaaagtg ctcatcattg  6120
gaaaacgttc ttcggggcga aaactctcaa ggatcttacc gctgttgaga tccagttcga  6180
tgtaacccac tcgtgcaccc aactgatctt cagcatcttt tactttcacc agcgtttctg  6240
ggtgagcaaa aacaggaagg caaaatgccg caaaaaaggg aataagggcg acacggaaat  6300
gttgaatact catactcttc ctttttcaat attattgaag catttatcag ggttattgtc  6360
tcatgagcgg atacatattt gaatgtattt agaaaaataa acaaataggg gttccgcgca  6420
catttccccg aaaagtgcca cctgacgtct aagaaaccat tattatcatg acattaacct  6480
ataaaaatag gcgtatcacg aggccctttc gtc                                6513
```

```
SEQ ID NO: 30          moltype = DNA  length = 6810
FEATURE                Location/Qualifiers
misc_feature           1..6810
                       note = construct pINT-fucP
source                 1..6810
                       mol_type = other DNA
                       organism = synthetic construct
SEQUENCE: 30
tcgcgcgttt cggtgatgac ggtgaaaacc tctgacacat gcagctcccg gagacggtca   60
cagcttgtct gtaagcggat gccgggagca gacaagcccg tcaggcgcg tcagcgggtg   120
ttggcgggtg tcgggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgaagatcct ttgatctttt   420
ctacggggtc tgacgctcag tggaacgaaa actcacgtta agggattttg gtcatgagat   480
tatcaaaaag gatcttcacc tagatccttt taaactagtg aagttaccat cacggaaaaa   540
ggttatgctg ctttttaagac ccacttttcac atttaagttg tttttctaat ccgcatatga   600
tcaattcaag gccgaataag aaggctggct ctgcaccttg gtgatcaaat aattcgatag   660
cttgtcgtaa taatggcggc atactatcag tagtaggtgt ttccctttct tctttagcga   720
cttgatcgtc ttgatcttcc aatacgcaac ctaaagtaaa atgccccact gcgctgagtg   780
catataatgc attctctagt gaaaaacctt gttggcataa aaaggctaat tgattttcga   840
gagtttcata ctgttttttct gtaggccgtg tacctaaatg tacttttgct ccatcgcgat   900
gacttagtaa agcacatcta aaactttttag cgttattacg taaaaaatct tgccagcttt   960
ccccttctaa agggcaaaag tgagtatggt gcctatctaa catctcaatg gctaaggcgt  1020
cgagcaaagc ccgcttattt tttacatgcc aatacaatgt aggctgctct acacctagct  1080
tctgggcgag tttacgggtt gttaaacctt cgattccgac ctcattaagc agctctaatg  1140
cgctgttaat cactttactt ttatctaaac gagacatact cttcctttttt caatattatt  1200
gaagcattta tcagggttat tgtctcatga gcggatacat acttggaatgt atttagaaaa  1260
ataaacaaat aggggttccg cgcacatttc cccgaaaagt gccacctgaa attggccaga  1320
tgattaattc ctaattttttg ttgacactct atcattgata gagttatttt accactccct  1380
atcagtgata gagaaaagtg aaatgaatag ttcgacaaaa atctagaaat aattttgttt  1440
aactttaaga aggagatata caagagctcg agtcgaagga gatagaacca tgggaaacac  1500
atcaatacaa acgcagagtt accgtgcggt agataaagat gcagggcaaa gcagaagtta  1560
cattattcca ttcgcgctgc tgtgctcact gttttttctt tgggcggtag ccaataacct  1620
taacgacatt ttattacctc aattccagca ggctttttacg ctgacaaatt tccaggctgg  1680
cctgatccaa tcggccttttt actttggtta tttcattatc ccaatccctg ctgggatatt  1740
gatgaaaaaa ctcagttata aagcagggat tattaccggg ttattttttat atgccttggg  1800
tgctgcatta ttctggcccg ccgcagaaat aatgaactac accttgtttt tagttggcct  1860
atttattatt gcagccggat taggttgtct ggaaactgcc gcaaacccctt ttgttacggt  1920
attagggccg gaaagtagtg gtcacttccg cttaaatctt gcgcaaacat ttaactcgtt  1980
tggcgcaatt atcgcggttg tctttgggca aagtcttatt ttgtctaacg tgccacatca  2040
atcgcaagac gttctcgata aaatgtctcc agagcaattg agtgcgtata aacacagcct  2100
ggtattatcg gtacagacac cttatatgat catcgtgact atcgtgttac tggtcgcccr  2160
gctgatcatg ctgacgaaat tcccggcatt gcagagtgat aatcacagtg acgccaaaca  2220
aggatcgttc tccgcatcgc tttctcgcct ggcgcgtatt cgccactggc gctgggcggt  2280
attagcgcaa ttctgctatg tcggcgcaca aacggcctgc tggagctatt tgattcgcta  2340
cgctgtagaa gaaattccag gtatgactgc aggctttgcc gctaactatt taaccggaac  2400
catggtgtgc ttctttattg gtcgtttcac cggtacctgg ctcatcagtc gcttcgcacc  2460
```

-continued

```
acacaaagtc ctggccgcct acgcattaat cgctatggca ctgtgcctga tctcagcctt   2520
cgctggcggt catgtgggct taatagccct gactttatgc agcgccttta tgtcgattca   2580
gtacccaaca atcttctcgc tgggcattaa gaatctcggc caggacacca aatatggttc   2640
gtccttcatc gttatgacca ttattggcgg cggtattgtc actccggtca tgggttttgt   2700
cagtgacgcg gcgggcaaca tccccactgc tgaactgatc cccgcactct gcttcgcggt   2760
catctttatc tttgcccgtt ccgttctca aacggcaact aactgataaa tcgatactag   2820
cataacccct tggggcctct aaacgcgtcg acacgcaaaa aggccatccg tcaggatggc   2880
cttctgctta atttgatgcc tggcagttta tggcgggcgt cctgcccgcc accctccggg   2940
ccgttgcttc gcaacgttca aatccgctcc cggcggattt gtcctactca ggagagcgtt   3000
caccgacaaa caacagataa aacgaaaggc ccagtctttc gactgagcct ttcgtttat   3060
ttgatgcctg gcagttccct actctcgcat ggggagaccc cacactacca tcatgtatga   3120
atatcctcct tagttcctat tccgaagttc ctattctcta gaaagtatag gaacttcggc   3180
gcgtcctacc tgtgacggaa gatcacttcg cagaataaat aaatcctggt gtccctgttg   3240
ataccgggaa gccctgggcc aacttttggc gaaaatgaga cgttgatcgg cacgtaagag   3300
gttccaactt tcaccataat gaaataagat cactaccggg cgtattttt gagttgtcga   3360
gattttcagg agctaaggaa gctaaaatgg agaaaaaaat cactggatat accaccgttg   3420
atatatccca atggcatcgt aaagaacatt ttgaggcatt tcagtcagtt gctcaatgta   3480
cctataacca gaccgttcag ctggatatta cggcctttt aaagaccgta aagaaaaata   3540
agcacaagtt ttatccggcc tttattcaca ttcttgcccg cctgatgaat gctcatccgg   3600
aattacgtat ggcaatgaaa gacggtgagc tggtgatatg ggatagtgtt cacccttgtt   3660
acaccgtttt ccatgagcaa actgaaacgt tttcatcgct ctggagtgaa taccacgacg   3720
atttccggca gtttctacac atatattcgc aagatgtggc gtgttacggt gaaaacctgg   3780
cctatttccc taaagggttt attgagaata tgtttttcgt ctcagccaat ccctgggtga   3840
gtttcaccag ttttgattta aacgtggcca atatggacaa cttcttcgcc cccgtttca   3900
ccatgggcaa atattatacg caaggcgaca aggtgctgat gccgctggcg attcaggttc   3960
atcatgccgt ttgtgatggc ttccatgtcg gcagatgctt aatgaataca acagtactgc   4020
gatgagtggc agggcggggc gtaaggcgcg ccatttaaat gaagttccta ttccgaagtt   4080
cctattctct agaaagtata ggaacttcga agcagctcca gcctacacaa tcgctcaaga   4140
cgtgtaatgc tgcaatctgc atgcaagctt ggcactggcc acgcaaaaag gccatccgtc   4200
aggatggcct tctgcttaat ttgatgcctg gcagtttatg gcgggcgtcc tgcccgccac   4260
cctccgggcc gttgcttcgc aacgttcaaa tccgctcccg gcggatttgt cctactcagg   4320
agagcgttca ccgacaaaca acagataaaa cgaaaggccc agtctttcga ctgagccttt   4380
cgttttattt gatgcctggc agttccctac tctcgcatgg ggagacccca cactaccatc   4440
ggggggccat cgatgcaggt ggcacttttc ggggaaatgt gcgcggaacc cctatttgtt   4500
tatttttcta aatacattca caatatatc cgctcatgag acaataaccc tgctgcagag   4560
gcctgcatgc aagcttggcg taatcatggt catagctgtt tcctgtgtga aattgttatc   4620
cgctcacaat tccacacaac atacgagccg gaagcataaa gtgtaaagcc tggggtgcct   4680
aatgagtgag ctaactcaca ttaattgcgt tgcgctcact gcccgctttc cagtcgggaa   4740
acctgtcgtg ccagctgcat taatgaatcg gccaacgcgc ggggagaggc ggtttgcgta   4800
ttgggcgctc ttccgcttcc tcgctcactg actcgctgcg ctcggtcgtt cggctgcggc   4860
gagcggtatc agctcactca aaggcggtaa tacggttatc cacagaatca ggggataacg   4920
caggaaagaa catgtgagca aaaggccagc aaaaggccag gaaccgtaaa aaggccgcgt   4980
tgctggcgtt tttccatagg ctccgccccc ctgacgagca tcacaaaaat cgacgctcaa   5040
gtcagaggtg gcgaaacccg acaggactat aaagatacca ggcgtttccc cctggaagct   5100
ccctcgtgcg ctctcctgtt ccgaccctgc cgcttaccgg atacctgtcc gcctttctcc   5160
cttcgggaag cgtggcgctt tctcatagct cacgctgtag gtatctcagt tcggtgtagg   5220
tcgttcgctc caagctgggc tgtgtgcacg aaccccccgt tcagcccgac cgctgcgcct   5280
tatccggtaa ctatcgtctt gagtccaacc cggtaagaca cgacttatcg ccactggcag   5340
cagccactgg taacaggatt agcagagcga ggtatgtagg cggtgctaca gagttcttga   5400
agtggtggcc taactacggc tacactagaa gaacagtatt tggtatctgc gctctgctga   5460
agccagttac cttcggaaaa agagttggta gctcttgatc cggcaaacaa accaccgctg   5520
gtagcggtgg tttttttgtt tgcaagcagc agattacgcg cagaaaaaaa ggatctcaag   5580
aagatccttt gatcttttct acgggtctg acgctcagtg gaacgaaaac tcacgttaag   5640
ggattttggt catgagatta tcaaaaagga tcttcaccta gatcctttta aattaaaaat   5700
gaagtttaa atcaatctaa agtatatatg agtaaacttg gtctgacagt taccaatgct   5760
taatcagtga ggcacctatc tcagcgatct gtctatttcg ttcatccata gttgcctgac   5820
tccccgtcgt gtagataact acgatacggg agggcttacc atctggcccc agtgctgcaa   5880
tgataccgcg agacccacgc tcaccggctc cagatttatc agcaataaac cagccagccg   5940
gaagggccga gcgcagaagt ggtcctgcaa ctttatccgc ctccatccag tctattaatt   6000
gttgccggga agctagagta agtagttcgc cagttaatag tttgcgcaac gttgttgcca   6060
ttgctacagg catcgtggtg tcacgctcgt cgtttggtat ggcttcattc agctccggtt   6120
cccaacgatc aaggcgagtt acatgatccc ccatgttgtg caaaaaagcg gttagctcct   6180
tcggtcctcc gatcgttgtc agaagtaagt tggccgcagt gttatcactc atggttatgg   6240
cagcactgca taattctctt actgtcatgc catccgtaag atgcttttct gtgactggtg   6300
agtactcaac caagtcattc tgagaatagt gtatgcggcg accgagttgc tcttgcccgg   6360
cgtcaatacg ggataatacc gcgccacata gcagaacttt aaaagtgctc atcattggaa   6420
aacgttcttc ggggcgaaaa ctctcaagga tcttaccgct gttgagatcc agttcgatgt   6480
aacccactcg tgcacccaac tgatcttcag catcttttac tttcaccagc gtttctgggt   6540
gagcaaaaac aggaaggcaa aatgccgcaa aaaagggaat aagggcgaca cggaaatgtt   6600
gaatactcat actcttcctt tttcaatatt attgaagcat ttatcagggt tattgtctca   6660
tgagcggata catatttgaa tgtatttaga aaaataaaca aataggggtt ccgcgcacat   6720
ttccccgaaa agtgccacct gacgtctaag aaaccattat tatcatgaca ttaacctata   6780
aaaataggcg tatcacgagg ccctttcgtc                                      6810
```

```
SEQ ID NO: 31          moltype = DNA   length = 6933
FEATURE                Location/Qualifiers
misc_feature           1..6933
                       note = construct pINT-mdeA
source                 1..6933
```

-continued

```
                       mol_type = other DNA
                       organism = synthetic construct
SEQUENCE: 31
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcaggcgcc  240
attcgccatt caggctgcgc aactgttggg aagggcgatc ggtgcgggcc tcttcgctat  300
tacgccagct ggcgaaaggg ggatgtgctg caaggcgatt aagttgggta acgccagggt  360
tttcccagtc acgacgttgt aaaacgacgg ccagtgaatt cgaagatcct ttgatctttt  420
ctacggggtc tgacgctcag tggaacgaaa actcacgtta agggattttg gtcatgagat  480
tatcaaaaag gatcttcacc tagatccttt taaactagtg aagttaccat cacggaaaaa  540
ggttatgctg cttttaagac ccactttcac atttaagttg tttttctaat ccgcatatga  600
tcaattcaag gccgaataag aaggctggct ctgcaccttg gtgatcaaat aattcgatag  660
cttgtcgtaa taatggcggc atactatcag tagtaggtgt ttcccttct tctttagcga  720
cttgatgctc ttgatcttcc aatacgcaac ctaaagtaaa atgccccact gcgctgagtg  780
catataatgc attctctagt gaaaaacctt gttggcataa aaaggctaat tgattttcga  840
gagtttcata ctgtttttct gtaggccgtg tacctaaatg tacttttgct ccatcgcgat  900
gacttagtaa agcacatcta aaacttttag cgttattacg taaaaaatct tgccagcttt  960
ccccttctaa agggcaaaag tgagtatggt gcctatctaa catctcaatg gctaaggcgt 1020
cgagcaaagc ccgcttattt tttacatgcc aatacaatgt aggctgctct acacctagct 1080
tctgggcgag tttacgggtt gttaaacctt cgattccgac ctcattaagc agctctaatg 1140
cgctgttaat cactttactt ttatctaaac gagacatact cttccttttt caatattatt 1200
gaagcattta tcagggttat tgtctcatga gcggatacat atttgaatgt atttagaaaa 1260
ataaacaaat aggggttccg cgcacatttc cccgaaaagt gccacctgaa attggccaga 1320
tgattaattc ctaattttg ttgacactct atcattgata gagttatttt accactccct 1380
atcagtgata gagaaaagtg aaatgaatag ttcgacaaaa atctagaaat aattttgttt 1440
aactttaaga aggagatata caagagctcg agtcgaagga gatagaacca tgtccaaaaa 1500
acaaaaactg acgatgatta ttacgatgct gatgggtggc ttcttcggtc tgctgaatga 1560
aacgctgctg gtgacggcac tgccgagcat catgaaagac ttcgaaattt cttatacgca 1620
ggttcaatgg ctgaccacgg catttctgct gaccaacggc atcgttattc cgctgtcagc 1680
tctggtcatt cagcgttaca ccacgcgcca agtttcctg gtcggtatct ctattttctt 1740
tctgggcacg ctgctgtcag gtctgtcgcc gcatttgcg accctgctgg ttgcgcgtat 1800
tatccaggca ctgggcgctg gtatcatgat gccgctgatg atgaccacga ttctggatgt 1860
cttccaaccg cacgaacgcg gcaaatatat gggcattttt ggtctggtga tcggtctggc 1920
accggcaatc ggtccgaccc tgagtggtta tctggttgaa tacttcaact ggcgttccct 1980
gtttcatgtg gttgcgccga tcgcggccgt tacctttctg attggcttca aaacgatcaa 2040
aaatgtgggt accacgatta aagttccgat cgactttatt tcagtcatct tctcggtgct 2100
gggctttggc ggtctgctgt atggtaccag ctctatttca gaaaaaggct tcgataatcc 2160
gatcgtcctg gtgtcgatga ttggcggtgt cgtgctggtt gcactgtttg tcctgcgtca 2220
gtaccgcctg agcaccccgc tgctgaactt cgctgtgttc aaaaacaaac aattcaccgt 2280
tggcattatc attatgggtg tgacgatggt tagcatgatc ggctctgaaa ccattctgcc 2340
gatctttgtt cagaacctgc tgcatcgtag tgcactggac tccggtctga cgctgctgcc 2400
gggtgcaatt gtgatggcct tcatgagcat gacctctggc gccctgtatg aaaaatttgg 2460
tccgcgcaat ctggcactgg tgggtatggc tattgttgtc atcaccacgg catatttgt 2520
ggttatggat gaacagacca gtacgattat gctggcaacc gtctacgcta ttcgcatggt 2580
gggcatcgcg ctgggtctga ttccggttat gacccatacg atgaaccagc tgaaaccgga 2640
aatgaatgcg cacggcagtt ccatgaccaa cacggtgcag caaattgccg gcagcatcgg 2700
taccgcagct ctgatcacga ttctgagtca cgcctccaaa aacttttcac cgaccatgtc 2760
ggattacaac ggtatgaaca aaatcgacat gatgaaccag atcaaagtcg ataccatgct 2820
gcatggctac cacgcgggt ttctgttcgc cctgctgatt accgtggtgt cgttcttctg 2880
ttcatttatg ctgcaaggca aaaagaaaga agtggattcc cgccagtaat aaatcgatac 2940
tagcataacc ccttggggcc tctaaacgcg tcgacacgca aaaaggccat ccgtcaggat 3000
ggccttctgc ttaatttgat gcctggcagt ttatggcggg cgtcctgccc gccaccctcc 3060
gggccgttgc ttcgcaacgt tcaaatccgc tcccggcgga tttgtcctac tcaggagagc 3120
gttcaccgac aaacaacaga taaaacgaaa ggcccagtct ttcgactgag cctttcgttt 3180
tatttgatgc ctggcagttc cctactctcg catgggaga ccccacacta ccatcatgta 3240
tgaatatcct ccttagttcc tattccgaag ttcctattct ctagaaagta taggaacttc 3300
ggcgcgtcct acctgtgacg gaagatcact tcgcagaata aataaatcct ggtgtccctg 3360
ttgataccgg gaagccctgg gccaacttt ggcgaaaatg agacgttgat cggcacgtaa 3420
gaggttccaa ctttcaccat aatgaaataa gatcactacc gggcgtattt tttgagttgt 3480
cgagattttc aggagctaag gaagctaaaa tggagaaaaa aatcactgga tataccaccg 3540
ttgatatatc ccaatggcat cgtaaagaac attttgaggc atttcagtca gttgctcaat 3600
gtacctataa ccagaccgtt cagctggata ttacggcctt tttaaagacc gtaaagaaaa 3660
ataagcacaa gttttatccg gcctttattc acattcttgc ccgcctgatg aatgctcatc 3720
cggaattacg tatggcaatg aaagacggtg agctggtgat atgggatagt gttcacccT 3780
gttacaccgt tttccatgag caaactgaaa cgttttcatc gctctggagt gaataccacg 3840
acgatttccg gcagtttcta cacatatatt cgcaagatgt ggcgtgttac ggtgaaaacc 3900
tggcctattt ccctaaaggg tttattgaga atatgttttt cgtctcagcc aatccctggg 3960
tgagtttcac cagttttgat ttaaacgtgg ccaatatgga caacttcttc gcccccgttt 4020
tcaccatggg caaatattat acgcaaggcg acaaggtgct gatgccgctg gcgattcagg 4080
ttcatcatcg cgtttgtgat ggcttccatg tcggcagatg cttaatgaat acaacagtac 4140
tgcgatgagt ggcaggcgg ggcgtaaggc gcgccattta aatgaagttc ctattccgaa 4200
gttcctctac tctagaaagt ataggaactt cgaagcagct ccagcctaca caatcgctca 4260
agacgtgtaa tgctgcaatc tgcatgcaag cttggcactg gccacgcaaa aaggccatcc 4320
gtcaggatgg ccttctgctt aatttgatgc ctggcagttt atggcgggcg tcctgcccgc 4380
caccctccgg gccgttgctt cgcaacgttc aaatccgctc ccggcggatt tgtcctactc 4440
aggagagcgt tcaccgacaa acaacagata aaacgaaagg cccagtcttt cgactgagcc 4500
tttcgtttta tttgatgcct ggcagttccc tactctcgca tggggagacc ccacactacc 4560
```

```
atcggggggc catcgatgca ggtggcactt ttcggggaaa tgtgcgcgga acccctattt  4620
gtttattttt ctaaatacat tcaaatatgt atccgctcat gagacaataa ccctgctgca  4680
gaggcctgca tgcaagcttg gcgtaatcat ggtcatagct gtttcctgtg tgaaattgtt  4740
atccgctcac aattccacac aacatacgag ccggaagcat aaagtgtaaa gcctggggtg  4800
cctaatgagt gagctaactc acattaattg cgttgcgctc actgcccgct ttccagtcgg  4860
gaaacctgtc gtgccagctg cattaatgaa tcggccaacg cgcggggaga ggcggtttgc  4920
gtattgggcg ctcttccgct tcctcgctca ctgactcgct gcgctcggtc gttcggctgc  4980
ggcgagcggt atcagctcac tcaaaggcgg taatacggtt atccacagaa tcagggata  5040
acgcaggaaa gaacatgtga gcaaaaggcc agcaaaaggc caggaaccgt aaaaaggccg  5100
cgttgctggc gtttttccat aggctccgcc cccctgacga gcatcacaaa aatcgacgct  5160
caagtcagag gtggcgaaac ccgacaggac tataaagata ccaggcgttt ccccctggaa  5220
gctccctcgt gcgctctcct gttccgaccc tgccgcttac cggatacctg tccgcctttc  5280
tcccttcggg aagcgtggcg ctttctcata gctcacgctg taggtatctc agttcggtgt  5340
aggtcgttcg ctccaagctg ggctgtgtgc acgaaccccc cgttcagccc gaccgctgcg  5400
ccttatccgg taactatcgt cttgagtcca acccggtaag acacgactta tcgccactgg  5460
cagcagccac tggtaacagg attagcagag cgaggtatgt aggcggtgct acagagttct  5520
tgaagtggtg gcctaactac ggctacacta gaagaacagt atttggtatc tgcgctctgc  5580
tgaagccagt taccttcgga aaaagagttg gtagctcttg atccggcaaa caaccaccg  5640
ctggtagcgg tggtttttt gtttgcaagc agcagattac gcgcagaaaa aaaggatctc  5700
aagaagatcc tttgatcttt tctacggggt ctgacgctca gtggaacgaa aactcacgtt  5760
aagggatttt ggtcatgaga ttatcaaaaa ggatcttcac ctagatcctt ttaaattaaa  5820
aatgaagttt taaatcaatc taaagtatat atgagtaaac ttggtctgac agttaccaat  5880
gcttaatcag tgaggcacct atctcagcga tctgtctatt tcgttcatcc atagttgcct  5940
gactccccgt cgtgtagata actacgatac gggagggctt accatctggc cccagtgctg  6000
caatgatacc gcgagaccca cgctcaccgg ctccagattt atcagcaata aaccagccag  6060
ccggaagggc cgagcgcaga agtggtcctg caactttatc cgcctccatc cagtctatta  6120
attgttgccg ggaagctaga gtaagtagtt cgccagttaa tagtttgcgc aacgttgttg  6180
ccattgctac aggcatcgtg gtgtcacgct cgtcgtttgg tatggcttca ttcagctccg  6240
gttcccaacg atcaaggcga gttacatgat cccccatgtt gtgcaaaaaa gcggttagct  6300
ccttcggtcc tccgatcgtt gtcagaagta agttggccgc agtgttatca ctcatggtta  6360
tggcagcact gcataattct cttactgtca tgccatccgt aagatgcttt tctgtgactg  6420
gtgagtactc aaccaagtca ttctgagaat agtgtatgcg gcgaccgagt tgctcttgcc  6480
cggcgtcaat acgggataat accgcgccac atagcagaac tttaaaagtg ctcatcattg  6540
gaaaacgttc ttcggggcga aaactctcaa ggatcttacc gctgttgaga tccagttcga  6600
tgtaacccac tcgtgcaccc aactgatctt cagcatcttt tactttcacc agcgtttctg  6660
ggtgagcaaa aacaggaagg caaaatgccg caaaaaaggg aataagggcg acacggaaat  6720
gttgaatact catactcttc ctttttcaat attattgaag catttatcag ggttattgtc  6780
tcatgagcgg atacatattt gaatgtattt agaaaaataa acaaataggg gttccgcgca  6840
catttccccg aaaagtgcca cctgacgtct aagaaaccat tattatcatg acattaacct  6900
ataaaaatag gcgtatcacg aggccctttc gtc                               6933
```

```
SEQ ID NO: 32            moltype = DNA  length = 7248
FEATURE                 Location/Qualifiers
misc_feature            1..7248
                        note = construct pINT-lmrA
source                  1..7248
                        mol_type = other DNA
                        organism = synthetic construct
SEQUENCE: 32
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg  120
ttggcgggtg tcgggctgg cttaactatg cggcatcaga gcagattgta ctgagagtgc  180
accatatgcg gtgtgaaata ccgcacagat gcgtaaggag aaaataccgc atcaggcgcc  240
attcgccatt caggctgcgc aactgttggg aaggggcgatc ggtgcgggcc tcttcgctat  300
tacgccagct ggcgaaaggg ggatgtgctg caaggcgatt aagttgggta acgccagggt  360
tttcccagtc acgacgttgt aaaacgacgg ccagtgaatt cgaagatcct ttgatctttt  420
ctacggggtc tgacgctcag tggaacgaaa actcacgtta agggattttg gtcatgagat  480
tatcaaaaag gatcttcacc tagatccttt taaactagtg aagttaccat cacggaaaaa  540
ggttatgctg cttttaagac ccactttcac atttaagttg tttttctaat ccgcatatga  600
tcaattcaag gccgaataag aaggctggct ctgcaccttg gtgatcaaat aattcgatag  660
cttgtcgtaa taatggcggc atactatcag tagtaggtgt ttcccttttct tctttagcga  720
cttgatgctc ttgatcttcc aatacgcaac ctaaagtaaa atgccccact gcgctgagtg  780
catataatgc attctctagt gaaaaacctt gttggcataa aaaggctaat tgattttcga  840
gagtttcata ctgttttct gtaggccgtg tacctaaatg tacttttgct ccatcgcgat  900
gacttagtaa agcacatcta aaactttttag cgttattacg taaaaaatct tgccagcttt  960
cccccttctaa agggcaaaag tgagtatggt gcctatctaa catctcaatg gctaaggcgt  1020
cgagcaaagc ccgcttattt tttacatgcc aatacaatgt aggctgctct acacctagct  1080
tctgggcgag tttacgggtt gttaaacctt cgattccgac ctcattaagc agctctaatg  1140
cgctgttaat cactttactt ttatctaaac gagacatact cttccttttt caatattatt  1200
gaagcattta tcaggttat tgtctcatga gcggatacat atttgaatgt atttagaaaa  1260
ataaacaaat aggggttccg cgcacatttc ccgaaaagt gccacctgaa attggccaga  1320
tgattaattc ctaatttttg ttgacactct atcattgata gagttatttt accactccct  1380
atcagtgata gagaaaagtg aaatgaatag ttcgacaaaa atctagaaat aattttgttt  1440
aactttaaga aggagatata caagagctcg agtcgaagga gagagaacca tggcgaaccg  1500
tatcgaaggc aaagctgtgg acaaaaactc aatcaaacat ttcattaaac tgatccgtgc  1560
cgcaaaaccg cgttacctgt ttttcattat cggtattctg gcgggtatcg tgggcaccct  1620
gattcagctg caagtcccga aaatggtgca gccgctggtt aactcttttg tcatgggcgt  1680
taatggcggt aaagttgccc tggtcattgc actgtatatc ggtagtgcag cagtctccgc  1740
aattgcagct atcgtgctgg gtatctttgg cgaaagcgtg gttaaaaacc tgcgtacgcg  1800
```

-continued

```
cgtttgggat aaaatgattc acctgccggt gaaatacttc gacgaagtta aaaccggtga  1860
aatgagctct cgtctggcga atgataccac gcaagtgaaa aacctgattg caaatagcat  1920
cccgcaggct tttacgtcta ttctgctgct ggtcggcagt atcgtgttca tgctgcagat  1980
gcaatggcgc ctgaccctgg ctatgattat cgcggttccg gtcgtgatgc tgattatgtt  2040
tccgatcatg acgttcggtc agaaaattgg ccgtacccgc caagatagcc tggcgaactt  2100
tcagggtatt gcctcagaat cgctgagcga aatccgtctg gtgaaaagtt ccaatgccga  2160
aaaacaggca tccaaaaaag ctgaaaacga cgttaatgca ctgtataaaa ttggtgtcaa  2220
agaagcgatc tttgatggcc tgatgagtcc ggtcatgatg ctgtccatga tgctgatgat  2280
cttcggtctg ctggcctatg gcatttacct gatcagcacg ggtgtgatgt ctctgggtac  2340
cctgctgggc atgatgatgt acctgatgaa cctgattggc gcggtgccga ccgttgccac  2400
gttttttcacc gaactggcga aagcctctgg tagtacgggc cgtctgaccg aactgctgga  2460
tgaagaacag gaagttctgc atcagggtga atcgctggat ctggaaggca aaaccctgag  2520
cgcacgtcac gtcgactttg cttatgatga ctctgaacaa attctgcgcg atatctcctt  2580
tgaagcgcag ccgaattcaa ttatcgcatt cgctggcccg agtggcggtg gcaaatcaac  2640
catcttttcg ctgctggaac gcttctacca accgacggcc ggtgaaatta ccatcgatgg  2700
ccagccgatt gacaacatct cactggaaaa ttggcgttcg cagattggtt cgttagccaa  2760
agactctgct attatggcgg gcacgatccg cgaaaacctg acctatggtc tggaaggcga  2820
ttacacggat gaagacctgt ggcaggtcct ggacctggcg tttgcccgtt cattcgtgga  2880
aaacatgccg gatcagctga ataccgaagt tggtgaacgc ggcgtcaaaa tttcgggtgg  2940
ccagcgtcaa cgcctggcaa tcgctcgtgc gtttctgcgc aatccgaaaa ttctgatgct  3000
ggatgaagcc accgcatctc tggactccga atcagaatcg atggtgcaga aagcgctgga  3060
tagtctgatg aaaggtcgta ccacgctggt gattgcccat cgcctgtcca cgatcgttga  3120
tgcagacaaa atctacttca tcgaaaaagg ccagatcacc ggtagcggca aacacaacga  3180
actggtcgca acccacccgc tgtacgcaaa atatgtctcg gaacaactga cggtcggcca  3240
ataataaatc gatactagca taaccccttg gggcctctaa acgcgtcgac acgcaaaaag  3300
gccatccgtc aggatggcct tctgcttaat ttgatgcctg gcagtttatg gcgggcgtcc  3360
tgcccgccac cctccgggcc gttgcttcgc aacgttcaaa tccgctcccg gcggatttgt  3420
cctactcagg agagcgttca ccgacaaaca acagataaaa cgaaaggccc agtctttcga  3480
ctgagccttt cgttttattt gatgcctggc agttccctac tctcgcatgg ggagacccca  3540
cactaccatc atgtatgaat atcctcctta gttcctattc cgaagttcct attctctaga  3600
aagtatagga acttcggcgc gtcctacctg tgacggaaga tcacttcgca gaataaataa  3660
atcctggtgt ccctgttgat accgggaagc cctgggccaa cttttggcga aaatgagacg  3720
ttgatcggca cgtaagaggt tccaactttc accataatga aataagatca ctaccgggcg  3780
tattttttga gttgtcgaga ttttcaggag ctaaggaagc taaaatggag aaaaaaatca  3840
ctggatatac caccgttgat atatcccaat ggcatcgtaa agaacatttt gaggcatttc  3900
agtcagttgc tcaatgtacc tataaccaga ccgttcagct ggatattacg gcctttttaa  3960
agaccgtaaa gaaaaataag cacaagtttt atccggcctt tattcacatt cttgcccgcc  4020
tgatgaatgc tcatccggaa ttacgtatgg caatgaaaga cggtgagctg gtgatatggg  4080
atagtgttca cccttgttac accgttttcc atgagcaaac tgaaacgttt tcatcgctct  4140
ggagtgaata ccacgacgat ttccggcagt ttctacacat atattcgcaa gatgtggcgt  4200
gttacggtga aaacctggcc tatttcccta aagggtttat tgagaatatg tttttcgtct  4260
cagccaatcc ctgggtgagt ttcaccagtt ttgatttaaa cgtggccaat atggacaact  4320
tcttcgcccc cgttttcacc atgggcaaat attatacgca aggcgacaag gtgctgatgc  4380
cgctggcgat tcaggttcat catgccgttt gtgatggctt ccatgtcggc agatgcttaa  4440
tgaatacaac agtactgcga tgagtggcag ggcggggcgt aaggcgcgcc atttaaatga  4500
agttcctatt ccgaagttcc tattctctag aaagtatagg aacttcgaag cagctccagc  4560
ctacacaatc gctcaagacg tgtaatgctg caatctgcat caagcttgg cactggccac  4620
gcaaaaaggc catccgtcag gatggccttc tgcttaattt gatgcctggc agtttatggc  4680
gggcgtcctg cccgccaccc tccgggccgt gcttcgcaa cgttcaaatc cgctcccggc  4740
ggatttgtcc tactcaggag agcgttcacc gacaaacaac agataaaacg aaaggcccag  4800
tctttcgact gagcctttcg ttttatttga tgcctggcag ttccctactc tcgcatgggg  4860
agaccccaca ctaccatcgg ggggccatcg atgcaggtgg cacttttcgg ggaaatgtgc  4920
gcggaacccc tatttgttta tttttctaaa tacattcaaa tatgtatccg ctcatgagac  4980
aataaccctg ctgcagaggc ctgcatgcaa gcttggcgta atcatggtca tagctgtttc  5040
ctgtgtgaaa ttgttatccg ctcacaattc cacacaacat acgagccgga agcataaagt  5100
gtaaagcctg gggtgcctaa tgagtgagct aactcacatt aattgcgttg cgctcactgc  5160
ccgctttcca gtcgggaaac ctgtcgtgcc agctgcatta tgaatcggc caacgcgcgg  5220
ggagaggcgg tttgcgtatt gggcgctctt ccgcttcctc gctcactgac tcgctgcgct  5280
cggtcgttcg gctgcggcga gcggtatcag ctcactcaaa ggcggtaata cggttatcca  5340
cagaatcagg ggataacgca ggaaagaaca tgtgagcaaa aggccagcaa aaggccagga  5400
accgtaaaaa ggccgcgttg ctggcgtttt tccataggct ccgcccccct gacgagcatc  5460
acaaaaatcg acgctcaagt cagaggtggc gaaacccgac aggactataa agataccagg  5520
cgtttccccc tggaagctcc ctcgtgcgct ctcctgttcc gaccctgccg cttaccggat  5580
acctgtccgc ctttctccct tcgggaagcg tggcgctttc tcatagctca cgctgtaggt  5640
atctcagttc ggtgtaggtc gttcgctcca agctgggctg tgtgcacgaa ccccccgttc  5700
agcccgaccg ctgcgcctta tccggtaact atcgtcttga gtccaacccg gtaagacacg  5760
acttatcgcc actggcagca gccactggta acaggattag cagagcgagg tatgtaggcg  5820
gtgctacaga gttcttgaag tggtggccta actacggcta cactagaaga acagtatttg  5880
gtatctgcgc tctgctgaag ccagttacct tcggaaaaag agttggtagc tcttgatccg  5940
gcaaacaaac caccgctggt agcggtggtt tttttgtttg caagcagcag attacgcgca  6000
gaaaaaaagg atctcaagaa gatcctttga tcttttctac ggggtctgac gctcagtgga  6060
acgaaaactc acgttaaggg attttggtca tgagattatc aaaaaggatc ttcacctaga  6120
tccttttaaa ttaaaaatga agttttaaat caatctaaag tatatatgag taaacttggt  6180
ctgacagtta ccaatgctta atcagtgagg cacctatctc agcgatctgt ctatttcgtt  6240
catccatagt tgcctgactc cccgtcgtgt agataactac gatacgggag ggcttaccat  6300
ctggccccag tgctgcaatg ataccgcgag acccacgctc accggctcca gatttatcag  6360
caataaacca gccagccgga agggccgagc gcagaagtgg tcctgcaact ttatccgcct  6420
ccatccagtc tattaattgt tgccgggaag ctagagtaag tagttcgcca gttaatagtt  6480
tgcgcaacgt tgttgccatt gctacaggca tcgtggtgtc acgctcgtcg tttggtatgg  6540
```

-continued

```
cttcattcag ctccggttcc caacgatcaa ggcgagttac atgatccccc atgttgtgca   6600
aaaaagcggt tagctccttc ggtcctccga tcgttgtcag aagtaagttg gccgcagtgt   6660
tatcactcat ggttatggca gcactgcata attctcttac tgtcatgcca tccgtaagat   6720
gcttttctgt gactggtgag tactcaacca agtcattctg agaatagtgt atgcggcgac   6780
cgagttgctc ttgcccggcg tcaatacggg ataataccgc gccacatagc agaactttaa   6840
aagtgctcat cattggaaaa cgttcttcgg ggcgaaaact ctcaaggatc ttaccgctgt   6900
tgagatccag ttcgatgtaa cccactcgtg cacccaactg atcttcagca tcttttactt   6960
tcaccagcgt ttctgggtga gcaaaaacag gaaggcaaaa tgccgcaaaa aagggaataa   7020
gggcgacacg gaaatgttga atactcatac tcttcctttt tcaatattat tgaagcattt   7080
atcagggtta ttgtctcatg agcggataca tatttgaatg tatttagaaa aataaacaaa   7140
taggggttcc gcgcacattt ccccgaaaag tgccacctga cgtctaagaa accattatta   7200
tcatgacatt aacctataaa aataggcgta tcacgaggcc ctttcgtc              7248
```

SEQ ID NO: 33          moltype = DNA   length = 6684
FEATURE                Location/Qualifiers
misc_feature           1..6684
                       note = construct pINT-Ps-setA
source                 1..6684
                       mol_type = other DNA
                       organism = synthetic construct
SEQUENCE: 33

```
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgaagatcct ttgatctttt   420
ctacggggtc tgacgctcag tggaacgaaa actcacgtta agggattttg gtcatgagat   480
tatcaaaaag gatcttcacc tagatccttt taaactagtg aagttaccat cacggaaaaa   540
ggttatgctg cttttaagac ccactttcac atttaagttg tttttctaat ccgcatatga   600
tcaattcaag gccgaataag aaggctggct ctgcaccttg gtgatcaaat aattcgatag   660
cttgtcgtaa taatggcggc atactatcag tagtaggtgt ttcccttttct tctttagcga   720
cttgatgctc ttgatcttcc aatacgcaac ctaaagtaaa atgccccact gcgctgagtg   780
catataatgc attctctagt gaaaaacctt gttggcataa aaaggctaat tgattttcga   840
gagtttcata ctgtttttct gtaggccgtg tacctaaatg tacttttgct ccatcgcgat   900
gacttagtaa agcacatcta aaactttag cgttattacg taaaaaatct tgccagcttt    960
ccccttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttcctttt caatattatt    1200
gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaattttg ttgacactct atcattgata gagttatttt accactcct     1380
atcagtgata gagaaaagtg aaatgaatag ttcgacaaaa atctagaaat aattttgttt   1440
aactttaaga aggagatata caagagctcg agtcgaagga gatagaacca tgaacgaaag   1500
ccagagctct catggcggtt catggctgtc ggttattgcg ctggccctgg cggcctttat   1560
cttcaatacc acggaattcg ttccggtcgc gctgctgtca gatattggcc gttcgtttga   1620
catgccgcca tcacaagtgg gtctgatgct gaccatctat gcgtgggtgg ttgccctgat   1680
gtcgctgccg atgatgctgc tgacccgcaa cgtcgaacgt cgcacgctgc tgattttgt    1740
gttcgtcgtg ttcatcggca gtcatctggt gagttccgtg gcgtcatcgt ttagcatgct   1800
gatgatttct cgtattggta tcgcactgtc ccacgctgtg ttttggagta tcaccgcatc   1860
cctggctgtg cgtgttgcac cggctggtaa acaggcccag gcactgggtc tgctggcaac   1920
cggttcagca ctggctatgg tcctgggtat tccgctgggc cgtgttgtcg gtgaactgct   1980
ggattggcgc accacgttcc tgagcattgc catcgtgaca gctctggtgg ttctgtgtct   2040
ggcacgtacc ctgccgctgc tgccgagtca gaatagtggt tccctgcgtt ccctgccgat   2100
gctgtttaaa cgtccggcgc tggttgcggc atatgttctg accgccctgg ttattacggc   2160
gcagtttacc gcctatacgt acattgaacc gttcgcacaa accatcgctc atctgtctgg   2220
caacatgacc acggcactgc tgctgctgtt tggcggtgct ggtattctgg gcacggtgct   2280
gttcagccgt tattctaatc gctacccgaa aggttttctg atcgcagcta ttagtatcat   2340
ggcaatgtgt ctgctgctgc tgctgccggc ctcccgcgat agctctctgc tggccgccct   2400
ggtcgtggtt tggggtattg cgggcatgtg tttcggcctg gcgctgcagg ccaaagttct   2460
gaacctggca agcgatgcta ccgacgtcgc gatggccctg ttttctggca tttataatgt   2520
tggtatcggc ggtggcgccc tgctgggttc actggttacg gacaccctgg gcttcaccga   2580
cgttggtatt gtcggtggcc tgctggccct gagcggcgtc gtgctgtgct gttttgccac   2640
ctatcgcttt gcacgtccgg tgggttctgc agctctgtaa taaatcgata ctagcataac   2700
cccttggggc ctctaaacgc gtcgacacgc aaaaaggcca tccgtcagga tggccttctg   2760
cttaatttga tgcctggcag tttatggcgg gcgtcctgcc cgccaccctc cgggccgttg   2820
cttcgcaacg ttcaaatccg ctcccggcgg atttgtccta ctcaggagag cgttcaccga   2880
caaacaacag ataaaacgaa aggcccagtc tttcgactga gcctttcgtt ttatttgatg   2940
cctggcagtt ccctactctc gcatgggag accccacact accatcatgt atgaatatcc    3000
tccttagttc ctattccgaa gttcctattc tctagaaagt ataggaactt cggcgcgtcc   3060
tacctgtgac ggaagatcac ttcgcagaat aaataaatcc tggtgtccct gttgataccg   3120
ggaagccctg ggccaacttt tggcgaaaat gagacgttga tcggcacgta agaggttcca   3180
actttcacca taatgaaata agatcactac cgggcgtatt ttttgagttg tcgagatttt   3240
caggagctaa ggaagctaaa atggagaaaa aaatcactgg atataccacc gttgatatat   3300
cccaatggca tcgtaaagaa catttgaggc atttcagtc agttgctcaa tgtacctata     3360
accagaccgt tcagctggat attacggcct ttttaaaagac cgtaaagaaa aataagcaca   3420
agttttatcg ggcctttatt cacattcttg cccgcctgat gaatgctcat ccggaattac   3480
```

-continued

```
gtatggcaat gaaagacggt gagctggtga tatgggatag tgttcaccct tgttacaccg   3540
ttttccatga gcaaactgaa acgttttcat cgctctggag tgaataccac gacgatttcc   3600
ggcagtttct acacatatat tcgcaagatg tggcgtgtta cggtgaaaac ctggcctatt   3660
tccctaaagg gtttattgag aatatgtttt tcgtctcagc caatccctgg gtgagtttca   3720
ccagttttga tttaaacgtg gccaatatgg acaacttctt cgcccccgtt ttcaccatgg   3780
gcaaatatta tacgcaaggc gacaaggtgc tgatgccgct ggcgattcag gttcatcatg   3840
ccgtttgtga tggcttccat gtcggcagat gcttaatgaa tacaacagta ctgcgatgag   3900
tggcagggcg gggcgtaagg cgcgccattt aaatgaagtt cctattccga agttcctatt   3960
ctctagaaag tataggaact tcgaagcagc tccagcctac acaatcgctc aagacgtgta   4020
atgctgcaat ctgcatgcaa gcttggcact ggccacgcaa aaaggccatc cgtcaggatg   4080
gccttctgct taatttgatg cctggcagtt tatggcgggc gtcctgcccg ccaccctccg   4140
ggccgttgct tcgcaacgtt caaatccgct cccggcggat ttgtcctact caggagagcg   4200
ttcaccgaca aacaacagat aaaacgaaag gcccagtctt tcgactgagc ctttcgtttt   4260
atttgatgcc tggcagttcc ctactctcgc atggggacga cccacactac catcgggggg   4320
ccatcgatgc aggtggcact tttcggggaa atgtgcgcgg aacccctatt tgtttatttt   4380
tctaaataca ttcaaatatg tatccgctca tgagacaata accctgctgc agaggcctgc   4440
atgcaagctt ggcgtaatca tggtcatagc tgtttcctgt gtgaaattgt tatccgctca   4500
caattccaca caacatacga gccggaagca taaagtgtaa agcctggggt gcctaatgag   4560
tgagctaact cacattaatt gcgttgcgct cactgcccgc tttccagtcg ggaaacctgt   4620
cgtgccagct gcattaatga atcggccaac gcgcggggag aggcggtttg cgtattgggc   4680
gctcttccgc ttcctcgctc actgactcgc tgcgctcggt cgttcggctg cggcgagcgg   4740
tatcagctca ctcaaaggcg gtaatacggt tatccacaga atcaggggat aacgcaggaa   4800
agaacatgtg agcaaaaggc cagcaaaagg ccaggaaccg taaaaaggcc gcgttgctgg   4860
cgtttttcca taggctccgc cccctgacg agcatcacaa aaatcgacgc tcaagtcaga   4920
ggtggcgaaa cccgacagga ctataaagat accaggcgtt tccccctgga agctccctcg   4980
tgcgctctcc tgttccgacc ctgccgctta ccggatacct gtccgccttt ctcccttcg    5040
gaagcgtggc gctttctcat agctcacgct gtaggtatct cagttcggtg taggtcgttc    5100
gctccaagct gggctgtgtg cacgaacccc cgttcagcc cgaccgctgc gccttatccg    5160
gtaactatcg tcttgagtcc aacccggtaa gacacgactt atcgccactg gcagcagcca    5220
ctggtaacag gattagcaga gcgaggtatg taggcggtgc tacagagttc ttgaagtggt    5280
ggcctaacta cggctacact agaagaacag tatttggtat ctgcgctctg ctgaagccag    5340
ttaccttcgg aaaaagagtt ggtagctctt gatccggcaa acaaaccacc gctggtagcg    5400
gtggtttttt tgtttgcaag cagcagatta cgcgcagaaa aaaaggatct caagaagatc    5460
ctttgatctt ttctacgggg tctgacgctc agtggaacga aaactcacgt taagggattt    5520
tggtcatgag attatcaaaa aggatcttca cctagatcct tttaaattaa aaatgaagtt    5580
ttaaatcaat ctaaagtata tatgagtaaa cttggtctga cagttaccaa tgcttaatca    5640
gtgaggcacc tatctcagcg atctgtctat ttcgttcatc catagttgcc tgactccccg    5700
tcgtgtagat aactacgata cgggagggct taccatctgg ccccagtgct gcaatgatac    5760
cgcgagaccc acgctcaccg gctccagatt tatcagcaat aaaccagcca gccggaaggg    5820
ccgagcgcag aagtggtcct gcaactttat ccgcctccat ccagtctatt aattgttgcc    5880
gggaagctag agtaagtagt tcgccagtta atagtttgcg caacgttgtt gccattgcta    5940
caggcatcgt ggtgtcacgc tcgtcgtttg gtatggcttc attcagctcc ggttcccaac    6000
gatcaaggcg agttacatga tccccccatgt tgtgcaaaaa agcggttagc tccttcggtc    6060
ctccgatcgt tgtcagaagt aagttggccg cagtgttatc actcatggtt atggcagcac    6120
tgcataattc tcttactgtc atgccatccg taagatgctt ttctgtgact ggtgagtact    6180
caaccaagtc attctgagaa tagtgtatgc ggcgaccgag ttgctcttgc ccggcgtcaa    6240
tacgggataa taccgcgcca catagcagaa ctttaaaagt gctcatcatt ggaaaacgtt    6300
cttcggggcg aaaactctca aggatcttac cgctgttgag atccagttcg atgtaaccca    6360
ctcgtgcacc caactgatct tcagcatctt ttactttcac cagcgtttct gggtgagcaa    6420
aaacaggaag gcaaaatgcc gcaaaaaagg gaataagggc gacacggaaa tgttgaatac    6480
tcatactctt ccttttttcaa tattattgaa gcatttatca gggttattgt ctcatgagcg    6540
gatacatatt tgaatgtatt tagaaaaata aacaaatagg ggttccgcgc acatttcccc    6600
gaaaagtgcc acctgacgtc taagaaacca ttattatcat gacattaacc tataaaaata    6660
ggcgtatcac gaggcccttt cgtc                                            6684
```

SEQ ID NO: 34        moltype = DNA  length = 6692
FEATURE              Location/Qualifiers
misc_feature        1..6692
                     note = construct pINT-Bb-setA
source              1..6692
                     mol_type = other DNA
                     organism = synthetic construct
SEQUENCE: 34
```
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc    240
attcgccatt caggctgcgc aactgttggg aagggcgatc ggtgcgggc tcttcgctat     300
tacgccagct ggcgaaaggg gatgtgctg caaggcgatt aagttgggt aacgccaggt    360
tttcccagtc acgacgttgt aaaacgacgg ccagtgaatt cgaagatcct ttgatctttt    420
ctacggggtc tgacgctcag tggaacgaaa actcacgtta agggattttg gtcatgagat    480
tatcaaaaag gatcttcacc tagatccttt taaactagtg aagttaccat cacggaaaaa    540
ggttatgctg cttttaagac ccactttcac atttaagttg ttttttctaat ccgcatatga    600
tcaattcaag gccgaataag aaggctggct ctgcaccttg gtgatcaaat aattcgatag    660
cttgtcgtaa taatggcggc atactatcag tagtaggtgt ttccctttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgtttttct gtaggccgtg tacctaaatg tacttttgct ccatcgcgat    900
gacttagtaa agcacatcta aaactttttag cgttattacg taaaaaatct tgccagcttt    960
```

```
cccccttctaa agggcaaaag tgagtatggt gcctatctaa catctcaatg gctaaggcgt 1020
cgagcaaagc ccgcttattt tttacatgcc aatacaatgt aggctgctct acacctagct 1080
tctgggcgag tttacgggtt gttaaacctt cgattccgac ctcattaagc agctctaatg 1140
cgctgttaat cactttactt ttatctaaac gagacatact cttccttttt caatattatt 1200
gaagcattta tcagggttat tgtctcatga gcggatacat atttgaatgt atttagaaaa 1260
ataaacaaat aggggttccg cgcacatttc cccgaaaagt gccacctgaa attggccaga 1320
tgattaattc ctaatttttg ttgacactct atcattgata gagttatttt accactccct 1380
atcagtgata gagaaaagtg aaatgaatag ttcgacaaaa atctagaaat aattttgttt 1440
aactttaaga aggagatata caagagctcg agtcgaagga gatagaacca tgaccattgc 1500
aacggtttcc cgcaaaaccg cttggctgcg tgtggttacc ctggccgttg ccgcctttat 1560
cttcaacacc acggaatttg tcccggtggg cctgctgagt gatattgcgc agtccttcgg 1620
catggaaacc gcccaagtgg gtattatgct gacgatctat gcctgggttg tggcactgat 1680
gagcctgccg tttatgctga tgacctctca ggtggaacgt cgccgtctgc tgattagcat 1740
ctttctgctg ttcatcgcaa gtcatgttct gtcctttctg gcgtggaatt tcaccgttct 1800
ggtcatttct cgcattggta tcgcgtttgc ccacgcaatt ttctggtcaa tcacggcttc 1860
gctggcgatt cgtatggctc cggcgggcaa gaaagcgcag gcactgagtc tgctggcgac 1920
cggtacggct ctggcgatgg ttctgggtct gccgatcggc cgcattgtcg gtcaatactt 1980
tggctggcgt accacgtttt tcgtgattgg cgttgtcgca gctatcaccc tgttctgcct 2040
gattaaactg ctgccgaaac tgccgagcga acatagtggt tccctgagct ctgtgccgaa 2100
actgtttcgc cgtccggcgc tggttaacat ctatgccctg attgcaatcg tggttaccgc 2160
acactacacg gcttatagtt acatcgaacc gttcgtgcag caaattgccg gcctgtccgc 2220
taactttgcg accctgctgc tgctgctgtt tggcggtgcg ggtattatcg gctctgttct 2280
gtttggtaaa tggggcaata aacatgccag cggtctggtc tctggcgcca ttgcactgat 2340
ggccgcatgt ctggtgctgc tgctgccggc agctcagggt gaactgaccc tggccggcct 2400
gtcactgttt tggggtattt cgatcatgat tgtcgcactg ggtatgcaag tgaaagttct 2460
ggctctggcc ccggatgcca ccgatgttgc catgagcctg ttttctggca tcttcaaacat 2520
cggcattggt gccggcgcac tgctgggtaa tcaggtgtca ctgcacattt caatgtcgga 2580
catcggtttt attggcgcca tcccggcaat tatcgctctg gtctggtcga ttctggtgtc 2640
cgccgttggc cggttgccct ggaagaacat ccgcaggcaa cccactaata aatcgatact 2700
agcataaccc cttggggcct ctaaacgcgt cgacacgcaa aaaggccatc cgtcaggatg 2760
gccttctgct taatttgatg cctggcagtt tatggcgggc gtcctgcccg ccacctccg 2820
ggccgttgct tcgcaacgtt caaatccgct cccgcggat ttgtcctact caggagagcg 2880
ttcaccgaca aacaacagat aaaacgaaag gcccagtctt tcgactgagc ctttcgtttt 2940
atttgatgcc tggcagttcc ctactctcgc atggggagac cccacactac catcatgtat 3000
gaatatcctc cttagttcct attccgaagt tcctattctc tagaaagtat aggaacttcg 3060
gcgcgtccta cctgtgacgg aagatcactt cgcagaataa ataaatcctg gtgtccctgt 3120
tgataccggg aagccctggg ccaacttttg gcgaaaatga gacgttgatc ggcacgtaag 3180
aggttccaac tttcaccata atgaaataag atcactaccg ggcgtatttt ttgagttgtc 3240
gagattttca ggagctaagg aagctaaaat ggagaaaaaa atcactggat ataccaccgt 3300
tgatatatcc caatggcatc gtaaagaaca ttttgaggca tttcagtcag ttgctcaatg 3360
tacctataac cagaccgttc agctggatat tacggccttt ttaaagaccg taaagaaaaa 3420
taagcacaag ttttatccgg cctttattca cattcttgcc cgcctgatga atgctcatcc 3480
ggaattacgt atggcaatga aagacggtga gctggtgata tgggatagtg ttcacccttg 3540
ttacaccgtt ttccatgagc aaactgaaac gttttcatcg ctctggagtg aataccacga 3600
cgatttccgg cagtttctac acatatattc gcaagatgtg gcgtgttacg gtgaaaacct 3660
ggcctatttc cctaaagggt ttattgagaa tatgtttttc gtctcagcca tccctgggt 3720
gagtttcacc agttttgatt taaacgtggc caatatggac aacttcttcg cccccgtttt 3780
caccatgggc aaatattata cgcaaggcga caaggtgctg atgccgctgg cgattcaggt 3840
tcatcatgcc gtttgtgatg gcttccatgt cggcagatgc ttaatgaata caacagtact 3900
gcgatgagtg gcagggcggg gcgtaaggcg cgccatttaa atgaagttcc tattccgaag 3960
ttcctattct ctagaaagta taggaacttc gaagcagctc cagcctacac aatcgctcaa 4020
gacgtgtaat gctgcaatct gcatgcaagc ttggcactgg ccacgcaaaa aggccatccg 4080
tcaggatggc cttctgctta atttgatgcc tggcagttta tggcgggcgt cctgcccgcc 4140
accctccggg ccgttgcttc gcaacgttca aatccgctcc cggcggattt gtcctactca 4200
ggagagcgtt caccgacaaa caacagataa aacgaaaggc ccagtctttc gactgagcct 4260
ttcgttttat ttgatgcctg gcagttccct actctcgcat ggggagaccc cacactacca 4320
tcggggggcc atcgatgcag gtggcacttt tcggggaaat gtgcgcggaa ccctatttg 4380
tttatttttc taaatacatt caaatatgta tccgctcatg agacaataac cctgctgcag 4440
aggcctgcat gcaagcttgg cgtaatcatg gtcatagctg tttcctgtgt gaaattgtta 4500
tccgctcaca attccacaca acatacgagc cggaagcata aagtgtaaag cctggggtgc 4560
ctaatgagtg agctaactca cattaattgc gttgcgctca ctgcccgctt tccagtcggg 4620
aaacctgtcg tgccagctgc attaatgaat cggccaacgc gcggggagag gcggtttgcg 4680
tattgggcgc tcttccgctt cctcgctcac tgactcgctg cgctcggtcg ttcggctgcg 4740
gcgagcggta tcagctcact caaaggcggt aatacggtta tccacagaat caggggataa 4800
cgcaggaaag aacatgtgag caaaaggcca gcaaaaggcc aggaaccgta aaaaggccgc 4860
gttgctggcg tttttccata ggctccgccc cctgacgag catcacaaaa atcgacgctc 4920
aagtcagagg tggcgaaacc cgacaggact ataaagatac caggcgtttc ccctggaag 4980
ctccctcgtg cgctctcctg ttccgaccct gccgcttacc ggatacctgt ccgcctttct 5040
cccttcggga agcgtggcgc tttctcatag ctcacgctgt aggtatctca gttcggtgta 5100
ggtcgttcgc tccaagctgg gctgtgtgca cgaacccccc gttcagcccg accgctgcgc 5160
cttatccggt aactatcgtc ttgagtccaa cccggtaaga cacgacttat cgccactggc 5220
agcagccact ggtaacagga ttagcagagc gaggtatgta ggcggtgcta cagagttctt 5280
gaagtggtgg cctaactacg gctacactag aagaacagta tttggtatct gcgctctgct 5340
gaagccagtt accttcggaa aaagagttgg tagctcttga tccggcaaac aaaccaccgc 5400
tggtagcggt ggtttttttg tttgcaagca gcagattacg cgcagaaaaa aaggatctca 5460
agaagatcct ttgatctttt ctacggggtc tgacgctcag tggaacgaaa actcacgtta 5520
agggattttg gtcatgagat tatcaaaaag gatcttcacc tagatccttt taaattaaaa 5580
atgaagtttt aaatcaatct aaagtatata tgagtaaact tggtctgaca gttaccaatg 5640
cttaatcagt gaggcaccta tctcagcgat ctgtctattt cgttcatcca tagttgcctg 5700
```

```
actccccgtc gtgtagataa ctacgatacg ggagggctta ccatctggcc ccagtgctgc    5760
aatgataccg cgagacccac gctcaccggc tccagattta tcagcaataa accagccagc    5820
cggaagggcc gagcgcagaa gtggtcctgc aactttatcc gcctccatcc agtctattaa    5880
ttgttgccgg gaagctagag taagtagttc gccagttaat agtttgcgca acgttgttgc    5940
cattgctaca ggcatcgtgg tgtcacgctc gtcgtttggt atggcttcat tcagctccgg    6000
ttcccaacga tcaaggcgag ttacatgatc ccccatgttg tgcaaaaaag cggttagctc    6060
cttcggtcct ccgatcgttg tcagaagtaa gttggccgca gtgttatcac tcatggttat    6120
ggcagcactg cataattctc ttactgtcat gccatccgta agatgctttt ctgtgactgg    6180
tgagtactca accaagtcat tctgagaata gtgtatgcgg cgaccgagtt gctcttgccc    6240
ggcgtcaata cgggataata ccgcgccaca tagcagaact ttaaaagtgc tcatcattgg    6300
aaaacgttct cgggggcgaa aactctcaag gatcttaccg ctgttgagat ccagttcgat    6360
gtaacccact cgtgcaccca actgatcttc agcatctttt actttcacca gcgtttctgg    6420
gtgagcaaaa acaggaaggc aaaatgccgc aaaaaaggga ataagggcga cacggaaatg    6480
ttgaatactc atactcttcc tttttcaata ttattgaagc atttatcagg gttattgtct    6540
catgagcgga tacatatttg aatgtattta gaaaaataaa caaataggg ttccgcgcac      6600
atttccccga aaagtgccac ctgacgtcta agaaaccatt attatcatga cattaaccta    6660
taaaaatagg cgtatcacga ggccctttcg tc                                  6692
```

```
SEQ ID NO: 35              moltype = DNA  length = 35
FEATURE                    Location/Qualifiers
misc_feature               1..35
                           note = Primer
source                     1..35
                           mol_type = other DNA
                           organism = synthetic construct
SEQUENCE: 35
ttactcagca ataaactgat attccgtcag gctgg                                35
```

```
SEQ ID NO: 36              moltype = DNA  length = 83
FEATURE                    Location/Qualifiers
misc_feature               1..83
                           note = Primer
source                     1..83
                           mol_type = other DNA
                           organism = synthetic construct
SEQUENCE: 36
ttgtaatctc gcgctcttca catcagactt tccatataga gcgtaatttc cgttaacgtc    60
ggtagtgctg accttgccgg agg                                            83
```

```
SEQ ID NO: 37              moltype = DNA  length = 53
FEATURE                    Location/Qualifiers
misc_feature               1..53
                           note = Primer
source                     1..53
                           mol_type = other DNA
                           organism = synthetic construct
SEQUENCE: 37
ctgtctctta tcacatctcc tgaaatggcc agatgtaatt cctaattttt gtt            53
```

```
SEQ ID NO: 38              moltype = DNA  length = 44
FEATURE                    Location/Qualifiers
misc_feature               1..44
                           note = Primer
source                     1..44
                           mol_type = other DNA
                           organism = synthetic construct
SEQUENCE: 38
ctgtctctta tcacatctca cattacatct gagcgattgt tagg                      44
```

```
SEQ ID NO: 39              moltype = DNA  length = 30
FEATURE                    Location/Qualifiers
misc_feature               1..30
                           note = Primer
source                     1..30
                           mol_type = other DNA
                           organism = synthetic construct
SEQUENCE: 39
gatcacatat gagagttctg gttaccggtg                                      30
```

```
SEQ ID NO: 40              moltype = DNA  length = 40
FEATURE                    Location/Qualifiers
misc_feature               1..40
                           note = Primer
source                     1..40
                           mol_type = other DNA
                           organism = synthetic construct
SEQUENCE: 40
gatcactcga gtcattaatc gggatatccc tgtggatggc                            40
```

```
SEQ ID NO: 41            moltype = DNA   length = 60
FEATURE                  Location/Qualifiers
misc_feature             1..60
                         note = Primer
source                   1..60
                         mol_type = other DNA
                         organism = synthetic construct
SEQUENCE: 41
gtcgatgaag ccctgaaaga cgcgcagact atgcacttca ttgaaaacaa aaacttcgtc   60

SEQ ID NO: 42            moltype = DNA   length = 60
FEATURE                  Location/Qualifiers
misc_feature             1..60
                         note = Primer
source                   1..60
                         mol_type = other DNA
                         organism = synthetic construct
SEQUENCE: 42
gatggccttt ttgcgtgtcg acgcggccgc ctagataaac aggatgatat ttttgccttg   60

SEQ ID NO: 43            moltype = DNA   length = 60
FEATURE                  Location/Qualifiers
misc_feature             1..60
                         note = Primer
source                   1..60
                         mol_type = other DNA
                         organism = synthetic construct
SEQUENCE: 43
caaggcaaaa atatcatcct gtttatctag gcggccgcgt cgacacgcaa aaaggccatc   60

SEQ ID NO: 44            moltype = DNA   length = 60
FEATURE                  Location/Qualifiers
misc_feature             1..60
                         note = Primer
source                   1..60
                         mol_type = other DNA
                         organism = synthetic construct
SEQUENCE: 44
gacgaagttt ttgttttcaa tgaagtgcat agtctgcgcg tctttcaggg cttcatcgac   60

SEQ ID NO: 45            moltype = DNA   length = 60
FEATURE                  Location/Qualifiers
misc_feature             1..60
                         note = Primer
source                   1..60
                         mol_type = other DNA
                         organism = synthetic construct
SEQUENCE: 45
atggcctttt tgcgtgtcga cgcggccgct taattcgagc gggtaaagat cttcatcagg   60

SEQ ID NO: 46            moltype = DNA   length = 60
FEATURE                  Location/Qualifiers
misc_feature             1..60
                         note = Primer
source                   1..60
                         mol_type = other DNA
                         organism = synthetic construct
SEQUENCE: 46
atggcctttt tgcgtgtcga cgcggccgct taattcgagc gggtaaagat cttcatcagg   60

SEQ ID NO: 47            moltype = DNA   length = 60
FEATURE                  Location/Qualifiers
misc_feature             1..60
                         note = Primer
source                   1..60
                         mol_type = other DNA
                         organism = synthetic construct
SEQUENCE: 47
ctgatgaaga tctttacccg ctcgaattaa gcggccgcgt cgacacgcaa aaaggccatc   60

SEQ ID NO: 48            moltype = DNA   length = 60
FEATURE                  Location/Qualifiers
misc_feature             1..60
                         note = Primer
source                   1..60
                         mol_type = other DNA
                         organism = synthetic construct
SEQUENCE: 48
cggggtacgc ttaatcaggt tatcaatcat agtctgcgcg tctttcaggg cttcatcgac   60
```

-continued

```
SEQ ID NO: 49              moltype = DNA   length = 60
FEATURE                    Location/Qualifiers
misc_feature               1..60
                           note = Primer
source                     1..60
                           mol_type = other DNA
                           organism = synthetic construct
SEQUENCE: 49
gtcgatgaag ccctgaaaga cgcgcagact atgagcggtg aacactatgt cattagcctg   60

SEQ ID NO: 50              moltype = DNA   length = 60
FEATURE                    Location/Qualifiers
misc_feature               1..60
                           note = Primer
source                     1..60
                           mol_type = other DNA
                           organism = synthetic construct
SEQUENCE: 50
gatggccttt ttgcgtgtcg acgcggccgc tcatttaaat tcgatgatca tcttgtcgtt   60

SEQ ID NO: 51              moltype = DNA   length = 60
FEATURE                    Location/Qualifiers
misc_feature               1..60
                           note = Primer
source                     1..60
                           mol_type = other DNA
                           organism = synthetic construct
SEQUENCE: 51
aacgacaaga tgatcatcga atttaaatga gcggccgcgt cgacacgcaa aaaggccatc   60

SEQ ID NO: 52              moltype = DNA   length = 60
FEATURE                    Location/Qualifiers
misc_feature               1..60
                           note = Primer
source                     1..60
                           mol_type = other DNA
                           organism = synthetic construct
SEQUENCE: 52
caggctaatg acatagtgtt caccgctcat agtctgcgcg tctttcaggg cttcatcgac   60

SEQ ID NO: 53              moltype = DNA   length = 60
FEATURE                    Location/Qualifiers
misc_feature               1..60
                           note = Primer
source                     1..60
                           mol_type = other DNA
                           organism = synthetic construct
SEQUENCE: 53
gtcgatgaag ccctgaaaga cgcgcagact atggatgaaa tcaaactgtc ggtggttatg   60

SEQ ID NO: 54              moltype = DNA   length = 60
FEATURE                    Location/Qualifiers
misc_feature               1..60
                           note = Primer
source                     1..60
                           mol_type = other DNA
                           organism = synthetic construct
SEQUENCE: 54
gatggccttt ttgcgtgtcg acgcggccgc tcattggcga cgccaatcga acgcaacgcg   60

SEQ ID NO: 55              moltype = DNA   length = 60
FEATURE                    Location/Qualifiers
misc_feature               1..60
                           note = Primer
source                     1..60
                           mol_type = other DNA
                           organism = synthetic construct
SEQUENCE: 55
cgcgttgcgt tcgattggcg tcgccaatga gcggccgcgt cgacacgcaa aaaggccatc   60

SEQ ID NO: 56              moltype = DNA   length = 60
FEATURE                    Location/Qualifiers
misc_feature               1..60
                           note = Primer
source                     1..60
                           mol_type = other DNA
                           organism = synthetic construct
SEQUENCE: 56
```

-continued

```
cataaccacc gacagtttga tttcatccat agtctgcgcg tctttcaggg cttcatcgac   60

SEQ ID NO: 57          moltype = DNA   length = 60
FEATURE                Location/Qualifiers
misc_feature           1..60
                       note = Primer
source                 1..60
                       mol_type = other DNA
                       organism = synthetic construct
SEQUENCE: 57
gtcgatgaag ccctgaaaga cgcgcagact atggaaaact atgtcgtctc tatccgcacc   60

SEQ ID NO: 58          moltype = DNA   length = 60
FEATURE                Location/Qualifiers
misc_feature           1..60
                       note = Primer
source                 1..60
                       mol_type = other DNA
                       organism = synthetic construct
SEQUENCE: 58
gatggccttt ttgcgtgtcg acgcggccgc tcatttgaac ggaacaatct ttttgtcatc   60

SEQ ID NO: 59          moltype = DNA   length = 60
FEATURE                Location/Qualifiers
misc_feature           1..60
                       note = Primer
source                 1..60
                       mol_type = other DNA
                       organism = synthetic construct
SEQUENCE: 59
gatgacaaaa agattgttcc gttcaaatga gcggccgcgt cgacacgcaa aaaggccatc   60

SEQ ID NO: 60          moltype = DNA   length = 60
FEATURE                Location/Qualifiers
misc_feature           1..60
                       note = Primer
source                 1..60
                       mol_type = other DNA
                       organism = synthetic construct
SEQUENCE: 60
ggtgcggata gagacgacat agttttccat agtctgcgcg tctttcaggg cttcatcgac   60

SEQ ID NO: 61          moltype = DNA   length = 60
FEATURE                Location/Qualifiers
misc_feature           1..60
                       note = Primer
source                 1..60
                       mol_type = other DNA
                       organism = synthetic construct
SEQUENCE: 61
gtcgatgaag ccctgaaaga cgcgcagact atgtcctcag ctttccatta cgtcattagc   60

SEQ ID NO: 62          moltype = DNA   length = 60
FEATURE                Location/Qualifiers
misc_feature           1..60
                       note = Primer
source                 1..60
                       mol_type = other DNA
                       organism = synthetic construct
SEQUENCE: 62
gatggccttt ttgcgtgtcg acgcggccgc tcattcaaat tcgataatca tggtgatttt   60

SEQ ID NO: 63          moltype = DNA   length = 60
FEATURE                Location/Qualifiers
misc_feature           1..60
                       note = Primer
source                 1..60
                       mol_type = other DNA
                       organism = synthetic construct
SEQUENCE: 63
aaaatcacca tgattatcga atttgaatga gcggccgcgt cgacacgcaa aaaggccatc   60

SEQ ID NO: 64          moltype = DNA   length = 60
FEATURE                Location/Qualifiers
misc_feature           1..60
                       note = Primer
source                 1..60
                       mol_type = other DNA
                       organism = synthetic construct
```

-continued

```
SEQUENCE: 64
gctaatgacg taatggaaag ctgaggacat agtctgcgcg tctttcaggg cttcatcgac   60

SEQ ID NO: 65         moltype = DNA   length = 60
FEATURE               Location/Qualifiers
misc_feature          1..60
                      note = Primer
source                1..60
                      mol_type = other DNA
                      organism = synthetic construct
SEQUENCE: 65
gtcgatgaag ccctgaaaga cgcgcagact atgaacgtga ataagccgac caccgaaaag   60

SEQ ID NO: 66         moltype = DNA   length = 60
FEATURE               Location/Qualifiers
misc_feature          1..60
                      note = Primer
source                1..60
                      mol_type = other DNA
                      organism = synthetic construct
SEQUENCE: 66
gatggccttt ttgcgtgtcg acgcggccgc tcagtattct tcaattttgt ccagttgata   60

SEQ ID NO: 67         moltype = DNA   length = 60
FEATURE               Location/Qualifiers
misc_feature          1..60
                      note = Primer
source                1..60
                      mol_type = other DNA
                      organism = synthetic construct
SEQUENCE: 67
tatcaactgg acaaaattga agaatactga gcggccgcgt cgacacgcaa aaaggccatc   60

SEQ ID NO: 68         moltype = DNA   length = 60
FEATURE               Location/Qualifiers
misc_feature          1..60
                      note = Primer
source                1..60
                      mol_type = other DNA
                      organism = synthetic construct
SEQUENCE: 68
cttttcggtg gtcggcttat tcacgttcat agtctgcgcg tctttcaggg cttcatcgac   60

SEQ ID NO: 69         moltype = DNA   length = 60
FEATURE               Location/Qualifiers
misc_feature          1..60
                      note = Primer
source                1..60
                      mol_type = other DNA
                      organism = synthetic construct
SEQUENCE: 69
gtgatcaacg ccgccagcgg tcgtcagact gtcgatgaag ccctgaaaga cgcgcagact   60

SEQ ID NO: 70         moltype = DNA   length = 60
FEATURE               Location/Qualifiers
misc_feature          1..60
                      note = Primer
source                1..60
                      mol_type = other DNA
                      organism = synthetic construct
SEQUENCE: 70
gcggccgcgt cgacacgcaa aaaggccatc catccgtcag gatggccttc tgcttaattt   60

SEQ ID NO: 71         moltype = DNA   length = 60
FEATURE               Location/Qualifiers
misc_feature          1..60
                      note = Primer
source                1..60
                      mol_type = other DNA
                      organism = synthetic construct
SEQUENCE: 71
aaattaagca gaaggccatc ctgacggatg gatggccttt ttgcgtgtcg acgcggccgc   60

SEQ ID NO: 72         moltype = DNA   length = 60
FEATURE               Location/Qualifiers
misc_feature          1..60
                      note = Primer
source                1..60
                      mol_type = other DNA
```

-continued

```
                            organism = synthetic construct
SEQUENCE: 72
agtctgcgcg tctttcaggg cttcatcgac agtctgacga ccgctggcgg cgttgatcac    60

SEQ ID NO: 73          moltype = DNA   length = 66
FEATURE                Location/Qualifiers
misc_feature           1..66
                       note = Primer
source                 1..66
                       mol_type = other DNA
                       organism = synthetic construct
SEQUENCE: 73
gtttaacttt aataaggaga tataccatgc tgacggaagt gcgcccggtc tctacgacga    60
aaccgc                                                               66

SEQ ID NO: 74          moltype = DNA   length = 66
FEATURE                Location/Qualifiers
misc_feature           1..66
                       note = Primer
source                 1..66
                       mol_type = other DNA
                       organism = synthetic construct
SEQUENCE: 74
cgacctgcag gcgcgccgag ctcgaattca tttgatgtat ttgcaataga acacagaaaa    60
gaccgt                                                               66

SEQ ID NO: 75          moltype = DNA   length = 66
FEATURE                Location/Qualifiers
misc_feature           1..66
                       note = Primer
source                 1..66
                       mol_type = other DNA
                       organism = synthetic construct
SEQUENCE: 75
gtgttctatt gcaaatacat caaatgaatt cgagctcggc gcgcctgcag gtcgacaagc    60
ttgcgg                                                               66

SEQ ID NO: 76          moltype = DNA   length = 69
FEATURE                Location/Qualifiers
misc_feature           1..69
                       note = Primer
source                 1..69
                       mol_type = other DNA
                       organism = synthetic construct
SEQUENCE: 76
gagaccgggc gcacttccgt cagcatggta tatctcctta ttaaagttaa acaaaattat    60
ttctacagg                                                            69

SEQ ID NO: 77          moltype = DNA   length = 62
FEATURE                Location/Qualifiers
misc_feature           1..62
                       note = Primer
source                 1..62
                       mol_type = other DNA
                       organism = synthetic construct
SEQUENCE: 77
gtatggtgac cctgtggcgc aaatgagaat tcgagctcgg cgcgcctgca ggtcgacaag    60
ct                                                                   62

SEQ ID NO: 78          moltype = DNA   length = 64
FEATURE                Location/Qualifiers
misc_feature           1..64
                       note = Primer
source                 1..64
                       mol_type = other DNA
                       organism = synthetic construct
SEQUENCE: 78
gcgctgccct gtttgatttt atccatggta tatctcctta ttaaagttaa acaaaattat    60
ttct                                                                 64

SEQ ID NO: 79          moltype = DNA   length = 63
FEATURE                Location/Qualifiers
misc_feature           1..63
                       note = Primer
source                 1..63
                       mol_type = other DNA
                       organism = synthetic construct
SEQUENCE: 79
cctgcaggcg cgccgagctc gaattctcat ttgcgccaca gggtcaccat acgtgccggc    60
```

-continued

```
agg                                                                          63

SEQ ID NO: 80          moltype = DNA   length = 66
FEATURE                Location/Qualifiers
misc_feature           1..66
                       note = Primer
source                 1..66
                       mol_type = other DNA
                       organism = synthetic construct
SEQUENCE: 80
gtttaacttt aataaggaga tataccatgg ataaaatcaa acagggcagc gcctctctgg   60
ttgtcg                                                              66

SEQ ID NO: 81          moltype = DNA   length = 57
FEATURE                Location/Qualifiers
misc_feature           1..57
                       note = Primer
source                 1..57
                       mol_type = other DNA
                       organism = synthetic construct
SEQUENCE: 81
cagactcgag ggtaccgacg tcctaataag tagatgaata tttatcagga cgaagat     57

SEQ ID NO: 82          moltype = DNA   length = 55
FEATURE                Location/Qualifiers
misc_feature           1..55
                       note = Primer
source                 1..55
                       mol_type = other DNA
                       organism = synthetic construct
SEQUENCE: 82
aactaaaggt ttattttcca tatgtatatc tccttcttat acttaactaa tatac       55

SEQ ID NO: 83          moltype = DNA   length = 64
FEATURE                Location/Qualifiers
misc_feature           1..64
                       note = Primer
source                 1..64
                       mol_type = other DNA
                       organism = synthetic construct
SEQUENCE: 83
taaatattca tctacttatt aggacgtcgg taccctcgag tctggtaaag aaaccgctgc   60
tgcg                                                                64

SEQ ID NO: 84          moltype = DNA   length = 59
FEATURE                Location/Qualifiers
misc_feature           1..59
                       note = Primer
source                 1..59
                       mol_type = other DNA
                       organism = synthetic construct
SEQUENCE: 84
gtataagaag gagatataca tatggaaaat aaacctttag tttcagtttt gatttgtgc    59

SEQ ID NO: 85          moltype = DNA   length = 75
FEATURE                Location/Qualifiers
misc_feature           1..75
                       note = Primer
source                 1..75
                       mol_type = other DNA
                       organism = synthetic construct
SEQUENCE: 85
taactttaag aaggagatat acaagagctc gagtcgaagg agatagaacc atggcaacag   60
catggtataa acaag                                                    75

SEQ ID NO: 86          moltype = DNA   length = 82
FEATURE                Location/Qualifiers
misc_feature           1..82
                       note = Primer
source                 1..82
                       mol_type = other DNA
                       organism = synthetic construct
SEQUENCE: 86
gcgtgtcgac gcgtttagag gcccccaaggg gttatgctag tatcgattta tcatttagcc   60
acggatagtt tataaatttt ac                                            82

SEQ ID NO: 87          moltype = DNA   length = 80
FEATURE                Location/Qualifiers
misc_feature           1..80
```

-continued

```
                              note = Primer
source                        1..80
                              mol_type = other DNA
                              organism = synthetic construct
SEQUENCE: 87
ggttctatct ccttcgactc gagctcttgt atatctcctt cttaaagtta aacaaaatta    60
tttctagatt tttgtcgaac                                                80

SEQ ID NO: 88      moltype = DNA   length = 63
FEATURE            Location/Qualifiers
misc_feature       1..63
                   note = Primer
source             1..63
                   mol_type = other DNA
                   organism = synthetic construct
SEQUENCE: 88
taaatcgata ctagcataac cccttggggc ctctaaacgc gtcgacacgc aaaaaggcca    60
tcc                                                                 63

SEQ ID NO: 89      moltype = DNA   length = 80
FEATURE            Location/Qualifiers
misc_feature       1..80
                   note = Primer
source             1..80
                   mol_type = other DNA
                   organism = synthetic construct
SEQUENCE: 89
gttcgacaaa aatctagaaa taattttgtt taactttaag aaggagatat acaagagctc    60
gagtcgaagg agatagaacc                                                80

SEQ ID NO: 90      moltype = DNA   length = 63
FEATURE            Location/Qualifiers
misc_feature       1..63
                   note = Primer
source             1..63
                   mol_type = other DNA
                   organism = synthetic construct
SEQUENCE: 90
ggatggcctt tttgcgtgtc gacgcgttta gaggccccaa ggggttatgc tagtatcgat    60
tta                                                                 63

SEQ ID NO: 91      moltype = DNA   length = 34
FEATURE            Location/Qualifiers
misc_feature       1..34
                   note = Primer
source             1..34
                   mol_type = other DNA
                   organism = synthetic construct
SEQUENCE: 91
atatgacgtc tcattagcgg tttttcagga gacg                                34

SEQ ID NO: 92      moltype = DNA   length = 35
FEATURE            Location/Qualifiers
misc_feature       1..35
                   note = Primer
source             1..35
                   mol_type = other DNA
                   organism = synthetic construct
SEQUENCE: 92
atatcatatg ccgtccgaag cattccgtcg tcacc                               35

SEQ ID NO: 93      moltype = DNA   length = 62
FEATURE            Location/Qualifiers
misc_feature       1..62
                   note = Primer
source             1..62
                   mol_type = other DNA
                   organism = synthetic construct
SEQUENCE: 93
taactttaat aaggagatat accatgacgc aatttaatcc cgttgatcat ccacatcgcc    60
gc                                                                  62

SEQ ID NO: 94      moltype = DNA   length = 67
FEATURE            Location/Qualifiers
misc_feature       1..67
                   note = Primer
source             1..67
                   mol_type = other DNA
                   organism = synthetic construct
```

-continued

```
SEQUENCE: 94
attttcgcga atccggagtg taaaagcttg cggccgcata atgcttaagt cgaacagaaa    60
gtaatcg                                                             67

SEQ ID NO: 95          moltype = DNA   length = 72
FEATURE                Location/Qualifiers
misc_feature           1..72
                       note = Primer
source                 1..72
                       mol_type = other DNA
                       organism = synthetic construct
SEQUENCE: 95
aagcattatg cggccgcaag cttttacact ccggattcgc gaaaatggat atcgctgact    60
gcgcgcaaac gc                                                        72

SEQ ID NO: 96          moltype = DNA   length = 68
FEATURE                Location/Qualifiers
misc_feature           1..68
                       note = Primer
source                 1..68
                       mol_type = other DNA
                       organism = synthetic construct
SEQUENCE: 96
tcaacgggat taaattgcgt catggtatat ctccttatta aagttaaaca aaattatttc    60
tacagggg                                                            68

SEQ ID NO: 97          moltype = DNA   length = 57
FEATURE                Location/Qualifiers
misc_feature           1..57
                       note = Primer
source                 1..57
                       mol_type = other DNA
                       organism = synthetic construct
SEQUENCE: 97
atggtgatgg ctgctgccca tttaaaccgc tttgactgcg tcggcaatac ggtgcgc       57

SEQ ID NO: 98          moltype = DNA   length = 60
FEATURE                Location/Qualifiers
misc_feature           1..60
                       note = Primer
source                 1..60
                       mol_type = other DNA
                       organism = synthetic construct
SEQUENCE: 98
gtttaacttt aataaggaga tataccatgc tgaacaacgc gatgtctgtt gttatcctgg    60

SEQ ID NO: 99          moltype = DNA   length = 53
FEATURE                Location/Qualifiers
misc_feature           1..53
                       note = Primer
source                 1..53
                       mol_type = other DNA
                       organism = synthetic construct
SEQUENCE: 99
cgcagtcaaa gcggtttaaa tgggcagcag ccatcaccat catcaccaca gcc           53

SEQ ID NO: 100         moltype = DNA   length = 59
FEATURE                Location/Qualifiers
misc_feature           1..59
                       note = Primer
source                 1..59
                       mol_type = other DNA
                       organism = synthetic construct
SEQUENCE: 100
tcgcgttgtt cagcatggta tatctcctta ttaaagttaa acaaaattat ttctacagg     59

SEQ ID NO: 101         moltype = DNA   length = 35
FEATURE                Location/Qualifiers
misc_feature           1..35
                       note = Primer
source                 1..35
                       mol_type = other DNA
                       organism = synthetic construct
SEQUENCE: 101
atatatcata tgtgcggtat cgttggtgct atcgc                               35

SEQ ID NO: 102         moltype = DNA   length = 36
FEATURE                Location/Qualifiers
misc_feature           1..36
```

-continued

```
                    note = Primer
source              1..36
                    mol_type = other DNA
                    organism = synthetic construct
SEQUENCE: 102
atatatgacg tcttattcca cggtcacgga tttcgc                          36
```